(12) United States Patent
Foitzik et al.

(10) Patent No.: US 9,238,644 B2
(45) Date of Patent: *Jan. 19, 2016

(54) VEGFR3 INHIBITORS

(71) Applicant: CANCER THERAPEUTICS CRC PTY LIMITED, Bundoora, Victoria (AU)

(72) Inventors: Richard Charles Foitzik, Parkville (AU); Benjamin Joseph Morrow, Parkville (AU); Catherine Fae Hemley, Parkville (AU); Gillian Elizabeth Lunniss, Parkville (AU); Michelle Ang Camerino, Parkville (AU); Danny Ganame, Bundoora (AU); Paul Anthony Stupple, Bundoora (AU); Romina Lessene, Bundoora (AU); Wilhelmus Johannes Antonius Kersten, Bundoora (AU); Andrew John Harvey, Thebarton (AU); Ian Peter Holmes, Parkville (AU)

(73) Assignee: CANCER THERAPEUTICS CRC PTY LIMITED, Bundoora, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/969,037

(22) Filed: Aug. 16, 2013

(65) Prior Publication Data
US 2014/0073620 A1    Mar. 13, 2014

Related U.S. Application Data

(60) Provisional application No. 61/684,202, filed on Aug. 17, 2012.

(51) Int. Cl.
| | | |
|---|---|---|
| C07D 401/14 | (2006.01) | |
| A61K 31/505 | (2006.01) | |
| C07D 413/12 | (2006.01) | |
| C07D 401/12 | (2006.01) | |
| C07D 403/12 | (2006.01) | |
| C07D 403/14 | (2006.01) | |
| C07D 239/42 | (2006.01) | |
| A61K 31/506 | (2006.01) | |

(52) U.S. Cl.
CPC ............ *C07D 413/12* (2013.01); *A61K 31/505* (2013.01); *A61K 31/506* (2013.01); *C07D 239/42* (2013.01); *C07D 401/12* (2013.01); *C07D 401/14* (2013.01); *C07D 403/12* (2013.01); *C07D 403/14* (2013.01)

(58) Field of Classification Search
CPC .. C07D 239/42; C07D 401/12; C07D 401/14; C07D 403/12; C07D 403/14; A61K 31/505; A61K 31/506
USPC .............. 544/295, 330, 331; 514/252.14, 275
See application file for complete search history.

(56) References Cited

FOREIGN PATENT DOCUMENTS

| | | |
|---|---|---|
| CN | 103113355 A | 5/2013 |
| WO | WO 03/032997 A1 | 4/2003 |
| WO | WO 2010/053438 A1 | 5/2010 |
| WO | WO 2010/111406 A2 | 9/2010 |
| WO | WO 2012/022408 A1 | 2/2012 |
| WO | WO 2012/110773 A1 | 8/2012 |
| WO | WO 2012/110774 A1 | 8/2012 |
| WO | WO 2012/115479 A2 | 8/2012 |
| WO | WO 2014/012942 A1 | 1/2014 |
| WO | WO 2014/027199 | * 2/2014 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Alitalo et al., Interaction of tumor cells and lymphatic vessels in cancer progression, Oncogene (2012), 31(42), 4499-4508.*
Bundgaard, Design of Prodrugs, p. 1, 1985.*
Wolff, Some consideration for prodrug design, Burger's Medicinal Chemistry and Drug Discovery, 5th Edition, vol. I Principles and Practice, pp. 975-977, 1995.*
Banker et al., Prodrugs, Modern Pharmaceutics, Third Edition and Expanded, pp. 451 and 596 (1996).*
Silverman, Prodrugs and Drug Delivery Systems, The Organic Chemistry of Drug Design and Drug Action, pp. 352-399, 1992.*
Written Opinion dated Sep. 24, 2013, issued in connection with PCT/AU2013/000913.
International Search Report dated Sep. 24, 2013, issued in connection with PCT/AU2013/000913.

(Continued)

*Primary Examiner* — Deepak Rao
(74) *Attorney, Agent, or Firm* — Nixon & Vanderhye P.C.

(57) ABSTRACT

This invention relates to a compound of the formula (I):

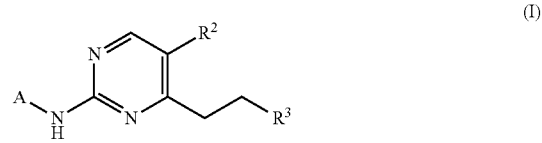

The invention also relates to processes for the preparation of the compound of the formula (I), pharmaceutical agents or compositions containing the compound or a method of using the compound for the treatment of proliferative diseases, such as cancer, as well as the treatment of diseases ameliorated by the control and/or inhibition of lymphangiogenesis.

61 Claims, No Drawings

(56) References Cited

OTHER PUBLICATIONS

CA 2 808 540 A1, dated Feb. 23, 2012 (equivalent to WO 2012/022408).
Coats et al, "Correlation analysis of pyrimidine folic acid antagonists as antibacterial agents .I.", European Journal of Medicinal Chemistry, (1979), 14(3), 261-270.
Murray et al, "Dimetalated Heterocycles as Synthetic Intermediates V. Dianions Derived from Certain 2-Hydroxy-4-methylpyrimidines, 2-Amino-4-methylpyrimidines, and Related Compounds", Journal of Organic Chemistry, 1974, vol. 39, No. 5, 595-600.
Kreutzberger et al, "Cyclisierungsreaktionen an 4-Nitrophenylguanidin", Chemiker-Zeitung, 1981, 105(7-7), 229-232.
ASX Announcement, May 16, 2013, Bionomics press release about CTx-0357927, "CTX and Bionomics' Program Reaches Key Milestone".
Hescot et al, "Pancreatic Atrophy—A New Late Toxic Effect of Sorafenib", The New England Journal of Medicine 369:15, pp. 475-476, Oct. 10, 2013.
Alam et al, "SAR131675, a Potent and Selective VEGFR-3-TK Inhibitor with Antilymphangiogenic, Antitumoral, and Antimetastatic Activities", Mol Cancer Ther; 11(8); 1637-49, 2012.
Loges et al, "Mechanisms of Resistance to Anti-Angiogenic Therapy and Development of Third-Generation Anti-Angiogenic Drug Candidates", Genes & Cancer 1(1) 12-25, 2010.
Duong et al, "Tumor Lymphangiogenesis as a Potential Therapeutic Target", Journal of Oncology, Article ID 204946, 23 pages, vol. 2012.
Meanwell, N. A. "Improving Drug Candidates by Design: A Focus on Physicochemical Properties as a Means of Improving Compound Disposition and Safety", Chemical Research in Toxicology 2011 24 (9), 1420-1456.
Kerns, E. H. & Di, L. (2008). "Drug-like Properties: Concepts, Structure Design and Methods" Lavergne, TN: Academic Press, pp. 45 and 152.
U.S. Patent Office, Office Action mailed Jul. 8, 2015 in U.S. Appl. No. 14/422,084, filed Feb. 17, 2015, Foitzik et al.
Jordan, V. C. "Tamoxifen: A Most Unlikely Pioneering Medicine", Nature Reviews: Drug Discovery, 2, 2003, 205.
Vippagunta, et al. "Crystalline Solids", Advanced Drug Delivery Reviews, 48, 2001, 18.
Hackam, et al. "Translation of Research Evidence From Animals to Humans", JAMA, 296(14), 2006, 1731-1732.

* cited by examiner

VEGFR3 INHIBITORS

This application claims priority to U.S. Provisional Application No. 61/684,202 filed 17 Aug. 2012, the entire contents of which is hereby incorporated by reference.

This invention relates to 2,4,5-substituted pyrimidines that inhibit vascular endothelial growth factor receptor 3 (VEGFR3), also known as Fms related tyrosine kinase 4 (FLT4), processes for their preparation and pharmaceutical agents or compositions containing such compounds. This invention also relates to a method of using such compounds for the treatment of proliferative diseases, such as cancer, as well as the treatment of diseases ameliorated by the control and/or inhibition of lymphangiogenesis.

BACKGROUND

Cancer remains a major cause of death in the 21st century. Consequently, considerable drug research and development effort is currently placed on the discovery of therapeutics that may provide life extending or curative options to cancer sufferers.

While there are many different varieties of cancer, each exhibiting a different array of genetic and growth properties, a common denominator among many solid cancer types is the ability to metastasise. Until the occurrence of metastasis, tumors are confined to one area of the body and may be controlled through surgical intervention and/or radiotherapy. However, metastasis causes cancer cells to spread to disparate parts of the body and while surgical intervention may remove the primary tumor lesion, removal of all metastatic lesions is very difficult to manage.

Tumor metastasis is a multistage process, involving the breakdown of extracellular matrix, invasion of local tissue parenchyma, intravasation into regional blood vessels and lymphatics, survival in the circulation and finally extravasation, survival and growth in secondary tissue sites (*Front. Biosci.* (*Elite Ed*). 2012; 4: 1888-1897).

Metastasis may occur through blood vessels or lymphatic vessels. Lymphatic vessels differ from blood vessels in several ways. Large collecting lymphatic vessels contain vascular smooth muscle cells in their wall, as well as valves, which prevent the backflow of lymph. However, lymphatic capillaries, unlike typical blood capillaries, lack pericytes and continuous basal lamina and contain large inter-endothelial valve-like openings (*J. Theor. Med.* 2003; 5: 59-66). Due to their greater permeability, lymphatic capillaries are more effective than blood capillaries in allowing tumor cells to pass. Experimental evidence demonstrates that lymphangiogenesis (the formation of new lymphatic vessels) within a growing tumor lesion promotes metastasis through lymphatic vessels. The control of lymphangiogenesis presents an attractive therapeutic strategy for preventing lymph node metastasis (*J. Clin. Onc.* 2007; 25: 4298-4307).

The lymphatic system is comprised of capillaries and larger collecting vessels continuously lined by endothelial cells which return extravasated fluid and macromolecules from the interstitial space back to the blood circulation. Metastasis to regional lymph nodes via lymphatic vessels is a tumor progression process that is common to many cancer types. The extent of lymph node involvement is a major determinant for the staging of many types of cancer and is an important prognostic factor that is used as the basis for surgical and radiation treatment intervention of the affected lymph nodes.

Molecular signalling through binding of the growth factors VEGFC or VEGFD to their membrane receptor VEGFR3 has been shown to play a central role in the process of lymphangiogenesis (*Brit. J. Cancer* 2006; 94: 1355-1360). Stimulation of the VEGFR3 receptor occurs through the phosphorylation of its intracellular region and triggers a downstream signalling cascade that drives lymphatic endothelial cell proliferation, migration and differentiation leading to formation of lymphatic vessels (*Exp. Cell Res.* 2006; 312: 575-583). Increased expression of VEGFC or VEGFD has been shown to promote tumor associated lymphangiogenesis enabling lymphatic-mediated metastasis to regional lymph nodes. These observations have been reported for several different tumor types, including colorectal (*Oncol. Rep.* 2009; 22: 1093-1100) lung (*Ann. Oncol.* 2010; 21: 223-231), gastric (*Surgery* 2009; 146: 896-905), kidney (*Oncol. Rep.* 2008; 20: 721-725) prostate (*Clin. Cancer Res.* 2004; 10: 5137-5144) and ovarian (*Cancer* 2004; 101: 1364-1374). Blockade of VEGFC, VEGFD/VEGFR3 mediated signalling has been shown to inhibit lymphangiogenesis and suppress lymph node metastasis in several tumor experimental models in rodents (*Ann. N.Y. Acad. Sci.* 2008; 113: 225-234; *Int. J. Cancer* 2009; 125: 2747-2756).

VEGFR3 is a transmembrane tyrosine kinase receptor that is broadly expressed in endothelial cells during embryogenesis (*Biochem. J.* 2011; 437: 169-183). In the latter stages of development VEGFR3 expression becomes restricted to developing lymphatic vessels. In adults, VEGFR3 expression is primarily restricted to lymphatic endothelium and a subset of CD34+ hematopoietic cells. In addition, fenestrated capillaries and veins in certain endocrine organs, as well as monocytes, macrophages and some dendritic cells (DCs), continue to express VEGFR3 in adults. Disruption of the VEGFR3 gene in mouse embryos results in the failure of vascular network formation and death after embryonic day 9.5 (*Biochem. J.* 2011; 437: 169-183). This observation demonstrates that VEGFR3 plays an essential role in the development of embryonic vasculature. In cancer, VEGFR3 is overexpressed in lymphatic sinuses in metastatic lymph nodes and in lymphangiomas. Furthermore, in many instances cancer cells themselves express VEGFR3. VEGFR3 expressing cancer cells have been shown to be dependent on VEGFR3/VEGFC signalling for their proliferation (*Eur. J. Canc.* 2011; 47: 2353-2363).

Based on the foregoing, it is apparent that inhibition of VEGFR3 signalling has strong potential as therapeutic strategy for mammalian subjects that have been diagnosed with a disease characterised by proliferation of endothelial cells that express this receptor. In the case of cancer, targeting VEGFR3 is likely to result in therapeutic benefit through suppression of lymphatic metastasis and suppression of growth in cancer cells that express VEGFR3.

Interestingly, and perhaps importantly from the view point of target selection within the VEGFR3 axis, in mice in which both the VEGFC and the VEGFD genes have been homozygously deleted, the blood vasculature develops normally, unlike the embryonic cardiovascular phenotype of VEGFR3 homozygous knockout mice: i.e. deletion of these two ligands is not the same as deletion of the receptor (*Mol. Cell. Biol.* 2008; 28: 4843-4850). These data raise the possibility that another ligand for VEGFR3 exists or that VEGFR3 may be able to act by an as-yet-unknown manner independent of its ligands VEGFC and VEGFD. The foregoing suggest that targeting VEGFR3 is more advantageous to blocking VEGFC/D-VEGFR3 signalling compared to targeting either VEGFC or VEGFD alone.

Whilst there are a number of studies reported involving tyrosine kinase inhibitors with various levels of VEGFR3 activity and selectivity (*Nat. Rev. Drug Discov.* 2006; 5: 835-

844; *Mol. Cancer Ther.* 2007; 6: 2012-2021; *Cancer Res.* 2009; 69: 8009-8016; *Mol. Cancer Ther.* 2012; 11: 1637-1649) these studies have some limitations, resulting in part at least from inhibition at other tyrosine kinases.

Nonetheless, collectively these studies strengthen the conclusion that inhibition of VEGFR3 suppresses or reduces lymphangiogenesis and/or lymphogenic metastasis.

Accordingly, compounds that selectively inhibit VEGFR3 would be useful for the treatment of proliferative diseases, such as cancer.

As described above, VEGFR3 plays an important role in the control of lymphangiogenesis. Accordingly, inhibitors of VEGFR3 may have utility in the treatment of diseases other than cancer where control/inhibition of lymphangiogenesis has a therapeutic benefit. The lymphatic system plays a major role in chronic inflammatory diseases and in transplant rejection. Inhibition of lymphangiogenesis through suppression of VEGFR3 function may provide a viable therapeutic strategy in these conditions.

For example, preclinical studies have demonstrated that the expression of VEGFR3 in the cornea and ocular surface is modified during corneal neovascularisation and that VEGFR3 mediates corneal dendritic cell migration to lymph nodes and induction of immunity to corneal transplant. High-risk corneal transplantation, where grafting is performed on inflamed and highly vascularized host beds, has a very poor success rate, with rejection rates as high as 90% (*J. Leukoc Biol.* 2003; 74: 172-178). In preclinical models, treatment with a VEGFR3 antibody leads to significant suppression of corneal graft rejection (*Nat. Med.* 2004; 10: 813-815).

Choroidal neovascularization (CNV), the creation of new blood vessels in the choroid layer of the eye, leads to chronic inflammation which is implicated in the pathogenesis of age related macular degeneration (AMD) and is driven by factors which include uncontrolled expression of the vascular endothelial growth factor (VEGF) family members VEGFA and VEGFC (*J. Cell. Physiol.* 2012; 227(1): 116-26). Treatments for AMD have been developed that target VEGFA, for example the anti-VEGFA antibodies ranibizumab and bevacizumab and the anti-VEGF aptamer pegaptanib, but to date no treatments have been clinically evaluated that mediate effects through modulation of VEGFC and its cognate receptor VEGFR3.

Accordingly, compounds that inhibit VEGFR3 may be useful for the prevention and/or treatment of eye diseases, for example corneal graft rejection and age related macular degeneration.

Furthermore, there is increasing evidence that lymphatic vessels have an active role in chronic inflammation of the skin. Lymphatic endothelial cell proliferation and lymphatic hyperplasia have been described in chronic skin inflammation in mice and have been reported for skin lesions in psoriasis patients (*Blood* 2004; 104: 1048-1057).

Accordingly, compounds that inhibit VEGFR3 may be useful for the prevention and/or treatment of skin inflammations, such as skin lesions in patients with psoriasis.

Lymphangiogenesis has also been found to be associated with kidney transplant rejection. VEGFC producing macrophages induce formation of new lymphatics which induce and support the maintenance of an alloreactive immune response in renal transplants (*Nat. Med.* 2006; 12: 230-234).

Accordingly, compounds that inhibit VEGFR3 may be useful for the prevention and/or treatment of rejection in renal transplantation.

Co-pending application WO2012/110773 discloses compounds which inhibit FAK and VEGFR3.

SUMMARY

The present inventors have discovered a particular class of compounds which are effective as VEGFR3 inhibitors. These compounds may exhibit selectivity for VEGFR3 over kinases such as FAK and/or VEGFR2.

In a first aspect, the present invention provides compounds of the following formula (I), isomers, salts, solvates, protected forms or prodrugs thereof:

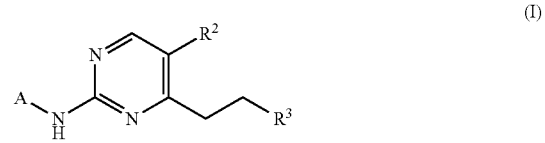

wherein:

A is selected from optionally substituted phenyl and an optionally substituted 5-10 membered heteroaryl group linked to the NH group through an aromatic ring carbon atom, in which the heteroaryl ring system contains 1 to 4 heteroatoms selected from N, O and S, and;

when A is optionally substituted phenyl, A may bear a substituent $R^{1A}$ which is not alpha to the NH group and may optionally further bear one or two substituents $R^{1B}$ which are not alpha to the NH group, where $R^{1A}$ is selected from:

(i) $CH(R^{C1})NZ^1Z^3$, where $R^{C1}$ is selected from H, $C_{1-2}$ alkyl, $Z^1$ is selected from H, $C_{1-3}$ alkyl optionally substituted by OH, $C(=O)OC_{1-4}$ alkyl and $C(=O)Me$, and $Z^3$ is H, or $Z^1$ and $Z^3$ together with the N to which they are attached form a 4-6 membered heterocycle containing at least one N and optionally one O;

(ii) $XNHZ^2$, where X is selected from $CMe_2$, cyclopropylidene, cyclobutylidene, cyclopentylidene and oxetanylidine and $Z^2$ is selected from H, $C_{1-3}$ alkyl optionally substituted by OH, $C(=O)OC_{1-3}$ alkyl and $C(=O)Me$;

(iii) a group selected from $R^{1A1}$ to $R^{1A13}$:

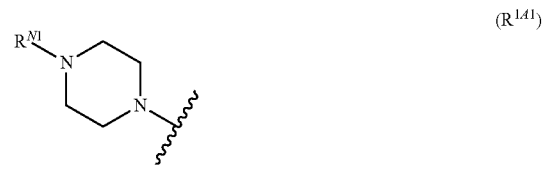

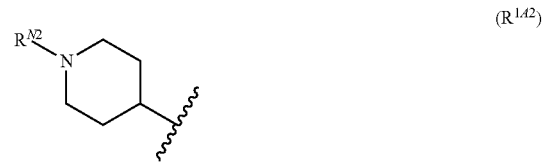

-continued

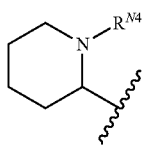
(R<sup>IA4</sup>)

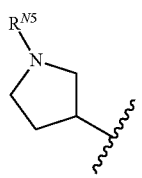
(R<sup>IA5</sup>)

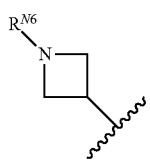
(R<sup>IA6</sup>)

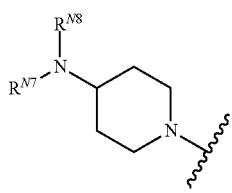
(R<sup>IA7</sup>)

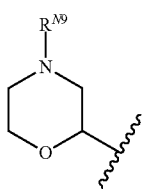
(R<sup>IA8</sup>)

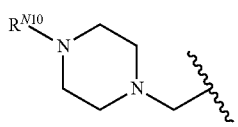
(R<sup>IA9</sup>)

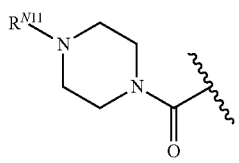
(R<sup>IA10</sup>)

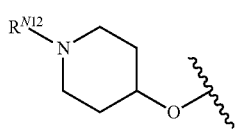
(R<sup>IA11</sup>)

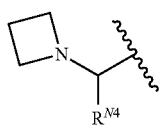
(R<sup>IA12</sup>)

-continued

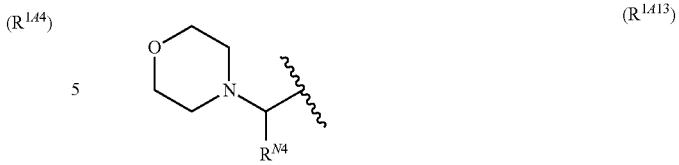
(R<sup>IA13</sup>)

wherein:
$R^{N1}$ is selected from H, $C_{1-4}$ alkyl, $C_{3-4}$ cycloalkyl and C(=O)Me;
$R^{N2}$ is selected from H, $C_{1-4}$ alkyl, $C_{3-4}$ cycloalkyl and C(=O)Me;
$R^{N3}$ is selected from H, $C_{1-4}$ alkyl, $C_{3-4}$ cycloalkyl and C(=O)Me;
$R^{N4}$ is selected from H and $CH_3$;
$R^{N5}$ is selected from H, $C_{1-4}$ alkyl, $C_{3-4}$ cycloalkyl and C(=O)Me;
$R^{N6}$ is selected from H, $C_{1-4}$ alkyl, $C_{3-4}$ cycloalkyl and C(=O)Me;
$R^{N7}$ and $R^{N8}$ are independently selected from H and $CH_3$;
$R^{N9}$ is selected from H, $C_{1-4}$ alkyl, $C_{3-4}$ cycloalkyl and C(=O)Me;
$R^{N10}$ is selected from H, $C_{1-4}$ alkyl, $C_{3-4}$ cycloalkyl and C(=O)Me;
$R^{N11}$ is selected from H, $C_{1-4}$ alkyl, $C_{3-4}$ cycloalkyl and C(=O)Me; and
$R^{N12}$ is selected from H, $C_{1-4}$ alkyl, $C_{3-4}$ cycloalkyl and C(=O)Me.

and where each $R^{1B}$ is independently selected from:
(i) $C_{1-3}$ alkyl;
(ii) $CF_3$;
(iii) F;
(iv) Cl;
(v) O—($C_{1-3}$ alkyl); and
(vi) CN;

when A is an optionally substituted 5-10 membered heteroaryl group, A may bear a single substituent $R^{1A}$ which is not alpha to the NH group, where $R^{1A}$ is as defined above, and may optionally further bear one, two or three substituents $R^{1C}$, where each $R^{1C}$ is independently selected from:
(i) $C_{1-3}$ alkyl optionally substituted with one to three substituents independently selected from F, OH and O—($C_{1-3}$ alkyl);
(ii) F;
(iii) Cl;
(iv) O—($C_{1-3}$ alkyl);
(v) CN;
(vi) =O, and
(vii) C(=O) ($C_{1-3}$ alkyl);

$R^2$ is selected from H, halo, $C_{1-4}$ alkyl, $CF_3$, $CF_2H$, CN and O—($C_{1-3}$ alkyl);

$R^3$ is selected from substituted phenyl and a substituted 6 membered heteroaryl group, where the heteroaryl ring system contains 1 or 2 N heteroatoms, where $R^3$ bears a substituent $R^4$ either alpha or beta to the —$C_2H_4$— group, and may additionally bear further substituents selected from F, methyl and $CF_3$; and $R^4$ is —Y—C(O)N($R^{N13}$)$Z^4$, where Y is selected from —CHCH$_3$—, —CH(CH$_2$CH$_3$)—, —C(CH$_3$)$_2$—, $C_{3-5}$ cycloalkylidene; $R^{N13}$ is selected from H and $CH_3$; and $Z^4$ is selected from H, $CH_3$ and $OCH_3$.

In some embodiments, the compounds of the first aspect of the present invention are of formula (I) as defined above with the proviso that the compound is not:

[Structure: 4-(piperidin-4-yl)phenyl-NH-pyrimidine(CF₃)-CH₂CH₂-phenyl-CH(CH₃)-C(O)NH₂]  or

[Structure: Boc-piperidine-phenyl-NH-pyrimidine(CF₃)-CH₂CH₂-phenyl-CH(CH₃)-C(O)NH₂]

In some embodiments, the compounds of the first aspect are of formula (I) as defined above with the proviso that:

when $R^3$ is selected from:

[Structures showing: R⁴-phenyl; R⁴-pyrazine; R⁴-pyrimidine; and R⁴-pyridine]

$R^4$ is —CH(CH$_3$)C(O)N(R$^{N13}$)Z$^4$;

A is either:

[Structure: R$^{1A}$-phenyl (para)]

where $R^{1A}$ is selected from

[Structure (R$^{141}$): R$^{N1}$-piperazine]

[Structure (R$^{142}$): R$^{N2}$-piperidine (4-position)]

[Structure (R$^{143}$): R$^{N3}$-piperidine (3-position)]

[Structure (R$^{144}$): R$^{N4}$-piperidine (2-position)]

[Structure (R$^{145}$): R$^{N5}$-pyrrolidine (3-position)]

[Structure (R$^{147}$): R$^{N7}$R$^{N8}$N-piperidine]

[Structure (R$^{148}$): R$^{N9}$-morpholine]

[Structure (R$^{149}$): R$^{N10}$-piperazine]

and $R^{N1}$ is selected from H, C$_{1-3}$ alkyl, and C(=O)Me;
$R^{N2}$ is selected from H, C$_{1-3}$ alkyl, and C(=O)Me;
$R^{N3}$ is selected from H, C$_{1-3}$ alkyl, and C(=O)Me;
$R^{N4}$ is selected from H and CH$_3$;
$R^{N5}$ is selected from H, C$_{1-3}$ alkyl, and C(=O)Me;
$R^{N7}$ and $R^{N8}$ are independently selected from H and CH$_3$;
$R^{N9}$ is selected from H, C$_{1-3}$ alkyl, and C(=O)Me;
$R^{N10}$ is selected from H, C$_{1-3}$ alkyl, and C(=O)Me;
or

[Structure: R$^{1A}$-phenyl (meta)]

where $R^{1A}$ is

[Structure (R$^{141}$): R$^{N1}$-piperazine]

-continued

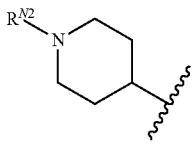
(R^{I42})

and $R^{N1}$ is selected from H, $C_{1-3}$ alkyl, and C(=O)Me;
$R^{N2}$ is selected from H, $C_{1-3}$ alkyl, and C(=O)Me;
then $R^2$ is not selected from $CF_3$, halo, $CF_2H$ and CN.

In some embodiments the compounds of the first aspect are of formula (I) as defined above, wherein when A is phenyl, Y is selected from —CH(CH$_2$CH$_3$)—, —C(CH$_3$)$_2$—, and $C_{3-5}$ cycloalkylidene.

A second aspect of the invention provides a process for the preparation of a compound of formula (I) or an isomer, salt, solvate, protected form or prodrug thereof of the first aspect, comprising:
reacting a compound of formula F1

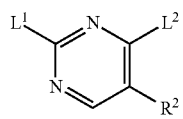
F1 with a compound of formula A-NH$_2$ to displace the group L and with a compound of the formula HC≡$R^3$ to displace the group $L^2$, or
with a compound of formula HC≡$R^3$ to displace the group $L^2$ and with a compound of formula A-NH$_2$ to displace the group $L^2$,
wherein $R^2$, A and $R^3$ areas defined in formula (I) above and $L^1$ and $L^2$ are leaving groups.

A third aspect of the invention provides a pharmaceutical agent comprising a compound of the formula (I) or isomers, salts, solvates, protected forms or prodrugs thereof of the first aspect.

There is also provided use of a compound of formula (I) or isomers, salts, solvates, protected forms or prodrugs thereof of the first aspect as a pharmaceutical agent.

There is further provided a compound of formula (I) or isomers, salts, solvates, protected forms or prodrugs thereof of the first aspect, for use as a pharmaceutical agent.

The pharmaceutical agent may be an anticancer agent, a lymphangiogenesis inhibitor, an antimetastasis agent or a VEGFR3 inhibitor.

A fourth aspect of the invention provides a composition comprising a compound or an isomer, salt, solvate, protected form or prodrug thereof of the first aspect and a pharmaceutically acceptable carrier or diluent.

A fifth aspect of the invention provides a compound or an isomer, salt, solvate, protected form or prodrug thereof of the first aspect, an agent of the third aspect or a composition of the fourth aspect for use in a method of therapy.

A sixth aspect of the invention provides for the use of a compound or an isomer, salt, solvate, protected form or prodrug thereof of the first aspect, an agent of the third aspect or a composition of the fourth aspect in the preparation of a medicament for treating a disease or condition ameliorated by the inhibition of VEGFR3. The sixth aspect of the invention also provides a compound or an isomer, salt, solvate, protected form or prodrug thereof of the first aspect, an agent of the third aspect or a composition of the fourth aspect for use in a method of treatment of a disease or condition ameliorated by the inhibition of VEGFR3.

A seventh aspect of the invention provides for the use of a compound or an isomer, salt, solvate, protected form or prodrug thereof of the first aspect, an agent of the third aspect or a composition of the fourth aspect in the preparation of a medicament for the treatment of cancer. The seventh aspect of the invention also provides a compound or an isomer, salt, solvate, protected form or prodrug thereof, an agent of the third aspect or a composition of the fourth aspect of the first aspect for use in a method for the treatment of cancer.

A further aspect of the invention provides a compound or an isomer, salt, solvate, protected form or prodrug thereof of the first aspect, an agent of the third aspect or a composition of the fourth aspect for use in a method of treatment of the human or animal body, preferably in the form of a pharmaceutical agent or composition.

Another aspect of the invention provides a method of inhibiting VEGFR3 in vitro or in vivo, comprising contacting a cell or cell lysates with an effective amount of a compound or an isomer, salt, solvate, protected form or prodrug thereof of the first aspect, an agent of the third aspect or a composition of the fourth aspect.

A still further aspect of the invention provides an anti-cancer treatment comprising a compound or an isomer, salt, solvate, protected form or prodrug thereof of the first aspect, an agent of the third aspect or a composition of the fourth aspect and an anti-tumour agent.

Each of the groups A, and $R^1$ to $R^4$ will be discussed in more detail below.

A

A is selected from optionally substituted phenyl and an optionally substituted 5-10 membered heteroaryl group linked to the NH group through an aromatic ring carbon atom, in which the heteroaryl ring system contains 1 to 4 heteroatoms selected from N, O and S.

If A is unsubstituted phenyl, it has the structure:

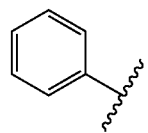
(A$^1$)

If A is substituted phenyl, the $R^{1A}$ group can either be meta or para, and so A can have the structures:

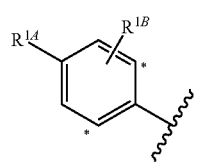
(A$^2$)

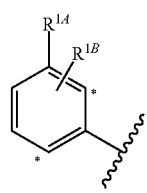
(A$^3$)

-continued

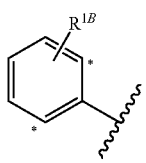 (A⁴)

where the R$^{1B}$ group cannot be alpha to the connection point to the rest of the compound (i.e., it cannot be in the asterixed positions).

When A is a 5-10 membered heteroaryl group linked to the NH group through an aromatic ring carbon atom, in which the heteroaryl ring system contains 1 to 4 heteroatoms selected from N, O and S, it is a monovalent moiety obtained by removing a hydrogen atom from an aromatic ring atom of an heteroaromatic compound (i.e. a compound having at least one heteroaromatic ring), which moiety has from 5 to 10 ring atoms. Preferably, each ring has from 5 to 7 ring atoms.

Examples of monocyclic heteroaryl groups include, but are not limited to, those derived from:

N$_1$: pyrrole (azole) (5-membered), pyridine (azine) (6-membered);
O$_1$: furan (oxole) (5-membered);
S$_1$: thiophene (thiole) (5-membered);
N$_1$O$_1$: oxazole (5-membered), isoxazole (5-membered), isoxazine (6-membered);
N$_2$O$_1$: oxadiazole (furazan) (5-membered);
N$_3$O$_1$: oxatriazole (5-membered);
N$_1$S$_1$: thiazole (5-membered), isothiazole (5-membered);
N$_2$: imidazole (1,3-diazole) (5-membered), pyrazole (1,2-diazole) (5-membered), pyridazine (1,2-diazine) (6-membered), pyrimidine (1,3-diazine) (6-membered) (e.g., cytosine, thymine, uracil), pyrazine (1,4-diazine) (6-membered);
N$_3$: triazole (5-membered), triazine (6-membered); and,
N$_4$: tetrazole (5-membered).

Examples of heteroaryl groups which comprise fused rings, include, but are not limited to, those derived from:

9-membered (with 2 fused rings) derived from benzofuran (O$_1$), isobenzofuran (O$_1$), indole (N$_1$), isoindole (N$_1$), indolizine (N$_1$), indoline (N$_1$), isoindoline (N$_1$), purine (N$_4$) (e.g., adenine, guanine), benzimidazole (N$_2$), indazole (N$_2$), benzoxazole (N$_1$O$_1$), benzisoxazole (N$_1$O$_1$), benzodioxole (O$_2$), benzofurazan (N$_2$O$_1$), benzotriazole (N$_3$), benzothiofuran (S$_1$), benzothiazole (N$_1$S$_1$), benzothiadiazole (N$_2$S);

10-membered (with 2 fused rings) derived from chromene (O$_1$), isochromene (O$_1$), chroman (O$_1$), isochroman (O$_1$), benzodioxan (O$_2$), quinoline (N$_1$), isoquinoline (N$_1$), quinolizine (N$_1$), benzoxazine (N$_1$O$_1$), benzodiazine (N$_2$), pyridopyridine (N$_2$), quinoxaline (N$_2$), quinazoline (N$_2$), cinnoline (N$_2$), phthalazine (N$_2$), naphthyridine (N$_2$), pteridine (N$_4$).

Thus, when A is a 5 to 10 membered heteroaryl group, it may be selected from any of the groups listed above.

If A is 6-membered heteroaryl, the R$^{1A}$ group can either be meta or para to the NH group. If A is 5-membered heteroaryl or a 7 to 10 membered heteroaryl, the R$^{1A}$ group is not alpha to the —NH— group. Thus, when A is 5-membered heteroaryl, the R$^{1A}$ group is beta to the —NH— group.

R$^{1A}$

R$^{1A}$ may have one of the following structures:
CH$_2$NZ$^1$Z$^3$;
CH(CH$_3$)NZ$^1$Z$^3$;
CH(C$_2$H$_5$)NZ$^1$Z$^3$;

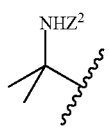 (R$^{LX1}$)

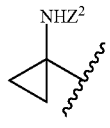 (R$^{LX2}$)

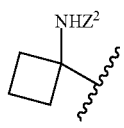 (R$^{LX3}$)

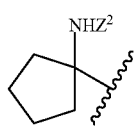 (R$^{LX4}$)

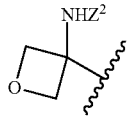 (R$^{LX5}$)

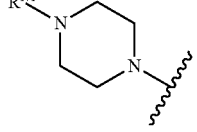 (R$^{LX6}$)

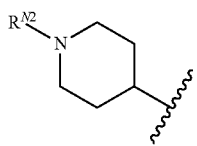 (R$^{LX7}$)

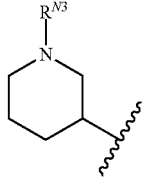 (R$^{LX8}$)

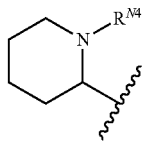 (R$^{LX9}$)

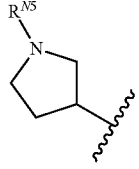 (R$^{LX10}$)

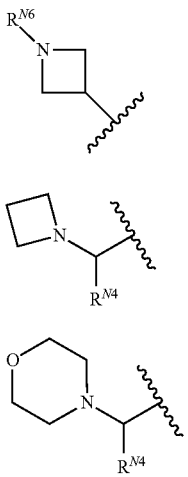

(R<sup>LX11</sup>)

(R<sup>1412</sup>)

(R<sup>1413</sup>)

wherein:
R$^{N1}$ is selected from H, C$_{1-4}$ alkyl, C$_{3-4}$ cycloalkyl and C(=O)Me;
R$^{N2}$ is selected from H, C$_{1-4}$ alkyl, C$_{3-4}$ cycloalkyl and C(=O)Me;
R$^{N3}$ is selected from H, C$_{1-4}$ alkyl, C$_{3-4}$ cycloalkyl and C(=O)Me;
R$^{N4}$ is selected from H and CH$_3$;
R$^{N5}$ is selected from H, C$_{1-4}$ alkyl, C$_{3-4}$ cycloalkyl and C(=O)Me;
R$^{N6}$ is selected from H, C$_{1-4}$ alkyl, C$_{3-4}$ cycloalkyl and C(=O)Me;
R$^{N7}$ and R$^{N8}$ are independently selected from H and CH$_3$;
R$^{N9}$ is selected from H, C$_{1-4}$ alkyl, C$_{3-4}$ cycloalkyl and C(=O)Me;
R$^{N10}$ is selected from H, C$_{1-4}$ alkyl, C$_{3-4}$ cycloalkyl and C(=O)Me;
R$^{N11}$ is selected from H, C$_{1-4}$ alkyl, C$_{3-4}$ cycloalkyl and C(=O)Me; and
R$^{N12}$ is selected from H, C$_{1-4}$ alkyl, C$_{3-4}$ cycloalkyl and C(=O)Me.

Each of R$^{N1}$, R$^{N2}$, R$^{N3}$, R$^{N5}$, R$^{N6}$, R$^{N9}$, R$^{N10}$, R$^{N11}$ and R$^{N12}$ is independently selected from H, C$_{1-4}$ alkyl (i.e. methyl, ethyl, prop-1-yl, prop-2-yl, n-butyl, iso-butyl, sec-butyl, tert-butyl), C$_{3-4}$ cycloalkyl (i.e. cyclopropyl, methylcyclopropyl, cyclobutyl) and C(=O)Me. Each of R$^{N4}$, R$^{N7}$ and R$^{N8}$ is independently selected from either H or methyl.

Z$^1$ is independently selected from H, C$_{1-3}$ alkyl (i.e. methyl, ethyl, prop-1-yl and prop-2-yl), optionally substituted by OH, C(=O)OC$_{1-4}$ alkyl (i.e. C(=O)O-methyl, C(=O)O-ethyl, C(=O)O-prop-1-yl, C(=O)O-prop-2-yl), C(=O)O-n-butyl, C(=O)O-iso-butyl, C(=O)O-sec-butyl, C(=O)O-tert-butyl) and C(=O)Me.

Z$^2$ is independently selected from H, C$_{1-3}$ alkyl (i.e. methyl, ethyl, prop-1-yl and prop-2-yl), optionally substituted by OH, C(=O)OC$_{1-3}$ alkyl (i.e. C(=O)O-methyl, C(=O)O-ethyl, C(=O)O-prop-1-yl and C(=O)O-prop-2-yl) and C(=O)Me.

Z$^3$ is H, or Z$^1$ and Z$^3$ together with N form a 4-6 membered heterocycle containing at least one N and optionally one O. Examples of suitable 4-6 membered heterocycle containing at least one N and optionally one O include azetidinyl, pyrrolidinyl, piperidinyl, piperazinyl, and morpholinyl.

R$^{1B}$

Each R$^{1B}$ group may be C$_{1-3}$ alkyl (i.e. methyl, ethyl, prop-1-yl and prop-2-yl), CF$_3$, F, Cl, O—C$_{1-3}$ alkyl (i.e. methoxy, ethoxy, prop-1-oxy and prop-2-oxy) or CN. These groups may be any available ring position on A, except that which is alpha to the NH group. There may be up to 2 R$^{1B}$ groups (i.e. 1 or 2).

R$^{1C}$

Each R$^{1C}$ group may be C$_{1-3}$ alkyl (i.e. methyl, ethyl, prop-1-yl and prop-2-yl) optionally substituted with one to three substituents selected from F, —OH, Cl, O—C$_{1-3}$ alkyl (i.e. methoxy, ethoxy, prop-1-oxy and prop-2-oxy), CN, =O or C(=O)Me. Examples of suitable optionally substituted C$_{1-3}$ alkyl groups include —CFH$_2$, —CF$_2$H, —CF$_3$, —CH$_2$CFH$_2$, —CH$_2$CF$_2$H, —CH$_2$CF$_3$, —CFHCH$_3$, —CF$_2$CH$_3$, —CH$_2$CH$_2$CFH$_2$, —CH$_2$CH$_2$CF$_2$H, —CH$_2$CH$_2$CF$_3$, —CH$_2$CFHCH$_3$, —CH$_2$CF$_2$CH$_3$, —CFHCH$_2$CH$_3$, —CF$_2$CH$_2$CH$_3$, —CH$_2$OH, —CH$_2$OCH$_3$, —CH(OH)CH$_3$, CH(OCH$_3$)CH$_3$, —CH$_2$CH$_2$OH, —CH$_2$CH$_2$OCH$_3$, —CH(OH)CH$_2$CH$_3$, CH(OCH$_3$)CH$_2$CH$_3$, —CH$_2$CH(OH)CH$_3$, —CH$_2$CH(OCH$_3$)CH$_3$, —CH$_2$CH$_2$CH$_2$OH and —CH$_2$CH$_2$CH$_2$OCH$_3$. These groups may be substituted at any available ring position on A. There may be up to 3 R$^{1C}$ groups (i.e. 1, 2 or 3) depending on the nature of A, and in particular on the number of ring atoms and ring heteroatoms, as well as whether R$^{1A}$ is present.

R$^2$

R$^2$ is selected from H, halo (i.e. F, Cl, Br, I), C$_{1-4}$ alkyl (i.e. methyl, ethyl, prop-1-yl and prop-2-yl, n-butyl, iso-butyl, sec-butyl, tert-butyl), CF$_3$, CF$_2$H, CN and methoxy.

In some embodiments, the halo group is either F or Cl.

R$^3$

R$^3$ is selected from substituted phenyl and a substituted 6 membered heteroaryl group, where the heteroaryl ring system contains 1 or 2 N heteroatoms.

When R$^3$ is substituted phenyl, it has the structure:

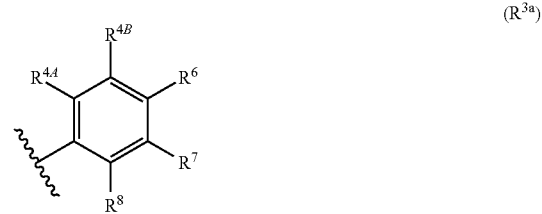

(R$^{3a}$)

where R$^6$, R$^7$ and R$^8$ are independently selected from H, F, methyl and CF$_3$. One of R$^{4A}$ and R$^{4B}$ is R$^4$, and the other is selected from H, F, methyl and CF$_3$.

When R$^3$ is a substituted 6 membered heteroaryl group, where the heteroaryl ring system contains 1 or 2 N heteroatoms, it may be selected from the any of the groups: pyridyl; pyridazinyl (1,2-diazinyl); pyrimidinyl (1,3-diazinyl); and pyrazinyl (1,4-diazinyl).

When R$^3$ is a substituted 6 membered heteroaryl group, it may have one of the following structures:

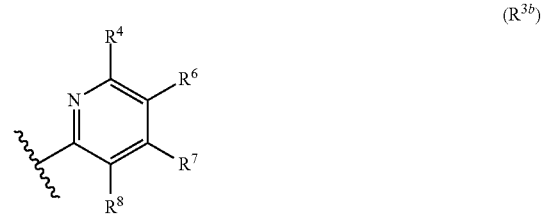

(R$^{3b}$)

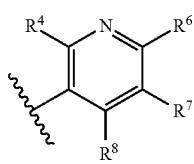 (R$^{3c}$)

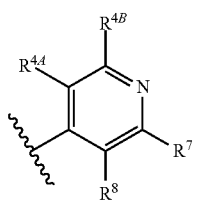 (R$^{3d}$)

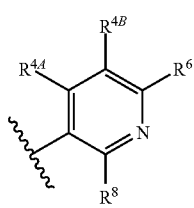 (R$^{3e}$)

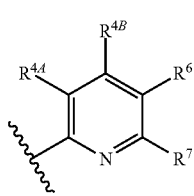 (R$^{3f}$)

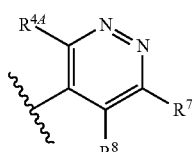 (R$^{3g}$)

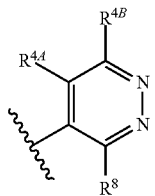 (R$^{3h}$)

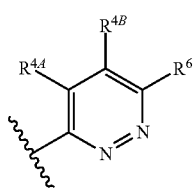 (R$^{3i}$)

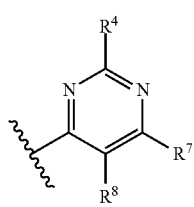 (R$^{3j}$)

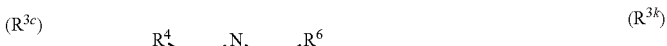 (R$^{3k}$)

 (R$^{3l}$)

 (R$^{3m}$)

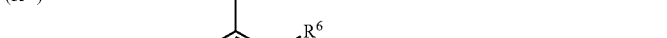 (R$^{3n}$)

where R$^6$, R$^7$ and R$^8$ (if present) are independently selected from H, F, methyl and CF$_3$. One of R$^{4A}$ and R$^{4B}$ (if present) is R$^4$, and the other is selected from H, F, methyl and CF$_3$.

When R$^4$ is alpha to the —C$_2$H$_4$-group, it may also be described as being ortho. When R$^4$ is beta to the —C$_2$H$_4$-group, it may also be described as being meta.

The further optional substituents on R$^3$ are independently selected from F, methyl and CF$_3$. These further groups may be at any available ring position on R$^3$, except that occupied by R$^4$. There may be up to 4 further optional substituents groups (i.e. 1, 2, 3 or 4) depending on the nature of R$^3$, and in particular on the number of ring heteroatoms.

R$^4$

R$^4$ is selected from groups of the following formulae:

 (R$^{4a}$)

 (R$^{4b}$)

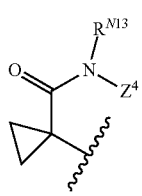(R^{N13})

(R^{4c})

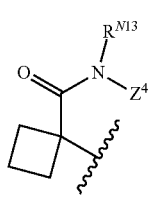(R^{N13})

(R^{4d})

$R^{N13}$ is selected from H and CH$_3$, and $Z^4$ is selected from H, CH$_3$ or OCH$_3$. Thus, $R^4$ can be of the following formulae:
(i) —Y—C(O)NH$_2$;
(ii) —Y—C(O)NHMe;
(iii) —Y—C(O)NMe$_2$;
(iv) —Y—C(O)N(OMe)H; and
(v) —Y—C(O)N(OMe)Me, where Y is selected from —CHCH$_3$—, —CH(CH$_2$CH$_3$)—, —C(CH$_3$)$_2$—, and C$_{3-5}$ cycloalkylidene.

Proviso

In some embodiments, compounds 12 and 155 of WO2012/110773 are disclaimed from the present application:

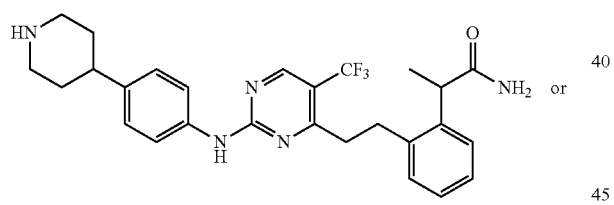

or

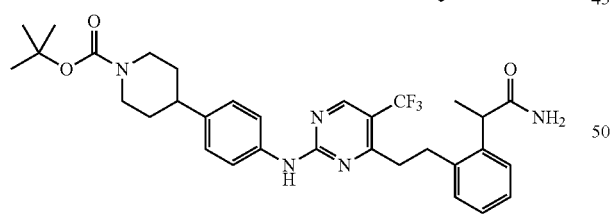

In other embodiments, the compounds of the present invention do not include those disclosed in WO2012/110773, which is incorporated herein by reference. In particular, when $R^3$ is selected from:

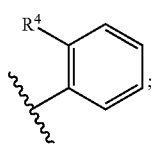 ; 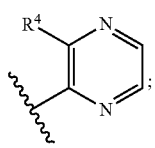 ;

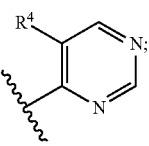 and 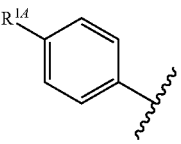 ;

$R^4$ is —CH(CH$_3$)C(O)N(R^{N13})Z^4$;

A is either:

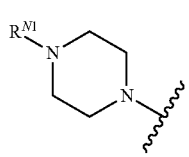

where $R^{14}$ is selected from

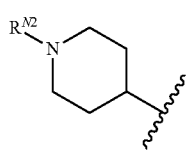(R^{141})

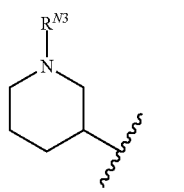(R^{142})

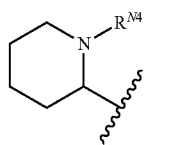(R^{143})

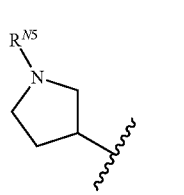(R^{144})

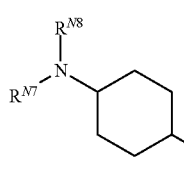(R^{145})

(R^{147})

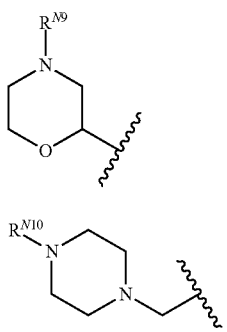

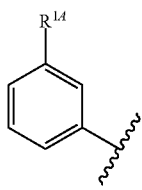

and $R^{N1}$ is selected from H, $C_{1-3}$ alkyl, and C(=O)Me;
$R^{N2}$ is selected from H, $C_{1-3}$ alkyl, and C(=O)Me;
$R^{N3}$ is selected from H, $C_{1-3}$ alkyl, and C(=O)Me;
$R^{N4}$ is selected from H and $CH_3$;
$R^{N5}$ is selected from H, $C_{1-3}$ alkyl, and C(=O)Me;
$R^{N7}$ and $R^{N8}$ are independently selected from H and $CH_3$;
$R^{N9}$ is selected from H, $C_{1-3}$ alkyl, and C(=O)Me;
$R^{N10}$ is selected from H, $C_{1-3}$ alkyl, and C(=O)Me;
or

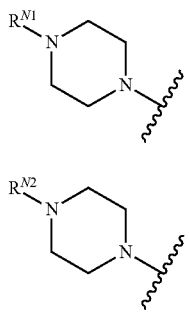

where $R^{14}$ is

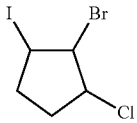

and $R^{N1}$ is selected from H, $C_{1-3}$ alkyl, and C(=O)Me;
$R^{N2}$ is selected from H, $C_{1-3}$ alkyl, and C(=O)Me;
then $R^2$ is not selected from $CF_3$, halo, $CF_2H$ and CN.

Thus, this proviso only applies when $R^4$ is —CH(CH$_3$)C(O)N($R^{N13}$)$Z^4$, i.e. when Y is —CH(CH$_3$)—.

In another embodiment the compounds of the first aspect are of formula (I), wherein
when A is phenyl, Y is selected from —CH(CH$_2$CH$_3$)—, —C(CH$_3$)$_2$—, and $C_{3-5}$ cycloalkylidene.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Alpha/Beta

The terms alpha and beta are used herein to indicate the relative position of substituent groups on rings. For the avoidance of doubt, their meaning is illustrated with the structure below:

wherein the bromo group is alpha to the chloro group, and the iodo group is beta to the chloro group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

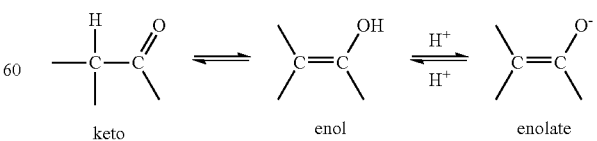

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al. *J. Pharm. Sci.*, 66, 1-19 (1977).

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g., a trihaloalkyl ester); a triC$_{1-7}$ alkylsilyl-C$_{1-4}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties. For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C1-7 alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl;

1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Selectivity

The selectivity of the compounds for inhibiting VEGFR3 over other kinases, such as FAK, and/or VEGFR2 can be demonstrated by cellular assay results (see, for example, the VEGFR3 and VEGFR2 assays described below).

Further Embodiments

The following embodiments and preferences may be combined with one another as appropriate.

A

In some embodiments, A is optionally substituted phenyl and can have the structures:

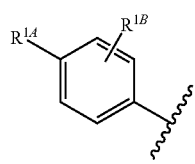
(A²)

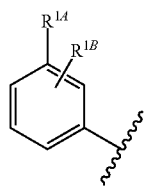
(A³)

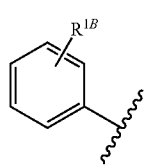
(A⁴)

where the $R^{1B}$ group cannot be alpha the connection point to the rest of the compound.

In these embodiments (i.e. when A is phenyl), it may be preferred that either there are no $R^{1B}$ substituents, or a single $R^{1B}$ substituent. If there is a single $R^{1B}$ substituent it is may be meta or para, so further preferred A groups include:

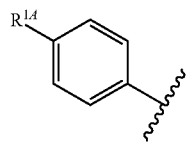
(A²ᴬ)

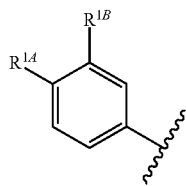
(A²ᴮ)

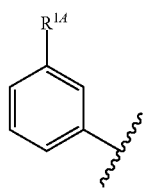
(A³ᴬ)

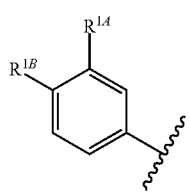
(A³ᴮ)

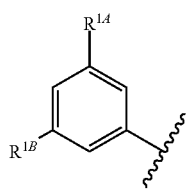
(A³ᶜ)

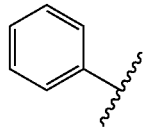
(A⁴ᴬ)

In some embodiments, A is an optionally substituted 6 membered heteroaryl group. 6 membered heteroaryl groups include, but are not limited to: pyridyl, isoxazinyl, pyridazinyl, pyrimidinyl, pyrazinyl and triazinyl.

In these embodiments, it may be preferred that A is pyridyl, which can have the structures:

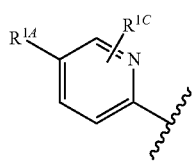
(A⁵)

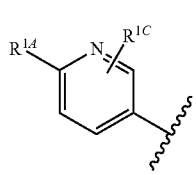
(A⁶)

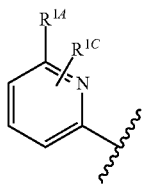 (A⁷)

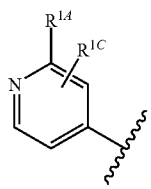 (A⁸)

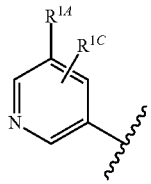 (A⁹)

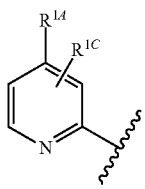 (A¹⁰)

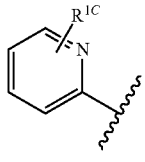 (A¹¹)

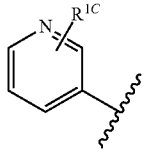 (A¹²)

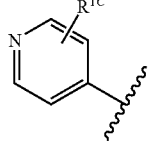 (A¹³)

In these embodiments, it is preferred that when $R^{1A}$ is present $R^{1C}$ is not an oxo (=O) group. Of these structures, $A^6$ may be further preferred.

In some embodiments (i.e. when A is 6 membered heteroaryl group), there may be no $R^{1C}$ substituents. Thus, when A is pyridyl and there are no $R^{1C}$ groups, it may have the structures:

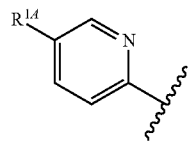 (A⁵ᴬ)

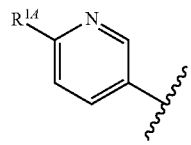 (A⁶ᴬ)

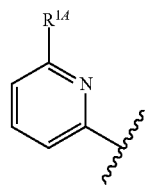 (A⁷ᴬ)

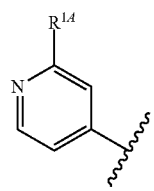 (A⁸ᴬ)

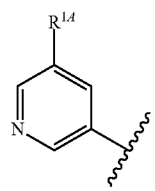 (A⁹ᴬ)

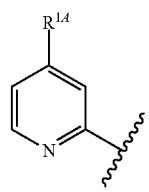 (A¹⁰ᴬ)

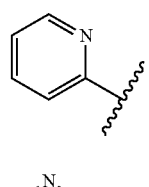 (A¹¹ᴬ)

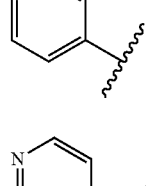 (A¹²ᴬ)

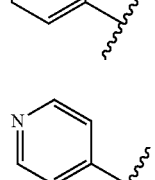 (A¹³ᴬ)

Of these structures $A^{6A}$ may be further preferred.

In other embodiments, (i.e. when A is 6 membered heteroaryl group), there may be no $R^{1A}$ substituents. Thus, when A is pyridyl and there are no $R^{1C}$ groups, the pyridyl group may be unsubstituted, or it may have one of more $R^{1C}$ groups. The pyridyl group may have one of the following structures:

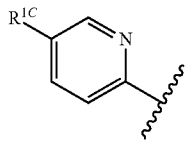
($A^{5A1}$)

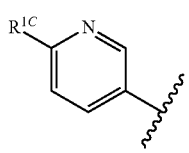
($A^{6A1}$)

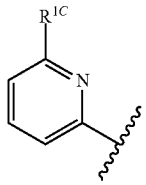
($A^{7A1}$)

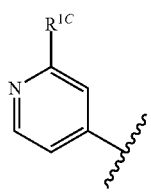
($A^{8A1}$)

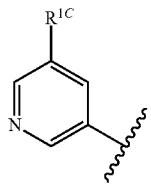
($A^{9A1}$)

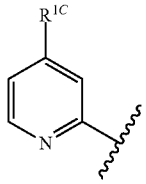
($A^{10A1}$)

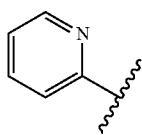
($A^{11A1}$)

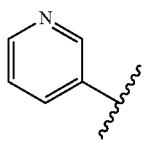
($A^{12A1}$)

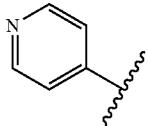
($A^{13A1}$)

Of these structures $A^{6A1}$ may be further preferred.

In some embodiments, A is an optionally substituted 5 membered heteroaryl group. 5 membered heteroaryl groups include, but are not limited to: pyrrolyl; furanyl; thiophenyl; oxazolyl; isoxazolyl; oxadiazolyl; oxatriazolyl; thiazolyl; isothiazolyl; imidazolyl; pyrazolyl; triazolyl and tetrazolyl.

In these embodiments, it may be preferred that A is pyrazolyl, which can have the structures:

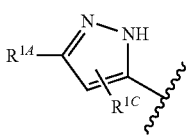
($A^{14}$)

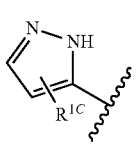
($A^{15}$)

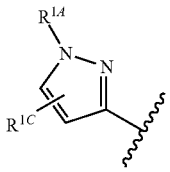
($A^{16}$)

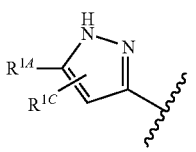
($A^{17}$)

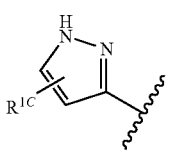
($A^{18}$)

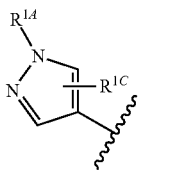
($A^{19}$)

($A^{20}$)

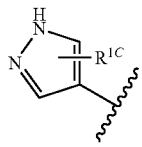
(A²¹)

In these embodiments, it is preferred that $R^{1C}$ is not an oxo (=O) group. Of these structures $A^{16}$ and $A^{18}$ may be further preferred.

In some embodiments (i.e. when A is a 5 membered heteroaryl group), there may be no $R^{1C}$ substituents. Thus, when A is pyrazolyl and there are no $R^{1C}$ groups, it may have the structures:

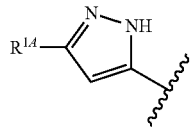
($A^{14A}$)

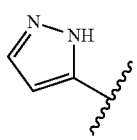
($A^{15A}$)

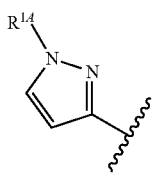
($A^{16A}$)

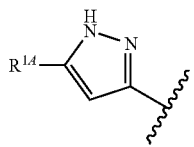
($A^{17A}$)

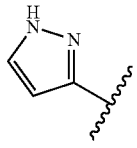
($A^{18A}$)

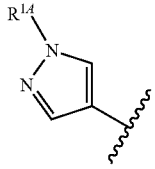
($A^{19A}$)

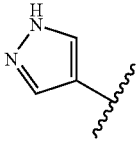
($A^{20A}$)

Of these structures $A^{19A}$ may be further preferred.

In other embodiments, (i.e. when A is 5 membered heteroaryl group), there may be no $R^{1A}$ substituents. Thus, when A is pyrazolyl and there are no $R^{1C}$ groups, the pyrazolyl group may be unsubstituted, or it may have one of more $R^{1C}$ groups. The pyrazolyl group may have one of the following structures:

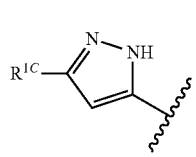
($A^{14A1}$)

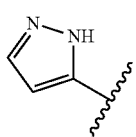
($A^{15A1}$)

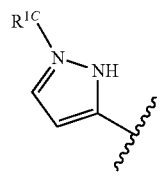
($A^{16A1}$)

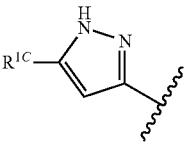
($A^{17A1}$)

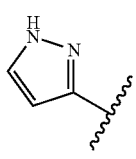
($A^{18A1}$)

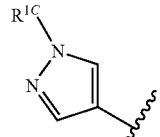
($A^{19A1}$)

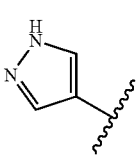
($A^{20A1}$)

Of these structures $A^{19A1}$ may be further preferred.

Thus particularly preferred structures for A include:

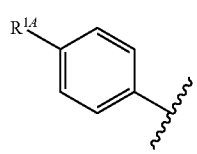
($A^{24}$)

-continued

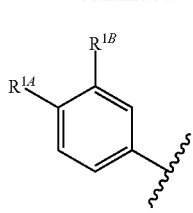
(A$^{2B}$)

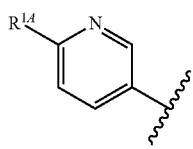
(A$^{6A}$)

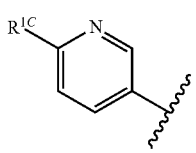
(A$^{6A1}$)

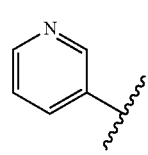
(A$^{12A}$)

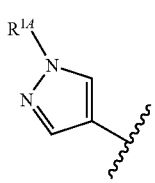
(A$^{19A}$)

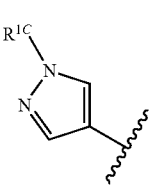
(A$^{19A1}$)

R$^{1A}$

In some embodiments where R$^{1A}$ is CH(R$^{C1}$)NZ$^1$Z$^3$, R$^{C1}$ is selected from H and C$_{1-2}$ alkyl, Z$^1$ may be any one of:
(i) H;
(ii) C$_{1-3}$ alkyl optionally substituted by OH, preferably Me, or CH$_2$CH$_2$OH;
(iii) C(=O)OC$_{1-4}$ alkyl, preferably C(=O)OMe or C(=O)OtBu; and
(iv) C(=O)Me.
and Z$^3$ may be H, or Z$^1$ and Z$^3$ together with the N to which they are attached form a 4-6 membered heterocycle containing one N and optionally one O.

In some of these embodiments, Z$^1$ may be selected from H and CH$_2$CH$_2$OH and Z$^3$ may be H. Thus, in these embodiments, R$^{1A}$ is selected from: CH$_2$NH$_2$; CH(CH$_3$)NH$_2$; CH(C$_2$H$_5$)NH$_2$; CH$_2$NHCH$_2$CH$_2$OH; CH(CH$_3$)NHCH$_2$CH$_2$OH; and CH(C$_2$H$_5$)NHCH$_2$CH$_2$OH.

In some embodiments where R$^{1A}$ is CH(R$^{C1}$)NZ$^1$Z$^3$, R$^{C1}$ may be selected from H and methyl and Z$^3$ may be H. Thus, in these embodiments, R$^{1A}$ is selected from: CH$_2$NHZ$^1$ and CH(CH$_3$)NHZ$^1$.

In some embodiments where R$^{1A}$ is CH(R$^{C1}$)NHZ$^1$, Z$^1$ may be selected from H and CH$_2$CH$_2$OH, and R$^{C1}$ may be selected from H and methyl. Thus, in these embodiments, R$^{1A}$ is selected from: CH$_2$NH$_2$; CH$_2$NHCH$_2$CH$_2$OH; CH(CH$_3$)NH$_2$; and CH(CH$_3$)NHCH$_2$CH$_2$OH.

In some embodiments where R$^{1A}$ is CH(R$^{C1}$)NZ$^1$Z$^3$, Z$^1$ and Z$^3$ may together with the N to which they are attached form a 4-6 membered heterocycle containing one N and optionally one O. In these embodiments, R$^{1A}$ is, for example, azetidinyl or morpholinyl.

In some embodiments where R$^{1A}$ is XNHZ$^2$, Z$^2$ may be any one of:
(i) H;
(ii) C$_{1-3}$ alkyl optionally substituted by OH, preferably Me, or CH$_2$CH$_2$OH;
(iii) C(=O)OC$_{1-3}$ alkyl, preferably C(=O)OMe; and
(iv) C(=O)Me.

In some embodiments where R$^{1A}$ is XNHZ$^2$, Z$^2$ may be H. Thus, in these embodiments, R$^{1A}$ has the structures:

(R$^{LX1A}$)

(R$^{LX2A}$)

(R$^{LX3A}$)

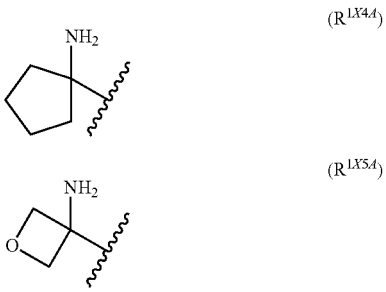
(R$^{LX4A}$)

(R$^{LX5A}$)

In some embodiments where R$^{1A}$ is XNHZ$^2$, Z$^2$ may be C(=O)OMe. Thus, in these embodiments, R$^{1A}$ has the structures:

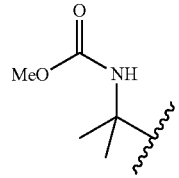
(R$^{LX1B}$)

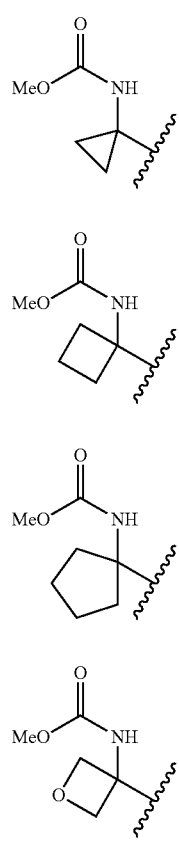

In some embodiments where $R^{1A}$ is $XNHZ^2$, X may be selected from $CMe_2$, and cyclobutylidene. Thus, in these embodiments, $R^{1A}$ has the structures:

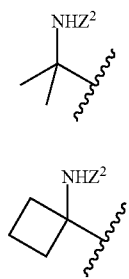

In some embodiments where $R^{1A}$ is $XNHZ^2$, $Z^2$ may be selected from H and C(=O)OMe, and X may be selected from $CMe_2$, and cyclobutylidene. Thus, in these embodiments, $R^{1A}$ has the structures:

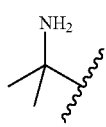

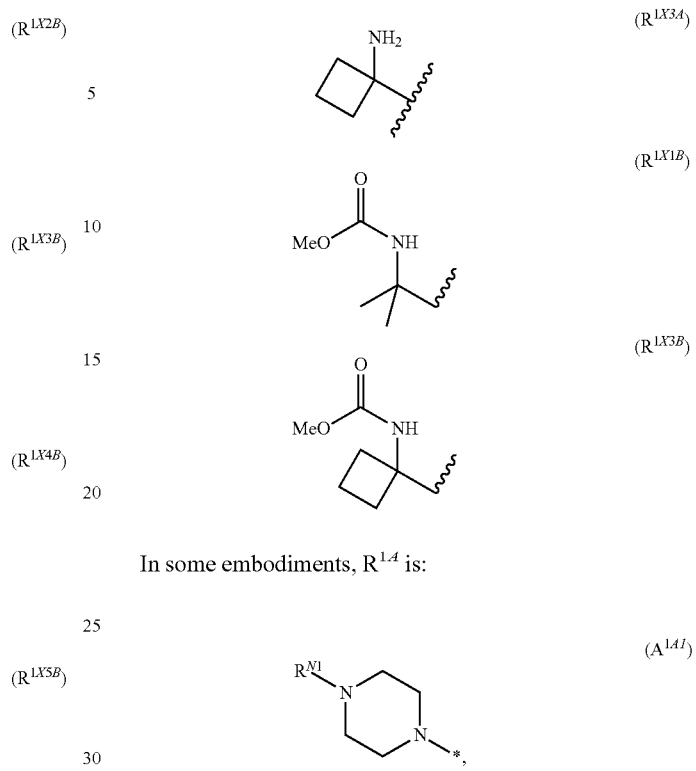

In some embodiments, $R^{1A}$ is:

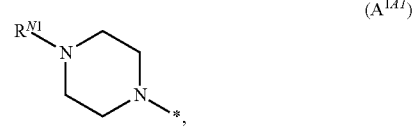

wherein $R^{N1}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N1}$ is C(=O)Me. In others of these embodiments, it may be preferred that $R^{N1}$ is H, methyl or ethyl.

In some embodiments, $R^{1A}$ is:

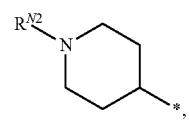

wherein $R^{N2}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N2}$ is C(=O)Me. In others of these embodiments, it may be preferred that $R^{N2}$ is H, methyl or ethyl, more preferably H or methyl.

In some embodiments, $R^{1A}$ is:

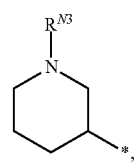

wherein $R^{N3}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N3}$ is C(=O)Me. In others of these embodiments, it may be preferred that $R^{N3}$ is H, methyl or ethyl, more preferably H or methyl.

In some embodiments, $R^{1A}$ is:

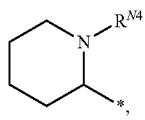

(A¹ᴬ⁴)

wherein $R^{N4}$ is selected from H or methyl. In some of these embodiments, it may be preferred that $R^{N4}$ is H.

In some embodiments, $R^{1A}$ is:

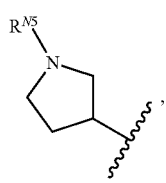

(R¹ᴬ⁵)

wherein $R^{N5}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N5}$ is C(=O)Me. In others of these embodiments, it may be preferred that $R^{N5}$ is H, methyl or ethyl, more preferably H or methyl.

In some embodiments, $R^{1A}$ is:

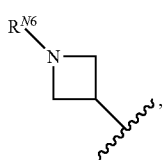

(R¹ᴬ⁶)

wherein $R^{N6}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N6}$ is C(=O)Me. In others of these embodiments, it may be preferred that $R^{N6}$ is H, methyl or ethyl, more preferably H or methyl.

In some embodiments, $R^{1A}$ is:

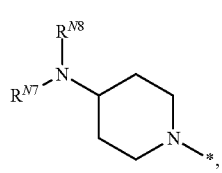

(A¹ᴬ⁷)

wherein $R^{N7}$ and $R^{N8}$ are both H or both methyl. In some of these embodiments, it may be preferred that $R^{N7}$ and $R^{N8}$ are both H.

In some embodiments, $R^{1A}$ is:

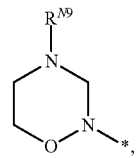

(A¹ᴬ⁸)

wherein $R^{N9}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N9}$ is C(=O)Me. In others of these embodiments, it may be preferred that $R^{N9}$ is H, methyl or ethyl, more preferably H or methyl.

In some embodiments, $R^{1A}$ is:

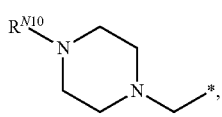

(R¹ᴬ⁹)

wherein $R^{N10}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N10}$ is C(=O)Me. In others of these embodiments, it may be preferred that $R^{N10}$ is H, methyl or ethyl, more preferably H or methyl.

In some embodiments, $R^{1A}$ is:

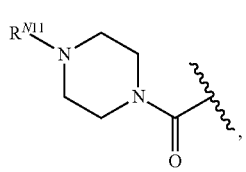

(R¹ᴬ¹⁰)

wherein $R^{N11}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{11}$ is C(=O)Me. In others of these embodiments, it may be preferred that $R^{N11}$ is H, methyl or ethyl, more preferably H or methyl.

In some embodiments, $R^{1A}$ is:

(R¹ᴬ¹¹)

wherein $R^{N12}$ is selected from H, $C_{1-4}$ alkyl (i.e. methyl, ethyl, prop-1-yl and prop-2-yl, n-butyl, iso-butyl, sec-butyl, tert-butyl), $C_{3-4}$ cycloalkyl (i.e. cyclopropyl, methylcyclopropyl, cyclobutyl) and C(=O)Me. In some of these embodiments, it may be preferred that $R^{N12}$ is C(=O)Me. In others of these embodiments, it may be preferred that $R^{N12}$ is H, methyl or ethyl, more preferably H or methyl.

Particularly preferred $R^{1A}$ groups include:

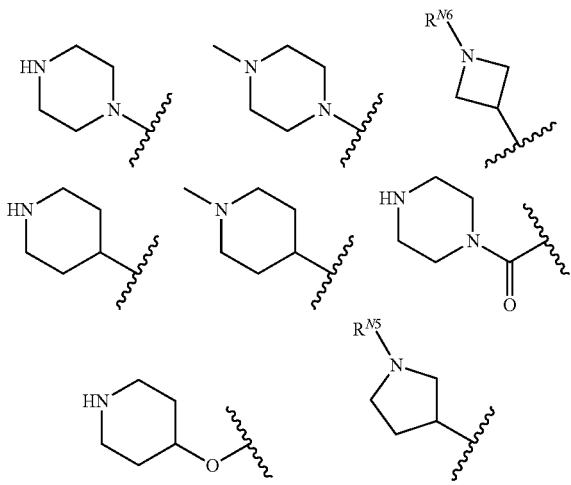

In some embodiments, $R^{1A}$ is selected from $R^{1A2}$ and $R^{1A6}$:

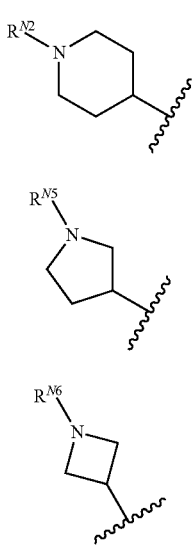

wherein:
$R^{N2}$ is selected from H and methyl;
$R^{N5}$ is selected from H and methyl; and
$R^{N6}$ is selected from H and methyl.

In some embodiments, $R^{1A}$ is selected from $R^{1A2}$ and $R^{1A6}$:

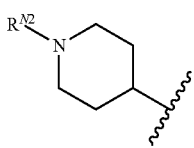

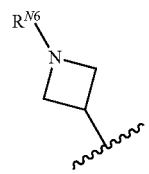

wherein:
$R^{N2}$ is selected from H and methyl; and
$R^{N6}$ is selected from H and methyl.

$R^{1B}$

In some embodiments, no $R^{1B}$ substituents are present.

In some embodiments, $R^{1B}$ is preferably $C_{1-3}$ alkyl and more preferably methyl.

In some embodiments, a single $R^{1B}$ substituent is present. It may be $C_{1-3}$ alkyl; $CF_3$; F; Cl; O—($C_{1-3}$alkyl); and CN. In some of these embodiments, it is preferably $C_{1-3}$ alkyl, and more preferably methyl.

$R^{1C}$

In some embodiments, no $R^{1C}$ substituents are present.

In the embodiments where $R^{1C}$ substituents are present, each $R^{1C}$ substituent is independently selected from:
(i) $C_{1-3}$ alkyl optionally substituted with one to three substituents selected from F, OH and OMe;
(ii) F;
(iii) Cl;
(iv) O—($C_{1-3}$ alkyl);
(v) CN;
(vi) =O, and
(vii) C(=O)Me.

In some embodiments, each $R^{1C}$ substituent is independently selected from:
(i) $C_{1-3}$ alkyl optionally substituted with one to three substituents selected from F, OH and OMe;
(ii) O—($C_{1-3}$ alkyl);
(v) CN; and
(vii) C(=O)Me.

In other embodiments, $R^{1C}$ is preferably $C_{1-3}$ alkyl optionally substituted with one to three F atoms and more preferably methyl or $CF_3$.

In some embodiments, a single $R^{1C}$ substituent is present. It may be $C_{1-3}$ alkyl; $CF_3$; F; Cl; O—($C_{1-3}$alkyl); CN; C(=O)Me; and =O. In some of these embodiments, it is preferably $C_{1-3}$ alkyl optionally substituted with one to three F substituents, and more preferably methyl or $CF_3$.

$R^2$

In some embodiments, $R^2$ is H.

In some embodiments, $R^2$ is halo (i.e. F, Cl, Br, I). In some of these embodiments, the halo group is either F or Cl.

In some embodiments, $R^2$ is $C_{1-4}$ alkyl (i.e. methyl, ethyl, prop-1-yl and prop-2-yl, n-butyl, iso-butyl, sec-butyl, tert-butyl). In some of these embodiments, the $C_{1-4}$ alkyl group is methyl or ethyl, and methyl may be preferred.

In some embodiments, $R^2$ is selected from $CF_3$ and $CF_2H$. In some of these embodiments, $R^2$ is $CF_3$.

In some embodiments, $R^2$ is CN.

In some embodiments, $R^2$ is methoxy.

In some embodiments, $R^2$ is selected from $CF_3$ and Cl.

$R^3$

In some embodiments, $R^3$ is substituted phenyl, and therefore it has the structure:

(R^{3a})

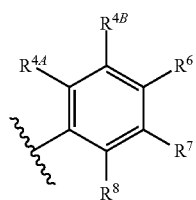

where $R^6$, $R^7$ and $R^8$ are independently selected from H, F, methyl and $CF_3$. One of $R^{4A}$ and $R^{4B}$ is $R^4$, and the other is selected from H, F, methyl and $CF_3$. In some of these embodiments, the group of $R^{4A}$ and $R^{4B}$ that is not $R^4$, and $R^6$, $R^7$ and $R^8$ are all H. In others of these embodiments, one of the group of $R^{4A}$ and $R^{4B}$ that is not $R^4$, $R^6$, $R^7$ and $R^8$ is not H, and therefore is F, methyl or $CF_3$. The group that is not H may preferably be $R^6$ or $R^7$.

In some embodiments, $R^3$ is substituted phenyl, $R^{4B}$, $R^6$, $R^7$ and $R^8$ are all H, and $R^{4A}$ is $R^4$.

In some embodiments, $R^3$ is a substituted 6 membered heteroaryl group, where the heteroaryl ring system contains 1 or 2 N heteroatoms. In these embodiments, it may be preferred that $R^3$ is pyridyl, which can have the structures:

(R^{3b})

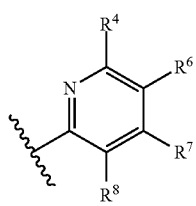

(R^{3c})

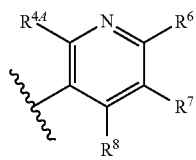

(R^{3d})

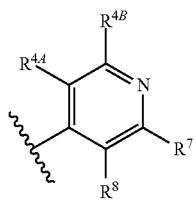

(R^{3e})

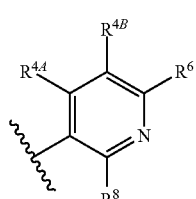

(R^{3f})

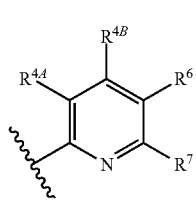

where $R^6$, $R^7$ and $R^8$ (if present) are independently selected from H, F, methyl and $CF_3$. One of $R^{4A}$ and $R^{4B}$ (if present) is $R^4$, and the other is selected from H, F, methyl and $CF_3$. Of these structures, $R^{3d}$ and $R^{3e}$ may be preferred. In some of these embodiments, the group of $R^{4A}$ and $R^{4B}$ that is not $R^4$, and $R^6$, $R^7$ and $R^8$ (if present) are all H. In others of these embodiments, one of the group of $R^{4A}$ and $R^{4B}$ that is not $R^4$, $R^6$, $R^7$ and $R^8$ (if present) is not H, and therefore is F, methyl or $CF_3$. In some embodiments, it may be preferred that a F substituent is not alpha to a ring nitrogen atom.

$R^4$

In some embodiments $R^4$ is alpha to the $-C_2H_4-$ group.
In some embodiments $R^4$ is beta to the $-C_2H_4-$ group.
The group $R^4$ is $-Y-C(O)(R^{N13})Z^4$.
In some embodiments, $R^{N13}$ is H.
In other embodiments, $R^{N13}$ is Me.
In some embodiments, $Z^4$ is H.
In other embodiments, $Z^4$ is Me.
In other embodiments, $Z^4$ is OMe.

Y can be any of $-CHCH_3-$, $-CH(CH_2CH_3)-$, $-C(CH_3)_2-$, $C_{3-5}$ cycloalkylidene.

In some embodiments, Y is selected from $CHCH_3-$, $-CH(CH_2CH_3)-$, $-C(CH_3)_2-$, and $C_{3-5}$ cycloalkylidene.

In some embodiments, Y is selected from $-CH(CH_2CH_3)-$, $-C(CH_3)_2-$, and $C_{3-5}$ cycloalkylidene.

In some embodiments, Y is selected from $Y^a$ to $Y^e$:

(Y^a)

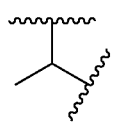

(Y^b)

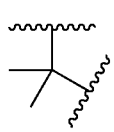

(Y^c)

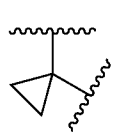

(Y^d)

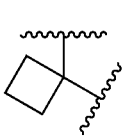

(Y^e)

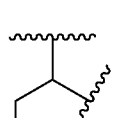

In some embodiments, Y is selected from $Y^b$, $Y^c$, $Y^d$ and $Y^e$.
In other embodiments, Y is selected from $Y^a$, $Y^b$, $Y^c$ and $Y^e$.
In some embodiments Y is selected from $Y^a$, $Y^c$, $Y^d$ and $Y^e$.

In some embodiments, $R^4$ is $-Y'-C(O)NH_2$, where Y' is selected from $-C(CH_3)_2-$, $-CH(CH_2CH_3)-$, cyclopropylidene and cyclobutylidene.

In some embodiments, $R^4$ is:

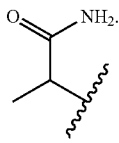

($R^{4a1}$)

In some embodiments, $R^4$ is:

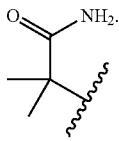

($R^{4b1}$)

In some embodiments, $R^4$ is:

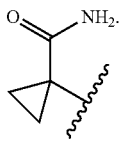

($R^{4c1}$)

In some embodiments, $R^4$ is:

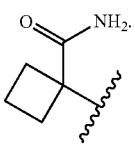

($R^{4d1}$)

In some embodiments of the present invention, the compounds are of formula (Ia) which is a compound of formula (I) of the first aspect or isomers, salts, solvates, protected forms or prodrugs thereof wherein:

A is selected from optionally substituted phenyl and an optionally substituted 5 or 6 membered heteroaryl group linked to the NH group through an aromatic ring carbon atom, in which the heteroaryl ring system contains 1 or 2 heteroatoms selected from N and O, and;

when A is optionally substituted phenyl, A may bear a substituent $R^{1A}$ which is not alpha to the NH group, where $R^{1A}$ is selected from:

(i) $CH(R^{C1})NZ^1Z^3$, where $R^{C1}$ is selected from H, $C_{1-2}$ alkyl, $Z^1$ is selected from H and $C_{1-3}$ alkyl substituted by $C(=O)OC_{1-4}$ alkyl or $C(=O)$Me and $Z^3$ is H, or $Z^1$ and $Z^3$ together with the N to which they are attached form a 4-6 membered heterocycle containing one N and optionally one O;

(iii) a group selected from:

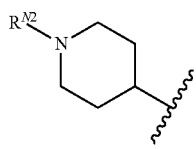

($R^{1A2}$)

-continued

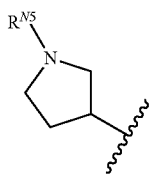

($R^{1A5}$)

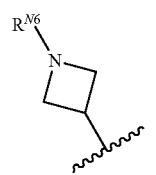

($R^{1A6}$)

wherein:
$R^{N2}$ is selected from H, $C_{1-3}$ alkyl and $C(=O)$Me;
$R^{N5}$ is selected from H and $C_{1-4}$ alkyl;
$R^{N6}$ is H;

when A is an optionally substituted 5 or 6 membered heteroaryl group, A may bear a single substituent $R^{1A}$ which is not alpha to the NH group, where $R^{1A}$ is as defined above, and may optionally further bear one or two substituents $R^{1C}$, where each $R^{1C}$ is independently selected from:

(i) $C_{1-3}$ alkyl optionally substituted with one to three substituents independently selected from F, OH and O—($C_{1-3}$alkyl);

(ii) O—($C_{1-3}$ alkyl);

(ii) CN; and $C(=O)$Me;

$R^2$ is selected from halo, $CH_3$ and $CF_3$;

$R^3$ is substituted phenyl, where $R^3$ bears a substituent $R^4$ either alpha or beta to the —$C_2H_4$— group, and may additionally bear a further substituent F; and $R^4$ is —Y—$C(O)N(R^{N13})Z^4$, where Y is selected from —CHCH$_3$—, —CH(CH$_2$CH$_3$)—, —C(CH$_3$)$_2$—, and $C_{3-4}$ cycloalkylidene; $R^{N13}$ is H; and $Z^4$ is H.

In some embodiments of the present invention, the compounds are of formula (Ib) which is a compound of formula (I) of the first aspect and formula (Ia) defined above or isomers, salts, solvates, protected forms or prodrugs thereof wherein:

A is selected from optionally substituted phenyl and an optionally substituted 5 or 6 membered heteroaryl group linked to the NH group through an aromatic ring carbon atom, in which the heteroaryl ring system contains 1 or 2 heteroatoms selected from N and O, and;

when A is optionally substituted phenyl, A may bear a substituent $R^{1A}$ which is not alpha to the NH group, where $R^{1A}$ is selected from:

(i) $CH(R^{C1})NZ^1Z^3$, where $R^{C1}$ is selected from H, $C_{1-2}$ alkyl, $Z^1$ is selected from H and $C_{1-3}$ alkyl substituted by $C(=O)OC_{1-4}$ alkyl or $C(=O)$Me and $Z^3$ is H;

(iii) a group selected from:

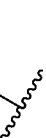

($R^{1A2}$)

(R^{N5}) pyrrolidine structure (R^{I.45})

(R^{N6}) azetidine structure (R^{I.46})

wherein:
$R^{N2}$ is selected from H, $C_{1-3}$ alkyl and C(=O)Me;
$R^{N5}$ is selected from H and $C_1$ alkyl;
$R^{N6}$ is H;
when A is an optionally substituted 5 or 6 membered heteroaryl group, A may bear a single substituent $R^{1.4}$ which is not alpha to the NH group, where $R^{1.4}$ is as defined above, and may optionally further bear one or two substituents $R^{1C}$, where each $R^{1C}$ is independently selected from:
  (i) $C_{1-3}$ alkyl optionally substituted with one to three substituents independently selected from F, OH or O—($C_{1-3}$ alkyl);
  (ii) O—($C_{1-3}$ alkyl);
  (ii) CN; and
  C(=O)Me;
$R^2$ is selected from halo, $CH_3$ and $CF_3$;
$R^3$ is substituted phenyl, where
  $R^3$ bears a substituent $R^4$ either alpha or beta to the —$C_2H_4$— group, and may additionally bear a further substituent F; and
  $R^4$ is —Y—C(O)N($R^{N13}$)$Z^4$, where Y is selected from —CHCH$_3$—, —CH(CH$_2$CH$_3$)—, —C(CH$_3$)$_2$—, and $C_{3-4}$ cycloalkylidene; $R^{N13}$ is H; and $Z^4$ is H.

In some embodiments of the present invention, the compounds are of formula (Ic) which is a compound of formula (I) of the first aspect and formulae (Ia) and (Ib) defined above or isomers, salts, solvates, protected forms or prodrugs thereof wherein:
A is selected from substituted phenyl and an optionally substituted 5 or 6 membered heteroaryl group linked to the NH group through an aromatic ring carbon atom, in which the heteroaryl ring system contains 1 or 2 heteroatoms selected from N and O, and;
when A is optionally substituted phenyl, A may bear a substituent $R^{1.4}$ which is not alpha to the NH group, where $R^{1.4}$ is selected from:
  (i) CH($R^{C1}$)N$Z^1Z^3$, where $R^{C1}$ is methyl, $Z^1$ is H and $Z^3$ is H;
  (iii) a group selected from:

(R^{N2}) piperidine structure (R^{I.42})

(R^{N5}) pyrrolidine structure (R^{I.45})

(R^{N6}) azetidine structure (R^{I.46})

wherein:
$R^{N2}$ is selected from H and methyl;
$R^{N5}$ is selected from H and methyl;
$R^{N6}$ is H;
when A is an optionally substituted 5 or 6 membered heteroaryl group, A may bear a single substituent $R^{1.4}$ which is not alpha to the NH group, where $R^{1.4}$ is as defined above, and may optionally further bear one or two substituents $R^{1C}$, where each $R^{1C}$ is independently selected from:
  (i) $CH_3$ or $CF_3$;
$R^2$ is selected from halo and $CF_3$;
$R^3$ is substituted phenyl, where
  $R^3$ bears a substituent $R^4$ either alpha or beta to the —$C_2H_4$— group, and may additionally bear a further substituent F; and
  $R^4$ is —Y—C(O)N($R^{N13}$)$Z^4$, where Y is selected from —CHCH$_3$—, —CH(CH$_2$CH$_3$)—, —C(CH$_3$)$_2$—, and cyclopropylidene; $R^{N13}$ is H; and $Z^4$ is H.

In some embodiments of the present invention, the compounds are of formula (Id) which is a compound of formula (I) of the first aspect and formulae (Ia) to (Ic) defined above or isomers, salts, solvates, protected forms or prodrugs thereof wherein:
A is selected from substituted phenyl and an optionally substituted pyrazolyl or pyridyl group linked to the NH group through an aromatic ring carbon atom, in which the heteroaryl ring system contains 1 or 2 heteroatoms selected from N and O, and; when A is optionally substituted phenyl, A may bear a substituent $R^{1.4}$ which is not alpha to the NH group, where $R^{1.4}$ is:

(R^{N2}) piperidine structure (R^{I.42})

wherein:
$R^{N2}$ is methyl;
when A is an optionally substituted pyrazolyl or pyridyl group, A may bear a single substituent $R^{1.4}$ which is not alpha to the NH group, where $R^{1.4}$ is as defined above, and may optionally further bear one or two substituents $R^{1C}$, where each $R^{1C}$ is independently selected from:
  (i) $CH_3$ or $CF_3$;
$R^2$ is selected from Cl and $CF_3$;
$R^3$ is substituted phenyl, where
  $R^3$ bears a substituent $R^4$ alpha to the —$C_2H_4$— group, and may additionally bear a further substituent F; and R⁴ is —Y—C(O)N(R^{N13})Z⁴, where Y is selected from —CHCH₃— and C₃ cycloalkylidene;
R^{N13} is H; and Z⁴ is H.

In some embodiments of the present invention, the compounds are of formula (Ie) or isomers, salts, solvates, protected forms or prodrugs thereof:

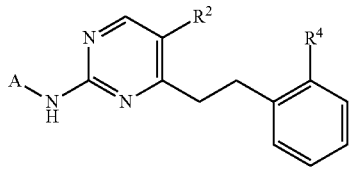
(Ie)

wherein:
A is selected from: optionally substituted phenyl and optionally substituted pyridyl, wherein A may bear one substituent R^{1A} which is not alpha to the NH group, where R^{1A} is selected from R^{1A2} and R^{1A6}:

(R^{1A2})

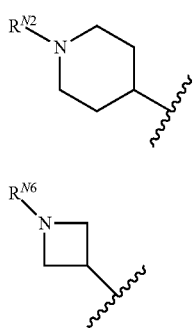

(R^{1A6})

wherein:
R^{N2} is selected from H and methyl;
R^{N6} is selected from H and methyl;
R² is selected from Cl, methyl and CF₃; and
R⁴ is —Y—C(O)NH₂, where Y is selected from —CHCH₃—, —C(CH₃)₂—, cyclopropylidene and cyclobutylidene;
with the proviso that:
when A is either:

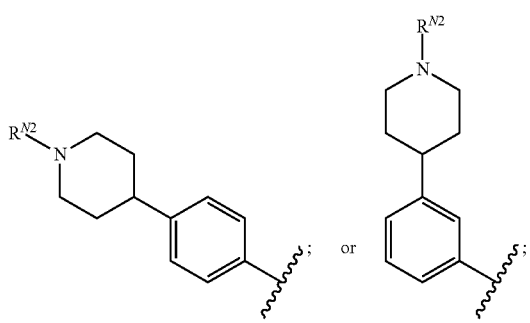

and R² is C₁ or CF₃, then R⁴ is not —CH(CH₃)C(O)NH₂.

In some embodiments of the present invention, the compounds are of formula (If) or isomers, salts, solvates, protected forms or prodrugs thereof:

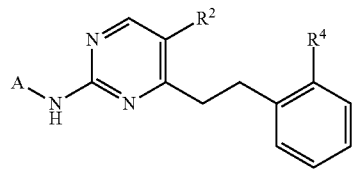
(If)

wherein:
A is selected from: optionally substituted phenyl and optionally substituted pyridyl, wherein A may bear one substituent R^{1A} which is not alpha to the NH group, where R^{1A} is selected from R^{1A2} and R^{1A6}:

(R^{1A2})

(R^{1A6})

wherein:
R^{N2} is selected from H and methyl;
R^{N6} is selected from H and methyl;
R² is selected from Cl, methyl and CF₃; and
R⁴ is —Y—C(O)NH₂, where Y is selected from —C(CH₃)₂—, cyclopropylidene and cyclobutylidene.

In some embodiments of the present invention, the compounds are of formula (Ig) or isomers, salts, solvates, protected forms or prodrugs thereof:

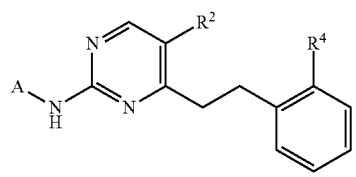
(Ig)

wherein
A is selected from an optionally substituted 5 or 6 membered heteroaryl group which contains 1 or 2 heteroatoms selected from N and O, wherein A may bear one substituent R^{1A} which is not alpha to the NH group, where R^{1A} is selected from R^{1A2}, R1A3 and R^{1A6}

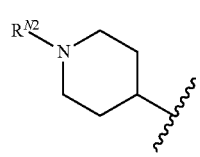
(R^{1A2})

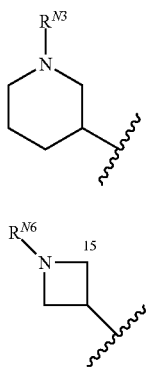

(R^{N3})

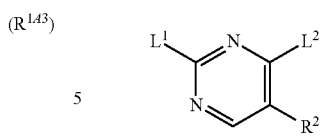

(R^{N6})

wherein:
$R^{N2}$ is selected from H and $C_{1-4}$ alkyl;
$R^{N3}$ is selected from H, $C_{1-3}$ alkyl, and C(=O)Me;
$R^{N6}$ is selected from H and $C_{1-4}$alkyl;
and may optionally further bear one substituent $R^{1C}$ selected from $CF_3$, $C_{1-3}$alkyl, $CH_2CF_3$, CN, C(=O)($C_{1-3}$alkyl), $CH(CH_3)NH_2$, $CHCF_2$, $OCH_3$, $CH(CH_3)NHCH_3$, $C_{1-3}$alkylOH and $C_{1-3}$alkylOMe;
$R^2$ is selected from halo, $C_{1-4}$alkyl and $CF_3$; and
$R^4$ is —Y—C(=O)NH$_2$, where Y is selected from —CHCH$_3$—, —C(CH$_3$)$_2$—, cyclopropylidene and cyclobutylidene.

In one embodiment of formula (Ig), A is selected from a 5 membered heteroaryl group which contains N such as optionally substituted pyrazolyl, a 5 membered heteroaryl group which contains N and O such as optionally substituted oxazolyl and a 6 membered heteroaryl group which contains N such as optionally substituted pyridinyl, optionally substituted pyrimidinyl and optionally substituted pyridazinyl, wherein A bears one substituent selected from R1A2, (R1A3) and R1A6 defined in formula (Ig) above and may optionally further bear one substituent R1C selected from CF3, C1-3alkyl, CH2CF3, CN, C(=O)Me, CH(CH3)NH2, CHCF2, OMe, CH(CH3)NHCH3, C1-3alkylOH and C1-3alkylOMe;
R2 is selected from Cl, Me and CF3; and
R4 is CHCH3C(=O)NH2.

In a further embodiment of formula (Ig), A is selected from a 5 membered heteroaryl group which contains N such as optionally substituted pyrazolyl wherein A bears one substituent selected from $R^{1A2}$ defined in formula (Ig) above;
$R^2$ is $CF_3$; and
$R^4$ is $CHCH_3C(=O)NH_2$.

The preferences expressed in relation to compounds of formula I also apply to compounds of formulae Ia to Ig, where appropriate.

Embodiments of the inventions are compounds of the examples, including compounds 1 to 77. Embodiments of particular interest include compounds 2, 3, 4, 5, 6, 7, 8, 13, 15, 19, 20, 33, 35, 45, 48, 49, 50, 56, 56-1A, 56-2A, 57, 57-1A, 57-2A, 68, and 70.

General Synthesis Methods

The compounds of the invention can be prepared by employing the following general methods and using procedures described in detail in the experimental section. The reaction conditions referred to are illustrative and non-limiting.

The process for the preparation of a compound of formula (I) or an isomer, salt, solvate, protected form or prodrug thereof, comprises reacting a compound of formula F1

F1 with a compound of formula A-NH$_2$ to displace the group $L^1$ and with a compound of the formula HC≡$R^3$ to displace the group $L^2$; or
with a compound of formula HC≡$R^3$ to displace the group $L^2$ and with a compound of formula A-NH$_2$ to displace the group $L^2$,
wherein $R^2$, A and $R^3$ areas defined in formula (I) above and $L^1$ and $L^2$ are leaving groups.

It will be appreciated that the compounds of formulae A-NH$_2$ and HC≡$R^3$ can be reacted with the compound of formula F1 separately or sequentially in any order or simultaneously.

The leaving groups $L^1$ and $L^2$ may be any suitable leaving groups, such as a halogen atom (F, Cl, Br, I), —SR or —SO$_2$R where R is a $C_{1-4}$ straight chain or branched alkyl group. In some embodiments, $L^1$ and $L^2$ may be the same or different and may be selected from the group consisting of Cl, Br, I, SMe, SO$_2$Me.

Compounds of formula I, as described above, can be prepared by synthetic strategies outlined below, wherein the definitions above apply:

Scheme A

Compounds of formula F1 may be reacted with substituted commercial or synthetic amino substituted compounds of formula F2 (as prepared in scheme C to N) to form intermediates of formula F3 where $L^1$ and $L^2$ may be the same or different and include Cl, Br, I, SMe, SO$_2$Me.

Compounds of the formula F1 may be prepared where $L^1$ and $L^2$ are different to allow regioselective substitution or when $L^1=L^2$ suitable reaction conditions can be employed (choice of solvent, reaction temperature, addition of a Lewis acid, for example ZnCl$_2$ in Et$_2$O) to allow $L^1$ to be selectively displaced over $L^2$. Where regiochemical mixtures and di-substitution are obtained the regioisomers may be separated by chromatography.

Compounds of the formula F1 where $L^1=L^2$ are either commercially available, for example 2,4-dichloro-5-(trifluoromethyl)pyrimidine, 2,4-dichloro-5-fluoropyrimidine, 2,4,5-trichloropyrimidine, 2,4-dichloro-5-bromopyrimidine, 2,4-dichloro-5-iodopyrimidine, 2,4-dichloro-5-methylpyrimidine, 2,4-dichloro-5-cyanopyrimidine or may be prepared readily from commercial starting materials. Where $R^2=CF_3$ and differentiation of $L^1$ and $L^2$ is desirable, the method outlined in scheme B may be employed.

Scheme B

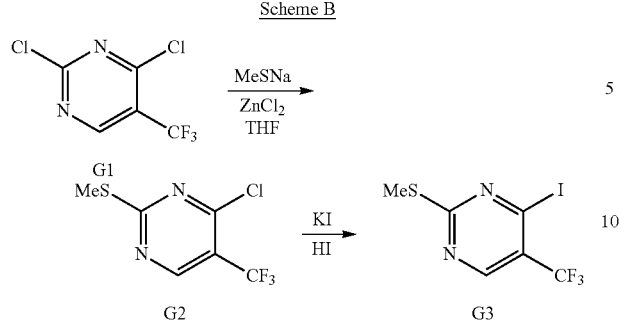

Commercially available 2,4-dichloro-5-(trifluoromethyl) pyrimidine (G1) can be selectively reacted with sodium thiomethoxide in the presence of zinc(II) chloride to give 2-thiomethyl-4-chloro-5-(trifluoromethyl)pyrimidine (G2). 2-Thiomethyl-4-chloro-5-(trifluoromethyl)pyrimidine (G2) can be further reacted, for example by conversion to 2-thiomethyl-4-iodo-5-(trifluoromethyl)pyrimidine (G3) under Finkelstein conditions and/or by oxidation with m-CPBA to give the corresponding sulfone if further differentiation of the 2 and 4-position is required or if additional activation is desirable.

Examples of commercially available amino compounds of the formula F2 include, but are not limited to those depicted in table 1.

TABLE 1

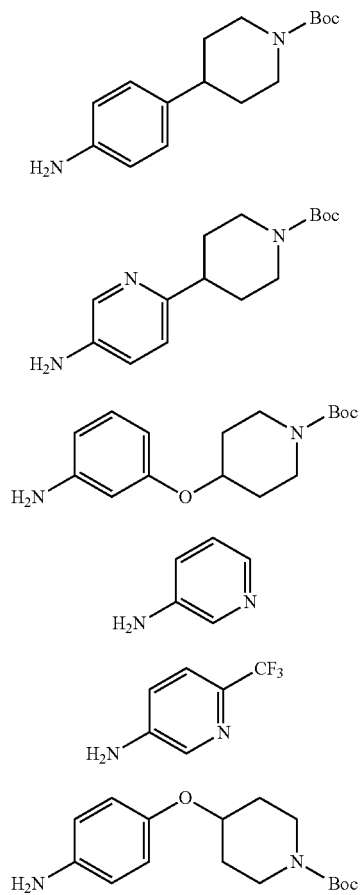

TABLE 1-continued

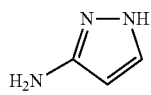

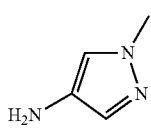

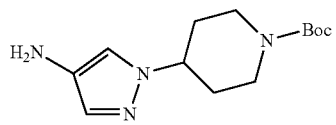 [SMILES: CC(C)(C)OC(=O)N1CCC(n2cc(N)cn2)CC1]

It will be appreciated that compounds of the formula F2, both commercial and synthetic, can be further modified either prior or post coupling to pyrimidines of the formula F1 via an extensive range of chemistries including, but not limited to hydrolysis, alkylation, acylation, electrophilic halogenation and Mitsunobu coupling.

In addition to commercially available amino compounds of the formula F2, numerous analogous nitro containing compounds are also commercially available including, but not limited to those depicted in table 2.

TABLE 2

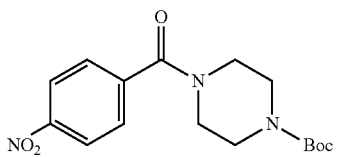 [SMILES: CC(C)(C)OC(=O)N1CCN(C(=O)c2ccc([N+](=O)[O-])cc2)CC1]

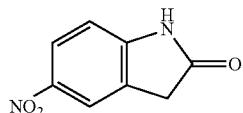

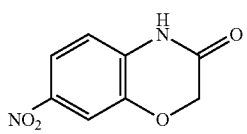 [SMILES: O=C1COc2cc([N+](=O)[O-])ccc2N1]

It will be appreciated that such compounds can be reduced under suitable conditions, for example in the presence of palladium under an atmosphere of hydrogen, to give amino compounds of the formula F2.

Synthetic amino compounds of the invention may be prepared via a range of procedures. It will be appreciated that heterocyclic analogues may also be prepared by analogous methods to those outlined below via substitution of phenyl containing starting materials with suitable heteroaromatic systems.

Scheme C

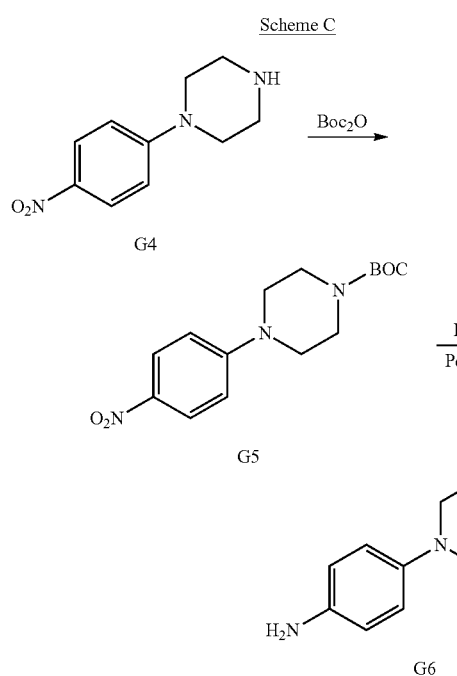

Commercially available 1-(4-nitrophenyl)piperazine (G4), or a salt thereof, can be reacted with Boc anhydride to give tert-butyl 4-(4-nitrophenyl)piperazine-1-carboxylate (G5). Subsequent reduction via hydrogenation in the presence of a catalyst, for example palladium on charcoal, gives the corresponding aniline, tert-butyl 4-(4-aminophenyl)piperazine-1-carboxylate (G6).

Scheme D

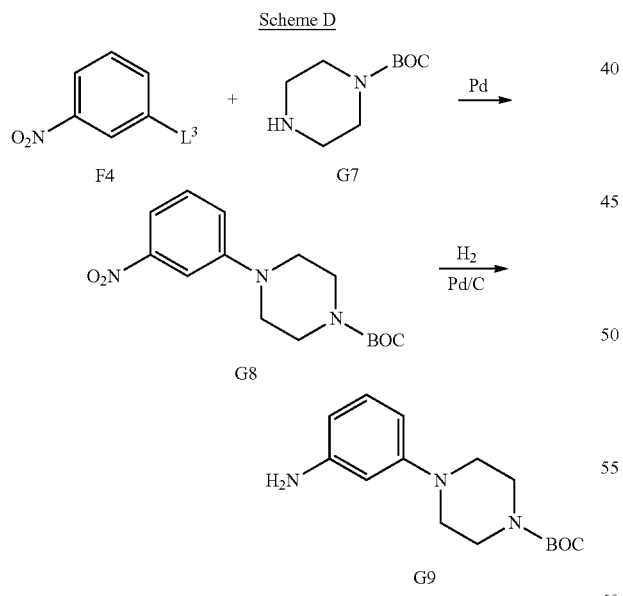

tert-Butyl 4-(3-aminophenyl)piperazine-1-carboxylate (G9) can be prepared by coupling of commercially available tert-butyl piperazine-1-carboxylate (G7) and compounds of the formula F4, where $L^3$=I or Br, in a Buchwald type reaction to give tert-butyl 4-(3-nitrophenyl)piperazine-1-carboxylate (G8). Reduction with hydrogen in the presence of a catalyst, for example palladium on charcoal, gives tert-butyl 4-(3-aminophenyl)piperazine-1-carboxylate (G9).

Scheme E

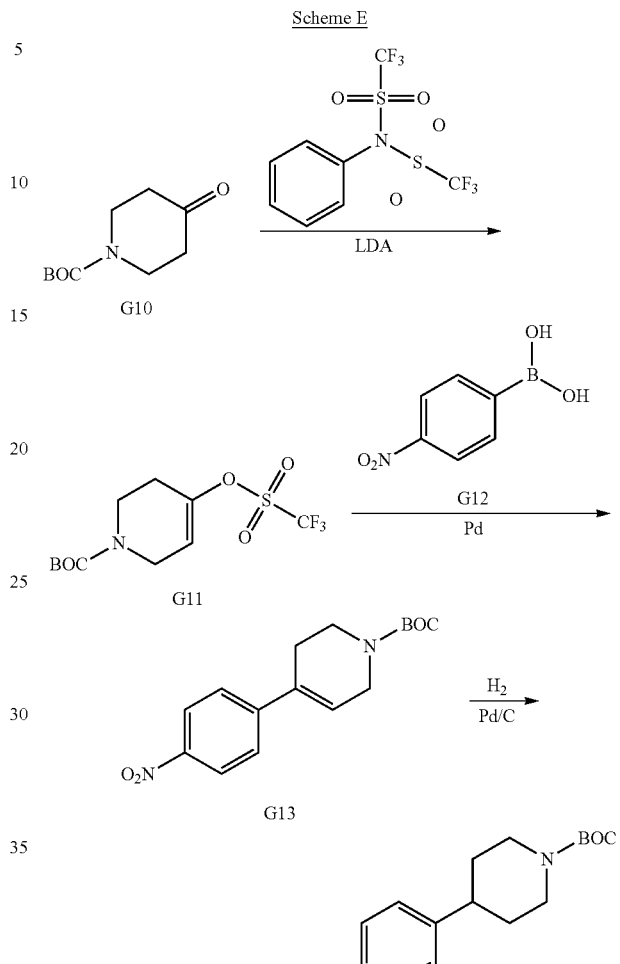

The corresponding 4-piperidine analogues of G6 can be prepared by a sequence of reactions starting with the conversion of commercially available tert-butyl 4-oxopiperidine-1-carboxylate (G10) to vinyl triflate G11. Coupling of G11 in a Suzuki type reaction with (4-nitrophenyl)boronic acid (G12) gives tetrahydropyridine G13. Subsequent reduction via hydrogenation in the presence of a catalyst, for example palladium on charcoal, gives tert-butyl 4-(4-aminophenyl)piperidine-1-carboxylate (G14).

Scheme F

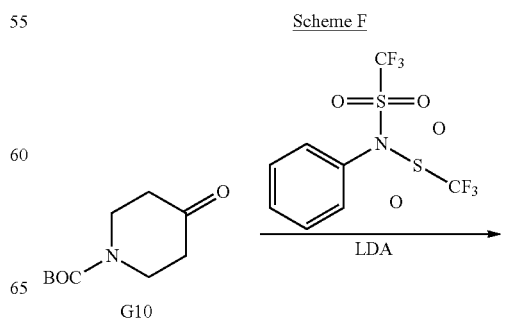

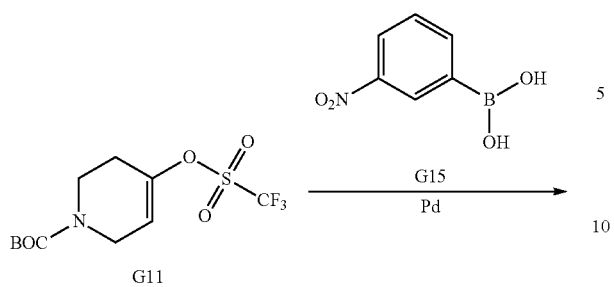

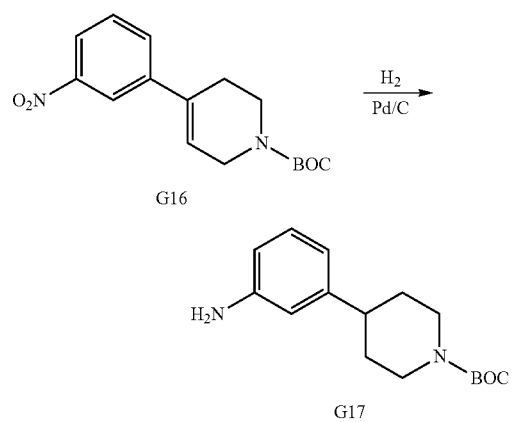

The corresponding 4-(3-aminophenyl)piperidine analogue of G9 can be prepared by a sequence of reactions starting with the conversion of commercially available tert-butyl 4-oxopiperidine-1-carboxylate (G10) to vinyl triflate G11. Coupling of G11 in a Suzuki type reaction with (3-nitrophenyl)boronic acid (G15) gives tetrahydropyridine G16. Subsequent reduction via hydrogenation in the presence of a catalyst, for example palladium on charcoal, gives tert-butyl 4-(3-aminophenyl)piperidine-1-carboxylate (G17).

Scheme G

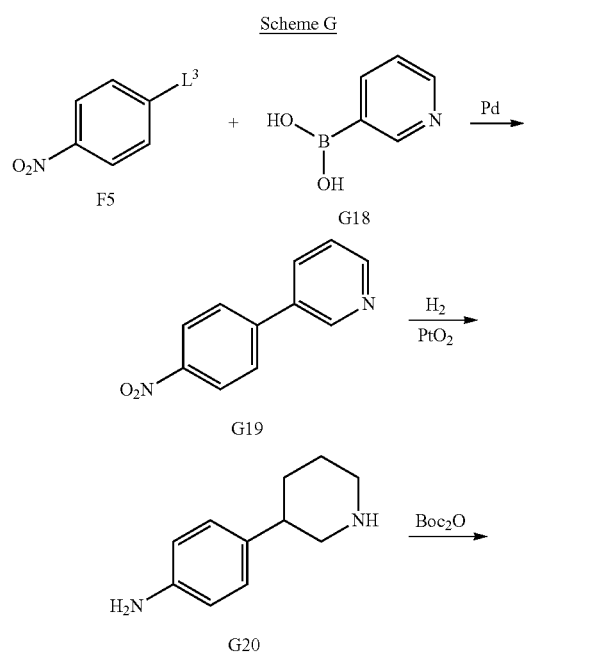

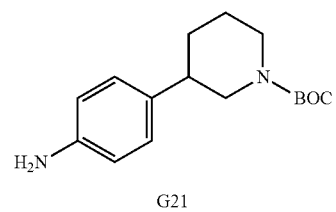

The 3-(4-aminophenyl)piperidine regioisomers of G14 can be prepared by reaction of commercially available compounds of the formula F5, where $L^3$=I or Br, with pyridin-3-ylboronic acid (G18) in a Suzuki type reaction to form 3-(4-nitrophenyl)pyridine (G19). Reduction of G19 with hydrogen in the presence of a catalyst, for example platinum oxide, gives 4-(piperidin-3-yl)aniline (G20) which may be protected using Boc anhydride to give tert-butyl 3-(4-aminophenyl)piperidine-1-carboxylate (G21).

Scheme H

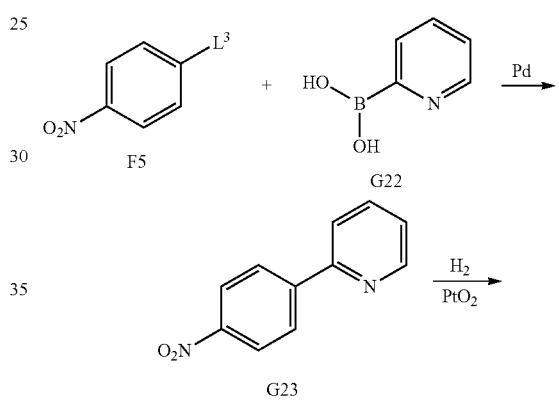

The 2-(4-aminophenyl)piperidine regioisomer of G14 can be prepared by reaction of commercially available compounds of the formula F5, where $L^3$=I or Br, with pyridin-2-ylboronic acid (G22) in a Suzuki type reaction to form 2-(4-nitrophenyl)pyridine (G23). Reduction of G23 with hydrogen in the presence of a catalyst, for example platinum oxide, gives 4-(piperidin-2-yl)aniline (G24) which may be protected using Boc anhydride to give tert-butyl 2-(4-aminophenyl)piperidine-1-carboxylate (G25).

Scheme I

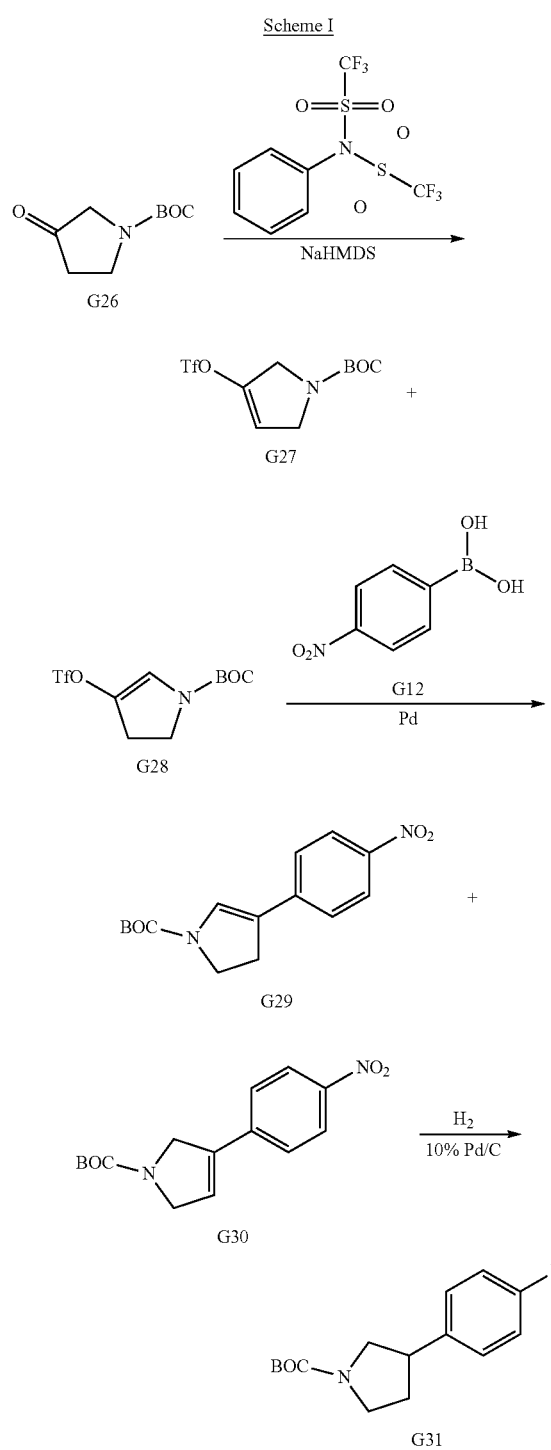

Scheme J

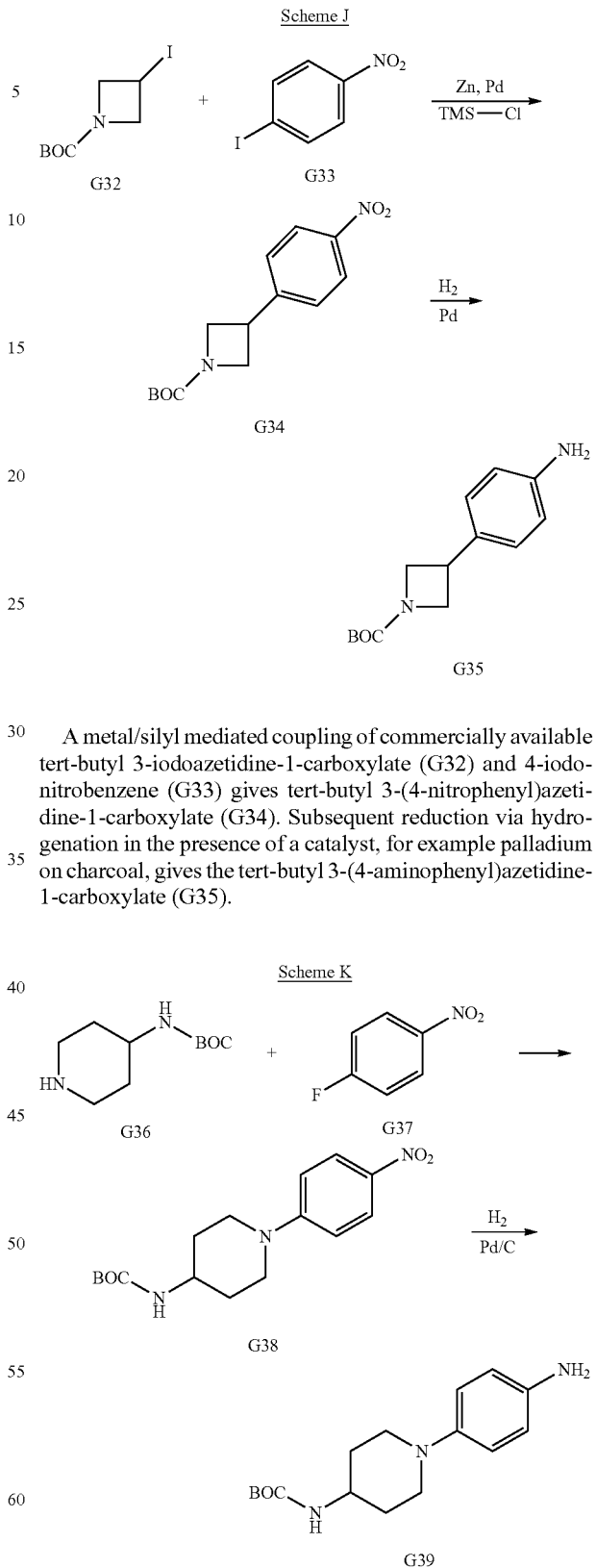

A metal/silyl mediated coupling of commercially available tert-butyl 3-iodoazetidine-1-carboxylate (G32) and 4-iodonitrobenzene (G33) gives tert-butyl 3-(4-nitrophenyl)azetidine-1-carboxylate (G34). Subsequent reduction via hydrogenation in the presence of a catalyst, for example palladium on charcoal, gives the tert-butyl 3-(4-aminophenyl)azetidine-1-carboxylate (G35).

Commercially available tert-butyl 3-oxopyrrolidine-1-carboxylate (G26) can be converted to a mixture of vinyl triflates G27 and G28 in the presence of a triflamide and a suitable base, for example NaHMDS. Coupling of the mixture with (4-nitrophenyl)boronic acid (G12) under Suzuki conditions gives dihydropyrroles G29 and G30. Reduction of this mixture using hydrogen in the presence of a catalyst, for example 10% palladium on charcoal, gives tert-butyl 3-(4-aminophenyl)pyrrolidine-1-carboxylate (G31).

tert-Butyl (1-(4-aminophenyl)piperidin-4-yl)carbamate (G39) can be prepared by nucleophilic aromatic substitution of commercially available tert-butyl piperidin-4-ylcarbamate (G36) and 1-fluoro-4-nitrobenzene (G37) under thermal conditions to give tert-butyl (1-(4-nitrophenyl)piperidin-4-yl)carbamate (G38). Reduction of G38 with hydrogen in the presence of a catalyst, for example 10% palladium on charcoal gives tert-butyl (1-(4-aminophenyl)piperidin-4-yl)carbamate (G39).

sulphonamide and subsequent re-protection with Boc anhydride gives carbamate G45. Reduction using hydrazine in the presence of iron(III) chloride gives tert-butyl 2-(4-aminophenyl)morpholine-4-carboxylate (G46).

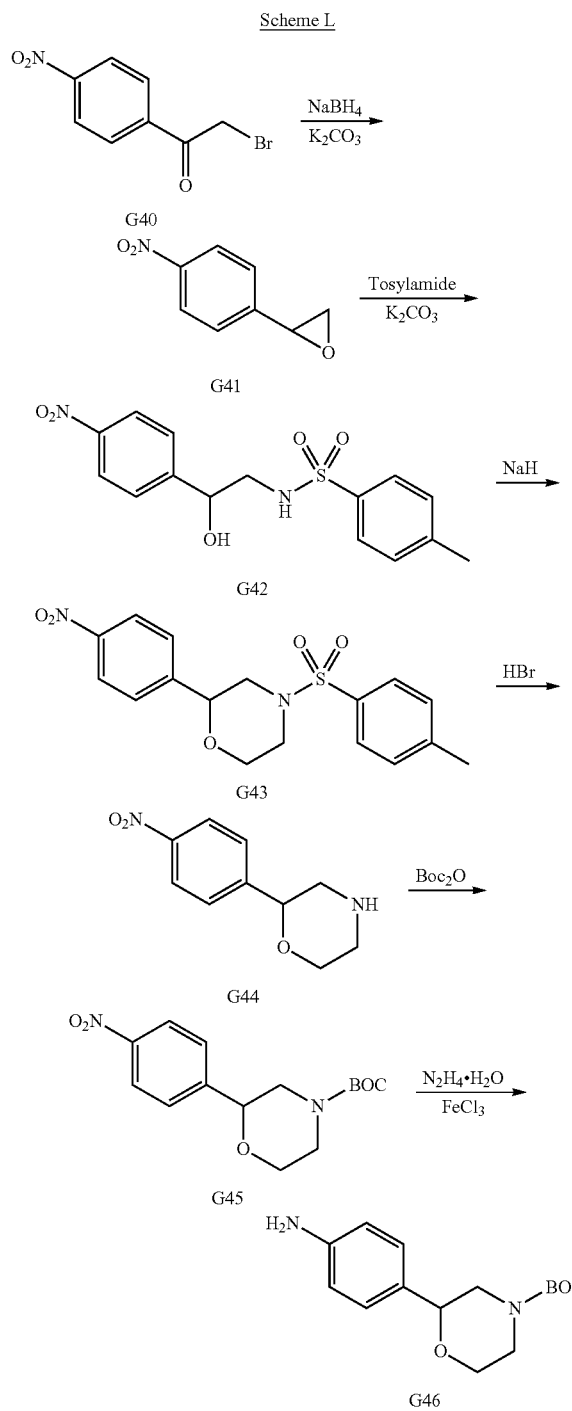

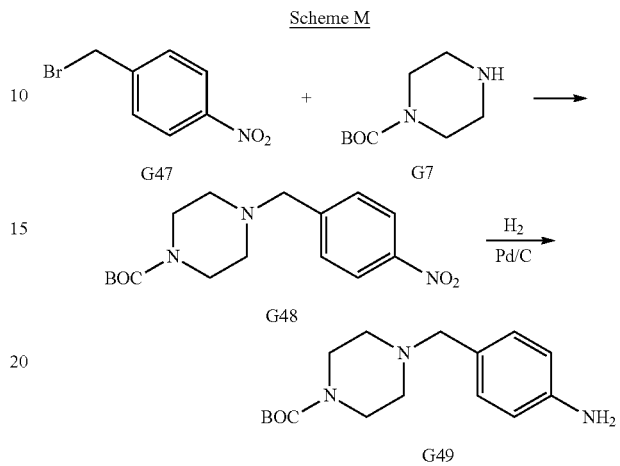

tert-Butyl 4-(4-aminobenzyl)piperazine-1-carboxylate (G49) can be prepared by the nucleophilic displacement of commercially available 1-(bromomethyl)-4-nitrobenzene (G47) with tert-butyl piperazine-1-carboxylate (G7) to give tert-butyl 4-(4-nitrobenzyl)piperazine-1-carboxylate (G48). Subsequent reduction with hydrogen in the presence of a catalyst, for example 10% palladium on charcoal, gives tert-butyl 4-(4-aminobenzyl)piperazine-1-carboxylate (G49).

Compounds of the formula F2 containing benzylamine or substituted benzylamines may either be purchased with suitable protecting groups in place to allow selective reaction at the aniline or synthesised using an Ellman type procedure as outlined in scheme N.

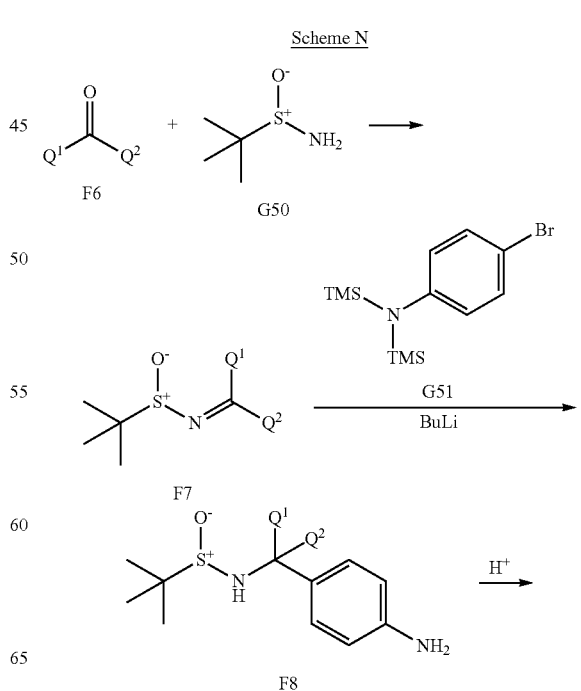

Commercially available 2-bromo-1-(4-nitrophenyl)ethanone (G40) can be reduced and cyclised to give epoxide G41. Opening of the epoxide with tosylamide followed by cyclisation with (2-bromoethyl)diphenylsulfonium trifluoromethanesulfonate gives morpholine G43. Cleavage of the

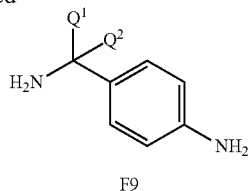

F9

Carbonyl compounds of the formula F6 can be reacted with 2-methylpropane-2-sulfinamide (G50) to give compounds of the formula F7. Compounds of the formula F7 can be reacted with anions prepared from suitably protected amino compounds, for example N-(4-bromophenyl)-1,1,1-trimethyl-N-(trimethylsilyl)silanamine (G51) treated with n-butyllithium, to give compounds of the formula F8. Hydrolysis of compounds of the formula F8 under acidic conditions, for example using aqueous hydrochloric acid, gives compounds of the formula F9. Where necessary, compounds of the formula F9 can be further protected to facilitate regiospecific reactivity. It will be appreciated that $Q^1$ and $Q^2$ may be the same or different and may be fused together to form a ring structure, for example as in cyclobutanone. Substituents $Q^1$ and $Q^2$ form either $R^{C1}$ or part of X in compounds of formula I. It will also be appreciated that anions of suitably protected amino heterocycles may be added to compounds of the formula F7 to give heterocyclic analogues of compounds of the formula F9.

Where compounds are required where $R^3$ is aryl or substituted aryl compounds of the formula F14 may be prepared as outlined in scheme O.

F12 that the nature of $Q^3$ can be readily changed. For example, a carboxylic acid may be converted to a corresponding ester or amide as required and conversely esters and amides can be hydrolysed to give carboxylic acids. Compounds of the formula F10 where $Q^3$ is an ester, may be deprotonated using a suitable base, for example LDA and the resulting anion quenched with an alkylating agent, for example methyl iodide, to give compounds of the formula F11 where Y is a monoalkylated species. A second deprotonation can then be carried out allowing the introduction of a second alkylating agent, which may be the same or different to the first alkylating agent employed, or to facilitate the cyclisation of a ring system where the first alkylating agent used was di-functional, for example 1,3-dibromopropane. Halogenation of compounds of the formula F11 gives compounds of the formula F12, for example 1-phenyl-1-cyclopropanecarboxylic acid can be readily iodinated in the presence of $Pd(OAc)_2$ and (diacetoxyiodo)benzene to give 1-(2-iodophenyl)cyclopropanecarboxylic acid. Compounds of the formula F12 may be reacted under Sonagashira type coupling conditions to give acetylenes of the formula F13 where $R^9$=TMS, TES or $C(CH_3)_2OH$. $R^9$ may then be removed to generate compounds of the formula F14. When $R^9$=TMS or TES potassium carbonate or tetra-n-butyl ammonium fluoride may be employed to induce this transformation. When $R^9$=$C(CH_3)_2OH$, sodium hydride in refluxing toluene may be used.

Alternatively, when compounds in which $R^3$=heteroaryl are desired heteroaryl analogues of F14 may be prepared as outlined in Schemes P, Q and R.

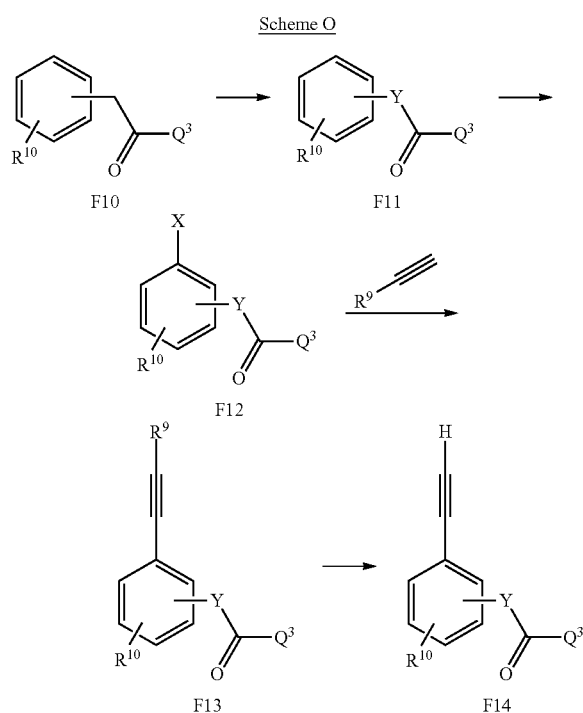

Scheme O

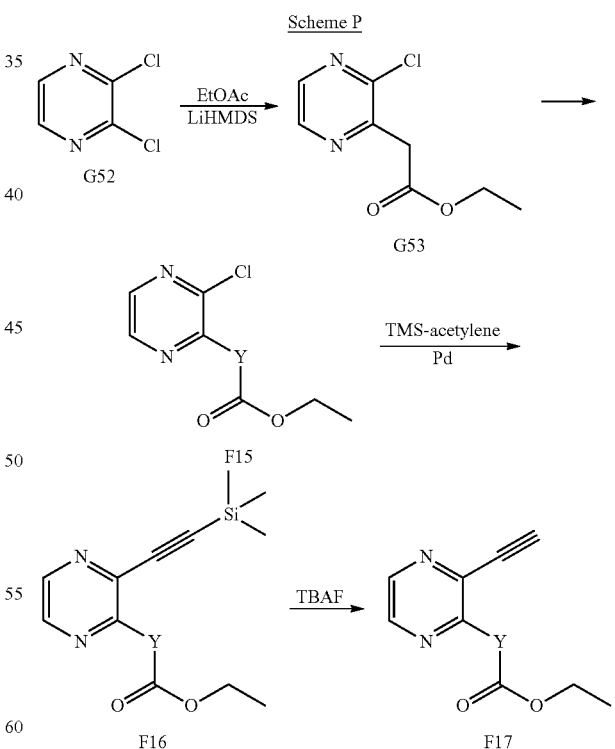

Scheme P

Compounds of the formula F10, F11 and F12, where $R^{10}$ are independently H, F, Me or $CF_3$; $Q^3$ may be OH, O-alkyl, $NH_2$ or substituted N and X=Cl, Br or I, are either commercially available or may be prepared synthetically. It will be appreciated that for compounds of the formula F10, F11 and For pyrazine containing analogues, 2,3-di-chloropyrazine (G52) can be reacted with ethyl acetate in the presence of LiHMDS to give ester G53. Deprotonation and alkylation, as described above for aryl analogues, gives compounds of the formula F15. Coupling of compounds of the formula F15 with TMS acetylene under Sonagashira conditions gives acetylenes of the formula F16. Removal of the trimethylsilyl group using TBAF gives compounds of the formula F17.

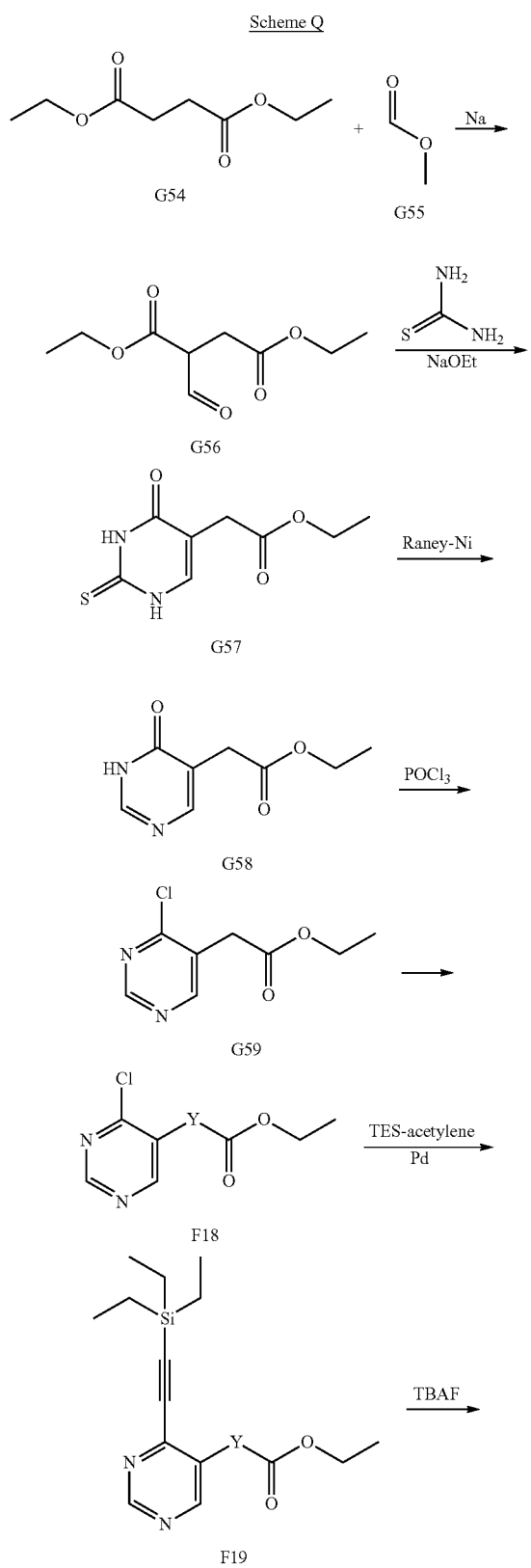

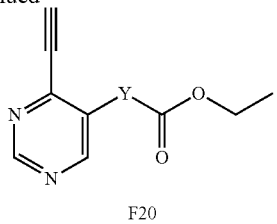

For pyrimidine analogues, diethyl succinate (G54) and ethyl formate (G55) can be condensed to give aldehyde G56 in the presence of sodium metal. Cyclisation using thiourea gives 4-oxo-2-thioxo-1,2,3,4-tetrahydropyrimidine (G57). Desulfurisation using Raney-nickel gives pyrimidone G58, which can be converted to 4-chloro pyrimidine G59 using phosphorous oxychloride. Deprotonation and alkylation, as described above for aryl analogues, gives compounds of the formula F18. Coupling of compounds of the formula F18 with TES-acetylene under Sonagashira conditions, followed by removal of the triethylsilyl group using TBAF gives compounds of the formula F20. It will be appreciated that the regioisomeric pyrimidine can be accessed by analogous series of reactions from the isomer of G57.

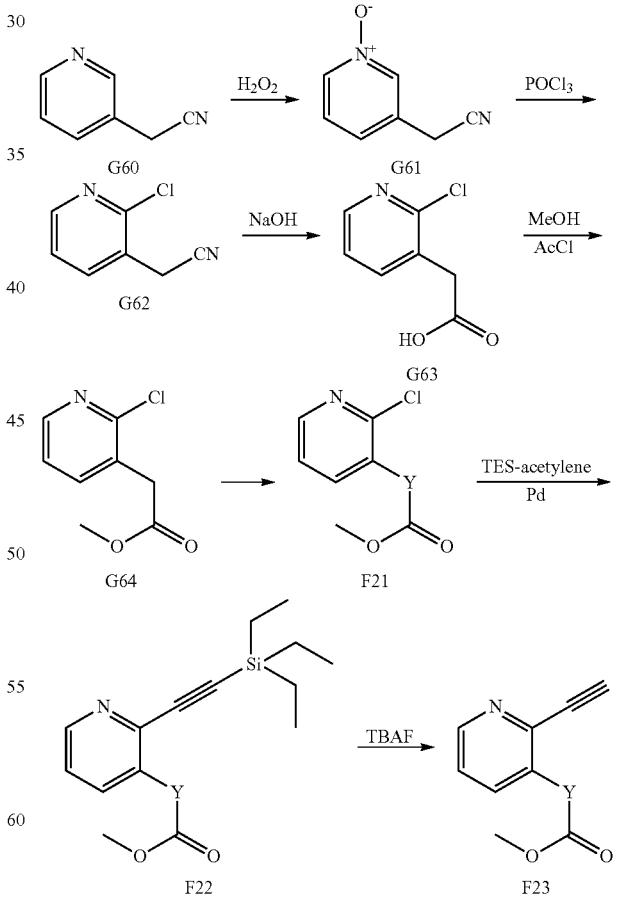

For 3-pyridyl acetates, 2-(pyridin-3-yl)acetonitrile (G60) can be oxidised to N-oxide G61. Chlorination with phosphorous oxychloride gives 2-chloropyridine G62 which can be hydrolysed with sodium hydroxide to acetic acid G63. Ester formation using methanol gives 2-chloropyridine ester G64. Deprotonation and alkylation, as described above for aryl analogues, gives compounds of the formula F21. Coupling of compounds of the formula F21 with TES-acetylene under Sonagashira conditions, followed by removal of the triethylsilyl group using TBAF gives compounds of the formula F23. It will be appreciated that the other regioisomeric pyridine analogues can be prepared using an analogous sequence starting from other commercially available pyridyl acetates.

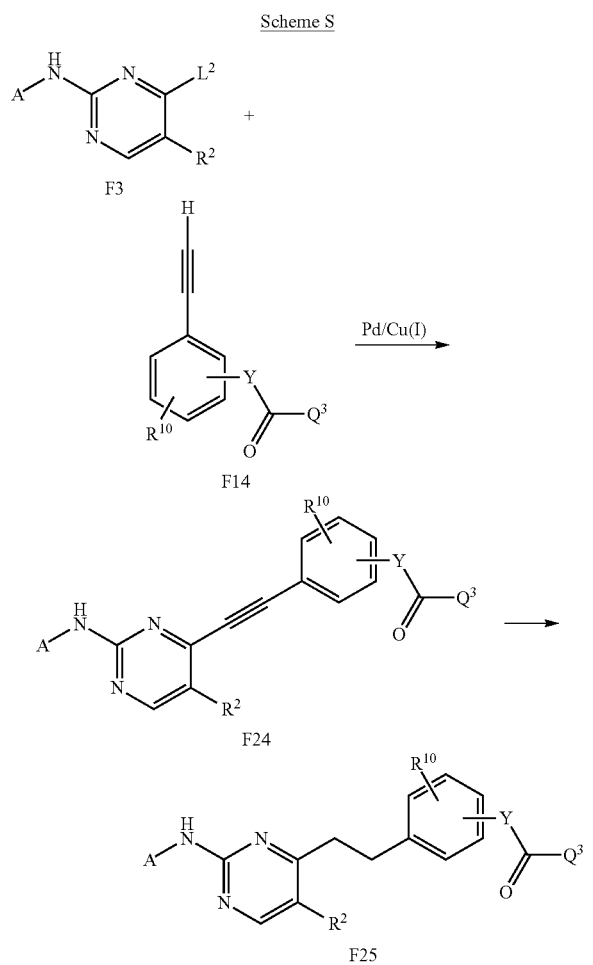

Pyrimidines of the formula F3 may be reacted with terminal acetylenes of the formula F14 to give acetylenes of the formula F24 in a Sonagashira type coupling. The acetylene in compounds of the formula F24 may be reduced to an alkane of the formula F25 using hydrogen gas in the presence of a transition metal catalyst. The exact choice of catalyst and conditions employed is dependant on the nature of $R^2$. For example, where $R^2$=F, $CF_3$, methyl or methoxy, 10% Pd/C may be used, where $R^2$=Cl, platinum oxide is employed. Functional group manipulation may be carried on compounds of the formula F25 if necessary. For example, compounds of the formula F25 where $Q^3$=O-alkyl (i.e. esters) may then be deprotected to give carboxylic acids of the formula F25 where $Q^3$=OH. In esters where $Q^3$=OMe, LiOH solutions may be employed. Where $Q^3$=Ot-Bu, acidic solutions, for example TFA in DCM may be used to facilitate hydrolysis. It will be appreciated that under acidic conditions Boc protecting groups in A will also be cleaved.

Compounds of the formula F25 where $Q^3$=OH may then be converted to amides and substituted amides as described in formula (I) using a suitable choice of amine in the presence of a coupling agents for example EDCl.HCl or HATU.

It will be appreciated that heteroaromatic analogues of compounds of the formula F14 (as described in schemes P, Q and R) may be coupled in an analogous manner to that described in scheme S and then further elaborated to amides as described above.

Compounds of the formula F25, in which $Q^3$=an amide or substituted amide may then be further modified by derivitisation of amine functionality present in A. For example, compounds of the formula F25 where A was prepared as described in schemes C to M, in which a tert-butyl carbamate is present, may be hydrolysed in the presence of mild acid, for example TFA, to give the parent amine. The amine functionality maybe further derivatised by reductive alkylation with formaldehyde in the presence of sodium triacetoxyborohydride to give N-Me analogues; by reductive alkylation with acetaldehyde in the presence of sodium triacetoxyborohydride to give N-Et analogues or the N-acetyl analogues may be prepared by reaction with a suitable acylating agent, for example acetic anhydride.

Alternatively, a complementary approach to that described scheme S can be employed, where $R^2$ is not $CF_3$, whereby pyrimidines of the formula F1 are initially coupled to acetylenes of the formula F14 as detailed in scheme T.

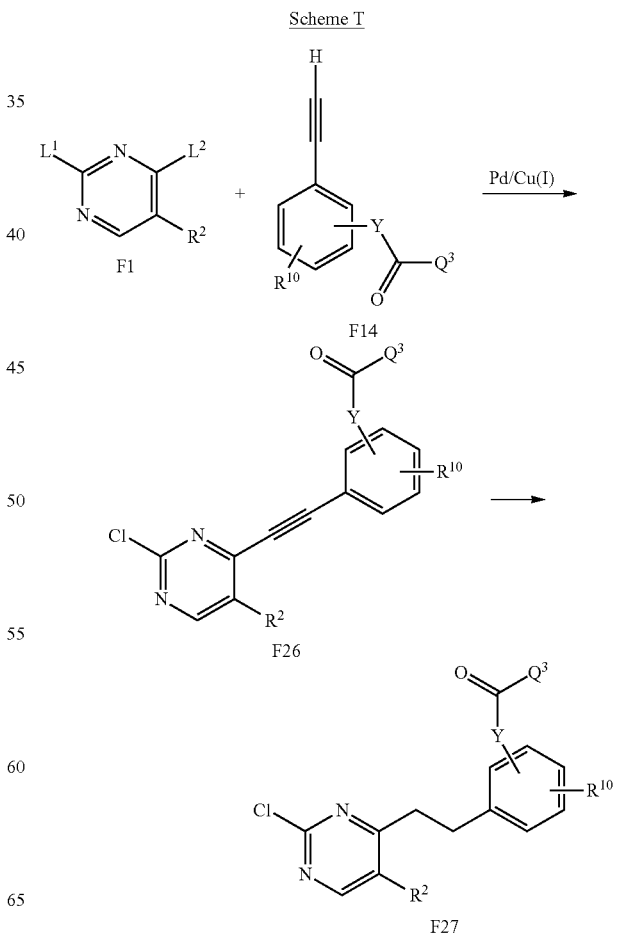

Pyrimidines of the formula F1 may be coupled to acetylenes of the formula F14 to give acetylenes of the formula F26 in a Sonagashira type coupling. Depending on the nature of $R^2$ these couplings may either be regioselective, or where mixtures are obtained, regioisomers may be separated by chromatography. The acetylene in compounds of the formula F26 may be reduced to an alkane of the formula F27 using hydrogen gas in the presence of a transition metal catalyst. The exact choice of catalyst and conditions employed is dependant on the nature of $R^2$. For example, where $R^2$=Me, 10% Pd/C may be used, where $R^2$=Cl, platinum oxide is employed. The desired amide may already be present in compounds of the formula F14, or alternatively an ester may be used and subsequently derivatised as described above.

Scheme U

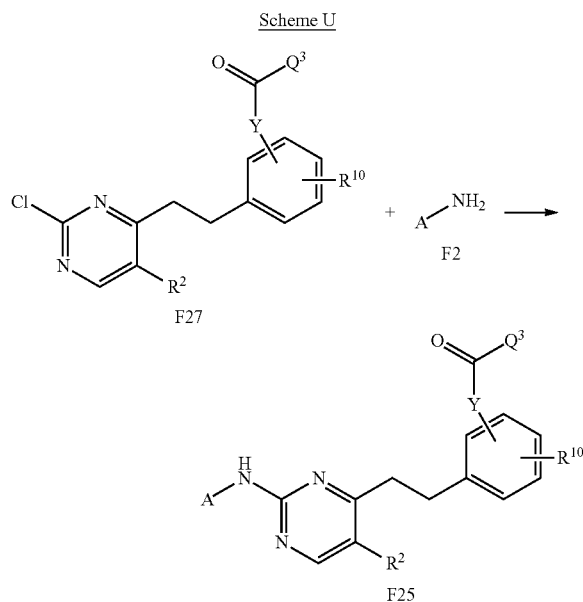

Compounds of the formula F27 may then be reacted with amino compounds of the formula F2, prepared as described above, to give compounds of the formula F25. Such couplings may either be mediated under acidic conditions, for example using trifluoroacetic acid in trifluoroethanol or using palladium catalysis in a Buchwald/Hartwig type coupling.

Compounds of the formula 25 may then be further elaborated as desired as described above.

Scheme V

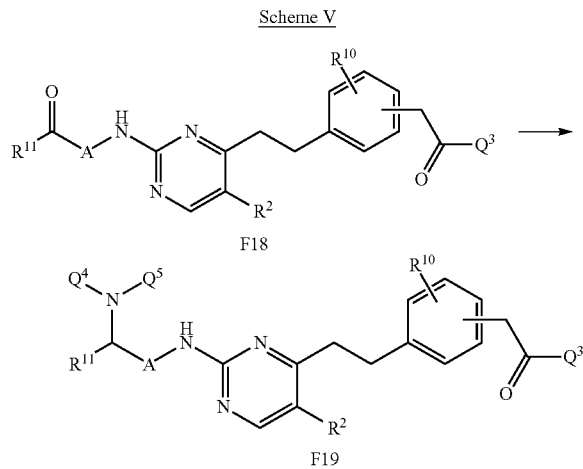

Aldehydes or ketones of formula F18 where $R^{11}$ is a hydrogen, an alkyl group or similar may be substituted with amines to form compounds of formula F19. It will be appreciated that in some cases $Q^4=Q^5=H$ forming a primary amine. Alternatively $Q^4=H$ and $Q^5=R$ to form a secondary amine. In some cases $Q^4=Q^5=R$, which will provide a secondary amine that may also have $Q^4$ and $Q^5$ fused together to form a ring structure, for example but not limited to azetidine, pyrrolidine, piperazine, morpholine and piperidine.

Use of Compounds of the Invention

The present invention provides active compounds, specifically, active 2,4,5-substituted pyrimidines.

The term "active", as used herein, pertains to compounds which are capable of inhibiting VEGFR3 activity and specifically includes both compounds with intrinsic activity (drugs) as well as prodrugs of such compounds, which prodrugs may themselves exhibit little or no intrinsic activity.

Assays which may be used in order to assess the VEGFR3 inhibition offered by a particular compound are described in the examples below.

The present invention further provides a method of inhibiting VEGFR3 activity in a cell, comprising contacting said cell with an effective amount of an active compound, preferably in the form of a pharmaceutically acceptable composition. Such a method may be practised in vitro or in vivo.

The present invention further provides active compounds which inhibit VEGFR3 activity, as well as methods of inhibiting VEGFR3 activity, comprising contacting a cell with an effective amount of an active compound, whether in vitro or in vivo.

Active compounds may also be used as part of an in vitro assay, for example, in order to determine whether a candidate host is likely to benefit from treatment with the compound in question.

The invention further provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

Cancer

The present invention provides active compounds which are anticancer agents. One of ordinary skill in the art is readily able to determine whether or not a candidate compound treats a cancerous condition for any particular cell type, either alone or in combination.

The invention provides the use of the active compounds for the treatment of cancer in the human or animal body. The invention further provides active compounds for use in a method of treatment of cancer in the human or animal body. Such a use or method may comprise administering to such a subject a therapeutically-effective amount of an active compound, preferably in the form of a pharmaceutical composition.

Examples of cancers include, but are not limited to, bone cancer, brain stem glioma, breast Cancer, cancer of the adrenal gland, cancer of the anal region, cancer of the bladder, cancer of the endocrine system, cancer of the oesophagus, cancer of the head or neck, cancer of the kidney or ureter, cancer of the liver, cancer of the parathyroid gland, cancer of the penis, cancer of the small intestine, cancer of the thyroid gland, cancer of the urethra, carcinoma of the cervix, carcinoma of the endometrium, carcinoma of the fallopian tubes, carcinoma of the renal pelvis, carcinoma of the vagina, carcinoma of the vulva, chronic or acute leukemia, colon cancer, melanoma such as cutaneous or intraocular melanoma, haemetological malignancies, Hodgkin's disease, lung cancer, lymphocytic lymphomas, neoplasms of the central nervous system (CNS), ovarian cancer, pancreatic cancer, pituitary adenoma, primary CNS lymphoma, prostate cancer, rectal cancer, renal cell carcinoma, sarcoma of soft tissue, skin cancer, spinal axis tumors, stomach cancer and uterine cancer. In some embodiments, the cancer is melanoma, breast cancer or head and neck cancer.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

Compounds of the present invention may also be useful in inhibiting lymphangiogenesis and/or suppressing lymph node metastasis. Compounds of the present invention may also be useful in preventing the spread of cancer and in the prevention of metastisis.

In one embodiment there is provided the use of a compound of formula (I) or an isomer, salt, solvate, protected form or prodrug thereof to prevent the spread of cancer or prevent metastasis. There is also provided a compound of formula (I) or an isomer, salt, solvate, protected form or prodrug thereof for use in a method for preventing the spread of cancer or preventing of metastasis.

In another embodiment there is provided an anti-cancer treatment comprising a compound of formula (I) or an isomer, salt, solvate, protected form or prodrug thereof and an anti-tumour agent.

The anti cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C5, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies A combination of particular interest is with docetaxel. Other possible combinations of interest include with gemcitabine, cisplatin and the camptothecin prodrug irinotecan.

Diseases Ameliorated by the Control and/or Inhibition of Lymphangiogenesis

The present invention provides active compounds which are useful in preventing and/or treating diseases or conditions ameliorated by the control and/or inhibition of lymphangiogenesis.

In one embodiment there is provided the use of a compound of formula (I) or an isomer, salt, solvate, protected form or prodrug thereof to inhibit, suppress or reduce lymphangiogenesis. There is also provided a compound of formula (I) or an isomer, salt, solvate, protected form or prodrug thereof for use in the method of inhibiting, suppressing or reducing lymphangiogenesis.

As discussed above, these diseases or conditions may include:

(a) eye diseases, for example corneal graft rejection and age related macular degeneration;

(b) skin inflammations, such as skin lesions in patients with psoriasis;

(c) rejection in renal transplantation.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein. In the examples below, in case the structures contain one or more stereogenic centres and the sterereochemistry is depicted in the diagram, the respective stereochemistry is assigned in an arbitrary absolute configuration. These structures depict single enantiomers as well as mixtures of enantiomers in all ratios, and/or mixtures of diastereoisomers in all ratios.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), ether or diethyl ether ($Et_2O$), ethyl acetate (EtOAc), triethylamine ($Et_3N$), dichloromethane(methylene chloride, DCM), trifluoroacetic acid (TFA), N,N-dimethylformamide (DMF), sodium sulphate ($Na_2SO_4$), tetrahydrofuran (THF), dimethylsulfoxide (DMSO), magnesium sulphate ($MgSO_4$), sodium hydrogen carbonate ($NaHCO_3$), tert-butanol (t-BuOH), 1-ethyl-3-(3-dimethylaminopropyl)carbodiimide hydrochloride salt (EDCl.HCl), tetra-n-butylammonium fluoride (TBAF), meta-chloroperbenzoic acid (mCPBA), hexamethyldisilazane sodium salt (NaHMDS), N,N-diisopropylethylamine (DIPEA), 1-hydroxybenzotriazole (HOBt), O-(7-azabenzotriazol-1-yl)-N,N,N',N'-tetramethyluronium hexafluorophosphate (HATU), tris(dibenzylideneacetone)dipalladium(0) ($Pd_2(dba)_3$), trans-dichlorobis(triphenylphosphine)palladium(II) ($PdCl_2(PPh_3)_2$), palladium(II) acetate ($Pd(OAc)_2$) tri-tert-butyl phosphonium tetrafluoroborate (t-$Bu_3$PH.$BF_4$), 4,5-bis(diphenylphosphino)-9,9-dimethylxanthene (Xantphos), triphenylphosphine ($PPh_3$) and 1,2-dichloroethane (DCE).

General Experimental Details

Unless otherwise stated the following generalisations apply.

[1]NMR spectra were recorded on either a Bruker Avance DRX300 (300 MHz) or a Bruker Ultrashield plus (400 MHz). The multiplicity of a signal is designated by the following abbreviations: s, singlet; d, doublet; dd, doublet of doublets; t, triplet; tt, triplet of triplets; td, triplet of doublets; q, quartet; br, broad; m, multiplet. All observed coupling constants, J, are reported in Hertz.

LC/MS data was generated using either an Agilent 6100 Series Single Quad LC/MS (LCMS-A) or Waters ZQ 3100 system (LCMS-B) or Finnigan LCG Advantage Max (LCMS-C) or Agilent 1200 Infinity Series (LCMS-D).

LCMS Method A (LCMS-A)

Instrument: Agilent 6100 Series Single Quad LC/MS

Agilent 1200 Series HPLC

Pump: 1200 Series G1311A Quaternary pump

Autosampler: 1200 Series G1329A Thermostatted Autosampler

Detector: 1200 Series G1314B Variable Wavelength Detector

LC Conditions:

Reverse Phase HPLC analysis

Column: Luna C8(2) 5µ 50×4.6 mm 100 A

Column temperature: 30° C.

Injection Volume: 5 µL

Solvent A: Water 0.1% Formic Acid

Solvent B: Acetonitrile 0.1% Formic Acid

Gradient: 5-100% B over 10 min

Detection: 254 nm or 214 nm

MS Conditions:

Ion Source Quadrupole

Ion Mode Multimode-ES

Drying gas temp: 300° C.

Vaporizer temperature: 200° C.

Capillary voltage (V): 2000 (positive)

Capillary voltage (V): 4000 (negative)

Scan Range: 100-1000

Step size: 0.1 sec

Acquisition time: 10 min

LCMS Method B (LCMS-B)

Instrument: Waters ZQ 3100 Mass Detector

Waters 2545-Pump

Waters SFO System Fluidics Organizer

Waters 2996 Diode Array Detector

Waters 2767 Sample Manager

LC Conditions:

Reverse Phase HPLC analysis

Column: XBridge TM C18 5 µm 4.6×100 mm

Injection Volume: 10 µL

Solvent A: Water 0.1% Formic Acid

Solvent B: Acetonitrile 0.1% Formic Acid

Gradient: 10-100% B over 10 min

Flow rate: 1.5 ml/min

Detection: 100-600 nm

MS Conditions

Ion Source: Single-quadrupole

Ion Mode: ES positive

Source Temp: 150° C.

Desolvation Temp: 350° C.

Detection: Ion counting

Capillary (KV): 3.00

Cone (V): 30
Extractor (V): 3
RF Lens (V): 0.1
Scan Range: 100-1000 Amu
Scan Time: 0.5 sec
Acquisition time: 10 min
Gas Flow: 100 L/hr
Desolvation: 650 L/hr
LCMS Method C (LCMS-C)
Instrument: Finnigan LCG Advantage Max
Finnigan Surveyor LC Pump
Finnigan Surveyor Autosampler
Finnigan Surveyor PDA Detector
LC Conditions:
Reverse Phase HPLC analysis
Column: Gemini 3 μm C18 20×4.0 mm 110 A
Injection Volume: 10 μL
Solvent A: Water 0.1% Formic Acid
Solvent B: Acetonitrile 0.1% Formic Acid
Gradient: 10-100% B over 10 min
Detection: 100-600 nm
MS Conditions
Ion Source: Ion trap
Ion Mode: ES positive
Temp: 300° C.
Detection: Ion counting
Scan Range: 80-1000 Amu
Scan Time: 0.2 sec
Acquisition time: 10 min
LCMS Method D (LCMS-D)
Instrument: Agilent 1200 Infinity Series
Pump: 1260 Infinity G1312B Binary pump
Auto Sampler: 1260 Infinity G1367E 1260 HiP ALS
Detector: 1290 Infinity G4212A 1290 DAD
LC Conditions:
Reverse Phase HPLC analysis
Column: Poroshell 120 EC-C18
Column temperature: 35° C.
Injection Volume: 1 μL
Solvent A: Water 0.1% Formic Acid
Solvent B: Acetonitrile 0.1% Formic Acid
Gradient: 5-100% B over 3.8 mins
Detection: monitored at 254 nm and 214 nm
MS Conditions:
Ion Source Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min
HPLC
Instrument: Waters Alliance HT
Detector: Waters 2996 Diode Array
Column: Reverse Phase Xbridge TM Prep C18 5 um 10×100 mm
Injection Volume: 50 uL
Solvent A: Water 0.1% Formic Acid
Solvent B: Acetonitrile 0.1% Formic Acid
Flow rate: 4.0 ml/min
Detection: 100-600 nm
Sample preparation: MeCN and MeOH
Preparative Mass-Directed LC (Prep-LCMS)
Instrument: Waters ZQ 3100-Mass Detector
Waters 2545-Pump
Waters SFO System Fluidics Organizer
Waters 2996 Diode Array Detector
Waters 2767 Sample Manager
LC Conditions:
Reverse Phase HPLC analysis
Column: XBridge TM C18 5 μm 19×50 mm
Injection Volume 500 μL
Solvent A: Water 0.1% Formic Acid
Solvent B: Acetonitrile 0.1% Formic Acid
Gradient: 25-100% B over 10 min
Flow rate: 19 mL/min
Detection: 100-600 nm
MS Conditions:
Ion Source: Single-quadrupole
Ion Mode: ES positive
Source Temp: 150° C.
Desolvation Temp: 350° C.
Detection: Ion counting
Capillary (KV)—3.00
Cone (V): 30
Extractor (V): 3
RF Lens (V): 0.1
Scan Range: 100-1000 Amu
Scan Time: 0.5 sec
Acquisition time: 10 min
Gas Flow
Desolvation L/hour-650
Cone L/hour-100
Chiral Separation and Characterisation Methods
Method A
SFC
Column: Chiralpak IC (250×21 mm), 5μ
Flow Rate: 40 mL/min
Mobile Phase: $CO_2$: 0.1% DEA in MeOH
Method B
SFC
Column: Chiralpak-IC (250×21 mm), 5μ
Flow Rate: 40 mL/min
Mobile Phase: $CO_2$: 0.5% DEA in IPA
Method C
SFC
Column: Chiralcel-ODH
Flow Rate: 3 mL/min
Mobile Phase: $CO_2$: 0.5% DEA in IPA
Method D
HPLC
Column: Chiralpak IC (250×10 mm), 5μ
Mobile Phase: n-Hexane:ethanol (80:20)
Flow rate: 5.0 mL/min
Method E
SFC
Column: Lux cellulose-4 (250×4.6 mm), 5μ
Mobile Phase: $CO_2$:methanol (70:30)
Flow rate: 3.0 mL/min
Method F
SFC
Column: Lux cellulose-2 (250×4.6 mm), 5μ
Flow Rate: 1.2 mL/min
Mobile Phase: $CO_2$: 0.5% DEA in methanol
Method G
HPLC
Column: Chiralpak ADH (250×4.6 mm), 5μ
Mobile Phase: n-Hexane:ethanol (80:20)
Flow rate: 1 mL/min Analytical thin-layer chromatography was performed on Merck silica gel 60F254 aluminium-backed plates which were visualised using fluorescence quenching under UV light or using an acidic anisaldehyde or a basic potassium permanganate dip. Flash chromatography was performed using either a Teledyne Isco CombiFlash Rf purification system using standard RediSep® cartridges or a Biotage Isolera purification system using either Grace, RediSep® or Biotage silica cartridges. Microwave irradiation was achieved using a CEM Explorer SP Microwave Reactor.

Where necessary, anhydrous solvents were prepared using a Braun purification system or purchased from Sigma-Aldrich.

Synthesis of Key Intermediates

Key Intermediate 1: 2-(2-Ethynylphenyl)butanamide (K1)

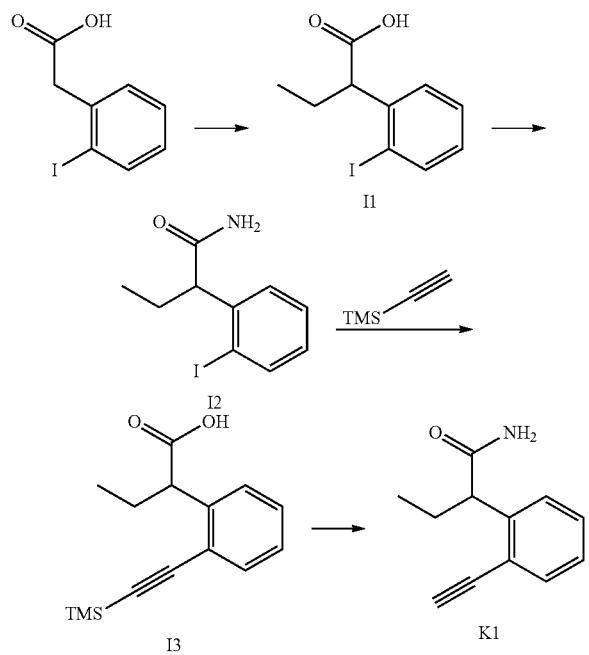

(a) 2-(2-Iodophenyl)butanoic acid (I1)

Lithium diisopropylamide solution (2.0 M in THF/heptane/ethylbenzene, 3.82 mL, 7.63 mmol) was added to dry THF (10 mL) under an atmosphere of nitrogen and cooled to 0° C. A solution of 2-(2-iodophenyl)acetic acid (500 mg, 1.91 mmol) in dry THF (15 mL) was then added dropwise. This solution was stirred for 40 minutes at 0° C. before the addition of iodoethane (0.92 mL, 11 mmol). The solution was returned to room temperature and stirred for 4 hours. The resulting mixture was quenched with the addition of $H_2O$ (10 mL) and then 2 M HCl (20 mL). The aqueous layer was extracted with EtOAc (3×30 mL), the organic layers were combined and washed with brine, dried over $MgSO_4$ and the solvent was evaporated under reduced pressure. The residue was adsorbed onto silica gel and purified using column chromatography (Biotage Isolera, $SiO_2$ cartridge, 0-40% EtOAc in petroleum benzine 40-60° C.) to give the title compound I1 as a pale yellow oil (479 mg, 87%); $^1$H NMR (400 MHz, $d_6$-DMSO) δ 12.49 (s, 1H), 7.88 (dd, J=7.9, 1.2 Hz, 1H), 7.39 (td, J=7.6, 1.2 Hz, 1H), 7.32 (dd, J=7.8, 1.7 Hz, 1H), 7.01 (J m, 1H), 3.77 (t, J=7.5 Hz, 1H), 1.98-1.86 (m, 1H), 1.73-1.60 (m, 1H), 0.85 (t, J=7.3 Hz, 3H).

(b) 2-(2-Iodophenyl)butanamide (I2)

HOBt (325 mg, 2.40 mmol), EDCl.HCl (461 mg, 2.40 mmol) and DIPEA (1.40 mL, 8.02 mmol) were added to a stirred solution of 2-(2-iodophenyl)butanoic acid (I1) (465 mg, 1.60 mmol) in dry THF (6 mL) and dry DMF (1 mL) under an atmosphere of nitrogen. After 10 minutes ammonium carbonate (770 mg, 8.02 mmol) was added in one portion and the resulting mixture stirred at room temperature for 24 hours. The volatiles were removed in vacuo and EtOAc (50 mL) and saturated aqueous $NaHCO_3$ (50 mL) were added to the residue. The aqueous phase was extracted with EtOAc (2×50 mL), then the combined organic extracts were washed with brine and dried over $MgSO_4$. The solvent was removed under reduced pressure and the resulting solid was purified by silica gel column chromatography (Biotage Isolera, $SiO_2$ cartridge, 0-50% EtOAc in petroleum benzine 40-60° C.) to give the title compound I2 as a white solid (398 mg, 86%); NMR (400 MHz, $d_6$-DMSO) δ 7.85 (dd, J=7.9, 1.2 Hz, 1H), 7.46 (dd, J=7.8, 1.7 Hz, 1H), 7.39 (s, 1H), 7.35 (td, J=7.6, 1.2 Hz, 1H), 7.02-6.92 (m, 2H), 3.59 (dd, J=8.8, 6.0 Hz, 1H), 1.92-1.78 (m, 1H), 1.65-1.51 (m, 1H), 0.86 (t, J=7.3 Hz, 3H). LCMS-A: rt 5.463 min; m/z 290 [M+H]$^+$.

(c) 2-(2-((Trimethylsilyl)ethynyl)phenyl)butanamide (I3)

Ethynyltrimethylsilane (0.11 mL, 0.80 mmol) and dry DMF (9.0 mL) was added to a mixture of 2-(2-iodophenyl)butanamide (I2) (193 mg, 0.668 mmol), $PdCl_2(PPh_3)_2$ (23 mg, 0.033 mmol), t-$Bu_3$PH.$BF_4$ (10 mg, 0.033 mmol) and CuI (6 mg, 0.033 mmol) under nitrogen. The resulting solution was degassed with a stream of nitrogen for 10 minutes before the addition of $Et_3N$ (3.0 mL). The resulting mixture was stirred at 60° C. under nitrogen for 16 hours then adsorbed onto silica gel and purified by column chromatography (Biotage Isolera, $SiO_2$ cartridge, 0-100% EtOAc in petroleum benzine 40-60° C.) to give the title compound I3 as a tan coloured solid (151 mg, 87); $^1$H NMR (400 MHz, $d_6$-DMSO) δ 7.46-7.39 (m, 2H), 7.34 (td, J=7.7, 1.4 Hz, 1H), 7.26 (br, 1H), 7.21 (td, J=7.5, 1.4 Hz, 1H), 6.97 (br, 1H), 3.80 (dd, J=8.9, 5.7 Hz, 1H), 1.95-1.80 (m, 1H), 1.69-1.55 (m, 1H), 0.85 (t, J=7.3 Hz, 3H), 0.25 (s, 9H). LCMS-A: rt 6.267 min; m/z 260 [M+H]$^+$.

(d) 2-(2-Ethynylphenyl)butanamide (K1)

To a solution of 2-(2-((trimethylsilyl)ethynyl)phenyl)butanamide (I3) (149 mg, 0.574 mmol) in DCM (10.0 mL) at 0° C. under nitrogen was added TBAF (1.0 M in THF, 0.86 mL, 0.86 mmol). The resulting mixture was stirred at 0° C. for 5 minutes then poured into water (50 mL). The organic phase was separated and the aqueous layer was extracted with DCM (2×40 mL). The combined organic layers were washed with brine (40 mL), dried over $MgSO_4$ and the solvent was removed in vacuo. The residue was adsorbed onto silica gel and purified by column chromatography (Biotage Isolera, $SiO_2$ cartridge, 0-75% EtOAc in petroleum benzine 40-60° C.) to give the title compound K1 as an off-white solid (104 mg, 97%); $^1$H NMR (400 MHz, $d_6$-DMSO) δ 7.50-7.43 (m, 2H), 7.35 (td, J=7.7, 1.5 Hz, 1H), 7.31 (s, 1H), 7.23 (td, J=7.5, 1.3 Hz, 1H), 6.93 (s, 1H), 4.37 (s, 1H), 3.85 (dd, J=8.6, 6.4 Hz, 1H), 1.97-1.83 (m, 1H), 1.61 (J m, 1H), 0.84 (t, J=7.3 Hz, 3H). LCMS-A: rt 5.265 min; m/z 188 [M+H]$^+$.

Key Intermediate 2: Methyl 1-(2-ethynylphenyl)cyclopropanecarboxylate (K2)

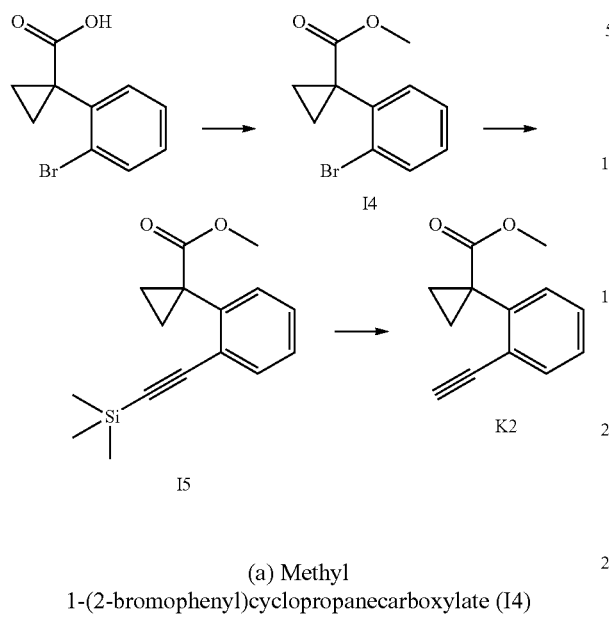

(a) Methyl 1-(2-bromophenyl)cyclopropanecarboxylate (I4)

A solution of 1-(2-bromophenyl)cyclopropanecarboxylic acid (500 mg, 2.07 mmol) in MeOH (10 mL) was treated with a solution of concentrated aqueous HCl (0.5 mL). The resulting mixture was stirred for 16 hours at room temperature and then heated to reflux and stirred for a further 24 hours. The volatiles were evaporated and the residue was dissolved in EtOAc. The organic layer was washed with saturated solution of NaHCO$_3$, brine and then dried over MgSO$_4$. The solvent was removed in vacuo to give the title compound I4 (400 mg, 76%) as an orange oil; $^1$H NMR (400 MHz, CDCl$_3$) δ 7.60-7.54 (m, 1H), 7.32-7.24 (m, 2H), 7.15 (m, 1H), 3.63 (s, 3H), 1.75 (d, J=3.1 Hz, 2H), 1.21 (q, J=4.0 Hz, 2H).

(b) Methyl 1-(2-((trimethylsilylethynyl)phenyl)cyclopropanecarboxylate (I5)

A solution of methyl 1-(2-bromophenyl)cyclopropanecarboxylate (I4) (658 mg, 2.58 mmol), PdCl$_2$(PPh$_3$)$_2$ (91 mg, 0.13 mmol) t-Bu$_3$PH.BF$_4$ (37 mg, 0.13 mmol), CuI (25 mg, 0.13 mmol) and ethynyltrimethylsilane (0.44 mL, 3.1 mmol) in dry DMF (5.0 mL) was degassed with nitrogen for 10 minutes before the addition of Et$_3$N (2.0 mL). After stirring at 65° C. under nitrogen for 16 hours the resulting mixture was adsorbed onto silica gel and purified by column chromatography (Biotage Isolera, SiO$_2$ cartridge, 0-20% EtOAc in petroleum benzine 40-60° C.) to give the title compound I5 as an orange oil (569 mg, 81%); $^1$H NMR (400 MHz, d$_6$-DMSO) δ 7.67-7.12 (m, 4H), 3.57-3.47 (m, 3H), 1.64-1.49 (m, 2H), 1.26-1.16 (m, 2H), 0.22-0.13 (m, 9H). LCMS-A: rt 6.977 min; m/z 273 [M+H]$^+$.

(c) Methyl 1-(2-ethynylphenyl)cyclopropanecarboxylate (K2)

To a solution of methyl 1-(2-((trimethylsilyl)ethynyl)phenyl)cyclopropanecarboxylate (I5) (568 mg, 2.09 mmol) in DCM (20.0 mL) at 0° C. was added TBAF (1.0 M in THF, 3.13 mL, 3.13 mmol). The resulting mixture was stirred at 0° C. for 10 minutes then poured into water (50 mL). The aqueous layer was extracted with DCM (2×50 mL), then the combined organic layers were washed with brine, dried over MgSO$_4$ and the solvent was removed in vacuo. The residue was adsorbed onto silica gel and purified by column chromatography (Biotage Isolera, SiO$_2$ cartridge, 0-25% EtOAc in petroleum benzine 40-60° C.) to give the title compound K2 as an off-white solid (140 mg, 34%); $^1$H NMR (400 MHz, d$_6$-DMSO) δ 7.46 (dt, J=7.5, 0.8 Hz, 1H), 7.40-7.25 (m, 3H), 4.32 (s, 1H), 3.52 (s, 3H), 1.54 (q, J=4.1 Hz, 2H), 1.25-1.19 (m, 2H). LCMS-A: rt 5.921 min; m/z 201 [M+H]$^+$.

Key Intermediate 3: tert-Butyl 4-(4-((4-chloro-5-(trifluoromethyl)pyrimidin-2-yl)amino)phenyl)piperidine-1-carboxylate (K3)

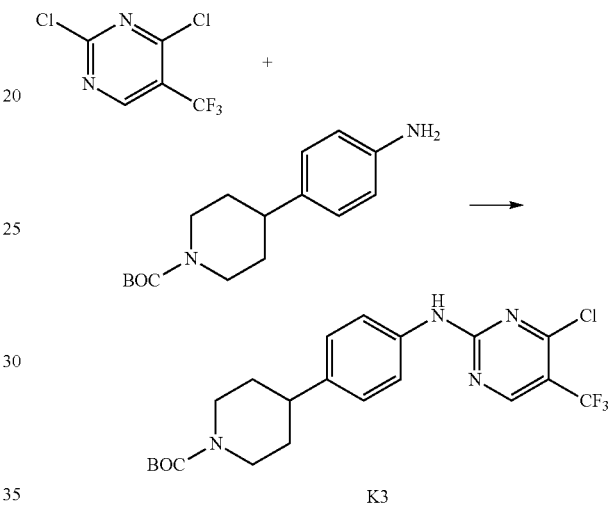

2,4-Dichloro-5-(trifluoromethyl)pyrimidine (4.122 g, 19.00 mmol) was stirred in a 1:1 t-BuOH:DCE mixture (400 mL) at room temperature. A 1.0 M ZnCl$_2$ solution in Et$_2$O (21.71 mL, 21.71 mmol) was added cautiously and the resulting mixture was stirred for 10 minutes. 1-Boc-4-(4-aminophenyl)piperidine (5.00 g, 18.1 mmol) was added followed by Et$_3$N (6.052 mL, 43.42 mmol) and stirring continued at room temperature overnight. The volatiles were evaporated to dryness and the resulting residue was suspended in water (500 mL). After sonication for 30 minutes the suspension was filtered and the filter cake was washed with water (2×100 mL) and dried under a high vacuum to yield the title compound K3 as a tan solid (8.11 g, 98%); $^1$H NMR (400 MHz, d$_6$-DMSO) δ 10.61 (s, 1H), 8.78 (s, 1H), 7.59 (d, J=8.4 Hz, 2H), 7.23 (d, J=8.5 Hz, 2H), 4.07 (d, J=11.1 Hz, 2H), 2.80 (s, 2H), 2.65 (t, J=12.0 Hz, 1H), 1.74 (d, J=12.3 Hz, 2H), 1.42 (s, 11H). LCMS-A: rt 6.834 min; m/z 457 [M+H]$^+$.

Key Intermediate 4: tert-Butyl 3-(4-((4-chloro-5-(trifluoromethyl)pyrimidin-2-yl)amino)phenyl)azetidine-1-carboxylate (K4)

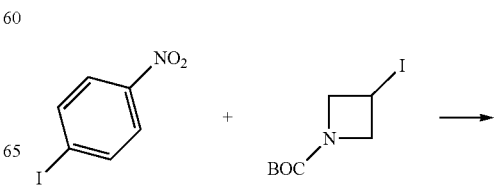

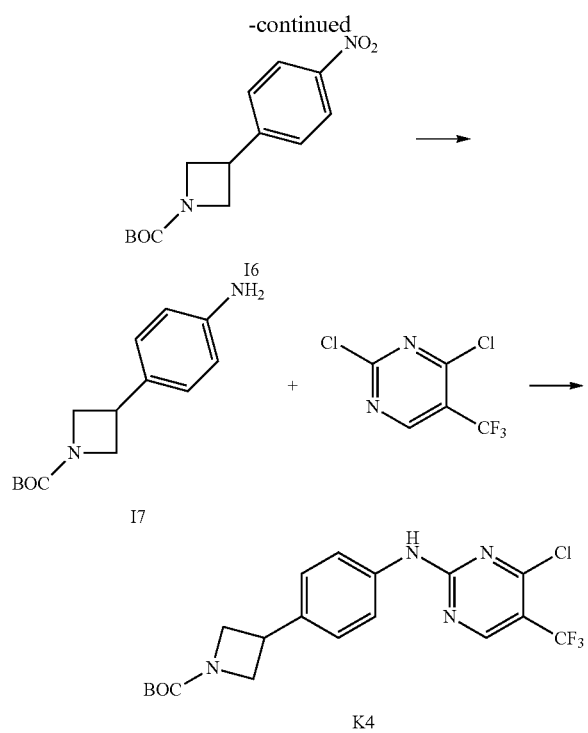

(a) tert-Butyl-3-(4-nitrophenyl)azetidine-1-carboxylate (I6)

1,2-Dibromoethane (0.146 mL, 1.69 mmol) was added to a vigorously stirred suspension of zinc dust (0.901 g, 13.8 mmol) in THF (3.5 mL) under a nitrogen atmosphere and the resulting suspension heated at 80° C. for 10 minutes. Trimethylsilyl chloride (0.202 mL, 1.59 mmol) in THF (1.75 mL) was added at room temperature and after stirring for 4 minutes a solution of tert-butyl 3-iodoazetidine-1-carboxylate (3.00 g, 10.6 mmol) in THF (3.5 mL) was added dropwise over a period of 15 minutes. The resulting mixture was stirred at room temperature for 2 hours then $Pd_2(dba)_3$ (0.155 g, 0.170 mmol) and tri-2-furylphosphine (0.143 g, 0.615 mmol) were added followed by 1-iodo-4-nitrobenzene (2.90 g, 11.7 mmol) in THF (18 mL). The resulting mixture was heated at 55° C. for 3 hours then quenched at room temperature with a saturated aqueous sodium chloride solution (15 mL). The aqueous phase was extracted with DCM (2×15 mL) then the combined organic fractions were dried (magnesium sulfate), filtered and evaporated in vacuo. The residue was purified using silica gel column chromatography (CombiFlash Rf, 40 g $SiO_2$ Cartridge, 10-40% EtOAc in cyclohexane) to give the title compound I6 as an orange oil (2.14 g, 72%); $^1$H NMR (300 MHz, $CDCl_3$) δ 8.24 (dd, J=6.8, 1.9 Hz, 2H), 7.51 (d, J=8.6 Hz, 2H), 4.41 (t, J=8.7 Hz, 2H), 3.98 (dd, J=8.5, 5.7 Hz, 2H), 3.89-3.81 (s, 1H), 1.49 (s, 9H).

(b) tert-Butyl 3-(4-aminophenyl)azetidine-1-carboxylate (I7)

A suspension of 10% Pd/C (0.320 g) and tert-butyl-3-(4-nitrophenyl)azetidine-1-carboxylate (I6) (2.14 g, 7.68 mmol) in EtOAc (16 mL) was stirred under a hydrogen atmosphere for 18 hours. Additional 10% Pd/C (1.00 g) was added and stirring continued for a further 20 hours. The resulting mixture was filtered through a pad of Celite, washing with EtOAc, and the filtrate concentrated in vacuo to give the title compound I7 as a light yellow/cream solid (1.80 g, 94%); $^1$H NMR (300 MHz, $CDCl_3$) δ 7.12 (d, J=8.3 Hz, 2H), 6.69 (dd, J=6.5, 1.9 Hz, 2H), 4.29 (t, J=8.7 Hz, 2H), 3.93 (dd, J=8.4, 6.1 Hz, 2H), 3.65 (brs, 2H), 1.55-1.68 (m, 1H), 1.48 (s, 9H). LCMS-B: rt 4.964 min; m/z 249 [M+H]$^+$.

(c) tert-Butyl 3-(4-((4-chloro-5-(trifluoromethyl)pyrimidin-2-yl)amino)phenyl)azetidine-1-carboxylate (K4)

Zinc chloride (1.0 M in $Et_2O$) (4.83 mL, 4.83 mmol) was added to a solution of 2,4-dichloro-5-(trifluoromethyl)pyrimidine (0.769 g, 3.54 mmol) in 1:1 dichloroethane/tert-butanol (64 mL) at room temperature under nitrogen. After stirring for 10 minutes, tert-butyl 3-(4-aminophenyl)azetidine-1-carboxylate (I7) (0.800 g, 3.22 mmol) was added followed by $Et_3N$ (1.08 mL, 7.73 mmol). The resulting mixture was stirred at room temperature for 20 hours then the volatiles removed in vacuo. Water was added to the solid residue and the resulting suspension sonicatated for 2 minutes. The suspension was filtered, and the filter cake dried then adsorbed onto silica gel and purified using column chromatography (CombiFlash Rf, 40 g $SiO_2$ Cartridge, 10-40% EtOAc in cyclohexane) to give a white solid. The solid was suspended in MeOH (7 mL) and sonicated for 30 seconds. The resulting suspension was filtered and the filter cake was washed with MeOH (3 mL) then dried to give the title compound K4 as a white solid (0.777 g, 56%); $^1$H NMR (300 MHz, $d_6$-DMSO) δ 10.6 (s, 1H), 8.79 (s, 1H), 7.66 (d, J=8.4 Hz, 2H), 7.33 (d, J=8.4 Hz, 2H), 4.23 (t, J=7.6 Hz, 2H), 3.80 (s, 3H), 1.40 (s, 9H). LCMS-B: rt 8.810 min; m/z 429 [M+H]$^+$.

Key Intermediate 5: tert-Butyl 4-(5-((4-chloro-5-(trifluoromethyl)pyrimidin-2-yl)amino)pyridin-2-yl)piperidine-1-carboxylate (K5)

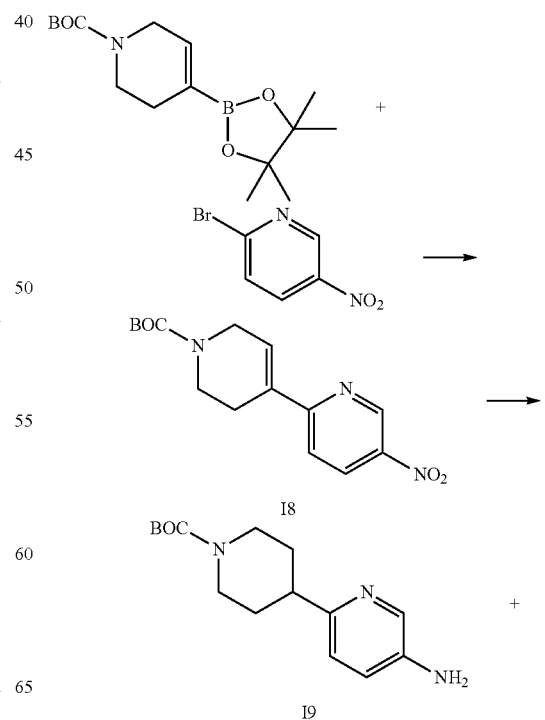

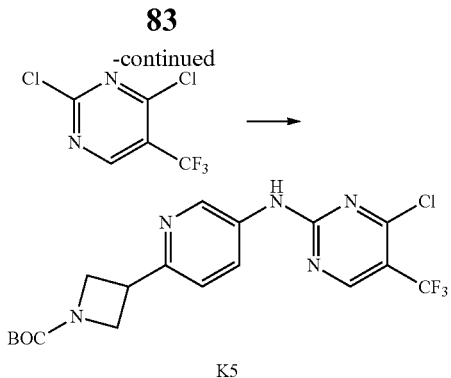

(a) tert-Butyl 5-nitro-5',6'-dihydro-[2,4'-bipyridine]-1'(2'H)-carboxylate (I8)

To a mixture of N-Boc-1,2,3,6-tetrahydropyridine-4-boronic acid pinacol ester (1.52 g, 4.93 mmol), 2-bromo-5-nitropyridine (1.00 g, 4.93 mmol) and PdCl$_2$(PPh$_3$)$_2$ (173 mg, 0.246 mmol) under nitrogen was added 1,4-dioxane (30 mL) followed by 3 M aqueous sodium carbonate (4.93 mL, 14.8 mmol). The resulting mixture was degassed with nitrogen for 10 minutes then heated at reflux for 16 hours. On cooling EtOAc (150 mL) was added and the resulting solution was washed with water (3×50 mL), brine (50 mL) then dried (Na$_2$SO$_4$). The volatiles were evaporated under reduced pressure to give a brown solid that was purified using silica gel column chromatography (Biotage Isolera, 40 g SiO$_2$ cartridge, 0-30% EtOAc in petroleum benzine 40-60° C.) to give the title compound I8 as a yellow solid (1.43 g, 95%); $^1$H NMR (400 MHz, CDCl$_3$) δ 9.37 (dd, J=2.6, 0.5 Hz, 1H), 8.43 (dd, J=8.8, 2.7 Hz, 1H), 7.53 (d, J=8.8 Hz, 1H), 6.95-6.83 (m, 1H), 4.20 (d, J=3.0 Hz, 2H), 3.67 (t, J=5.6 Hz, 2H), 2.70-2.63 (m, 2H), 1.49 (s, 9H). LCMS-A: rt 6.140 min; m/z 304 [M−H]$^−$.

(b) tert-Butyl 4-(5-aminopyridin-2-yl)piperidine-1-carboxylate (I9)

A slurry of 10% Pd/C (500 mg) in DMF (5 mL) was added to a solution of tert-butyl 5-nitro-5',6'-dihydro-[2,4'-bipyridine]-1'(2'H)-carboxylate (I8) (1.40, 4.59 mmol) in DMF (45 mL) and the resulting mixture was stirred under a hydrogen atmosphere for 16 hours at room temperature. EtOAc (100 mL) was added and the resulting suspension was filtered through a Celite pad, washing with EtOAc (150 mL). The volatiles were removed under reduced pressure and the residue was purified by silica gel column chromatography (Biotage Isolera, 40 g Si cartridge, 0-100% EtOAc in petroleum benzine 40-60° C. and then 0-20% MeOH in EtOAc) to give the title compound I9 as a yellow oil (1.18 g, 93%); $^1$H NMR (400 MHz, CDCl$_3$) δ 8.03 (dd, J=2.4, 1.0 Hz, 1H), 7.00-6.87 (m, 2H), 4.22 (brs, 2H), 3.59 (brs, 2H), 2.85-2.67 (m, 3H), 1.86 (m, 2H), 1.72-1.59 (m, 2H), 1.46 (s, 9H). LCMS-A: rt 4.416 min; m/z 278 [M+H]$^+$.

(c) tert-Butyl 4-(5-((4-chloro-5-(trifluoromethyl)pyrimidin-2-yl)amino)pyridin-2-yl)piperidine-1-carboxylate (K5)

A 1.0 M ZnCl$_2$ solution in Et$_2$O (1.14 mL, 1.14 mmol) was added cautiously to a stirred solution of 2,4-dichloro-5-(trifluoromethyl)pyrimidine (217 mg, 0.999 mmol) in a 1:1 t-BuOH:DCE mixture (50 mL) at room temperature. After completion of the addition stirring was continued for 20 minutes then tert-butyl 4-(5-aminopyridin-2-yl)piperidine-1-carboxylate (I9) (263 mg, 0.952 mmol) followed by Et$_3$N (0.159 mL, 1.14 mmol) were added. The resulting mixture was stirred at room temperature for 48 hours then the volatiles were evaporated under reduced pressure and the resulting residue was purified using silica gel column chromatography (Biotage Isolera, 24 g SiO$_2$ cartridge, 0-55% EtOAc in petroleum benzine 40-60° C.) to give the title compound K5 as a white solid (155 mg, 36%); $^1$H NMR (400 MHz, d$_6$-DMSO) δ 10.75 (s, 1H), 8.82 (s, 1H), 8.73 (d, J=2.4 Hz, 1H), 8.00 (dd, J=8.5, 2.4 Hz, 1H), 7.30 (d, J=8.5 Hz, 1H), 4.11-4.01 (m, 2H), 2.93-2.75 (m, 3H), 1.81 (d, J=11.1 Hz, 2H), 1.63-1.50 (m, 2H), 1.41 (s, 9H). LCMS-A: rt 5.604 min; m/z 458, 460 [M+H]$^+$.

Key Intermediate 6:
1-(2-Ethynylphenyl)cyclopropanecarboxamide (K6)

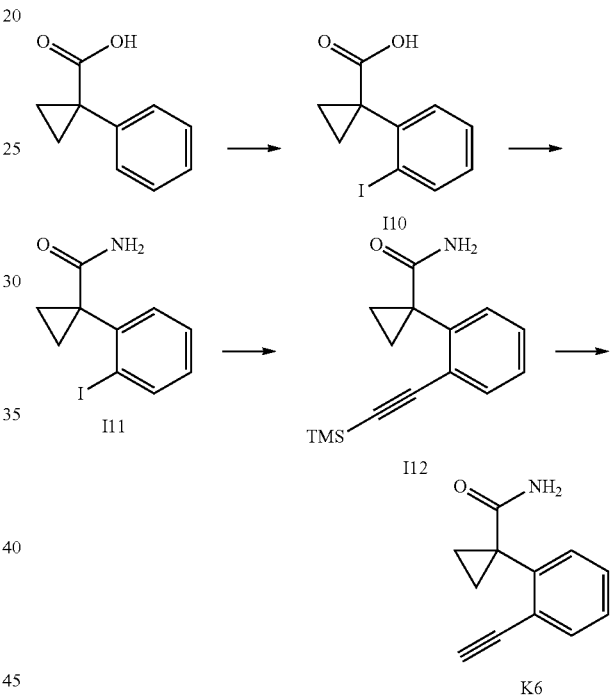

(a) 1-(2-Iodophenyl)cyclopropanecarboxylic Acid (I10)

A solution of 1-phenyl-1-cyclopropanecarboxylic acid (2.00 g, 12.3 mmol), Pd(OAc)$_2$ (0.138 g, 0.617 mmol), iodine (2.34 g, 9.24 mmol) and (diacetoxyiodo)benzene (2.97 g, 9.24 mmol) in DMF (10 mL) was stirred at 60° C. for 18 hours covered aluminium foil. Additional iodine (2.34 g, 9.24 mmol) and (diacetoxyiodo)benzene (2.97 g, 9.24 mmol) were added and stirring was continued at 60° C. for a further 8 hours. A final addition of iodine (2.34 g, 9.24 mmol) and (diacetoxyiodo)benzene (2.97 g, 9.24 mmol) was performed and stirring was continued at 60° C. for a further 16 hours. The resulting mixture was partitioned between EtOAc and water and the aqueous phase was extracted several times with EtOAc. The combined organic extracts were washed with a 10% aqueous solution of sodium metabisulfate (3×30 mL), 10% aqueous citric acid (2×30 mL), water, brine, dried (MgSO$_4$), filtered and evaporated. The residue was purified using silica gel column chromatography (CombiFlash Rf, 80 g SiO$_2$ Cartridge, 30-40% EtOAc in cyclohexane) to give the title compound I10 as a cream solid (3.11 g, 87%); $^1$H NMR (300 MHz, CDCl$_3$) δ 7.88 (d, J=8.0 Hz, 1H), 7.28-7.35 (m 2H), 6.97-7.03 (m, 1H), 2.13 (brs, 2H), 1.30 (brs, 2H).

(b) 1-(2-Iodophenyl)cyclopropanecarboxamide (I11)

HOBt (1.89 g, 14.0 mmol) and EDCl.HCl (2.69 g, 14.0 mmol) were added to a solution of 1-(2-iodophenyl)cyclopropanecarboxylic acid (I10) (3.11 g, 10.8 mmol) in DMF (6 mL), THF (29 mL) and Et$_3$N (9.4 mL, 54 mmol). After 15 minutes ammonium carbonate (7.95 g, 86.4 mmol) was added and the resulting mixture was stirred at room temperature for 20 hours. The volatiles were removed in vacuo and water (150 mL) was added to the residue resulting in the formation of a suspension. The suspension was sonicated for several minutes, filtered and the filter cake dried to give the title compound I11 as an off white solid (2.55 g, 82%); $^1$H NMR (300 MHz, d$_6$-DMSO) δ 7.87 (d, J=7.6 Hz, 1H), 7.36-7.38 (m, 2H), 7.02-7.08 (m, 1H), 6.96 (brs, 1H), 6.05 (brs, 1H), 1.52 (brs, 2H), 0.96 (brs, 2H). LCMS-B: rt 5.800 min; m/z 288 [M+H]$^+$.

(c) 1-(2-((Trimethylsilyl)ethynyl)phenyl)cyclopropanecarboxamide (I12)

A solution of 1-(2-iodophenyl)cyclopropanecarboxamide (I11) (1.53 g, 85.3 mmol), ethynyltrimethylsilane (1.05 mL, 7.46 mmol), PdCl$_2$(PPh$_3$)$_2$ (0.037 g, 0.053 mmol), t-Bu$_3$PH.BF$_4$ (0.031 g, 0.11 mmol) and copper(I) iodide (0.020 g, 0.11 mmol) in DMF (10 mL) was stirred under a nitrogen atmosphere at 50° C. for 26 hours. The volatiles were evaporated in vacuo and the resulting black residue was purified using silica gel column chromatography (CombiFlash Rf, 24 g SiO$_2$ Cartridge, 5-20% EtOAc in cyclohexane) to give the title compound I12 as a dark yellow amorphous solid (1.09 g, 79%); $^1$H NMR (300 MHz, CDCl$_3$) δ 7.52 (d, J=7.1 Hz, 1H), 7.26-7.50 (m, 3H), 5.26 (brs, 2H), 1.72 (dq, J=4.1 Hz, 2H) 1.16 (dq, J=3.9 Hz, 2H), 0.26 (s, 9H). LCMS-B: rt 7.446 min; m/z 258 [M+H]$^+$.

(d) 1-(2-Ethynylphenyl)cyclopropanecarboxamide (K6)

A cooled (5° C. water/ice bath) solution of 1-(2-((trimethylsilyl)ethynyl)phenyl)cyclopropanecarboxamide (I12) (1.09 g, 4.23 mmol) in DCM (20 mL) containing acetic acid (0.315 mL, 5.50 mmol) was slowly treated with a 1 M solution of TBAF in THF (5.08 mL, 5.08 mmol). The resulting mixture was stirred at room temperature for 2 hours then water (30 mL) was added. The aqueous layer was extracted with DCM (2×15 mL), then the combined organic extracts were washed with water, brine, dried (MgSO$_4$), filtered and evaporated in vacuo to give the title compound as a tan solid (0.780 g, 99%); $^1$H NMR (300 MHz, CDCl$_3$) δ 7.57 (d, J=6.7 Hz, 1H), 7.31-7.45 (m, 3H), 5.46 (brs, 1H), 5.27 (brs, 1H), 3.38 (s, 1H), 1.75 (dq, J=4.0 Hz, 2H) 1.18 (dq, J=3.7 Hz, 2H). LCMS-B: rt 5.489 min; m/z 186 [M+H]$^+$.

Synthesis of Key Intermediate 7:
2-(2-Ethynylphenyl)propanamide (K7)

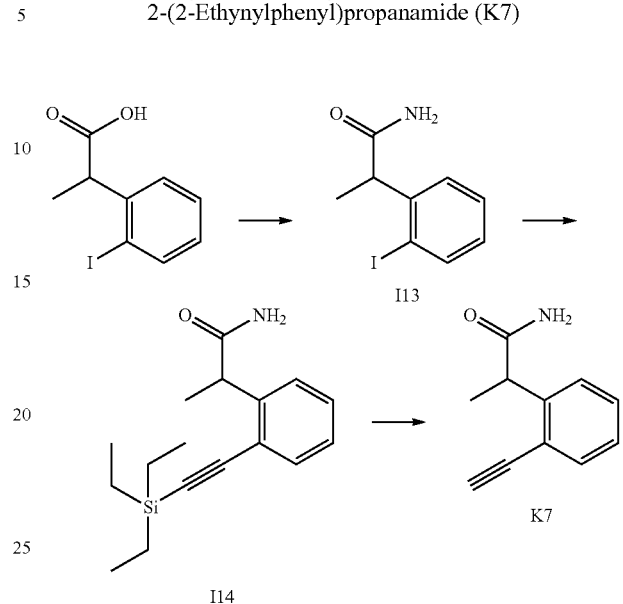

Method 1

(a) 2-(2-Iodophenyl)propanamide (I13)

A solution of 2-(2-iodophenyl)propanoic acid (9.73 g, 35.2 mmol) in THF (24 mL), DMF (4 mL) and DIPEA (30.7 mL, 0.176 mol) was stirred with HOBt (7.14 g, 52.9 mmol) and EDCl.HCl (10.1 g, 52.9 mmol) for 10 minutes at room temperature under N$_2$. Ammonium carbonate (16.9 g, 0.176 mol) was then added and the reaction mixture was stirred overnight at room temperature. The volatiles were removed under reduced pressure before sat. aq. NaHCO$_3$ (100 mL) was added to the residue. The aqueous phase was extracted with EtOAc (3×100 mL) and the combined organics were washed with brine, dried over MgSO$_4$ and the volatiles were removed in vacuo to give the impure title compound I13 as a pale yellow solid (~95% purity, 10.05 g, >95%). LCMS-D: rt 3.12 min; m/z 276 [M+H]$^+$.

Alternative synthesis of
2-(2-Iodophenyl)propanamide (I13)

Thionyl chloride (9.00 mL, 123 mmol) was added to 2-iodo-phenacetic acid (16.0 g, 58.0 mmol) and the mixture was stirred at 40° C. for 2 hours. The volatiles were removed in vacuo before EtOAc (40 mL) and 28% ammonium hydroxide aqueous solution (17.9 mL. 118 mmol) were added. The mixture was stirred at room temperature overnight before EtOAc (200 mL) and water (100 mL) were added. The layers were separated and the aqueous phase was extracted with EtOAc (2×100 mL). The combined organics were washed with brine (100 mL), dried (Na$_2$SO$_4$) and concentrated in vacuo to give the title compound I13 as a solid (15.7 g, 98%).

(b) 2-(2-((Triethylsilyl)ethynyl)phenyl)propanamide (I14)

A mixture of 2-(2-iodophenyl)propanamide I13 (12.4 g, 45.2 mmol), ethynyltriethylsilane (9.72 mL, 54.2 mmol), PdCl$_2$(PPh$_3$)$_2$ (0.634 g, 0.904 mmol), tri-tert-butylphosphonium tetrafluoroborate (0.262 g, 0.904 mmol) and CuI (0.172 g, 0.904 mmol) in DMF (46 mL) was stirred under a nitrogen atmosphere at 70° C. for 4 hours. The volatiles were removed in vacuo and the crude residue was purified by silica gel column chromatography (Combiflash Rf, 0-30% EtOAc in cyclohexane) to give the title compound I14 as an orange oil (8.9 g, 68%). LCMS-B: rt 3.845 min; m/z 288 [M+H]$^+$.

(c) 2-(2-Ethynylphenyl)propanamide (K7)

A cooled (0° C. water/ice bath) solution of 2-(2-((triethylsilyl)ethynyl)phenyl)propanamide I14 (7.17 g, 24.9 mmol) in THF (40 mL) was slowly treated with a 1.0 M solution of tetrabutylammonium fluoride in THF (26.2 mL, 26.2 mmol) under a nitrogen atmosphere. The resulting mixture was stirred at 0° C. for 5 minutes before a sat. aq. NaHCO$_3$ solution was added. The mixture was extracted with EtOAc (3 times), the combined organic extracts were washed with brine, dried (Na$_2$SO$_4$) and evaporated in vacuo to give the crude product. The crude product was purified by silica gel column chromatography (Combiflash Rf, 30-80% EtOAc in cyclohexane) to give the title compound K7 as a cream solid (3.69 g, 85%). LCMS-B: rt 3.031 min; m/z 174 [M+H]$^+$.

Method 2

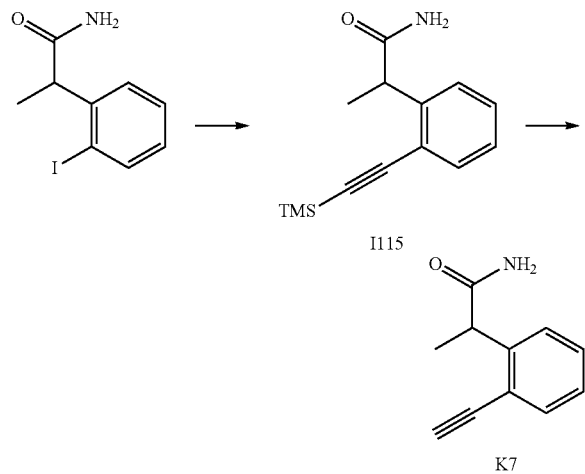

(a) 2-(2-((Trimethylsilyl)ethynyl)phenyl)propanamide (I15)

A mixture of 2-(2-iodophenyl)propanamide I13 (16.5 g, 0.060 mol), CuI (0.229 g, 1.20 mmol), tri-tert-butylphosphonium tetrafluoroborate (0.348 g, 1.20 mmol), PdCl$_2$(PPh$_3$)$_2$ (0.421 g, 0.600 mmol) and trimethylsilylacetylene (10.3 mL, 0.072 mol) in DMF (60 mL) was bubbled with N$_2$ for 10 minutes. Et$_3$N (50 mL) was then added and the mixture was stirred under nitrogen at 60° C. for 5 hours. The reaction mixture was cooled and the volatiles were removed in vacuo. The dark brown residue was adsorbed onto silica and purified by column chromatography (Biotage Isolera, 120 g SiO$_2$ cartridge, 0-30% EtOAc in petroleum benzine 40-60° C.) to give the title compound I15 as an orange oil (11.5 g, 78%). LCMS-D: rt 3.49 min; m/z 246 [M+H]$^+$.

(b) 2-(2-Ethynylphenyl)propanamide (K7)

A 1.0 M solution of TBAF in THF (45.6 mL, 45.6 mmol) was added to a solution of 2-(2-((trimethylsilyl)ethynyl)phenyl)propanamide I15 (9.33 g, 38.0 mmol) in THF (200 mL) and the mixture was stirred for 10 minutes. The reaction mixture was diluted with sat. aq. NaHCO$_3$ (200 mL), and the aqueous layer was extracted with DCM (3×150 mL). The combined organics were adsorbed onto silica and purified by silica gel column chromatography (Biotage Isolera, 120 g SiO$_2$ cartridge, 0-80% EtOAc in petroleum benzine 40-60° C.) to yield the title compound K7 as a tan solid (5.11 g, 76%). LCMS-D: rt 3.03 min; m/z 174 [M+H]$^+$.

Synthesis of Key Intermediate 8: tert-Butyl 4-(4-((4-chloro-5-(trifluoromethyl)pyrimidin-2-yl)amino)-1H-pyrazol-1-yl)piperidine-1-carboxylate (K8)

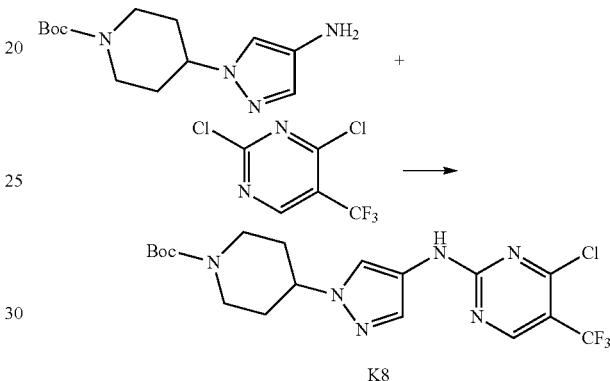

A 1.0 M solution of ZnCl$_2$ in Et$_2$O (22.5 mL, 22.5 mmol) was added to a solution of 2,4-dichloro-5-(trifluoromethyl)pyrimidine (4.48 g, 20.7 mmol) in t-BuOH (50 mL) and DCE (50 mL) and the mixture was stirred for 10 minutes. The mixture was diluted with t-BuOH (50 mL) and DCE (50 mL) before tert-butyl 4-(4-amino-1H-pyrazol-1-yl)piperidine-1-carboxylate (5.00 g, 18.8 mmol) and Et$_3$N (3.14 mL, 22.5 mmol) were added. Stirring was continued overnight and the volatiles were subsequently removed in vacuo. The resultant residue was suspended in acetone (50 mL) then water (500 mL) and sonicated for 15 minutes before the solid was removed by vacuum filtration and the filter cake washed with water (100 mL). The solid was suspended in acetone (25 mL), filtered and the filter cake was washed with petroleum benzine 40-60° C. (200 mL) to give the title compound K8 as a light pink solid (6.57 g, 78%). LCMS-D: rt 3.618 min; m/z 445.1 [M−H]$^−$.

Example 1

Synthesis of 2-(2-(2-(2-((4-(piperidin-4-yl)phenyl)amino)-5-(trifluoromethyl)pyrimidin-4-yl)ethyl)phenyl)butanamide (1)

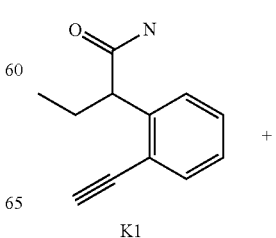

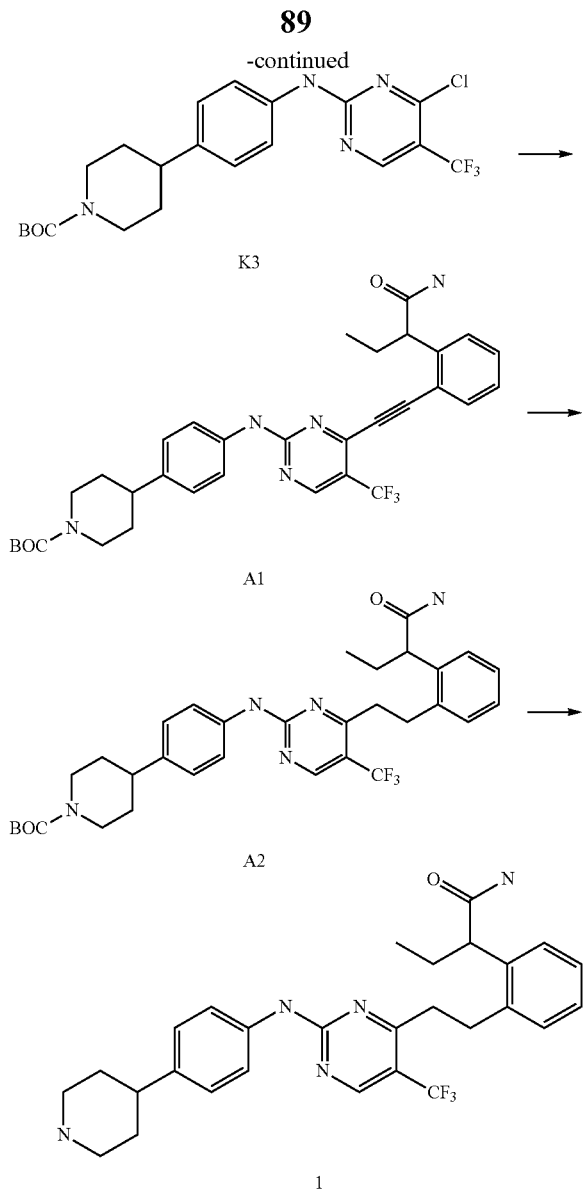

(a) tert-Butyl 4-(4-((4-((2-(1-amino-1-oxobutan-2-yl)phenyl)ethynyl)-5-(trifluoromethyl)pyrimidin-2-yl)amino)phenyl)piperidine-1-carboxylate (A1)

A mixture of tert-butyl 4-(4-((4-chloro-5-(trifluoromethyl)pyrimidin-2-yl)amino)phenyl)piperidine-1-carboxylate (K3) (193 mg, 0.422 mmol), PdCl₂(PPh₃)₂ (15 mg, 0.021 mmol), t-Bu₃PH.BF₄ (6 mg, 0.021 mmol), CuI (4 mg, 0.021 mmol) and 2-(2-ethynylphenyl)butanamide (K1) (87 mg, 0.47 mmol) in DMF (3.0 mL) was degassed with nitrogen for 10 minutes. Et₃N (1.0 mL) was added and the resulting mixture was heated under microwave irradiation at 120° C. for 20 minutes. The volatiles were removed under reduced pressure and the residue was adsorbed onto silica gel then purified by column chromatography (Biotage Isolera, SiO₂ cartridge, 0-100% EtOAc in petroleum benzine 40-60° C.) to give the title compound A1 as a yellow solid (175 mg, 68%); ¹H NMR (400 MHz, d₆-DMSO) δ 10.39 (s, 1H), 8.88-8.76 (m, 1H), 7.67 (d, J=8.5 Hz, 2H), 7.63-7.47 (m, 3H), 7.37 (td, J=7.4, 1.6 Hz, 1H), 7.27-7.17 (m, 3H), 7.01 (s, 1H), 4.07 (s, 2H), 3.89 (dd, J=8.6, 6.4 Hz, 1H), 2.80 (br, 2H), 2.64 (J m, 1H), 1.98-1.90 (m, 1H), 1.74 (d, J=12.7 Hz, 2H), 1.70-1.60 (m, 1H), 1.55-1.44 (m, 2H), 1.42 (s, 9H), 0.87 (t, J=7.3 Hz, 3H). LCMS-A: rt 6.726 min; m/z 606 [M−H]⁻.

(b) tert-Butyl 4-(4-((4-(2-(1-amino-1-oxobutan-2-yl)phenethyl)-5-(trifluoromethyl)pyrimidin-2-yl)amino)phenyl)piperidine-1-carboxylate (A2)

A suspension of 10% Pd/C (100 mg), tert-butyl 4-(4-((4-((2-(1-amino-1-oxobutan-2-yl)phenyl)ethynyl)-5-(trifluoromethyl)pyrimidin-2-yl)amino)phenyl)piperidine-1-carboxylate (A1) (167 mg, 0.275 mmol) and Et₃N (1.0 mL) in DMF (10 mL) was stirred under an atmosphere of hydrogen for 16 hours. The resulting mixture was diluted with EtOAc (60 mL), filtered through Celite then the solvent removed under reduced pressure to give the title compound A2 as a yellow oil (412 mg, 98%); ¹H NMR (400 MHz, d₆-DMSO) δ 10.15 (s, 1H), 8.67 (s, 1H), 7.67 (d, J=8.6 Hz, 2H), 7.49-7.42 (m, 1H), 7.31 (s, 1H), 7.22-7.14 (m, 5H), 6.87 (s, 1H), 4.06 (d, J=10.5 Hz, 2H), 3.61 (dd, J=8.8, 6.1 Hz, 1H), 3.29-2.94 (m, 4H), 2.88-2.74 (m, obscured by solvent), 2.70-2.59 (m, 1H), 2.04-1.92 (m, 1H), 1.74 (d, J=12.6 Hz, 2H), 1.61-1.43 (m, 3H), 1.41 (s, 9H), 0.83 (t, J=7.3 Hz, 3H). LCMS-A: rt 6.722 min; m/z 612 [M+H]⁺.

(c) 2-(2-(2-(2-((4-(Piperidin-4-yl)phenyl)amino)-5-(trifluoromethyl)pyrimidin-4-yl)ethyl)phenyl)butanamide (1)

A solution of TFA (0.84 mL, 11 mmol) and tert-butyl 4-(4-((4-(2-(1-amino-1-oxobutan-2-yl)phenethyl)-5-(trifluoromethyl)pyrimidin-2-yl)amino)phenyl)piperidine-1-carboxylate (A2) (168 mg, 0.275 mmol) in DCM (20 mL) was stirred for 24 hours at room temperature under a nitrogen atmosphere. The volatiles were removed in vacuo and the residue was taken up in MeOH and loaded onto an SCX cartridge (10 g). The column was eluted with 5 column volumes of MeOH and then 5 column volumes of 5% v/v aqueous ammonia in MeOH to elute the amine product. The ammoniacal filtrate was evaporated under reduced pressure and the residue was taken up in DCM (~2 mL). Cyclohexane (~10 mL) was added and the resulting suspension sonicated for 10 minutes. The precipitate was isolated by filtration to give the title compound 1 as an off-white solid (100 mg, 71%); ¹H NMR (400 MHz, d₆-DMSO) δ 10.14 (s, 1H), 8.67 (s, 1H), 7.66 (d, J=8.6 Hz, 2H), 7.51-7.43 (m, 1H), 7.31 (s, 1H), 7.22-7.10 (m, 5H), 6.87 (s, 1H), 3.61 (dd, J=8.8, 6.1 Hz, 1H), 3.22-2.89 (m, 6H), 2.62-2.53 (m, 3H), 2.07-1.91 (m, 1H), 1.67 (d, J=12.0 Hz, 2H), 1.62-1.42 (m, 3H), 0.87-0.80 (m, 3H). LCMS-A: rt 4.973 min; m/z 512 [M+H]⁺.

Example 1-1A and 1-2A

Separation of 2-(2-(2-(2-((4-(Piperidin-4-yl)phenyl)amino)-5-(trifluoromethyl)pyrimidin-4-yl)ethyl)phenyl)butanamide (1)

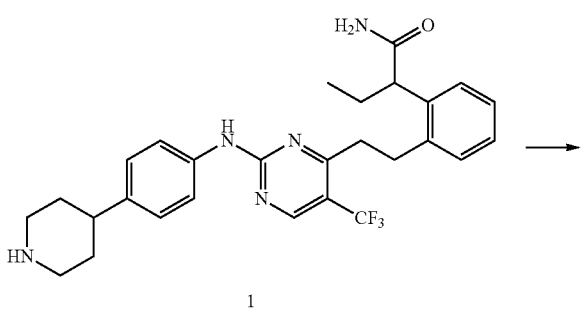

1

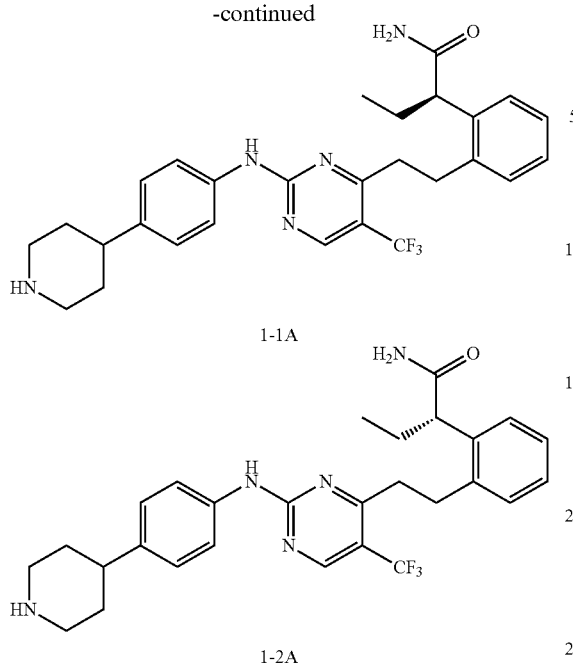

Racemic 2-(2-(2-(2-((4-(Piperidin-4-yl)phenyl)amino)-5-(trifluoromethyl)pyrimidin-4-yl)ethyl)phenyl)butanamide (1) was separated using the chiral separation Method C. The absolute configuration of each enantiomer has not been determined empirically.

Enantiomer A of 2-(2-(2-(2-((4-(Piperidin-4-yl)phenyl)amino)-5-(trifluoromethyl)pyrimidin-4-yl)ethyl)phenyl)butanamide (1-1A), Chiral Characterisation Method C: rt 5.58 min, enantiomeric purity>99%. Enantiomer B of 2-(2-(2-(2-((4-(Piperidin-4-yl)phenyl)amino)-5-(trifluoromethyl)pyrimidin-4-yl)ethyl)phenyl)butanamide (1-2A), Chiral Characterisation Method C: rt 3.82 min, enantiomeric purity 97.4%.

Example 2

Synthesis of 1-(2-(2-(2-((4-(piperidin-4-yl)phenyl)amino)-5-(trifluoromethyl)pyrimidin-4-yl)ethyl)phenyl)cyclopropanecarboxamide (2)

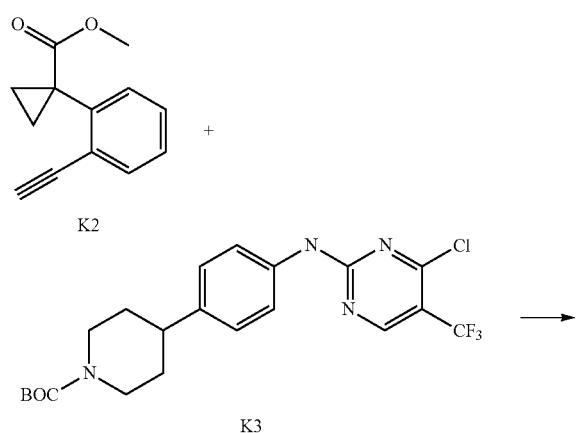

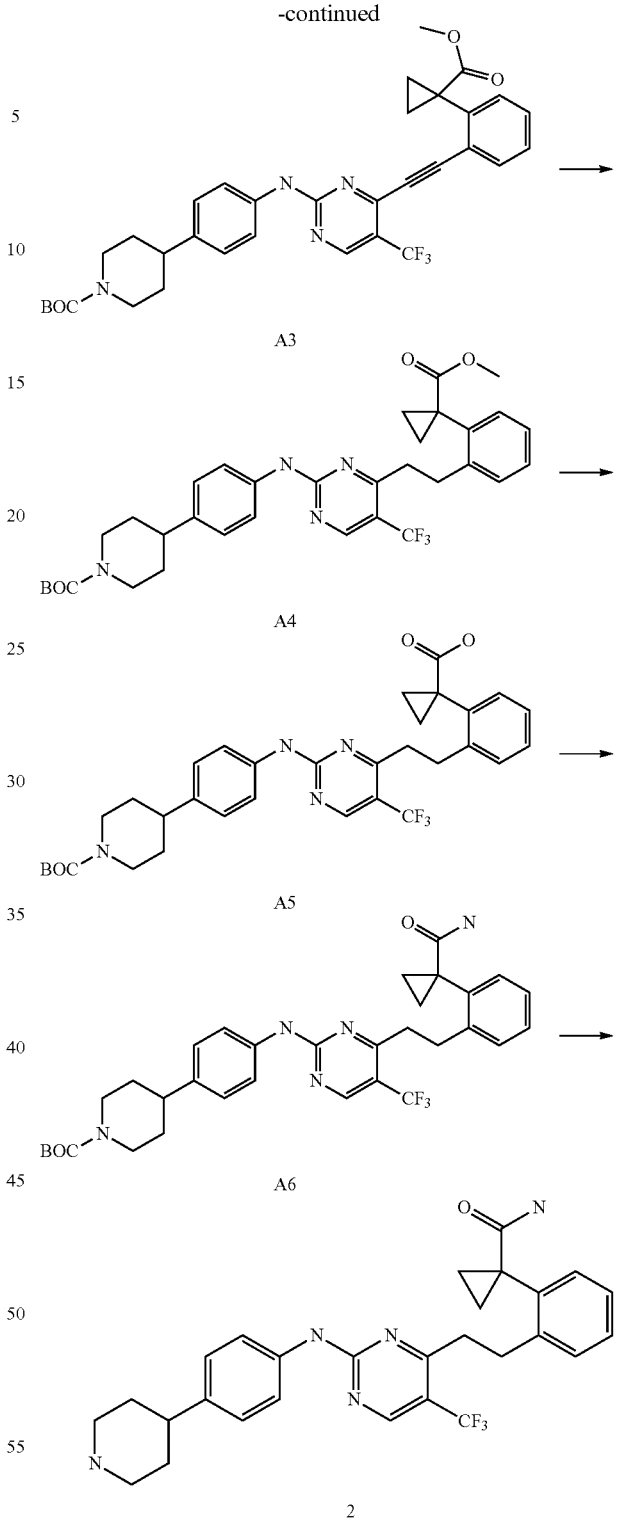

(a) tert-Butyl 4-(4-((4-((2-(1-(methoxycarbonyl)cyclopropyl)phenyl)ethynyl)-5-(trifluoromethyl)pyrimidin-2-yl)amino)phenyl)piperidine-1-carboxylate (A3)

A solution of tert-butyl 4-(4-((4-chloro-5-(trifluoromethyl)pyrimidin-2-yl)amino)phenyl)piperidine-1-carboxylate (K3) (262 mg, 0.574 mmol), PdCl$_2$(PPh$_3$)$_2$ (20 mg, 0.029 mmol,) t-Bu$_3$PH.BF$_4$ (8 mg, 0.03 mmol), CuI (5 mg, 0.03 mmol) and methyl 1-(2-ethynylphenyl)cyclopropanecarboxylate (K2) (138 mg, 0.689 mmol) in DMF (5.0 mL) was degassed with nitrogen for 10 minutes. Et$_3$N (1.0 mL) was added and the resulting mixture heated under microwave irradiation for 20 minutes at 120° C. The resulting mixture was adsorbed onto silica gel and purified by column chromatography (Biotage Isolera, SiO$_2$ cartridge, 0-40% EtOAc in petroleum benzine 40-60° C.) to give the title compound A3 as a yellow solid (308 mg, 86%); $^1$H NMR (400 MHz, d$_6$-DMSO) δ 10.37 (s, 1H), 8.79 (s, 1H), 7.67 (d, J=8.2 Hz, 2H), 7.60 (dd, J=7.6, 1.0 Hz, 1H), 7.54-7.38 (m, 3H), 7.21 (d, J=8.6 Hz, 2H), 4.07 (d, J=11.6 Hz, 2H), 3.52 (s, 3H), 2.80 (s, 2H), 2.65 (J m, 1H), 1.74 (d, J=12.4 Hz, 2H), 1.64 (q, J=4.0 Hz, 2H), 1.49 (td, J=12.6, 4.1 Hz, 2H), 1.42 (s, 9H), 1.29 (q, J=4.2 Hz, 2H). LCMS-A: rt 7.083 min; m/z 619 [M−H]$^-$.

(b) tert-Butyl 4-(4-((4-(2-(1-(methoxycarbonyl)cyclopropyl)phenethyl)-5-(trifluoromethyl)pyrimidin-2-yl)amino)phenyl)piperidine-1-carboxylate (A4)

A suspension of 10% Pd/C (200 mg), tert-butyl 4-(4-((2-(1-(methoxycarbonyl)cyclopropyl)phenyl)ethynyl)-5-(trifluoromethyl)pyrimidin-2-yl)amino)phenyl)piperidine-1-carboxylate (A3) (0.302 g, 0.487 mmol) and Et$_3$N (1.0 mL) in DMF (10 mL) was stirred under an atmosphere of hydrogen for 16 hours. The resulting mixture was diluted with EtOAc (60 mL) and filtered through Celite. The filtrate was evaporated under reduced pressure to give the title compound A4 as a yellow oil (494 mg, 99%); $^1$H NMR (400 MHz, d$_6$-DMSO) δ 10.15 (s, 1H), 8.68 (s, 1H), 7.67 (d, J=8.6 Hz, 2H), 7.33-7.26 (m, 3H), 7.22-7.17 (m, 3H), 4.07 (d, J=11.6 Hz, 2H), 3.49 (s, 3H), 3.15-3.07 (m, 2H), 3.07-3.00 (m, 2H), 2.86-2.75 (m, peaks obscured by solvent), 2.70-2.58 (m, 1H), 1.74 (d, J=11.3 Hz, 2H), 1.58 (d, J=3.4 Hz, 2H), 1.48 (dt, J=12.6, 6.2 Hz, 2H), 1.42 (s, 9H), 1.21 (s, 2H). LCMS-A: rt 7.175 min; m/z 625 [M+H]$^+$.

(c) 1-(2-(2-(2-((4-(1-tert-Butoxycarbonyl)piperidin-4-yl)phenyl)amino)-5-(trifluoromethyl)pyrimidin-4-yl)ethyl)phenyl)cyclopropanecarboxylic acid (A5)

A solution of tert-butyl 4-(4-((4-(2-(1-(methoxycarbonyl)cyclopropyl)phenethyl)-5-(trifluoromethyl)pyrimidin-2-yl)amino)piperidine-1-carboxylate (A4) (0.304 g, 0.487 mmol) and LiOH.H$_2$O (204 mg, 4.87 mmol) in THF (7 mL), MeOH (7 mL) and H$_2$O (1.5 mL) was stirred at room temperature overnight. The resulting mixture was then heated to 40° C. and stirred for 3.5 days. The volatiles were removed under reduced pressure and the residue was taken up in EtOAc (50 mL). Aqueous HCl (2 M, 50 mL) was added cautiously and the layers were separated. The aqueous phase was extracted with EtOAc (2×50 mL), and then the combined organics were washed with brine and dried over MgSO$_4$. The solvent was removed in vacuo to give the title compound A5 as a yellow oil (680 mg, 98%); LCMS-A: rt 6.793 min; m/z 609 [M−H]$^-$.

(d) tert-Butyl 4-(4-((4-(2-(1-carbamoylcyclopropyl)phenethyl)-5-(trifluoromethyl)pyrimidin-2-yl)amino)phenyl)piperidine-1-carboxylate (A6)

HOBt (99 mg, 0.73 mmol), EDCl.HCl (140 mg, 0.73 mmol) and DIPEA (0.42 mL, 2.43 mmol) were added to a stirred solution of 1-(2-(2-(2-((4-(1-(tert-butoxycarbonyl)piperidin-4-yl)phenyl)amino)-5-(trifluoromethyl)pyrimidin-4-yl)ethyl)phenyl)cyclopropanecarboxylic acid (A5) (297 mg, 0.486 mmol) in dry THF (6 mL) and dry DMF (1 mL) under an atmosphere of nitrogen. After 10 minutes ammonium carbonate (234 mg, 2.43 mmol) was added in one portion and the resulting solution was stirred at 40° C. for 72 hours. The volatiles were removed in vacuo and EtOAc (50 mL) and saturated NaHCO$_3$ (50 mL) were added to the residue. After separating the organic layer, the aqueous phase was extracted with EtOAc (2×50 mL). The organic extracts were combined, washed with brine and dried over MgSO$_4$. The volatiles were removed under reduced pressure and the residue was purified by silica gel column chromatography (Biotage Isolera, SiO$_2$ cartridge, 0-60% EtOAc in petroleum benzine 40-60° C.) to give the title compound A6 as a yellow solid (131 mg, 44%); $^1$H NMR (400 MHz, d$_6$-DMSO) δ 10.15 (s, 1H), 8.67 (s, 1H), 7.67 (d, J=8.5 Hz, 2H), 7.32 (dd, J=13.9, 5.0 Hz, 3H), 7.26-7.14 (m, 3H), 6.98 (s, 1H), 5.99 (s, 1H), 4.05 (dd, J=15.7, 8.8 Hz, 2H), 3.13 (dd, J=25.3, 9.9 Hz, 4H), 2.93-2.70 (m, 2H), 2.63 (t, J=12.2 Hz, 1H), 1.74 (d, J=12.5 Hz, 2H), 1.41 (s, 13H), 0.97 (s, 2H). LCMS-A: rt 6.720 min; m/z 610 [M+H]$^+$.

(e) 1-(2-(2-(2-((4-(Piperidin-4-yl)phenyl)amino)-5-(trifluoromethyl)pyrimidin-4-yl)ethyl)phenyl)cyclopropanecarboxamide (2)

A solution of TFA (0.65 mL, 8.5 mmol) and tert-butyl 4-(4-((4-(2-(1-carbamoylcyclopropyl)phenethyl)-5-(trifluoromethyl)pyrimidin-2-yl)amino)phenyl)piperidine-1-carboxylate (A6) (0.13 mg, 0.21 mmol) in DCM (20 mL) was stirred for 24 hours at room temperature under nitrogen. The volatiles were removed in vacuo and the residue was taken up in MeOH and loaded onto an SCX cartridge (10 g). The column was eluted with 5 column volumes of MeOH and then 5 column volumes of 5% v/v aqueous ammonia in MeOH to elute the amine product. The ammoniacal filtrate was evaporated under reduced pressure and the resulting solid was dried under high vacuum to give the title compound 2 as a white solid (100 mg, 93%); $^1$H NMR (400 MHz, d$_6$-DMSO) δ 10.14 (s, 1H), 8.67 (s, 1H), 7.66 (d, J=8.6 Hz, 2H), 7.37-7.27 (m, 3H), 7.25-7.14 (m, 3H), 6.99 (s, 1H), 6.00 (s, 1H), 3.22-3.13 (m, 2H), 3.13-3.06 (m, 2H), 3.01 (d, J=11.9 Hz, 2H), 2.62-2.52 (m, peaks obscured by solvent), 1.67 (d, J=10.7 Hz, 2H), 1.57-1.40 (m, 4H), 0.97 (s, 2H). LCMS-A: rt 4.963 min; m/z 510 [M+H]$^+$.

Example 3

Synthesis of 1-(2-(2-(2-((4-(1-methylpiperidin-4-yl)phenyl)amino)-5-(trifluoromethyl)pyrimidin-4-yl)ethyl)phenyl)cyclopropanecarboxamide (3)

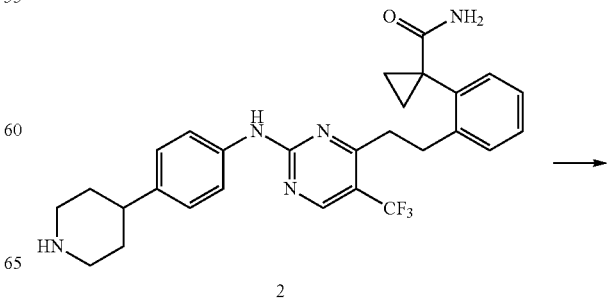

-continued

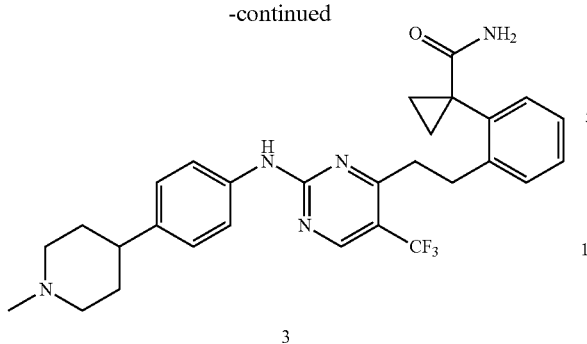

3

Formaldehyde (37 wt % in H$_2$O; 8.8 µL, 0.12 mmol) was added to a solution of 1-(2-(2-(2-((4-(piperidin-4-yl)phenyl)amino)-5-(trifluoromethyl)pyrimidin-4-yl)ethyl)phenyl)cyclopropanecarboxamide (2) (20 mg, 39 µmol) in MeOH (5.0 mL) under an atmosphere of nitrogen. The resulting mixture was stirred for 10 minutes at room temperature then sodium triacetoxyborohydride (33 mg, 0.16 mmol) was added in one portion and stirring continued for 2.5 hours. The volatiles were removed in vacuo and the residue was diluted with EtOAc (20 mL) and saturated aqueous NaHCO$_3$ (20 mL). The layers were separated and the aqueous layer was extracted with EtOAc (2×20 mL). The combined organic layers were washed with brine (20 mL), dried over MgSO$_4$ and the volatiles were removed under reduced pressure. The residue was dissolved in DCM (1 mL) to which cyclohexane (5 mL) was added to form a cloudy suspension. The solvent was removed in vacuo and the resulting solid was dried under high vacuum to give the title compound 3 as a white powder (18 mg, 88%); $^1$H NMR (400 MHz, d$_6$-DMSO) δ 10.15 (s, 1H), 8.67 (s, 1H), 7.66 (d, J=8.5 Hz, 2H), 7.40-7.27 (m, 3H), 7.22 (dd, J=14.4, 8.0 Hz, 3H), 6.99 (s, 1H), 6.01 (s, 1H), 3.21-3.05 (m, 4H), 2.88 (d, J=10.9 Hz, 2H), 2.50-2.30 (m, 1H), 2.21 (s, 3H), 1.99 (s, 2H), 1.79-1.58 (m, 4H), 1.44 (s, 2H), 0.97 (s, 2H). LCMS-A: 5.028 min; m/z 524 [M+H]$^+$.

Example 4

Synthesis of 1-(2-(2-(2-((4-(azetidin-3-yl)phenyl)amino)-5-(trifluoromethyl)pyrimidin-4-yl)ethyl)phenyl)cyclopropanecarboxamide (4)

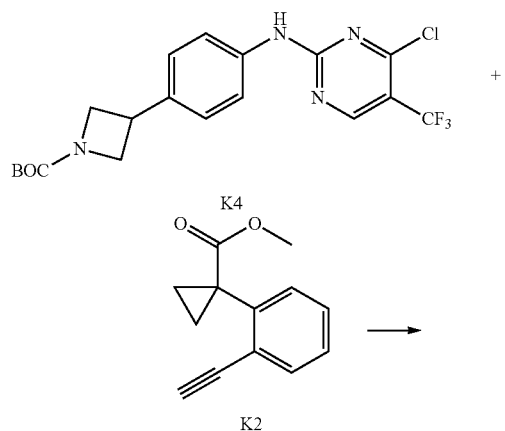

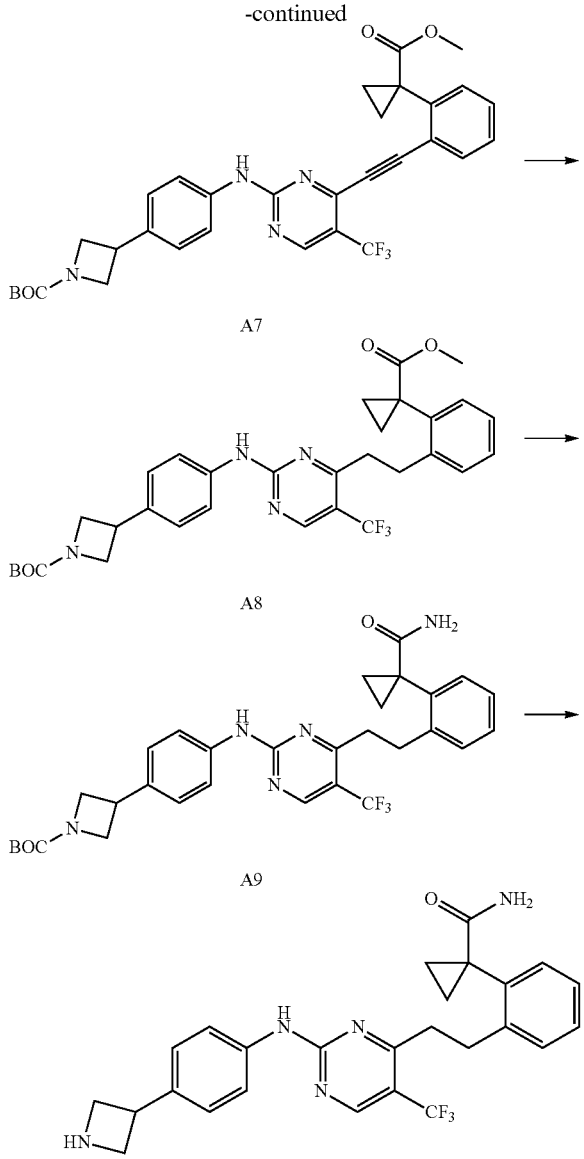

(a) tert-Butyl 3-(4-((4-((2-(1-(methoxycarbonyl)cyclopropyl)phenyl)ethynyl)-5-(trifluoromethyl)pyrimidin-2-yl)amino)phenyl)azetidine-1-carboxylate (A7)

A solution of tert-butyl 3-(4-((4-chloro-5-(trifluoromethyl)pyrimidin-2-yl)amino)phenyl)azetidine-1-carboxylate (K4) (260 mg, 0.606 mmol), PdCl$_2$(PPh$_3$)$_2$ (21 mg, 0.030 mmol), PPh$_3$ (16 mg, 0.061 mmol), CuI (12 mg, 0.061 mmol) and methyl 1-(2-ethynylphenyl)cyclopropanecarboxylate (K2) (146 mg, 0.728 mmol) in DMF (3.0 mL) was degassed with nitrogen for 10 minutes. Et$_3$N (1.0 mL) was added and the resulting mixture heated under microwave irradiation at 120° C. for 20 minutes. The resulting mixture was adsorbed onto silica and purified by silica gel column chromatography (Biotage Isolera, 40 g SiO$_2$ cartridge, 0-25% EtOAc in petroleum benzine 40-60° C.) to give the title compound A7 as an orange oil (359 mg, >95%); $^1$H NMR (400 MHz, d$_6$-DMSO) δ 10.45 (s, 1H), 8.82 (s, 1H), 7.75 (d, J=8.4 Hz, 2H), 7.61 (dd, J=7.5, 1.0 Hz, 1H), 7.55-7.38 (m, 3H), 7.32 (d, J=8.6 Hz, 2H), 4.32-4.17 (m, 2H), 3.89-3.74 (m, 3H), 3.52 (s, 3H), 1.64 (q, J=4.0 Hz, 2H), 1.40 (s, 9H), 1.29 (q, J=4.2 Hz, 2H). LCMS-A: rt 6.550 min; m/z 593 [M+H]$^+$.

(b) tert-Butyl 3-(4-((4-(2-(1-(methoxycarbonyl)cyclopropyl)phenethyl)-5-(trifluoromethyl)pyrimidin-2-yl)amino)phenyl)azetidine-1-carboxylate (A8)

A suspension of 10% Pd/C (200 mg), tert-butyl 3-(4-((4-((2-(1-(methoxycarbonyl)cyclopropyl)phenyl)ethynyl)-5-(trifluoromethyl)pyrimidin-2-yl)amino)phenyl)azetidine-1-carboxylate (A7) (353 mg, 0.596 mmol) and Et$_3$N (1.5 mL) in DMF (10 mL) was stirred with under a hydrogen atmosphere for 16 hours. The resulting mixture was diluted with EtOAc (60 mL), filtered through Celite and the volatiles were removed under reduced pressure. The residue was adsorbed onto silica gel and purified by column chromatography (Biotage Isolera, 24 g SiO$_2$ cartridge, 0-40% EtOAc in petroleum benzine 40-60° C.) to give the title compound A8 as yellow oil (353 mg, 99%); $^1$H NMR (400 MHz, d$_6$-DMSO) δ 10.22 (s, 1H), 8.69 (s, 1H), 7.74 (d, J=8.6 Hz, 2H), 7.32-7.26 (m, 5H), 7.22-7.16 (m, 1H), 4.24 (t, J=7.4 Hz, 2H), 3.87-3.71 (m, 3H), 3.49 (s, 3H), 3.17-2.98 (m, 4H), 1.58 (d, J=3.3 Hz, 2H), 1.40 (s, 9H), 1.19 (s, 2H). LCMS-A: rt 6.650 min; m/z 595 [M–H]$^-$.

(c) tert-Butyl 3-(4-((4-(2-(1-carbamoylcyclopropyl)phenethyl)-5-(trifluoromethyl)pyrimidin-2-yl)amino)phenyl)azetidine-1-carboxylate (A9)

A solution of tert-butyl 3-(4-((4-(2-(1-(methoxycarbonyl)cyclopropyl)phenethyl)-5-(trifluoromethyl)pyrimidin-2-yl)amino)phenyl)azetidine-1-carboxylate (A8) (347 mg, 0.582 mmol) and LiOH.H$_2$O (293 mg, 6.98 mmol) in THF (7.0 mL), MeOH (7.0 mL) and H$_2$O (2.0 mL) was stirred at room temperature for 3 days. LiOH.H$_2$O (147 mg, 3.49 mmol) was added and the resulting mixture was heated at 35° C. for 16 hours. EtOAc (50 mL) and aqueous HCl (2 M, 50 mL) were added cautiously, then the layers were separated and the aqueous phase was extracted with EtOAc (2×50 mL). The organic layers were combined, washed with brine, dried (MgSO$_4$) then evaporated to dryness. The residue was dissolved in THF (12 mL) and DMF (2.0 mL), to which HOBt (157 mg, 1.16 mmol), EDCl.HCl (223 mg, 1.16 mmol) and DIPEA (0.507 mL, 2.91 mmol) were added under an atmosphere of nitrogen. After 10 minutes ammonium carbonate (280 mg, 2.91 mmol) was added in one portion and the resulting mixture was stirred at room temperature for 16 hours, then 40° C. for a further 24 hours. The volatiles were removed in vacuo and EtOAc (20 mL) and saturated NaHCO$_3$ (20 mL) were added. The layers were separated then the aqueous phase extracted with EtOAc (2×20 mL). The organic extracts were combined, washed with brine, dried (MgSO$_4$) then evaporated to dryness. The residue was purified by silica gel column chromatography (Biotage Isolera, 24 g SiO$_2$ cartridge, 10-50% EtOAc in petroleum benzine 40-60° C.) to give the title compound A9 as a white solid (179 mg, 53%); $^1$H NMR (400 MHz, d$_6$-DMSO) δ 10.22 (s, 1H), 8.69 (s, 1H), 7.73 (d, J=8.6 Hz, 2H), 7.37-7.27 (m, 5H), 7.26-7.19 (m, 1H), 6.98 (s, 1H), 5.99 (s, 1H), 4.23 (t, J=7.7 Hz, 2H), 3.88-3.70 (m, 3H), 3.21-3.14 (m, 2H), 3.14-3.07 (m, 2H), 1.44 (d, J=3.5 Hz, 2H), 1.40 (s, 9H), 0.97 (s, 2H). LCMS-A: rt 6.168 min; m/z 582 [M+H]$^+$.

(d) 1-(2-(2-(2-((4-(azetidin-3-yl)phenyl)amino)-5-(trifluoromethyl)pyrimidin-4-yl)ethyl)phenyl)cyclopropanecarboxamide (4)

A solution of TFA (0.916 mL, 12.0 mmol) and tert-butyl 3-(4-((4-(2-(1-carbamoylcyclopropyl)phenethyl)-5-(trifluoromethyl)pyrimidin-2-yl)amino)phenyl)azetidine-1-carboxylate (A9) (174 mg, 0.299 mmol) in DCM (10 mL) was stirred for 16 hours at room temperature under nitrogen. The volatiles were removed in vacuo and the residue was taken up in MeOH and loaded onto an SCX cartridge (10 g). The column was eluted with 5 column volumes of MeOH and then 5 column volumes of 5% v/v aqueous ammonia in MeOH to elute the amine product. The ammoniacal filtrate was evaporated under reduced pressure and dried under high vacuum to give the title compound 4 as a yellow solid (129 mg, 90%); $^1$H NMR (400 MHz, d$_6$-DMSO) δ 10.19 (s, 1H), 8.68 (s, 1H), 7.77-7.67 (m, 2H), 7.38-7.26 (m, 5H), 7.26-7.18 (m, 1H), 6.99 (s, 1H), 6.00 (s, 2H), 3.86 (s, 3H), 3.71 (s, 2H), 3.22-3.13 (m, 2H), 3.13-3.05 (m, 2H), 1.44 (s, 2H), 0.96 (s, 2H). LCMS-A: rt 4.591 min; m/z 482 [M+H]$^+$.

Example 5

Synthesis of 1-(2-(2-(2-((6-(piperidin-4-yl)pyridin-3-yl)amino)-5-(trifluoromethyl)pyrimidin-4-yl)ethyl)phenyl)cyclopropanecarboxamide (5)

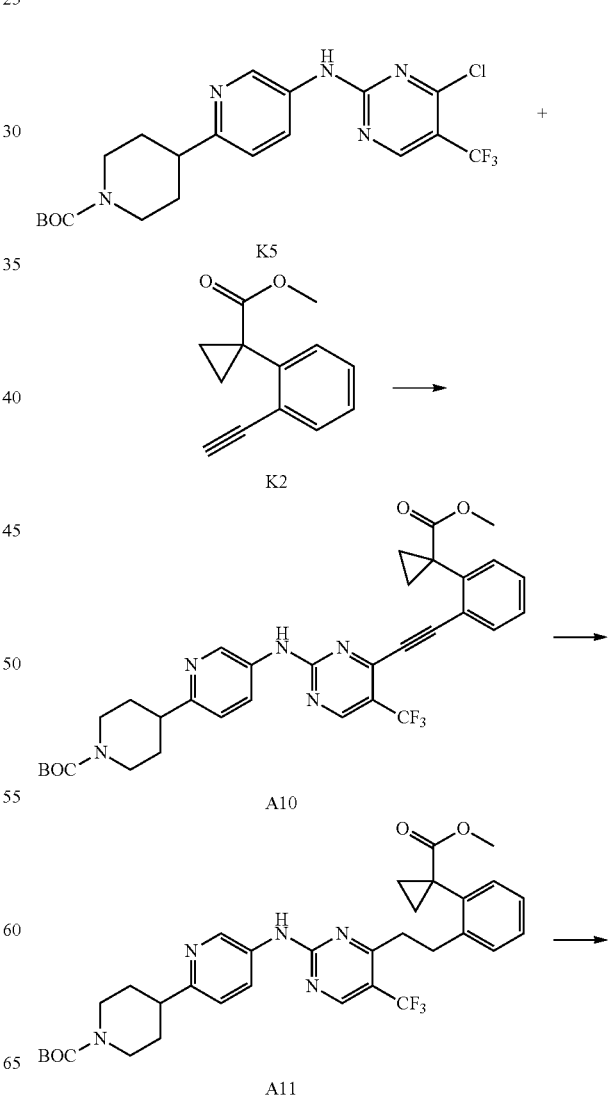

-continued

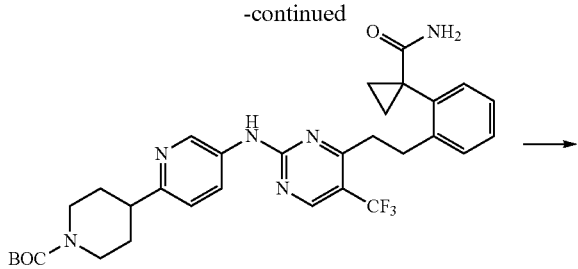

A12

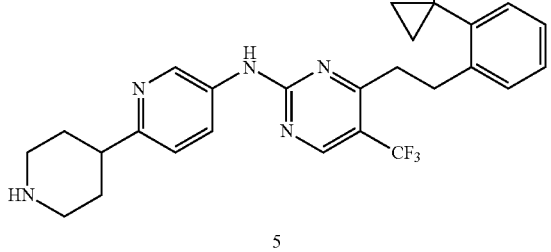

5

(a) tert-Butyl 4-(5-((4-((2-(1-(methoxycarbonyl)cyclopropyl)phenyl)ethynyl)-5-(trifluoromethyl)pyrimidin-2-yl)amino)pyridin-2-yl)piperidine-1-carboxylate (A10)

A stirred suspension of tert-butyl 4-(5-((4-chloro-5-(trifluoromethyl)pyrimidin-2-yl)amino)pyridin-2-yl)piperidine-1-carboxylate (K5) (152 mg, 0.332 mmol), PdCl$_2$(PPh$_3$)$_2$ (12 mg, 0.017 mmol), PPh$_3$ (9 mg, 0.03 mmol), CuI (6 mg, 0.03 mmol) and methyl 1-(2-ethynylphenyl)cyclopropanecarboxylate (K2) (80 mg, 0.40 mmol) in DMF (4.0 mL) was degassed with nitrogen for 10 minutes. Et$_3$N (1.0 mL) was added and the resulting mixture heated under microwave irradiation at 120° C. for 20 minutes. The volatiles were removed in vacuo and the residue was adsorbed onto silica gel and purified by column chromatography (Biotage Isolera, 24 g SiO$_2$ cartridge, 0-60% EtOAc in petroleum benzine 40-60° C. then 10-45% EtOAc in petroleum benzine 40-60° C.) to give the title compound A10 as yellow oil (141 mg, 68%); $^1$H NMR (400 MHz, d$_6$-DMSO) δ 10.53 (s, 1H), 8.84 (s, 1H), 8.77 (d, J=2.5 Hz, 1H), 8.12 (d, J=6.5 Hz, 1H), 7.61 (dd, J=7.6, 1.0 Hz, 1H), 7.54-7.38 (m, 3H), 7.28 (d, J=8.5 Hz, 1H), 4.05 (br, 2H), 3.51 (s, 3H), 2.94-2.72 (m, 3H), 1.81 (d, J=10.5 Hz, 2H), 1.63 (q, J=4.1 Hz, 2H), 1.61-1.49 (m, 2H), 1.41 (s, 9H), 1.29 (q, J=4.2 Hz, 2H). LCMS-A: rt 5.913 min; m/z 622 [M+H]$^+$.

(b) tert-Butyl 4-(5-((4-(2-(1-(methoxycarbonyl)cyclopropyl)phenethyl)-5-(trifluoromethyl)pyrimidin-2-yl)amino)pyridin-2-yl)piperidine-1-carboxylate (A11)

A suspension of tert-butyl 4-(5-((4-((2-(1-(methoxycarbonyl)cyclopropyl)phenyl)ethynyl)-5-(trifluoromethyl)pyrimidin-2-yl)amino)pyridin-2-yl)piperidine-1-carboxylate (A10) (134 mg, 0.216 mmol), 10% Pd/C (100 mg) and Et$_3$N (1.0 mL) in DMF (10 mL) was stirred under an atmosphere of hydrogen for 16 hours. The resulting mixture was diluted with EtOAc (60 mL) and filtered through Celite. The filtrate was evaporated in vacuo and the resulting residue was adsorbed onto silica gel and purified by column chromatography (Biotage Isolera, 24 g SiO$_2$ cartridge, 10-50% EtOAc in petroleum benzine 40-60° C.) to give the title compound A11 as a colourless oil (117 mg, 87%); $^1$H NMR (400 MHz, CDCl$_3$) δ 8.65 (d, J=2.6 Hz, 1H), 8.57 (s, 1H), 8.15 (dd, J=8.5, 2.7 Hz, 1H), 7.45 (s, 1H), 7.34-7.27 (m, 3H), 7.24-7.15 (m, 2H), 4.26 (s, 2H), 3.60 (s, 3H), 3.22-3.07 (m, 4H), 2.92-2.76 (m, 3H), 1.92 (d, J=11.4 Hz, 2H), 1.79-1.65 (m, 4H), 1.48 (s, 9H), 1.22-1.18 (m, 2H). LCMS-A: rt 5.971 min; m/z 626 [M+H]$^+$.

(c) tert-Butyl 4-(5-((4-(2-(1-carbamoylcyclopropyl)phenethyl)-5-(trifluoromethyl)pyrimidin-2-yl)amino)pyridin-2-yl)piperidine-1-carboxylate (A12)

A solution of tert-butyl 4-(5-((4-(2-(1-(methoxycarbonyl)cyclopropyl)phenethyl)-5-(trifluoromethyl)pyrimidin-2-yl)amino)pyridin-2-yl)piperidine-1-carboxylate (A11) (112 mg, 0.179 mmol) and LiOH.H$_2$O (90 mg, 2.2 mmol) in THF (7.0 mL), MeOH (7.0 mL) and H$_2$O (2.0 mL) was stirred at 35° C. for 24 hours. Additional LiOH.H$_2$O (45 mg, 1.1 mmol) was added and stirring continued at 35° C. for 16 hours. Further LiOH.H$_2$O (45 mg, 1.07 mmol) was added and stirring was continued at 35° C. for 3 days. The volatiles were removed in vacuo and the residue diluted with EtOAc (20 mL) and aqueous HCl (2 M, 20 mL). The layers were separated and the aqueous phase was extracted with EtOAc (2×50 mL). The combined organics extracts were washed with brine and dried over MgSO$_4$. The volatiles were removed in vacuo and the residue dissolved in anhydrous THF (9.0 mL) and anhydrous DMF (1.5 mL) then HOBt (48 mg, 0.36 mmol), EDCl.HCl (68 mg, 0.36 mmol) and diisopropylamine (0.310 mL, 2.21 mmol) were added under an atmosphere of nitrogen. After 10 minutes of stirring ammonium carbonate (86 mg, 0.89 mmol) was added in one portion and the resulting mixture was stirred at room temperature for 16 hours. The temperature was raised to 40° C. and stirring was continued for a further 24 hours. The volatiles were removed in vacuo before EtOAc (20 mL) and saturated NaHCO$_3$ (20 mL) were added to the residue. After separating the layers, the aqueous phase was extracted with EtOAc (2×20 mL) then the combined organic extracts were washed with brine and dried over MgSO$_4$. The volatiles were removed under reduced pressure and the residue was purified by silica gel column chromatography (Biotage Isolera, 24 g SiO$_2$ cartridge, 10-100% EtOAc in petroleum benzine 40-60° C.) to give the title compound A12 as a white solid (77 mg, 71%); $^1$H NMR (400 MHz, d$_6$-DMSO) δ 10.32 (s, 1H), 8.76 (d, J=2.5 Hz, 1H), 8.72 (s, 1H), 8.14 (d, J=6.7 Hz, 1H), 7.37-7.26 (m, 4H), 7.26-7.18 (m, 1H), 6.98 (s, 1H), 6.02 (s, 1H), 4.05 (d, J=12.7 Hz, 2H), 3.21-3.07 (m, 4H), 2.87-2.75 (m, 3H), 1.81 (d, J=11.1 Hz, 2H), 1.56 (qd, J=13.0, 4.4 Hz, 2H), 1.47-1.38 (m, 11H), 0.97 (s, 2H). LCMS-A: rt 5.273 min; m/z 611 [M+H]$^+$.

(d) 1-(2-(2-(2-((6-(Piperidin-4-yl)pyridin-3-yl)amino)-5-(trifluoromethyl)pyrimidin-4-yl)ethyl)phenyl)cyclopropanecarboxamide (5)

A solution of TFA (0.386 mL, 5.04 mmol) and tert-butyl 4-(5-((4-(2-(1-carbamoylcyclopropyl)phenethyl)-5-(trifluoromethyl)pyrimidin-2-yl)amino)pyridin-2-yl)piperidine-1-carboxylate (A12) (0.077 g, 0.13 mmol) in DCM (10.0 mL) was stirred at room temperature for 3.5 h under N$_2$. The volatiles were removed in vacuo and the residue was dissolved in DCM (~1 mL). Cyclohexane (~5 mL) was added until a white precipitate formed. The resulting suspension was sonicated for 10 minutes and the solid was isolated by filtration and dried to give the title compound 5 as an off-white solid (0.042 g, 65%); $^1$H NMR (400 MHz, d$_6$-DMSO) δ 10.31 (s, 1H), 8.75 (d, J=2.4 Hz, 1H), 8.72 (s, 1H), 8.13 (d, J=7.3 Hz, 1H), 7.39-7.18 (m, 5H), 6.98 (s, 1H), 6.02 (s, 1H), 3.19-3.05 (m, 6H), 2.81-2.59 (m, 3H), 1.79 (d, J=11.0 Hz, 2H), 1.63 (qd, J=12.5, 3.8 Hz, 2H), 1.47-1.41 (m, 2H), 1.02-0.92 (m, 2H). LCMS-A: rt 4.445 min; m/z 511 [M+H]$^+$.

Example 6

Synthesis of 1-(2-(2-(5-chloro-2-(pyridin-3-ylamino)pyrimidin-4-yl)ethyl)phenyl)cyclopropanecarboxamide (6)

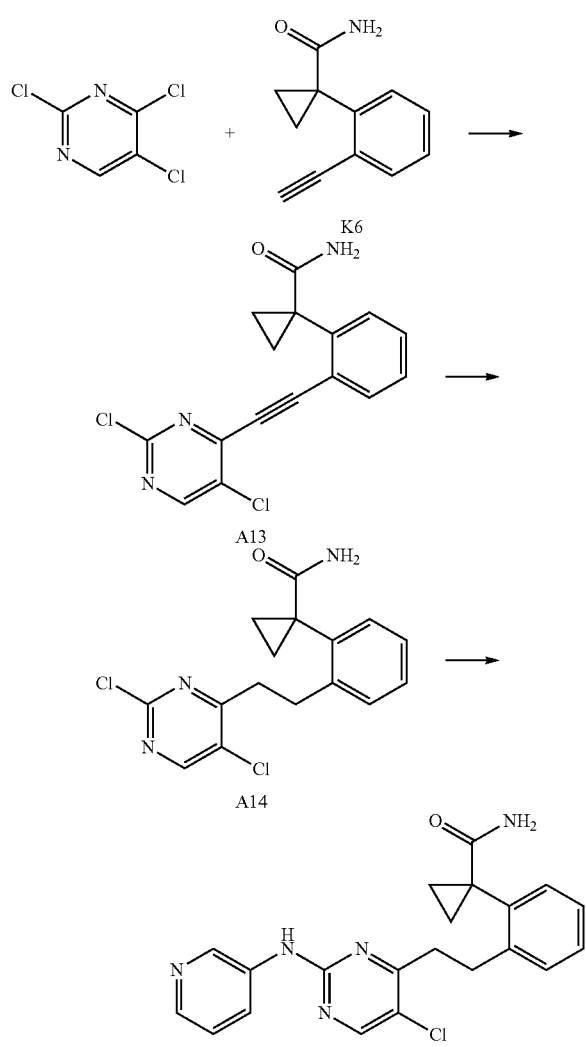

(a) 1-(2-((2,5-Dichloropyrimidin-4-yl)ethynyl)phenyl)cyclopropanecarboxamide (A13)

PdCl$_2$(PPh$_3$)$_2$ (16 mg, 0.023 mmol) was added to a stirred solution of 1-(2-ethynylphenyl)cyclopropanecarboxamide (K6) (0.420 g, 2.26 mmol), 2,4,5-trichloropyrimidine (0.338 mL, 2.94 mmol), Et$_3$N (1.26 mL, 9.07 mmol) and copper(I) iodide (8.6 mg, 0.045 mmol) in 1,4-dioxane (4.5 mL). The resulting mixture was stirred at 60° C. for 2.5 hours under a nitrogen atmosphere before being diluted with petroleum benzine 40-60° C. (25 mL). The resultant precipitate was filtered, dried, washed with water (50 mL) and dried to give the title compound A13 as light coloured tan solid (0.570 g, 75%); $^1$H NMR (300 MHz, d$_6$-DMSO) δ 9.01 (s, 1H), 7.72 (d, J=7.1 Hz, 1H), 7.41-7.57 (m, 3H), 6.97 (brs, 1H), 6.20 (brs, 1H), 1.53 (dq, J=4.0 Hz, 2H) 1.06 (dq, J=3.7 Hz, 2H). LCMS-B: rt 6.593 min; m/z 332 [M+H]$^+$.

(b) 1-(2-(2-(2,5-Dichloropyrimidin-4-yl)ethyl)phenyl)cyclopropanecarboxamide (A14)

A suspension of 1-(2-((2,5-dichloropyrimidin-4-yl)ethynyl)phenyl)cyclopropanecarboxamide (A13) (0.536 g, 1.61 mmol) and platinum oxide (0.110 g, 0.484 mmol) in DIPEA (16 mL) and MeOH (3 mL) was stirred under a hydrogen atmosphere for 58 hours. The resulting mixture was filtered through a pad of Celite and the filtrate concentrated in vacuo. The residue was diluted with water and EtOAc and filtered through a pad of Celite. The filtrate was extracted with EtOAc (2×20 mL) and the combined organic fractions were washed with water (3×20 mL), brine, dried (magnesium sulfate), filtered and concentrated in vacuo. The residue was adsorbed onto silica gel and purified by column chromatography (CombiFlash Rf, 24 g SiO$_2$ Cartridge, 30-60% EtOAc in cyclohexane) to give the title compound A14 as a white solid (375 mg, 69%); $^1$H NMR (300 MHz, CDCl$_3$) δ 8.52 (s, 1H), 7.43 (d, J=7.2 Hz, 1H), 7.28-7.31 (m, 3H), 5.37 (d, J=17 Hz, 2H), 3.27 (brs, 4H), 1.76 (brs, 2H), 1.16 (brs, 2H). LCMS-B: rt 5.30 min; m/z 337 [M+H]$^+$.

(c) 1-(2-(2-(5-chloro-2-(pyridin-3-ylamino)pyrimidin-4-yl)ethyl)phenyl)cyclopropanecarboxamide (6)

A suspension of 1-(2-(2-(2,5-dichloropyrimidin-4-yl)ethyl)phenyl)cyclopropanecarboxamide (A14) (100 mg, 297 μmol), Cs$_2$CO$_3$ (291 mg, 892 μmol) and 3-aminopyridine (56.0 mg, 595 μmol) in 1,4-dioxane (2.0 mL) was sonicated for 10 minutes. To this Xantphos (6.88 mg, 11.9 μmol) and Pd(OAc)$_2$ (1.33 mg, 5.95 μmol) were added and the resulting mixture heated under microwave irradiation for 20 minutes at 120° C. The resulting mixture was adsorbed onto silica gel and purified by column chromatography (Biotage Isolera, 24 g SiO$_2$ cartridge, 0-50% MeOH in EtOAc) to yield a tan solid. This was sonicated for 10 min in water (50 mL) and filtered to give the title compound 6 as a green solid (29 mg, 25%); $^1$H NMR (400 MHz, CDCl$_3$) δ 8.80-8.74 (d, J=2.5 Hz, 1H), 8.33 (s, 1H), 8.32-8.28 (dd, J=4.7, 1.3 Hz, 1H), 8.18-8.12 (m, 1H), 7.47-7.42 (d, J=7.2 Hz, 1H), 7.38-7.34 (m, 3H), 7.34-7.25 (m, 2H), 5.56 (s, 1H), 5.37 (s, 1H), 3.34-3.14 (m, 4H), 1.78 (s, 2H), 1.16 (s, 2H). LCMS-A: rt 4.502 min; m/z 394 [M+H]$^+$.

Example 7

Synthesis of 1-(2-(2-(5-chloro-2-(pyridin-3-ylamino)pyrimidin-4-yl)ethyl)phenyl)cyclopropanecarboxamide (7)

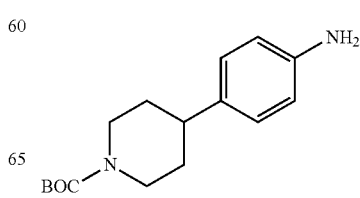

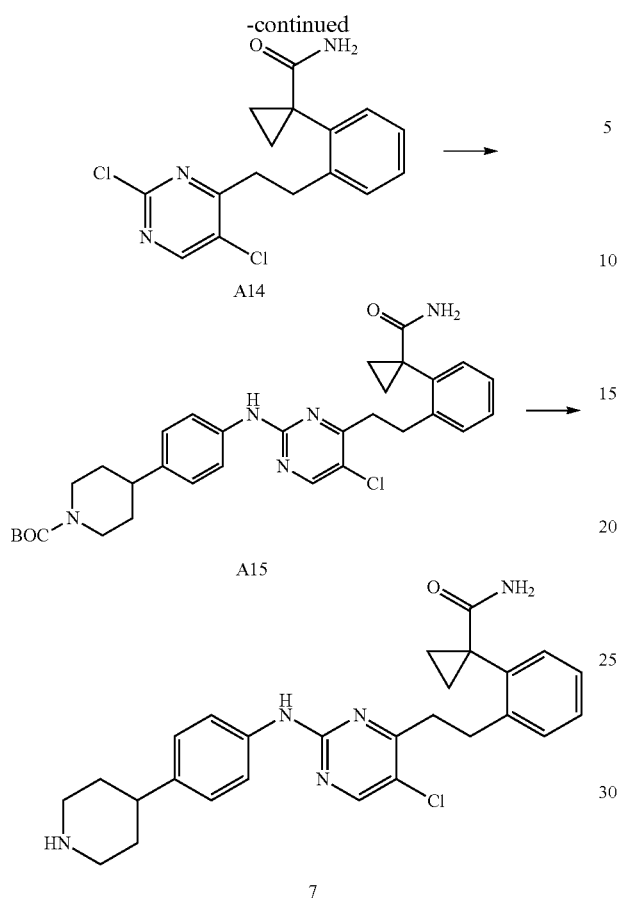

A14

A15

7

(a) tert-Butyl 4-(4-((4-(2-(1-carbamoylcyclopropyl)phenethyl)-5-chloropyrimidin-2-yl)amino)phenyl)piperidine-1-carboxylate (A15)

A suspension of 1-(2-(2-(2,5-dichloropyrimidin-4-yl)ethyl)phenyl)cyclopropanecarboxamide (A14) (100 mg, 297 μmol), Cs₂CO₃ (291 mg, 892 μmol) and tert-butyl 4-(4-aminophenyl)piperidine-1-carboxylate (164 mg, 595 μmol) in 1,4-dioxane (2.0 mL) was sonicated for 10 min. To this Xantphos (6.88 mg, 11.9 μmol) and Pd(OAc)₂ (1.33 mg, 5.95 μmol) were added and the resulting mixture heated under microwave irradiation for 20 min at 120° C. The resulting mixture was adsorbed onto silica gel and purified by column chromatography (Biotage Isolera, 24 g SiO₂ cartridge, 0-100% EtOAc in petroleum benzine 40-60° C.) to give the title compound A15 as a yellow oil (121 mg, 71%); ¹H NMR (400 MHz, CDCl₃) δ 8.25-8.22 (s, 1H), 7.54-7.46 (m, 3H), 7.43-7.38 (dt, J=7.4, 1.0 Hz, 1H), 7.34-7.29 (m, 2H), 7.29-7.22 (m, 1H), 7.19-7.12 (m, 2H), 5.93-5.80 (s, 1H), 5.41-5.26 (s, 1H), 4.39-4.18 (s, 2H), 3.31-3.06 (m, 4H), 2.90-2.69 (t, J=11.8 Hz, 2H), 2.69-2.54 (tt, J=12.0, 3.4 Hz, 1H), 1.88-1.68 (t, J=15.8 Hz, 4H), 1.68-1.53 (qd, J=13.0, 4.4 Hz, 2H), 1.53-1.46 (s, 9H), 1.19-1.07 (s, 2H). LCMS-A: rt 6.326 min; m/z 577 [M+H]⁺.

(b) 1-(2-(2-(5-chloro-2-((4-(piperidin-4-yl)phenyl)amino)pyrimidin-4-yl)ethyl)phenyl)cyclopropanecarboxamide (7)

TFA (1.0 mL) was added to a solution of tert-butyl 4-(4-((4-(2-(1-carbamoylcyclopropyl)phenethyl)-5-chloropyrimidin-2-yl)amino)phenyl)piperidine-1-carboxylate (A15) (121 mg, 210 μmol) in DCM (5 mL) and the resulting mixture was stirred at room temperature for 16 hours. Saturated aqueous Na₂CO₃ was added until the solution was basic then EtOAc (50 mL) and water (50 mL) were added. The organic layer was separated, washed with brine (20 mL), dried over MgSO₄ then the volatiles removed in vacuo. The resulting residue was adsorbed onto silica gel and the resulting material washed with MeOH (300 mL) then 1 M NH₃ in MeOH/EtOH (1:1) (300 mL). The volatiles from the ammoniacal washing were removed in vacuo and the resultant gum sonicated in Et₂O (20 mL) to give a precipitate that was collected by filtration. Air drying of the filter cake gave the product 7 as a white solid (55 mg, 55%); ¹H NMR (400 MHz, CDCl₃) δ 8.28 (s, 1H), 7.52-7.46 (d, J=8.6 Hz, 2H), 7.46-7.41 (d, J=7.3 Hz, 1H), 7.37-7.32 (d, J=5.0 Hz, 2H), 7.31-7.25 (m, 2H, obscured), 7.23-7.18 (d, J=8.5 Hz, 2H), 7.15 (s, 1H), 5.33 (s, 2H), 3.34-3.12 (m, 6H), 2.84-2.71 (td, J=12.2, 2.3 Hz, 2H), 2.71-2.56 (tt, J=12.1, 3.7 Hz, 1H), 1.92-1.59 (m, 6H, obscured), 1.15 (s, 2H). LCMS-A: rt 4.527 min; m/z 477 [M+H]⁺.

Example 8

Synthesis of 1-(2-(2-(5-chloro-2-((4-(1-methylpiperidin-4-yl)phenyl)amino)pyrimidin-4-yl)ethyl)phenyl)cyclopropanecarboxamide (8)

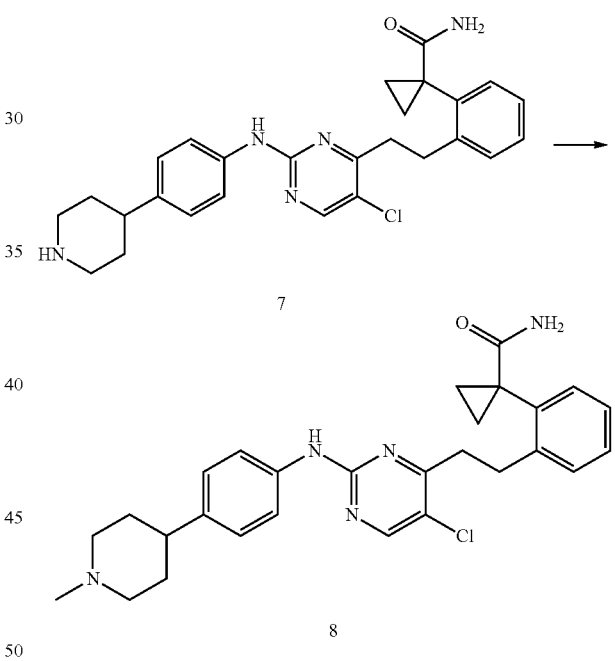

Formaldehyde (37 wt % in H₂O; 14 μL, 0.19 mmol) was added to a solution of 1-(2-(2-(5-chloro-2-((4-(piperidin-4-yl)phenyl)amino)pyrimidin-4-yl)ethyl)phenyl)cyclopropanecarboxamide (7) (30 mg, 63 μmol) in MeOH (5.0 mL) under an atmosphere of nitrogen. The resulting mixture was stirred for 10 minutes at room temperature before the addition of sodium triacetoxyborohydride (53 mg, 0.25 mmol). Stirring was continued for 2.5 hours at room temperature before the volatiles were removed in vacuo and the resulting residue was partitioned between EtOAc (20 mL) and saturated aqueous NaHCO₃ (20 mL). The layers were separated and the aqueous layer was extracted with EtOAc (2×20 mL). The combined organic layers were washed with brine (20 mL), dried over MgSO₄ and the volatiles evaporated in vacuo. The residue was dissolved in acetone (0.5 mL) and petroleum benzine 40-60° C. (25 mL) was added. The resulting green precipitate was isolated by filtration and dried under high vacuum to give the title compound 8 as a green solid (8 mg, 26%); ¹H NMR (400 MHz, CDCl$_3$) δ 8.18 (s, 1H), 7.41 (d, J=8.5 Hz, 2H), 7.34 (d, J=7.3 Hz, 1H), 7.30-7.23 (m, 3H), 7.12 (d, J=8.5 Hz, 2H), 5.55 (s, 1H), 5.25 (s, 1H), 3.13 (J m, 6H), 2.52-2.41 (m, 1H), 2.38 (s, 3H), 2.23 (t, J=11.8 Hz, 2H), 1.89 (dd, J=25.4, 12.3 Hz, 2H), 1.80 (d, J=12.3 Hz, 2H), 1.68 (s, 2H), 1.06 (s, 2H). LCMS-A: rt 4.611 min; m/z 491 [M+H]$^+$.

Example 9

Synthesis of 1-(2-(2-(5-chloro-2-((6-(trifluoromethyl)pyridin-3-yl)amino)pyrimidin-4-yl)ethyl)phenyl)cyclopropanecarboxamide (9)

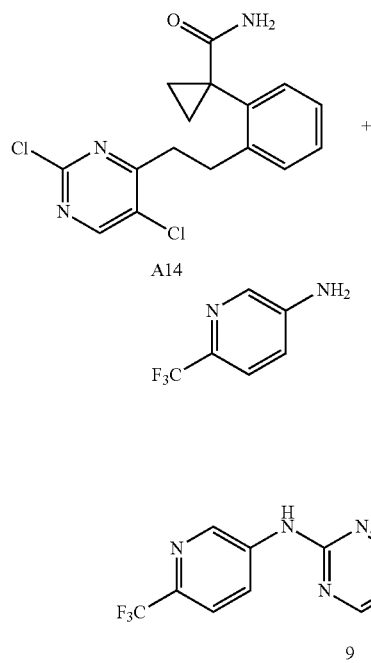

A suspension of 1-(2-(2-(2,5-dichloropyrimidin-4-yl)ethyl)phenyl)cyclopropanecarboxamide (A14) (150 mg, 446 μmol), Cs$_2$CO$_3$ (436 mg, 1.34 mmol) and 5-amino-2-trifluoromethylpyridine (145 mg, 892 μmol) in 1,4-dioxane (3 mL) was sonicated for 10 minutes. Xantphos (10.3 mg, 17.8 μmol) and Pd(OAc)$_2$ (2.00 mg, 8.92 μmol) were added and the resulting mixture was heated under microwave irradiation for 20 minutes at 120° C. The resulting mixture was adsorbed onto silica gel and purified by column chromatography (Biotage Isolera, 40 g SiO$_2$ cartridge, 0-100% EtOAc in petroleum benzine 40-60° C. then 0-40% MeOH in EtOAc). The purified solid was dissolved in acetone (0.2 mL) and petroleum benzene 40-60° C. (30 mL) added. The precipitate was collected by vacuum filtration and the filter cake dried under high vacuum to yield the title compound 9 as a tan solid (62 mg, 30%); $^1$H NMR (400 MHz, CDCl$_3$) δ 8.87 (d, J=2.6 Hz, 1H), 8.43-8.34 (m, 2H), 7.69 (d, J=8.7 Hz, 1H), 7.60 (s, 1H), 7.45 (d, J=8.2 Hz, 1H), 7.36 (dd, J=7.8, 3.1 Hz, 2H), 7.30 (d, J=4.9 Hz, 1H), 5.39 (d, J=8.9 Hz, 2H), 3.35-3.17 (m, 4H), 1.78 (s, 2H), 1.16 (s, 2H). LCMS-A: rt 4.816 min; m/z 462 [M+H]$^+$.

Example 10

Synthesis of 1-(2-(2-(5-(trifluoromethyl)-2-(6-(trifluoromethyl)pyridin-3-yl)amino)pyrimidin-4-yl)ethyl)phenyl)cyclopropanecarboxamide (10)

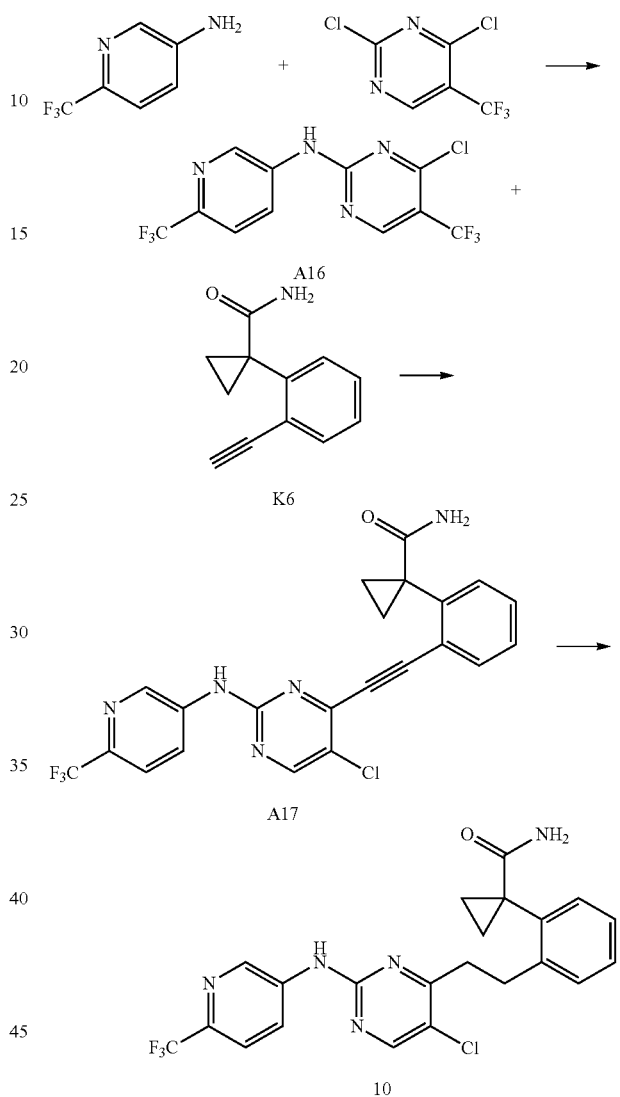

(a) 4-Chloro-5-(trifluoromethyl)-N-(6-(trifluoromethyl)pyridin-3-yl)pyrimidin-2-amine (A16)

A 1.0 M solution of zinc chloride in Et$_2$O (18.5 mL, 18.5 mmol) was added to a solution of 2,6-dichloro-5-trifluoromethylpyrimidine (2.81 g, 13.0 mmol) in t-BuOH/DCE (1:1, 50 mL) at 0° C. over a period of 20 minutes then the resulting mixture was stirred for 1 hour. A solution of 5-amino-2-trifluoromethylpyrimidine (2.00 g, 12.3 mmol) and DIPEA (3.22 mL, 18.5 mmol) in t-BuOH/DCE (1:1, 30 mL) was added over 20 minutes then the resulting mixture was stirred at room temperature for 4 days, before heating to 40° C. and stirred for a further 24 hours. The volatiles were removed under reduced pressure to give a solid residue. Water (100 mL) was added and the suspension sonicated for 30 minutes. The resulting mixture was extracted with EtOAc (3×100 mL) and CHCl$_3$ (100 mL). The organic extracts were combined, passed through a phase separation cartridge and the volatiles were evaporated under reduced pressure. The residue was purified by silica gel column chromatography (Biotage Isolera, 2×40 g SiO$_2$, 0-25% EtOAc in petroleum benzine 40-60°

C.) to give the title compound A16 as a white solid (1.78 g, 42%); $^1$H NMR (400 MHz, d$_6$-DMSO) δ 11.21 (s, 1H), 9.02 (d, J=2.5 Hz, 1H), 8.96-8.89 (m, 1H), 8.40 (dd, J=8.6, 2.2 Hz, 1H), 7.92 (d, J=8.6 Hz, 1H). LCMS-A: rt 5.931 min; m/z 343 [M+H]$^+$.

(b) 1-(2-((5-(Trifluoromethyl)-2-(6-(trifluoromethyl)pyridin-3-yl)amino)pyrimidin-4-yl)ethynyl)phenyl)cyclopropanecarboxamide (A17)

A solution of 1-(2-ethynylphenyl)cyclopropanecarboxamide (K6) (0.100 g, 0.540 mmol) in DMF (2.0 mL) was added to 4-chloro-5-(trifluoromethyl)-N-(6-(trifluoromethyl)pyridin-3-yl)pyrimidin-2-amine (A16) (0.185 g, 0.540 mmol), PdCl$_2$(PPh$_3$)$_2$ (0.019 g, 0.027 mmol), t-Bu$_3$PH.BF$_4$ (0.016 g, 0.054 mmol) and CuI (0.010 g, 0.054 mmol) under nitrogen. The mixture was degassed with nitrogen for 10 minutes then Et$_3$N (1.0 mL) was then added and the resulting mixture was heated under microwave irradiation at 120° C. for 15 minutes. The volatiles were removed under reduced pressure, the residue was adsorbed onto silica and purified by silica gel column chromatography (Biotage Isolera, 24 g silica cartridge, 0-100% EtOAc in petroleum benzine 40-60° C.) to give the title compound A17 as a yellow solid (0.157 g, 59%); $^1$H NMR (400 MHz, d$_6$-DMSO) δ 11.05 (s, 1H), 9.05-8.93 (m, 2H), 8.64 (d, J=6.3 Hz, 1H), 7.93 (d, J=8.7 Hz, 1H), 7.62 (dd, J=7.6, 0.9 Hz, 1H), 7.58-7.39 (m, 3H), 7.00 (s, 1H), 6.17 (s, 1H), 1.54 (q, J=3.8 Hz, 2H), 1.10-1.02 (m, 2H). LCMS-A: rt 5.851 min; m/z 492.2 [M+H]$^+$.

(c) 1-(2-(2-(5-(Trifluoromethyl)-2-(6-(trifluoromethyl)pyridin-3-yl)amino)pyrimidin-4-yl)ethyl)phenyl)cyclopropanecarboxamide (10)

A suspension of 10% Pd/C (0.145 g) and 1-(2-((5-(trifluoromethyl)-2-((6-(trifluoromethyl)pyridin-3-yl)amino)pyrimidin-4-yl)ethynyl)phenyl)cyclopropanecarboxamide (A17) (0.157 g, 0.320 mmol) in Et$_3$N (1 mL) and DMF (10 mL) was stirred under an atmosphere of hydrogen for 16 hours at 40° C. The resulting mixture was filtered through Celite and the filtrate concentrated under reduced pressure. The residue was adsorbed onto silica gel and purified by silica gel column chromatography (Biotage Isolera, 24 g SiO$_2$ cartridge, 0-55% EtOAc in petroleum benzine 40-60° C.) to give the title compound 10 as a white solid (0.108 g, 68%); $^1$H NMR (400 MHz, d$_6$-DMSO) δ 10.84 (s, 1H), 9.01 (d, J=2.2 Hz, 1H), 8.84 (s, 1H), 8.58 (dd, J=8.6, 2.1 Hz, 1H), 7.93 (d, J=8.7 Hz, 1H), 7.40-7.28 (m, 3H), 7.27-7.19 (m, 1H), 7.01 (s, 1H), 6.04 (s, 1H), 3.27-3.08 (m, 4H), 1.44 (d, J=3.4 Hz, 2H), 1.02-0.91 (m, 2H). LCMS-A: rt 5.959 min; m/z 496 [M+H]$^+$.

Example 11

Synthesis of 1-(2-(2-(5-chloro-2-(oxazol-2-ylamino)pyrimidin-4-yl)ethyl)phenyl)cyclopropanecarboxamide (11)

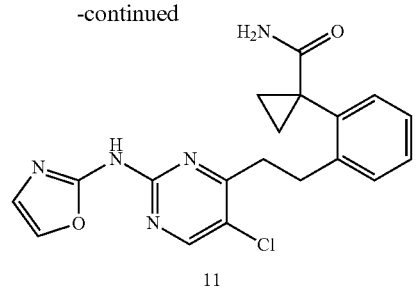

1-(2-(2-(5-Chloro-2-(oxazol-2-ylamino)pyrimidin-4-yl)ethyl)phenyl)cyclopropanecarboxamide (11)

A suspension of 1-(2-(2-(2,5-dichloropyrimidin-4-yl)ethyl)phenyl)cyclopropanecarboxamide A14 (0.150 g, 0.446 mmol), Cs$_2$CO$_3$ (436 mg, 1.34 mmol) and 2-aminoxazole (75.0 mg, 0.892 mmol) in 1,4-dioxane (3 mL) was sonicated for 10 minutes. Xantphos (10 mg, 18 μmol) and Pd(II) acetate (2.0 mg, 8.9 μmol) were added and the reaction was irradiated in the microwave for 20 minutes at 120° C. The resulting mixture was adsorbed onto silica gel and purified by column chromatography (Biotage Isolera, 24 g SiO$_2$ cartridge, 0-100% EtOAc in cyclohexane then 0-20% MeOH in EtOAc) to give a solid. Acetone (0.5 mL) followed by cyclohexane (25 mL) was added and the mixture was sonicated for 10 minutes. The resulting precipitate was collected by filtration and the filter cake was washed with cyclohexane (25 mL) and dried under high vacuum to give the title compound 11 as a white solid (10 mg, 6%). LCMS-B: rt 4.64 min; m/z 384.0 [M+H]$^+$.

Example 12

Synthesis of 1-(2-(2-(5-chloro-2-(pyrimidin-5-ylamino)pyrimidin-4-yl)ethyl)phenyl)cyclopropanecarboxamide (12)

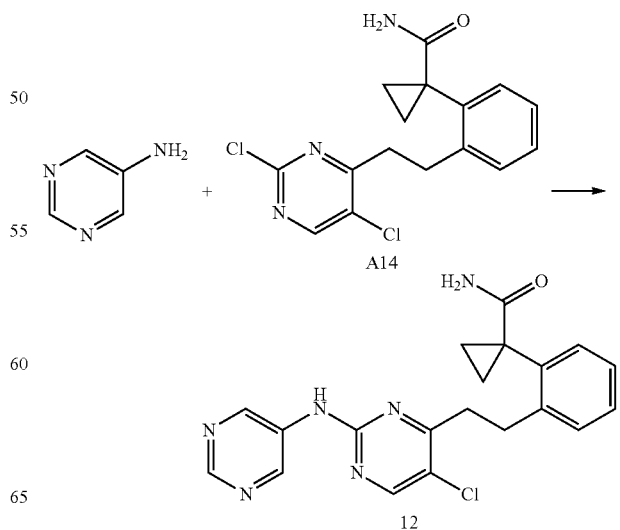

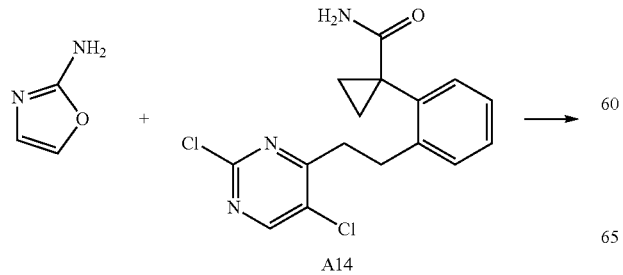

1-(2-(2-(5-Chloro-2-(pyrimidin-5-ylamino)pyrimidin-4-yl)ethyl)phenyl)cyclopropanecarboxamide (12)

A suspension of 1-(2-(2-(2,5-dichloropyrimidin-4-yl)ethyl)phenyl)cyclopropanecarboxamide A14 (0.100 g, 0.297 mmol), Cs₂CO₃ (0.291 g, 0.892 mmol) and 5-aminopyrimidine (56.6 mg, 0.595 mmol) in 1,4-dioxane (3 mL) was sonicated for 10 minutes. Xantphos (6.9 mg, 12 μmol) and Pd(II) acetate (1.3 mg, 5.9 μmol) were added and the reaction was irradiated in the microwave at 120° C. for 20 minutes. The resulting mixture was adsorbed onto silica gel and purified by column chromatography (Biotage Isolera, 40 g SiO₂ cartridge, 0-100% EtOAc in petroleum benzine 40-60° C. then 0-40% MeOH in EtOAc) to give a solid which was suspended in 0.5 M aqueous citric acid (50 mL) and sonicated for 10 minutes. The precipitate was collected by filtration and the filter cake was washed with 2 M aqueous NaOH (100 mL), cyclohexane (100 mL) and air dried to give the title compound 12 as a yellow solid (25 mg, 21%). LCMS-B: rt 4.89 min; m/z 395.0 [M+H]⁺.

Example 13

Synthesis of 1-(2-(2-(5-Chloro-2-((1-methyl-1H-pyrazol-4-yl)amino)pyrimidin-4-yl)ethyl)phenyl)cyclopropanecarboxamide (13)

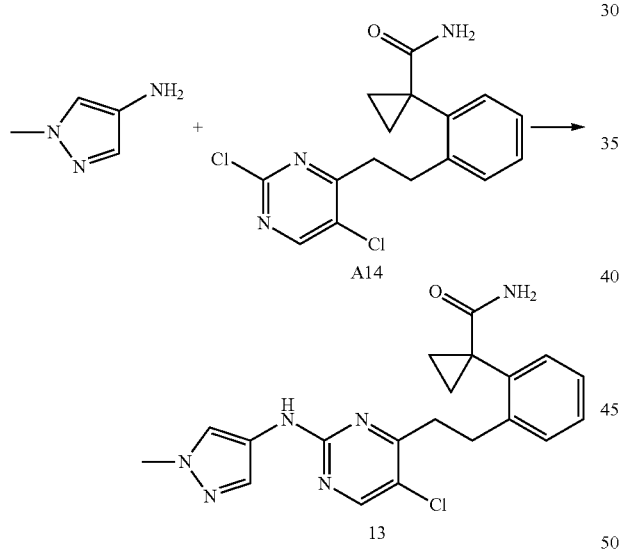

1-(2-(2-(5-Chloro-2-((1-methyl-1H-pyrazol-4-yl)amino)pyrimidin-4-yl)ethyl)phenyl)cyclopropanecarboxamide (13)

A solution of 1-(2-(2-(2,5-dichloropyrimidin-4-yl)ethyl)phenyl)cyclopropanecarboxamide A14 (1.50 g, 4.46 mmol) in 1,4-dioxane (25 mL) containing 4-amino-1-methylpyrazole (0.520 g, 5.35 mmol) and p-toluenesulfonic acid (0.085 g, 0.45 mmol) was heated under microwave irradiation at 120° C. for 7 hours. The volatiles were removed in vacuo and the residue was adsorbed onto silica gel and the product was separated using silica column chromatography (Combiflash Rf, 40 g SiO₂ Cartridge, 60-100% EtOAc in cyclohexane and then 0-5% MeOH in DCM) to give the title compound 13 as a light orange foam (1.01 g, 56%). ¹H NMR (300 MHz, d6-DMSO) δ 9.64 (s, 1H), 8.37 (s, 1H), 7.87 (s, 1H), 7.46 (s, 1H), 7.22-7.36 (m, 4H), 7.00 (brs, 1H), 6.01 (brs, 1H), 3.81 (s, 3H), 3.09 (brs, 4H), 1.45-1.44 (m, 2H), 1.00-0.99 (m, 2H). LCMS-B: rt 6.318 min; m/z 397 [M+H]⁺.

Example 14

Synthesis of 1-(2-(2-(2-((1-(azetidin-3-yl)-1H-pyrazol-4-yl)amino)-5-chloropyrimidin-4-yl)ethyl)phenyl)cyclopropanecarboxamide (14)

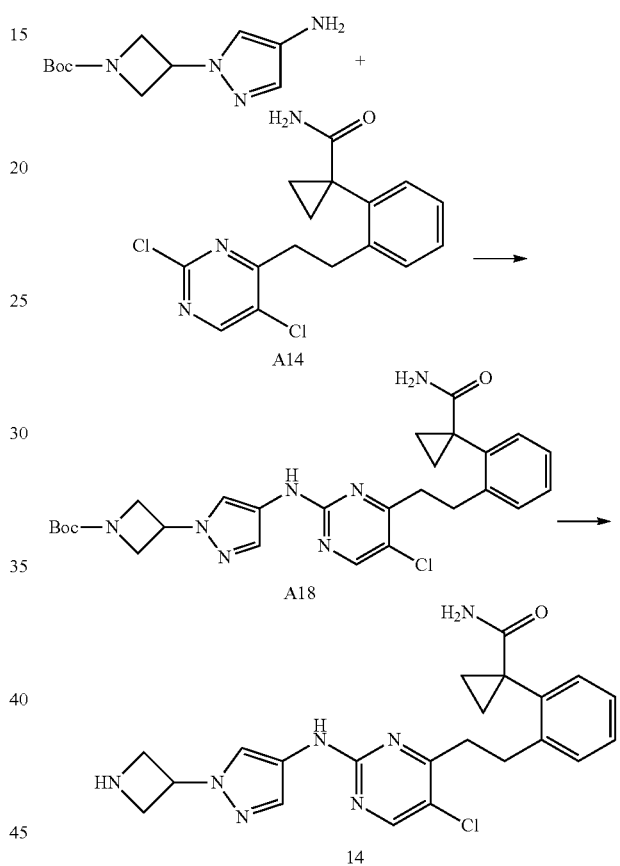

(a) tert-Butyl 3-(4-((4-(2-(1-carbamoylcyclopropyl)phenethyl)-5-chloropyrimidin-2-yl)amino)-1H-pyrazol-1-yl)azetidine-1-carboxylate (A18)

A suspension of 1-(2-(2-(2,5-dichloropyrimidin-4-yl)ethyl)phenyl)cyclopropanecarboxamide A14 (0.100 g, 0.297 mmol), Cs₂CO₃ (0.291 g, 0.892 mmol) and tert-butyl 3-(4-amino-1H-pyrazol-1-yl)azetidine-1-carboxylate (0.142 g, 0.595 mmol) in dioxane (3 mL) was sonicated for 10 minutes. Xantphos (6.9 mg, 12 μmol) and Pd(II) acetate (1.3 mg, 5.9 μmol) were added to the suspension and the mixture was irradiated in the microwave for 20 minutes at 120° C. The resulting mixture was adsorbed onto silica gel and purified by column chromatography (Biotage Isolera, 24 g SiO₂ cartridge, 0-100% EtOAc in petroleum benzine 40-60° C. then 0-40% MeOH in EtOAc) to give the title compound A18 as a yellow oil (110 mg, 69%). LCMS-A: rt 6.349 min; m/z 538.3 [M+H]⁺.

(b) 1-(2-(2-(2-((1-(Azetidin-3-yl)-1H-pyrazol-4-yl)amino)-5-chloropyrimidin-4-yl)ethyl)phenyl)cyclopropanecarboxamide (14)

TFA (1 mL) was added to a solution of tert-butyl 3-(4-((4-(2-(1-carbamoylcyclopropyl)phenethyl)-5-chloropyrimidin-2-yl)amino)-1H-pyrazol-1-yl)azetidine-1-carboxylate A18 (0.110 g, 0.204 mmol) in DCM (5 mL) and the reaction was stirred for 16 hours. The volatiles were removed in vacuo and the resultant residue loaded onto an SCX cartridge (5 g). The cartridge was washed with MeOH (100 mL) and then with 5% NH$_4$OH in MeOH (100 mL). The basic fractions were combined and the solvent was removed in vacuo to give the title compound 14 as a tan solid (61 mg, 68%). $^1$H NMR (400 MHz, d$_4$-MeOD) δ 8.27 (s, 1H), 8.09 (s, 1H), 7.65 (s, 1H), 7.44-7.37 (m, 2H), 7.34 (m, 1H), 7.27 (m, 1H), 5.36-5.18 (m, 1H), 4.15 (m, 2H), 3.96 (m, 2H), 3.20 (m, 4H), 1.63 (m, 2H), 1.20-1.05 (m, 2H). LCMS-C: rt 4.30 min; m/z 438.0 [M+H]$^+$.

Example 15

Synthesis of 1-(2-(2-(5-chloro-2-((6-(piperidin-4-yl)pyridin-3-yl)amino)pyrimidin-4-yl)ethyl)phenyl)cyclopropanecarboxamide (15)

(a) tert-Butyl 4-(5-((4-(2-(1-carbamoylcyclopropyl)phenethyl)-5-chloropyrimidin-2-yl)amino)pyridin-2-yl)piperidine-1-carboxylate (A19)

A suspension of 1-(2-(2-(2,5-dichloropyrimidin-4-yl)ethyl)phenyl)cyclopropanecarboxamide A14 (0.150 g, 0.446 mmol), Cs$_2$CO$_3$ (0.436 g, 1.34 mmol) and tert-butyl 4-(5-aminopyridin-2-yl)piperidine-1-carboxylate 19 (247 mg, 0.892 mmol) in 1,4-dioxane (3 mL) was sonicated for 10 minutes. Xantphos (10 mg, 18 µmol) and Pd(II) acetate (2.0 mg, 8.9 µmol) were added and the mixture was irradiated in the microwave at 120° C. for 20 minutes. The mixture was adsorbed onto silica gel and purified by column chromatography (Biotage Isolera, 24 g SiO$_2$ cartridge, 0-100% EtOAc in cyclohexane) to give the title compound A19 as a yellow oil (79 mg, 31%). LCMS-C: rt 4.92 min; m/z 577.0 [M+H]$^+$.

(b) 1-(2-(2-(5-Chloro-2-((6-(piperidin-4-yl)pyridin-3-yl)amino)pyrimidin-4-yl)ethyl)phenyl)cyclopropanecarboxamide (15)

TFA (1 mL) was added to a solution of tert-butyl 4-(5-((4-(2-(1-carbamoylcyclopropyl)phenethyl)-5-chloropyrimidin-2-yl)amino)pyridin-2-yl)piperidine-1-carboxylate A19 (79.0 mg, 0.137 mmol) in DCM (5 mL) and stirred for 16 hours. The volatiles were removed in vacuo and the resultant residue loaded onto an SCX cartridge (5 g). The cartridge was washed with MeOH (100 mL) and then with 5% NH$_4$OH in MeOH (100 mL). The basic fractions were combined and the solvent was removed in vacuo to give the title compound 15 as a white solid (50 mg, 77%). $^1$H NMR (400 MHz, d$_4$-MeOD) δ 8.74 (s, 1H), 8.36 (s, 1H), 8.21 (dd, J=8.6, 2.7 Hz, 1H), 7.45-7.22 (m, 5H), 3.30-3.17 (m, 6H), 2.95-2.80 (m, 3H), 1.99-1.96 (m, 2H), 1.86-1.76 (m, 2H), 1.64-1.63 (m, 2H), 1.19-1.07 (m, 2H). LCMS-C: rt 4.17 min; m/z 477.1 [M+H]$^+$.

Example 16

Synthesis of 1-(2-(2-(5-chloro-2-(5-(1-methylpiperidin-3-yl)pyridin-3-ylamino)pyrimidin-4-yl)ethyl)phenyl)cyclopropanecarboxamide (16)

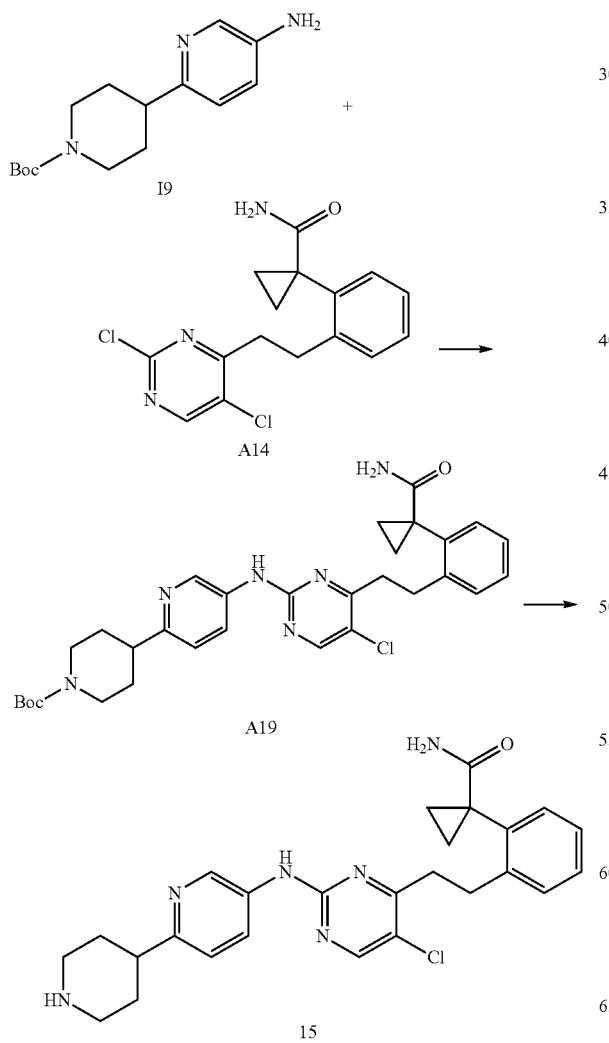

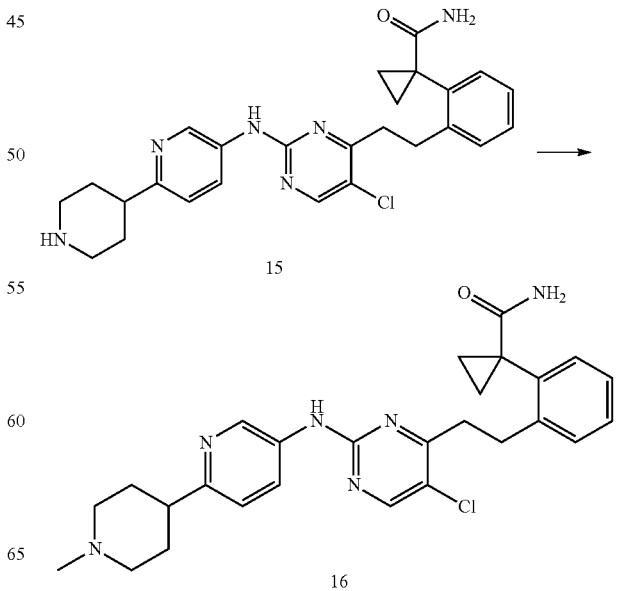

1-(2-(2-(5-Chloro-2-(5-(1-methylpiperidin-3-yl)pyridin-3-ylamino)pyrimidin-4-yl)ethyl)phenyl)cyclopropanecarboxamide (16)

Formaldehyde (32.8 µL, 0.440 mmol, 37 wt % in H₂O) was added to a suspension of 1-(2-(2-(5-chloro-2-((6-(piperidin-4-yl)pyridin-3-yl)amino)pyrimidin-4-yl)ethyl)phenyl)cyclopropanecarboxamide 15 (42.0 mg, 0.088 mmol) in MeOH (1.10 mL) under an atmosphere of nitrogen. Sodium triacetoxyborohydride (187 mg, 0.881 mmol) was then added in one portion and the mixture was stirred at room temperature overnight. The volatiles were removed in vacuo and the residue was diluted with EtOAc (10 mL) and sat. aq. NaHCO₃ (10 mL). The layers were separated and the aqueous layer was extracted with EtOAc (2×15 mL). The combined organic layers were washed with water (20 mL) and brine (20 mL) and dried over Na₂SO₄. The solvent was removed under reduced pressure to yield a white solid which was purified by prep-LCMS to give the title compound 16 as a white solid (5.90 mg, 14%). ¹H NMR (300 MHz, CDCl₃) δ 8.69 (brs, 1H), 8.28 (s, 1H), 8.10 (dd, J=8.47, 2.53 Hz, 1H), 7.55-7.62 (m, 1H), 7.43 (d, J=7.04 Hz, 1H), 7.32-7.36 (m, 2H), 7.20-7.32 (m, 1H), 5.94 (brs, 1H), 5.40 (brs, 1H), 3.32-3.42 (m, 4H), 3.22-3.32 (m, 2H), 3.12-3.21 (m, 2H), 2.80-2.92 (m, 1H), 2.59-2.73 (m, 3H), 2.05-2.33 (m, 4H), 1.72-1.79 (m, 2H), 1.10-1.17 (m, 2H). LCMS-C: rt 5.08 min; m/z 491.3 [M+H]⁺.

Example 17

Synthesis of 1-(2-(2-(5-chloro-2-((1-(piperidin-4-yl)-1H-pyrazol-4-yl)amino)pyrimidin-4-yl)ethyl)phenyl)cyclopropanecarboxamide (17)

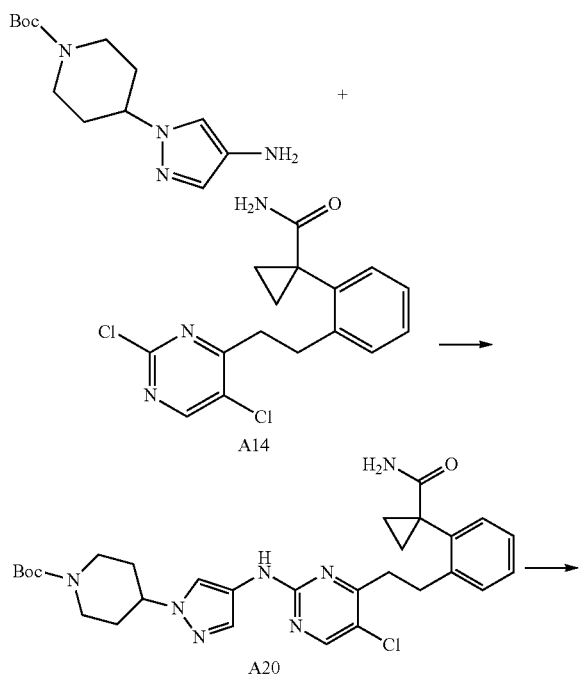

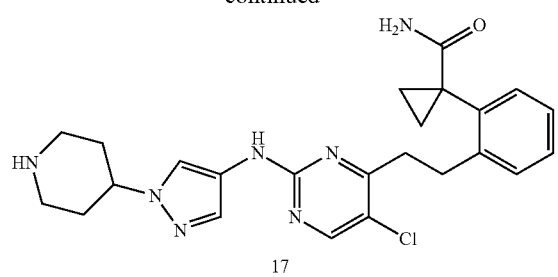

(a) tert-Butyl 4-(4-((4-(2-(1-carbamoylcyclopropyl)phenethyl)-5-chloropyrimidin-2-yl)amino)-1H-pyrazol-1-yl)piperidine-1-carboxylate (A20)

A suspension of 1-(2-(2-(2,5-dichloropyrimidin-4-yl)ethyl)phenyl)cyclopropanecarboxamide A14 (0.100 g, 0.297 mmol), Cs₂CO₃ (0.291 g, 0.892 mmol) and tert-butyl 4-(4-amino-1H-pyrazol-1-yl)piperidine-1-carboxylate (0.158 g, 0.595 mmol) in 1,4-dioxane (2 mL) was sonicated for 10 minutes. Xantphos (6.9 mg, 12 µmol) and Pd(II) acetate (1.3 mg, 5.9 µmol) were added and the mixture was irradiated in the microwave at 120° C. for 20 minutes. The mixture was adsorbed onto silica gel and purified by column chromatography (Biotage Isolera, 40 g SiO₂ cartridge, 0-100% EtOAc in cyclohexane then 0-10% MeOH in EtOAc) to give the title compound A20 as a brown solid (21 mg, 12%). LCMS-C: rt 5.54 min; m/z 565.9 [M+H]⁺.

(b) 1-(2-(2-(5-Chloro-2-((1-(piperidin-4-yl)-1H-pyrazol-4-yl)amino)pyrimidin-4-yl)ethyl)phenyl)cyclopropanecarboxamide (17)

TFA (1 mL) was added to a solution of tert-butyl 4-(4-((4-(2-(1-carbamoylcyclopropyl)phenethyl)-5-chloropyrimidin-2-yl)amino)-1H-pyrazol-1-yl)piperidine-1-carboxylate A20 (0.021 g, 0.037 mmol) in DCM (5 mL) and the mixture was stirred for 16 hours. The volatiles were removed in vacuo and the resultant residue loaded onto a SCX cartridge (5 g). The cartridge was washed with MeOH (100 mL) and then with 5% NH₄OH in MeOH (100 mL). The basic fractions were combined, the solvent was removed in vacuo and the resultant residue purified by prep-LCMS to give the title compound 17 as a yellow solid (3.6 mg, 21%). LCMS-B: rt 4.711 min; m/z 466.2 [M+H]⁺.

Example 18

Synthesis of 1-(2-(2-(5-chloro-2-((1-(1-methylpiperidin-4-yl)-1H-pyrazol-4-yl)amino)pyrimidin-4-yl)ethyl)phenyl)cyclopropanecarboxamide (18)

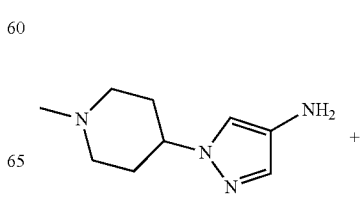

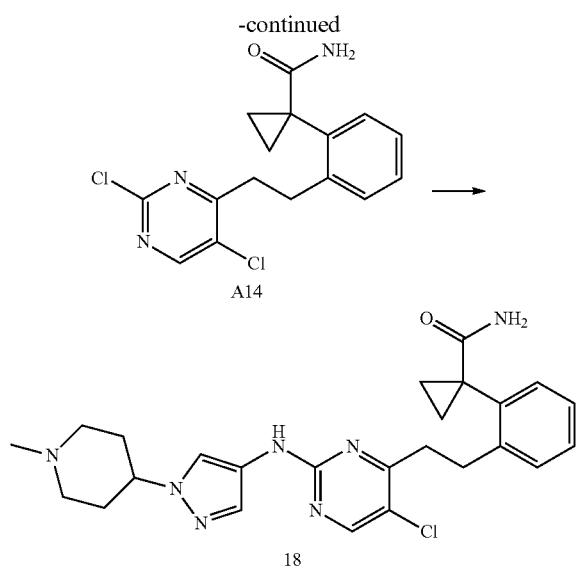

1-(2-(2-(5-Chloro-2-((1-(1-methylpiperidin-4-yl)-1H-pyrazol-4-yl)amino)pyrimidin-4-yl)ethyl)phenyl)cyclopropanecarboxamide (DGG_011_20_06) (CTX-0358024)

A solution of 1-(2-(2-(2,5-dichloropyrimidin-4-yl)ethyl)phenyl)cyclopropanecarboxamide A14 (0.060 g, 0.21 mmol) in MeOH (1.0 mL) and water (0.1 mL) containing 1-(1-methylpiperidin-4-yl)-1H-pyrazol-4-amine (0.039 g, 0.21 mmol) was heated at 70° C. for 48 hours. The mixture was adsorbed onto silica gel and purified by silica column chromatography (Combiflash Rf, 4 g SiO₂ Cartridge, 0-50% MeOH in DCM). Further purification by HPLC (eluting with 30-100% gradient in acetonitrile containing 0.1% formic acid and water containing 0.1% formic acid, flow rate 4.0 mL/min) gave the title compound 18 as a light yellow solid (0.015 g, 17%). LCMS-C: rt 4.31 min; m/z 480 [M+H]⁺.

Example 19

Synthesis of 1-(2-(2-(2-(1H-pyrazol-4-ylamino)-5-chloropyrimidin-4-yl)ethyl)phenyl)cyclopropanecarboxamide (19)

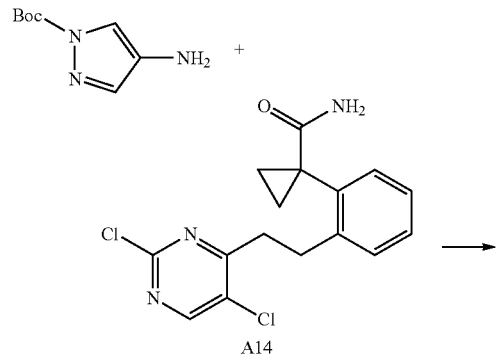

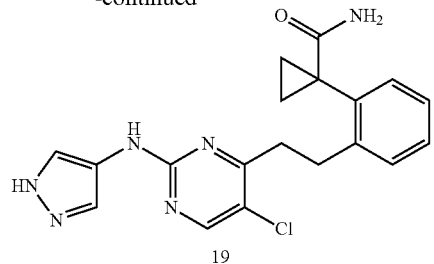

1-(2-(2-(2-(1H-Pyrazol-4-ylamino)-5-chloropyrimidin-4-yl)ethyl)phenyl)cyclopropanecarboxamide (19)

A solution of 1-(2-(2-(2,5-dichloropyrimidin-4-yl)ethyl)phenyl)cyclopropanecarboxamide A14 (0.070 g, 0.21 mmol) and tert-butyl 4-amino-1H-pyrazole-1-carboxylate (0.11 g, 0.63 mmol) was stirred in MeOH:water (10:1 ratio, 4 mL) at 70° C. for 2 hours and then at 90° C. for 16 hours. The volatiles were removed in vacuo and the residue was purified by silica gel column chromatography (Combiflash Rf, 0-15% MeOH in DCM) to give the title compound 19 as a light yellow solid (0.015 g, 19%). ¹H NMR (300 MHz, d₆-DMSO) δ 0.93-1.02 (m, 2H), 1.38-1.49 (m, 2H), 3.04-3.16 (m, 4H), 6.03 (brs, 1H), 6.98 (brs, 1H), 7.18-7.39 (m, 4H), 7.48-7.72 (m, 1H), 7.79-8.00 (m, 1H), 8.37 (s, 1H), 9.62 (s, 1H). LCMS-C: rt 4.92 min; m/z 383 [M+H]⁺.

Example 20

Synthesis of 1-(2-(2-(5-chloro-2-(1-(pyrrolidin-3-yl)-1H-pyrazol-4-ylamino)pyrimidin-4-yl)ethyl)phenyl)cyclopropanecarboxamide (20)

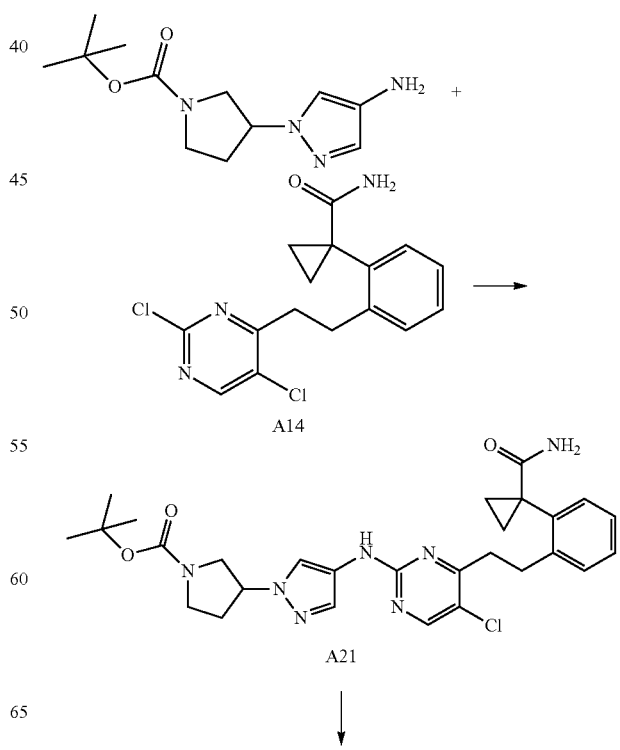

117

-continued

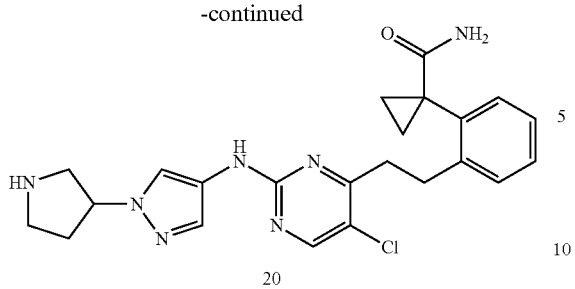

20

(a) tert-Butyl 3-(4-(4-(2-(1-carbamoylcyclopropyl) phenethyl)-5-chloropyrimidin-2-ylamino)-1H-pyrazol-1-yl)pyrrolidine-1-carboxylate (A21)

A stirred solution of 1-(2-(2-(2,5-dichloropyrimidin-4-yl) ethyl)phenyl)cyclopropanecarboxamide A14 (0.150 g, 0.446 mmol), 4-amino-1-(1-Boc-pyrrolidin-3-yl)-1H-pyrazole (0.225 g, 0.892 mmol) in MeOH (10 mL) and water (1.0 mL) was heated at 70° C. for 2 days. Additional 4-amino-1-(1-boc-pyrrolidin-3-yl)-1H-pyrazole (0.125 g, 0.446 mmol) was added and the mixture was heated for a further 16 hours at reflux. After cooling the solvent was removed to afford a crude red oil which was purified by silica gel column chromatography (0-100% EtOAc in cyclohexane) to give the title compound A21 as a red oil (0.164 g, 67% yield). LCMS-C: rt 5.51 min; m/z 551.9 [M+H]$^+$.

(b) 1-(2-(2-(5-Chloro-2-(1-(pyrrolidin-3-yl)-1H-pyrazol-4-ylamino)pyrimidin-4-yl)ethyl)phenyl) cyclopropanecarboxamide (20)

To a stirred solution of tert-butyl 3-(4-(4-(2-(1-carbamoylcyclopropyl)phenethyl)-5-chloropyrimidin-2-ylamino)-1H-pyrazol-1-yl)pyrrolidine-1-carboxylate A21 (0.164 g, 0.297 mmol) in DCM (5 mL) was added 4 M HCl solution in 1,4-dioxane (0.223 mL). The mixture was stirred for 5 hours before additional 4 M HCl in dioxane (3 eq.) was added and the mixture stirred for another 16 hours. Another portion of 4 M HCl in 1,4-dioxane (2 mL) was added and the mixture was stirred for 16 hours. The solvent was removed and the residue was diluted with 1 M HCl aq. (~5 mL) and washed with EtOAc (2×10 mL). The aqueous layer was basified with 1 M NaOH and extracted with EtOAc (3×10 mL). The combined organics were dried (MgSO$_4$), filtered and concentrated in vacuo to give a crude white paste that was purified by flash chromatography (0-100% EtOAc in cyclohexane) to give the title compound as a red oil. Further purification by HPLC (Gradient: 20-100%, Acetonitrile 0.1% formic acid in water 0.1% formic acid, 12 min) gave the title compound 20 as a clear gum (0.012 g, 9% yield). $^1$H NMR (300 MHz, MeOD) δ 1.14 (d, J=3.30 Hz, 2H), 1.64 (d, J=3.30 Hz, 2H), 2.32-2.44 (m, 1H), 2.46-2.65 (m, 1H), 3.12-3.26 (m, 4H), 3.43-3.54 (m, 1H), 3.60-3.80 (m, 3H), 5.21-5.32 (m, 1H), 7.23-7.45 (m, 4H), 7.64 (s, 1H), 8.08 (m, 1H), 8.29 (m, 1H). LCMS-C: rt 4.29 min; m/z 452 [M+H]$^+$.

118

Example 21

Synthesis of 1-(2-(2-(5-chloro-2-(1-(1-methylpyrrolidin-3-yl)-1H-pyrazol-4-ylamino)pyrimidin-4-yl) ethyl)phenyl)cyclopropanecarboxamide (21)

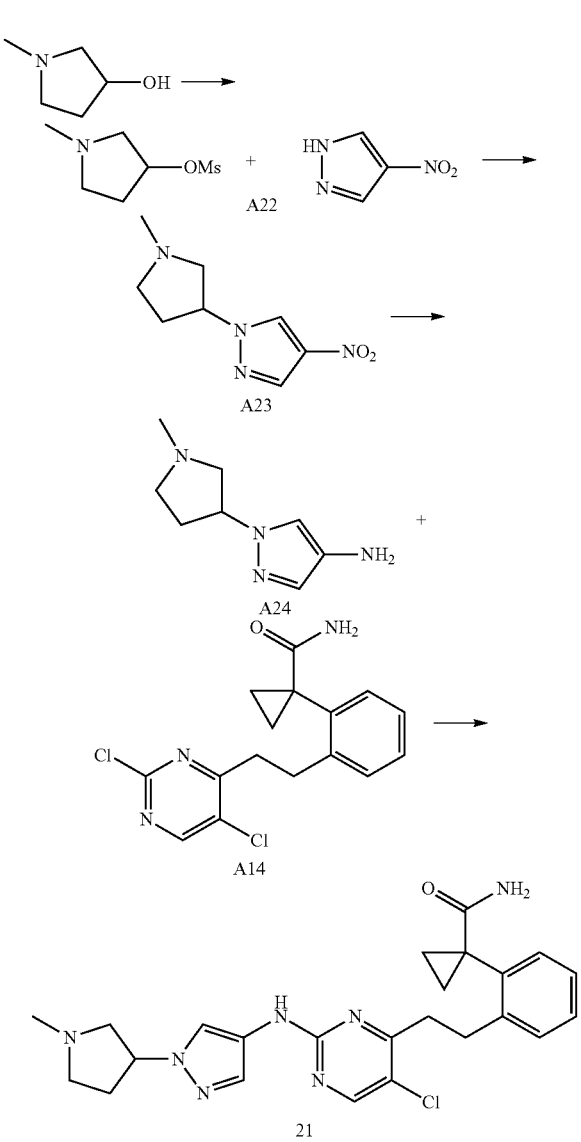

(a) 1-Methylpyrrolidin-3-yl methanesulfonate (A22)

3-Hydroxy-1-methylpyrroldine (0.543 mL, 4.94 mmol) was dissolved in DCM (10 mL) and cooled to 0° C. Et$_3$N (0.827 mL, 5.93 mmol), methanesulfonyl chloride (0.421 mL, 5.44 mmol) and DMAP (0.006 g, 0.05 mmol) were added and the mixture was stirred for 16 hours at room temperature. The mixture was diluted with CHCl$_3$ (5 mL) and washed with sat. NaHCO$_3$ (5 mL) and water (2×5 mL). The organic layer was concentrated in vacuo to give the title compound A22 as a yellow oil (0.717 g, 81% yield). $^1$H NMR (300 MHz, CDCl$_3$) δ 1.85-2.24 (m, 6H), 2.38-2.74 (m, 3H), 2.76-2.91 (m, 3H), 4.95 (m, 1H).

(b) 1-(1-Methylpyrrolidin-3-yl)-4-nitro-1H-pyrazole (A23)

4-Nitro-1H-pyrazole (0.452 g, 4.00 mmol) was dissolved in DMF (8 mL) and cooled to 0° C. NaH (0.192 g, 60% dispersion in oil, 4.80 mmol) was added and the mixture was stirred for 10 minutes. 1-Methylpyrrolidin-3-yl methanesulfonate A22 (0.717 g, 4.00 mmol) was added and the mixture was stirred for 16 hours at 100° C. The mixture was diluted with EtOAc (5 mL) and washed with sat. NH$_4$Cl (5 mL) and water (4×5 mL). The organics were concentrated in vacuo affording a crude pale yellow oil which was purified by flash chromatography (0-30% MeOH in DCM) to give the title compound A23 as a pale yellow oil (0.575 g, 73% yield). LCMS-B: rt 1.12 min; m/z 197 [M+H]$^+$.

(c) 1-(1-Methylpyrrolidin-3-yl)-1H-pyrazol-4-amine (A24)

A solution of 1-(1-methylpyrrolidin-3-yl)-4-nitro-1H-pyrazole A23 (0.575 g, 2.93 mmol) and 10% Pd/C (0.061 g) in EtOH (15 mL) was stirred under a hydrogen atmosphere for 16 hours. The reaction mixture was filtered through Celite and the solvent was removed in vacuo to give the title compound A24 as a red oil (0.555 g, quantitative). $^1$H NMR (300 MHz, MeOD) δ 2.27-2.42 (m, 1H), 2.72-2.76 (m, 2H), 3.02-3.10 (m, 1H), 3.46-3.55 (m, 1H), 3.70-3.85 (m, 4H), 5.14-5.26 (m, 1H), 7.33 (s, 1H), 7.46 (m, 1H).

(d) 1-(2-(2-(5-Chloro-2-(1-(1-methylpyrrolidin-3-yl)-1H-pyrazol-4-ylamino)pyrimidin-4-yl)ethyl)phenyl)cyclopropanecarboxamide (21)

A stirred solution of 1-(2-(2-(2,5-dichloropyrimidin-4-yl)ethyl)phenyl)cyclopropanecarboxamide A14 (0.085 g, 0.25 mmol), 1-(1-methylpyrrolidin-3-yl)-1H-pyrazol-4-amine A24 (0.046 g, 0.278 mmol) and TsOH (0.003 g, 0.02 mmol) in 1,4-dioxane (4 mL) was stirred at 120° C. in the microwave for 60 minutes followed by 150° C. for 2 hours and then 160° C. for 2 hours. After cooling, the solvent was removed to afford a crude red oil that was purified by flash chromatography (0-30% MeOH in DCM) followed by HPLC (Gradient: 20-100%, Acetonitrile 0.1% formic acid in water 0.1% formic acid, 12 min) to give the title compound 21 as a clear gum (0.008 g, 7% yield). LCMS-C: rt 4.34 min; m/z 466 [M+H]$^+$.

Example 22

Synthesis of 1-(2-(2-(5-chloro-2-(pyridazin-4-ylamino)pyrimidin-4-yl)ethyl)phenyl)cyclopropanecarboxamide (22)

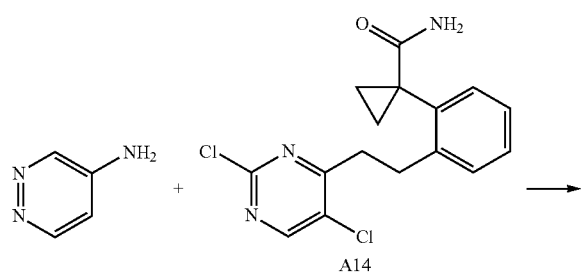

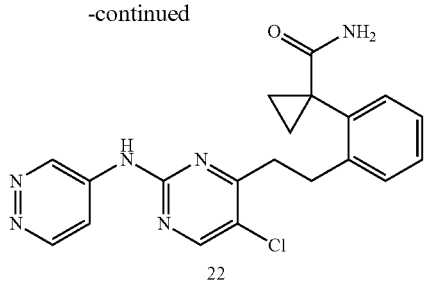

(a) 1-(2-(2-(5-Chloro-2-(pyridazin-4-ylamino)pyrimidin-4-yl)ethyl)phenyl)cyclopropanecarboxamide (22)

A mixture of 1-(2-(2-(2,5-dichloropyrimidin-4-yl)ethyl)phenyl)cyclopropanecarboxamide A14 0.080 g, 0.24 mmol), 4-aminopyridazine (0.045 g, 0.48 mmol), Xantphos (0.0055 g, 0.010 mmol) and Cs$_2$CO$_3$ (0.23 g, 0.71 mmol) in 1,4-dioxane (4 mL) was bubbled with nitrogen for 10 minutes. Palladium(II) acetate (0.0011 g, 0.0049 mmol) was added and the mixture was heated in the microwave at 120° C. for 25 minutes. The volatiles were removed in vacuo and the residue was purified by silica gel column chromatography (Combiflash Rf, 0-15% MeOH in DCM) to give the title compound 22 as a light yellow solid (0.010 g, 11%). LCMS-C: rt 4.34 min; m/z 395 [M+H]$^+$.

Example 23

Synthesis of 1-(2-(2-(5-chloro-2-(phenylamino)pyrimidin-4-yl)ethyl)phenyl)cyclopropanecarboxamide (23)

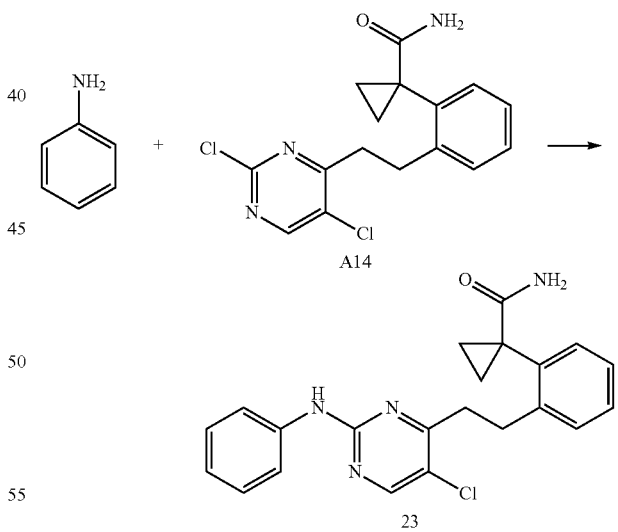

(a) 1-(2-(2-(5-Chloro-2-(phenylamino)pyrimidin-4-yl)ethyl)phenyl)cyclopropanecarboxamide (23)

A solution of 1-(2-(2-(2,5-dichloropyrimidin-4-yl)ethyl)phenyl)cyclopropanecarboxamide A14 (0.080 g, 0.24 mmol) in 1,4-dioxane (1.0 mL) containing aniline (0.043 mL, 0.48 mmol) and p-toluenesulfonic acid (4.5 mg, 0.024 mmol) was heated under microwave irradiation at 120° C. for 4 hours. The reaction mixture was adsorbed onto silica gel and purified by silica column chromatography (Combiflash Rf, 12 g SiO$_2$ Cartridge, 20-50% EtOAc in cyclohexane) to give the title product 23 as a light yellow foam (0.044 g, 46%). LCMS-B: rt 7.718 min; m/z 393 [M+H]$^+$.

Example 24

Synthesis of tert-Butyl (1-(4-((4-(2-(1-carbamoylcyclopropyl)phenethyl)-5-chloropyrimidin-2-yl)amino) phenyl)ethyl)carbamate (24)

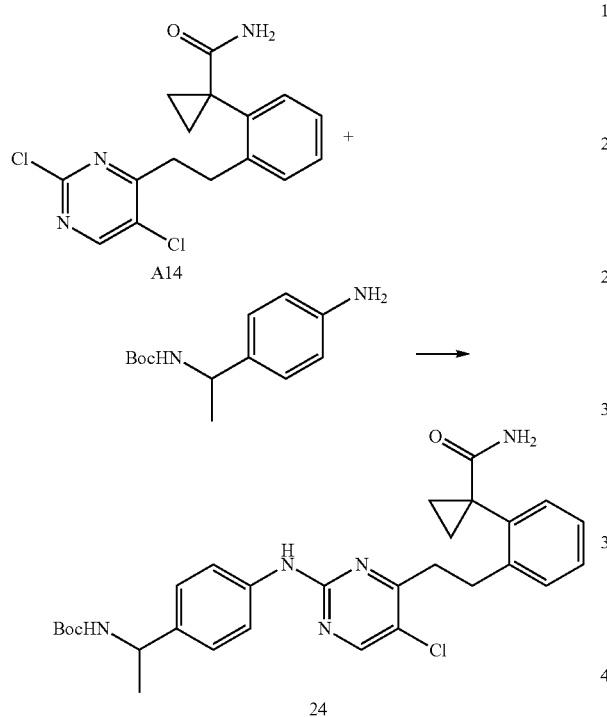

tert-Butyl (1-(4-((4-(2-(1-carbamoylcyclopropyl) phenethyl)-5-chloropyrimidin-2-yl)amino)phenyl) ethyl)carbamate (24)

A mixture of 1-(2-(2-(2,5-dichloropyrimidin-4-yl)ethyl) phenyl)cyclopropanecarboxamide A14 (0.080 g, 0.24 mmol), tert-butyl 1-(4-aminophenyl)ethylcarbamate (0.067 g, 0.29 mmol), Xantphos (0.0057 g, 0.010 mmol) and Cs$_2$CO$_3$ (0.23 g, 0.71 mmol) in 1,4-dioxane (4 mL) was bubbled with nitrogen for 10 minutes. Palladium(II) acetate (0.0010 g, 0.0045 mmol) was added and the mixture was heated at 120° C. under microwave irradiation for 25 minutes. The mixture was partitioned between water and EtOAc. The layers were separated and the aqueous was extracted with EtOAc (2 times). The combined organic extracts were washed with brine, dried (Na$_2$SO$_4$) and the solvent evaporated in vacuo to give the crude product. Purification by silica gel column chromatography (Combiflash Rf, 0-100% EtOAc in cyclohexane) gave the title compound 24 as a colourless oil (0.015 g, 12%). LCMS-C: rt 5.79 min; m/z 536 [M+H]$^+$.

Example 24A

Synthesis of 1-(2-(2-(2-((4-(1-aminoethyl)phenyl) amino)-5-chloropyrimidin-4-yl)ethyl)phenyl)cyclopropanecarboxamide (24A)

1-(2-(2-(2-((4-(1-Aminoethyl)phenyl)amino)-5-chloropyrimidin-4-yl)ethyl)phenyl)cyclopropanecarboxamide (24A)

To a solution of tert-butyl (1-(4-((4-(2-(1-carbamoylcyclopropyl)phenethyl)-5-chloropyrimidin-2-yl)amino)phenyl) ethyl)carbamate 24 (0.012 g, 0.022 mmol) in DCM (1 mL) was added trifluoroacetic acid (0.5 mL). The mixture was stirred at ambient temperature for 2 hours before the volatiles were removed in vacuo. The crude residue was loaded onto an SCX cartridge conditioned with methanol. The cartridge was washed with methanol and then 2 N ammonia in ethanol. The basic fractions were combined and the solvent removed in vacuo to give the title compound 24A as a colourless oil (0.009 g, 92%). LCMS-C: rt 4.41 min; m/z 436 [M+H]$^+$.

Example 25

Synthesis of 1-(2-(2-(5-Chloro-2-((3-methyl-1H-pyrazol-4-yl)amino)pyrimidin-4-yl)ethyl)phenyl) cyclopropanecarboxamide (25)

-continued

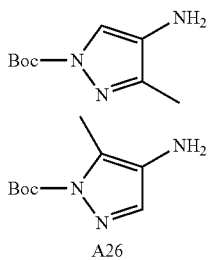

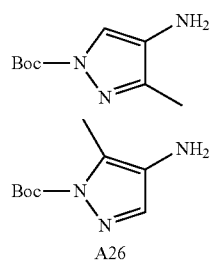

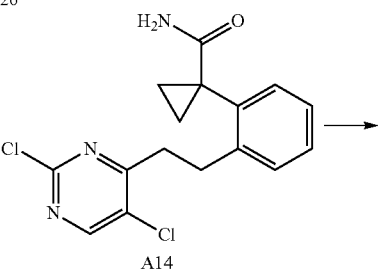

(a) tert-Butyl 3-methyl-4-nitro-1H-pyrazole-1-carboxylate or tert-butyl 5-methyl-4-nitro-1H-pyrazole-1-carboxylate (A25)

Di-tert-butyl dicarbonate (5.15 g, 23.6 mmol) and 4-dimethylaminopyridine (0.481 g, 3.93 mmol) were added to a solution of 3-methyl-4-nitropyrazole (2.50 g, 19.7 mmol) in DCM (100 mL) and the mixture was stirred at room temperature for 16 hours. The reaction mixture was washed with water (100 mL), brine (100 mL), dried (phase separator) and concentrated under reduced pressure. The residue was adsorbed onto $SiO_2$ and purified by column chromatography (Biotage Isolera, 2×40 g $SiO_2$ cartridges, 0-50% EtOAc in petroleum benzine 40-60° C.) to give the title compound A25 as a white solid (2.54 g, 57%). LCMS-D: rt 3.39 min; no product ion detected.

(b) tert-Butyl 4-amino-3-methyl-1H-pyrazole-1-carboxylate or tert-butyl 4-amino-5-methyl-1H-pyrazole-1-carboxylate (A26)

A solution of tert-butyl 3-methyl-4-nitro-1H-pyrazole-1-carboxylate or tert-butyl 5-methyl-4-nitro-1H-pyrazole-1-carboxylate (isomer not determined) A25 (1.50 g, 6.60 mmol) in EtOH (75 mL) was stirred over 10% Pd/C (wetted with ca. 53% water, 0.150 g) under an atmosphere of $H_2$ at room temperature for 16 hours. The mixture was diluted with EtOAc (50 mL) and filtered through Celite. Evaporation of the volatiles in vacuo gave the title compound A26 as a pink solid (1.30 g, >95%). LCMS-D: rt 2.78 min; m/z 198 [M+H]+.

(c) 1-(2-(2-(5-Chloro-2-((3-methyl-1H-pyrazol-4-yl)amino)pyrimidin-4-yl)ethyl)phenyl)cyclopropanecarboxamide (25)

A mixture of 1-(2-(2-(2,5-dichloropyrimidin-4-yl)ethyl)phenyl)cyclopropanecarboxamide A14 (0.120 g, 0.357 mmol), tert-butyl 4-amino-3-methyl-1H-pyrazole-1-carboxylate or tert-butyl 4-amino-5-methyl-1H-pyrazole-1-carboxylate (isomer not determined) A26 (0.141 g, 0.714 mmol) and p-toluenesulfonic acid monohydrate (0.007 g, 0.04 mmol) in 1,4-dioxane (2.0 mL) was stirred in a microwave reactor at 120° C. for 3 hours. The reaction mixture was adsorbed onto $SiO_2$ and purified by column chromatography (Biotage Isolera, 24 g $SiO_2$ cartridge, 0-10% MeOH in DCM) to give the title compound 25 as a white solid (0.035 g, 25%). LCMS-A: rt 5.62 min; m/z 397 [M+H]+.

Example 26

Synthesis of 1-(2-(2-(5-Chloro-2-((1,3-dimethyl-1H-pyrazol-4-yl)amino)pyrimidin-4-yl)ethyl)phenyl)cyclopropanecarboxamide (26)

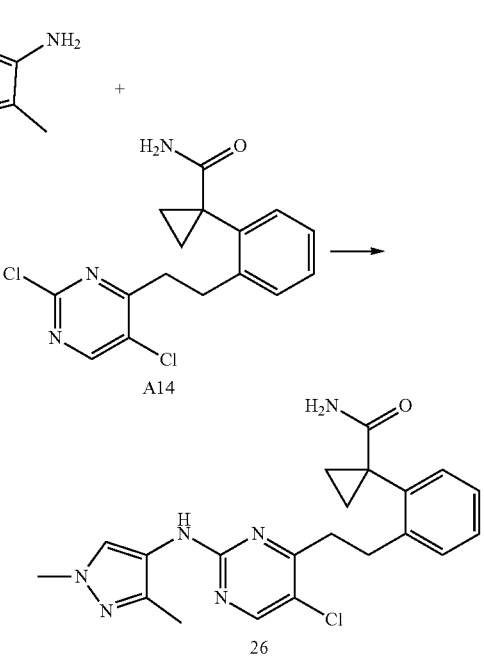

(a) 1-(2-(2-(5-Chloro-2-((1,3-dimethyl-1H-pyrazol-4-yl)amino)pyrimidin-4-yl)ethyl)phenyl)cyclopropanecarboxamide (26)

A mixture of 1-(2-(2-(2,5-dichloropyrimidin-4-yl)ethyl)phenyl)cyclopropanecarboxamide A14 (0.100 g, 0.297 mmol), 1,3-dimethyl-1H-pyrazol-4-amine (0.070 g, 0.63 mmol) and p-toluenesulfonic acid monohydrate (0.006 g, 0.032 mmol) in 1,4-dioxane (1.0 mL) was stirred in the microwave at 120° C. for 2 hours. Additional 1,4-dioxane (1.5 mL) was added and the reaction mixture was stirred in the microwave at 120° C. for a further 4 hours. The reaction mixture was adsorbed onto SiO₂ and purified by column chromatography (Biotage Isolera, 24 g SiO₂ cartridge, 15-100% EtOAc in petroleum benzine 40-60° C.). Fractions containing suspected product were combined and adsorbed onto silica and purified by column chromatography (Biotage Isolera, 12 g SiO₂, 0-5% MeOH in DCM) to give the title compound 26 as a pale yellow solid (0.030 g, 25%). LCMS-D: rt 3.24 min; m/z 411 [M+H]⁺.

Example 27

Synthesis of 1-(2-(2-(5-chloro-2-((5-methyl-1H-pyrazol-3-yl)amino)pyrimidin-4-yl)ethyl)phenyl)cyclopropanecarboxamide (27)

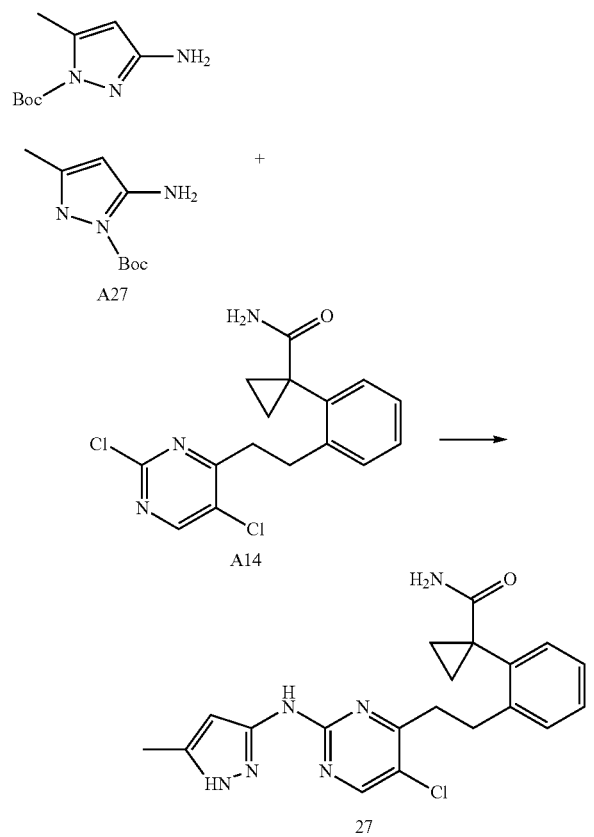

(a) Mixture of tert-butyl 3-amino-5-methyl-1H-pyrazole-1-carboxylate and tert-butyl 5-amino-3-methyl-1H-pyrazole-1-carboxylate (A27)

Di-tert-butyl dicarbonate (531 mg, 2.57 mmol) was added to a mixture of 3-amino-5-methylpyrazole (250 mg, 2.57 mmol) and KOH (289 mg, 5.15 mmol) in THF (25 mL). The reaction mixture was stirred at room temperature overnight and the volatiles were removed in vacuo. The resulting gum was diluted with EtOAc (100 mL) and washed with water (100 mL). The organic layer was separated, adsorbed onto silica gel and purified by silica gel column chromatography (Biotage Isolera, 24 g SiO₂ cartridge, 0-50% EtOAc in petroleum benzine 40-60° C.) to give the title compound/s A27 as a white solid (154 mg, 30%). LCMS-A: rt 5.237 min.

Note: No assignment of Boc position on the pyrazole was made.

(b) 1-(2-(2-(5-Chloro-2-((5-methyl-1H-pyrazol-3-yl)amino)pyrimidin-4-ylethyl)phenyl)cyclopropanecarboxamide (27)

A suspension of 1-(2-(2-(2,5-dichloropyrimidin-4-yl)ethyl)phenyl)cyclopropanecarboxamide A14 (263 mg, 0.781 mmol), Cs₂CO₃ (509 mg, 1.56 mmol) and a mixture of tert-butyl 3-amino-5-methyl-1H-pyrazole-1-carboxylate and tert-butyl 5-amino-3-methyl-1H-pyrazole-1-carboxylate A27 (154 mg, 0.781 mmol) in 1,4-dioxane (5 mL) was sonicated for 10 minutes. Xantphos (23 mg, 0.039 mmol) and Pd₂(dba)₃ (36 mg, 0.039 mmol) were added and the mixture was irradiated in the microwave at 120° C. for 20 minutes. The resulting mixture was adsorbed onto silica gel and purified by column chromatography (Biotage Isolera, 40 g SiO₂ cartridge, 0-100% EtOAc in petroleum benzine 40-60° C.) to give a yellow oil which was dissolved in DCM (5.0 mL). TFA (1.0 mL) was added and the mixture was stirred at room temperature for 2 hours before the addition of sat. aq. Na₂CO₃ (20 mL) and water (100 mL). The resultant precipitate was collected by filtration, adsorbed onto silica gel and purified by silica gel column chromatography (Biotage Isolera, 12 g SiO₂ cartridge, 0-100% EtOAc in petroleum benzine 40-60° C. then 0-30% MeOH in EtOAc) to give the title compound 27 as a yellow solid (8 mg, 3%). LCMS-A: rt 5.412 min; m/z 397.2 [M+H]⁺.

Example 28

Synthesis of 1-(2-(2-(5-Chloro-2-((1-methyl-1H-pyrazol-3-yl)amino)pyrimidin-4-yl)ethyl)phenyl)cyclopropanecarboxamide (28)

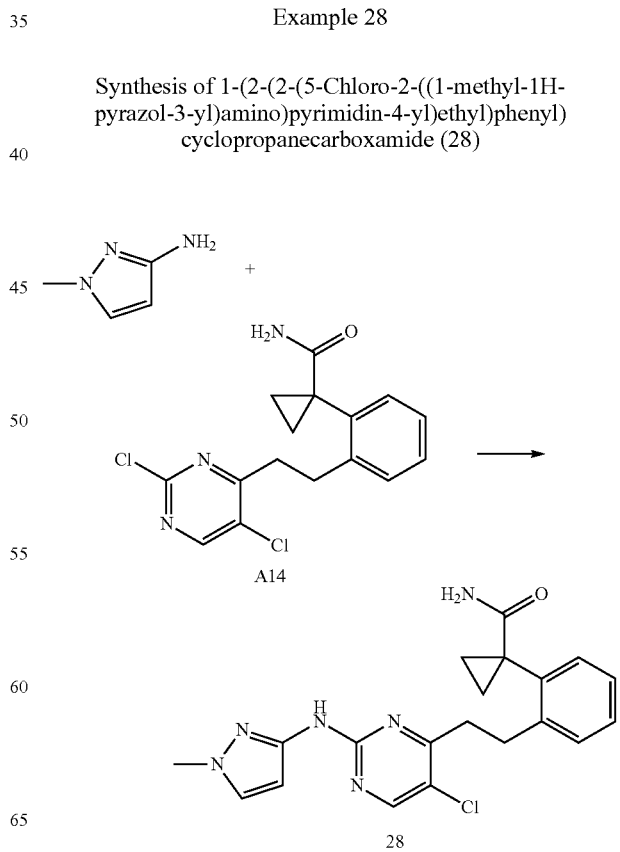

1-(2-(2-(5-Chloro-2-((1-methyl-1H-pyrazol-3-yl)amino)pyrimidin-4-yl)ethyl)phenyl)cyclopropanecarboxamide (28)

A mixture of 1-(2-(2-(2,5-dichloropyrimidin-4-yl)ethyl)phenyl)cyclopropanecarboxamide A14 (0.100 g, 0.297 mmol), 1-methyl-1H-pyrazole-3-amine (0.058 g, 0.595 mmol) and p-toluenesulfonic acid monohydrate (0.006 g, 0.030 mmol) in 1,4-dioxane (2.0 mL) was stirred in a microwave reactor at 120° C. for 3 hours. The reaction mixture was adsorbed onto SiO$_2$ and purified by column chromatography (Biotage Isolera, 24 g SiO$_2$ cartridge, 0-5% MeOH in DCM) to give a gummy solid. The solid was suspended in a mixture of Et$_2$O and petroleum benzine 40-60° C. (1:1) and sonicated for 10 minutes. The precipitate was isolated by vacuum filtration and dried to give the title compound 28 as a yellow solid (0.014 g, 12%). LCMS-D: rt 3.26 min; m/z 397 [M+H]$^+$.

Example 29

Synthesis of 1-(2-(2-(5-chloro-2-((1-(2,2,2-trifluoroethyl)-1H-pyrazol-4-yl)amino)pyrimidin-4-yl)ethyl)phenyl)cyclopropanecarboxamide (29)

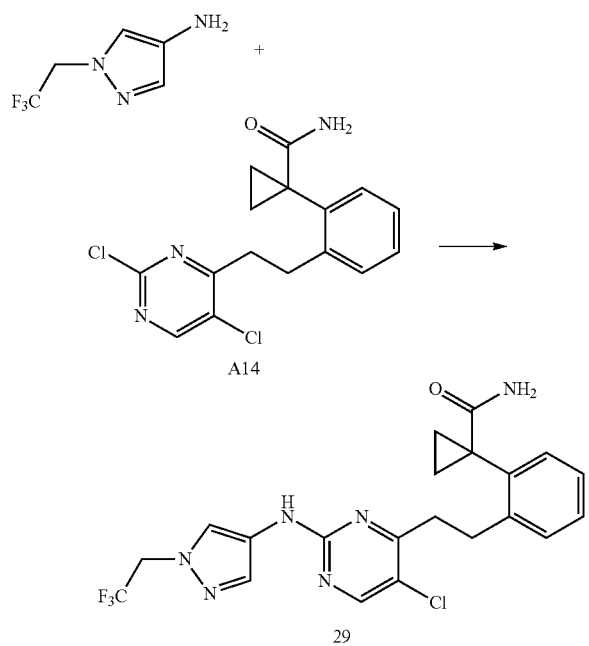

1-(2-(2-(5-Chloro-2-((1-(2,2,2-trifluoroethyl)-1H-pyrazol-4-yl)amino)pyrimidin-4-yl)ethyl)phenyl)cyclopropanecarboxamide (29)

A mixture of 1-(2,2,2-trifluoroethyl)-1H-pyrazol-4-amine (0.160 g, 0.967 mmol), 1-(2-(2-(2,5-dichloropyrimidin-4-yl)ethyl)phenyl)cyclopropanecarboxamide A14 (0.101 g, 0.300 mmol) and TsOH.H$_2$O (0.010 g, 0.051 mmol) in 1,4-dioxane (2.0 mL) was heated to 120° C. for 3 hours in the microwave. The mixture was concentrated under reduced pressure and purified using silica gel column chromatography (0-100% EtOAc in petroleum benzine 40-60° C.) to give the title compound 29 (0.036 g, 26%). LCMS-D: rt 3.402 min; m/z 465.2 [M+H]$^+$.

Example 30

Synthesis of 1-(2-(2-(5-chloro-2-((1-isopropyl-1H-pyrazol-4-yl)amino)pyrimidin-4-yl)ethyl)phenyl)cyclopropanecarboxamide (30)

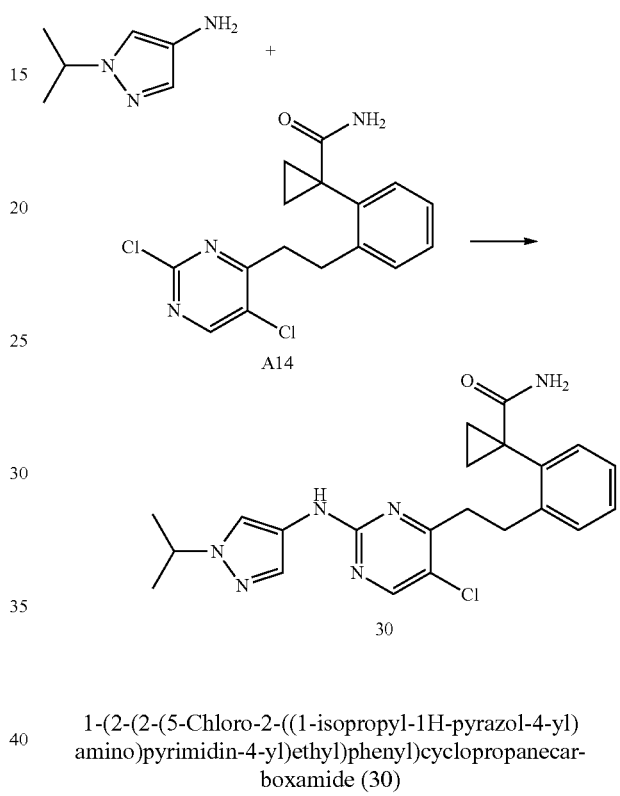

1-(2-(2-(5-Chloro-2-((1-isopropyl-1H-pyrazol-4-yl)amino)pyrimidin-4-yl)ethyl)phenyl)cyclopropanecarboxamide (30)

A mixture of 1-isopropylpyrazol-4-amine (0.083 g, 0.66 mmol), 1-(2-(2-(2,5-dichloropyrimidin-4-yl)ethyl)phenyl)cyclopropanecarboxamide A14 (0.110 g, 0.327 mmol) and TsOH.H$_2$O (0.013 g, 0.066 mmol) in 1,4-dioxane (2.0 mL) was heated in the microwave to 100° C. for 3 hours. The mixture was concentrated under reduced pressure and purified by silica gel column chromatography (0-100% EtOAc in petroleum benzine 40-60° C. then 0-10% MeOH in EtOAc) to give the title compound 30 (0.094 g, 68%). LCMS-D: rt 3.355 min; m/z 425.3 [M+H]$^+$.

Example 31

Synthesis of 1-(2-(2-(5-chloro-2-((6-cyanopyridin-3-yl)amino)pyrimidin-4-yl)ethyl)phenyl)cyclopropanecarboxamide (31)

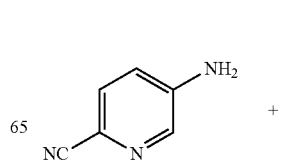

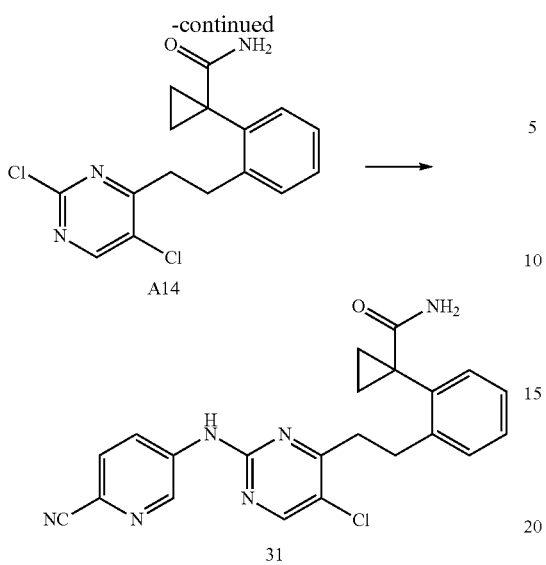

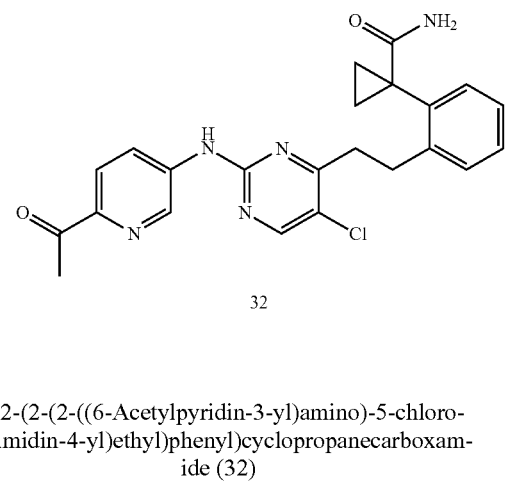

1-(2-(2-(5-Chloro-2-(((6-cyanopyridin-3-yl)amino)pyrimidin-4-yl)ethyl)phenyl)cyclopropanecarboxamide (31)

A solution of 1-(2-(2-(2,5-dichloropyrimidin-4-yl)ethyl)phenyl)cyclopropanecarboxamide A14 (0.300 g, 0.892 mmol) in THF (2.5 mL) containing 5-amino-2-pyridinecarbonitrile (0.213 g, 1.78 mmol), Cs$_2$CO$_3$ (0.872 g, 2.67 mmol), Xantphos (0.021 g, 0.036 mmol) and palladium (II) acetate (4 mg, 0.018 mmol) was heated under microwave irradiation for 30 minutes at 120° C. The reaction mixture was adsorbed onto silica gel and purified by silica column chromatography (Combiflash Rf, 12 g SiO$_2$ Cartridge, 0-10% MeOH in DCM) to give the title compound 31 as a cream solid (0.262 g, 70%). LCMS-B: rt 7.13 min; m/z 419 [M+H]$^+$.

Example 32

Synthesis of 1-(2-(2-(2-((6-acetylpyridin-3-yl)amino)-5-chloropyrimidin-4-yl)ethyl)phenyl)cyclopropanecarboxamide (32)

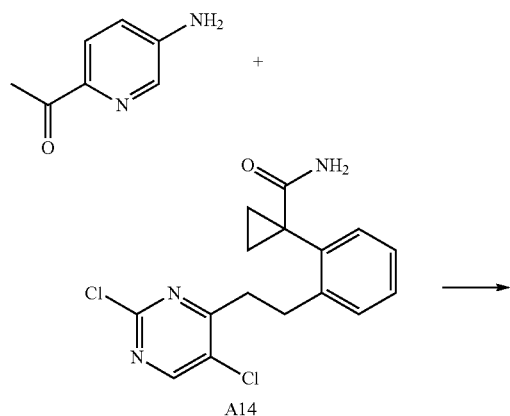

1-(2-(2-(2-((6-Acetylpyridin-3-yl)amino)-5-chloropyrimidin-4-yl)ethyl)phenyl)cyclopropanecarboxamide (32)

A solution of 1-(2-(2-(2,5-dichloropyrimidin-4-yl)ethyl)phenyl)cyclopropanecarboxamide A14 (0.200 g, 0.595 mmol) in 1,4-dioxane (2.0 mL) containing 1-(5-aminopyridin-2-yl)ethanone (0.121 g, 0.892 mmol), Cs$_2$CO$_3$ (0.581 g, 1.78 mmol), Xantphos (0.014 g, 0.024 mmol) and palladium (II) acetate (2.67 mg, 0.012 mmol) was heated under microwave irradiation for 30 minutes at 120° C. The reaction mixture was adsorbed onto silica gel and purified by silica column chromatography (Combiflash Rf, 4 g SiO$_2$ Cartridge, 0-10% MeOH in DCM) to give title compound 32 as a light cream solid (0.183 g, 70%). LCMS-B: rt 6.98 min; m/z 437 [M+H]$^+$.

Example 33

Synthesis of 1-(2-(2-(2-((6-(1-aminoethyl)pyridin-3-yl)amino)-5-chloropyrimidin-4-yl)ethyl)phenyl)cyclopropanecarboxamide (33)

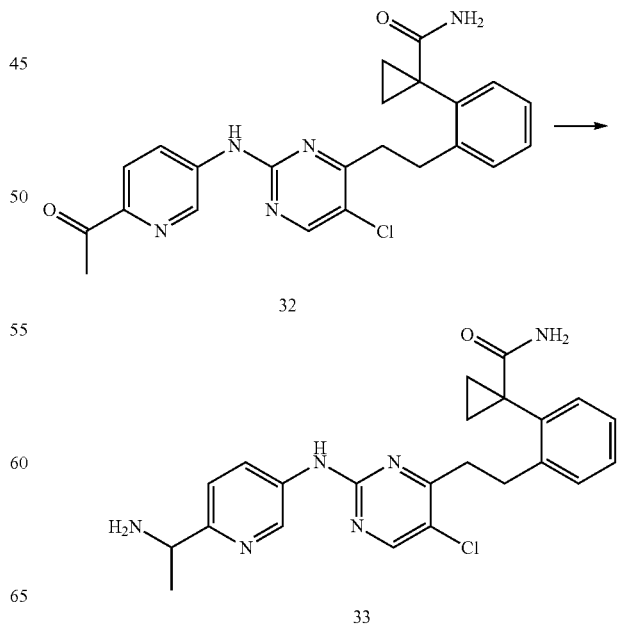

1-(2-(2-(2-((6-(1-Aminoethyl)pyridin-3-yl)amino)-5-chloropyrimidin-4-yl)ethyl)phenyl)cyclopropanecarboxamide (33)

Ammonium acetate (0.587 g, 7.61 mmol) was added to a solution of 1-(2-(2-(2-((6-Acetylpyridin-3-yl)amino)-5-chloropyrimidin-4-yl)ethyl)phenyl)cyclopropanecarboxamide 32 (0.166 g, 0.381 mmol) in MeOH (5 mL) and THF (5 mL) and the mixture was stirred for 20 minutes under a nitrogen atmosphere. Sodium cyanoborohydride (0.017 g, 0.27 mmol) was added and the mixture was stirred for 5 hours. Additional sodium cyanoborohydride (0.017 g, 0.27 mmol) was added and the mixture was stirred for 22 hours at 35° C. Water (10 mL) was added to the mixture which was then acidified with 20% aqueous hydrochloride (10 mL). The aqueous phase was washed with Et$_2$O (2×30 mL) and then basified with solid potassium hydroxide to pH 10. The aqueous phase was extracted with DCM (3×30 mL) and the combined organics were washed with brine, dried (Na$_2$SO$_4$), adsorbed onto silica and purified by silica column chromatography (Combiflash Rf, 12 g SiO$_2$ Cartridge, 0-30% MeOH in DCM) to give the title compound 33 as a white solid (0.101 g, 60%). LCMS-B: rt 4.32 min; m/z 437 [M+H]$^+$.

Example 34

Synthesis of 1-(2-(2-(5-chloro-2-((1-(difluoromethyl)-1H-pyrazol-4-yl)amino)pyrimidin-4-yl)ethyl)phenyl)cyclopropanecarboxamide (34)

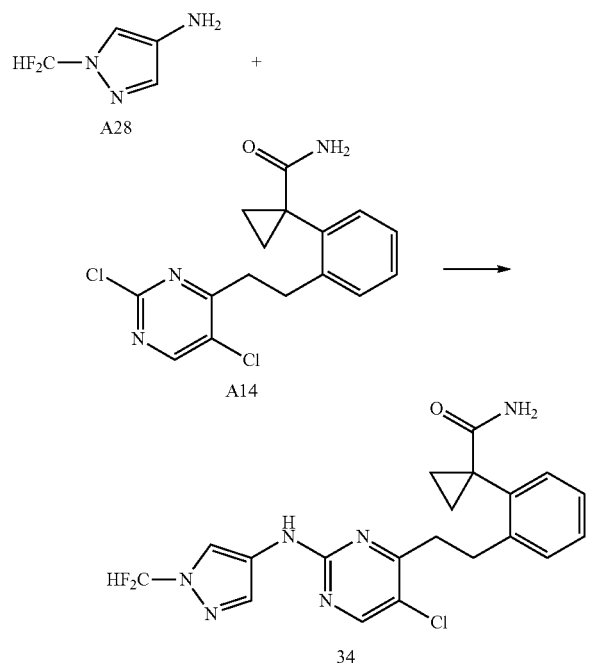

1-(2-(2-(5-Chloro-2-((1-(difluoromethyl)-1H-pyrazol-4-yl)amino)pyrimidin-4-yl)ethyl)phenyl)cyclopropanecarboxamide (34)

A mixture of 1-(2-(2-(2,5-dichloropyrimidin-4-yl)ethyl)phenyl)cyclopropanecarboxamide A14 (0.076 g, 0.225 mmol), 1-(difluoromethyl)-1H-pyrazol-4-amine A28 (0.030 g, 0.23 mmol) and p-toluenesulfonic acid monohydrate (0.004 g, 0.023 mmol) in 1,4-dioxane (4.0 mL) was stirred in a microwave reactor at 120° C. for 2 hours. The volatiles were evaporated in vacuo and the residue was purified by column chromatography (Biotage Isolera, 12 g SiO$_2$ cartridge, 0-5% MeOH in DCM). Fractions containing suspected product were combined and the solvent removed in vacuo to give a residue that was purified further by column chromatography (Biotage Isolera, 12 g SiO$_2$ cartridge, 0-60% EtOAc in petroleum benzine 40-60° C.). Fractions containing suspected product were combined, the solvent was removed in vacuo and the resulting solid purified by prep-LCMS to give the title compound 34 as a white solid (0.005 g, 5%). LCMS-B: rt 3.41 min; m/z 433 [M+H]$^+$.

Example 35

Synthesis of 2-(2-(2-(2-(1H-pyrazol-4-ylamino)-5-chloropyrimidin-4-yl)ethyl)phenyl)propanamide (35)

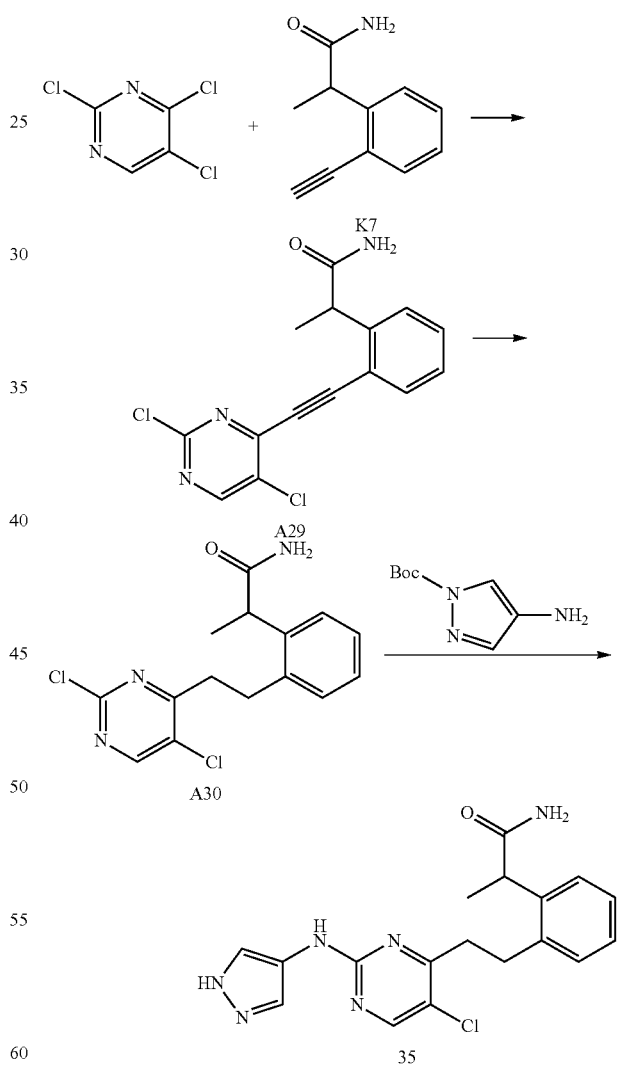

(a) 2-(2-((2,5-Dichloropyrimidin-4-yl)ethynyl)phenyl)propanamide (A29)

To a solution of 2-(2-ethynylphenyl)propanamide K7 (2.5 g, 14 mmol) and 2,4,5-trichloropyrimidine (2.2 mL, 19 mmol) in 1,4-dioxane (27 mL) and Et₃N (8.1 mL, 58 mmol) containing CuI (0.055 g, 0.29 mmol) was added PdCl₂(PPh₃)₂ (0.10 g, 0.14 mmol). The reaction mixture was heated at 60° C. for 2.5 hours under a nitrogen atmosphere. The solvent was removed in vacuo and the residue was diluted with 20% Et₂O in cyclohexane. The precipitate was filtered, washed with water and dried in vacuo to give the title compound A29 as a light brown solid (4.52 g, 98%). LCMS-C: rt 5.10 min; m/z 320 [M+H]⁺.

(b) 2-(2-(2-(2,5-Dichloropyrimidin-4-yl)ethyl)phenyl)propanamide (A30)

A solution of 2-(2-((2,5-dichloropyrimidin-4-yl)ethynyl)phenyl)propanamide A29 (1.0 g, 3.1 mmol) in DMF (55 mL) and MeOH (5 mL) was stirred with platinum(II)oxide (0.21 g, 0.94 mmol) under an atmosphere of hydrogen for 120 hours at ambient temperature. The reaction mixture was diluted with EtOAc and filtered through a plug of Celite. The filter cake was washed with EtOAc and the solvents were removed in vacuo to give a crude residue that was purified by silica gel column chromatography (Combiflash Rf, 0-90% EtOAc in cyclohexane), giving the title compound A30 as an off white solid (0.65 g, 64%). LCMS-C: rt 4.98 min; m/z 324 [M+H]⁺.

(C) 2-(2-(2-(2-(1H-Pyrazol-4-ylamino)-5-chloropyrimidin-4-yl)ethyl)phenyl)propanamide (35)

A solution of 2-(2-(2-(2,5-dichloropyrimidin-4-yl)ethyl)phenyl)propanamide A30 (0.10 g, 0.31 mmol) and tert-butyl 4-amino-1H-pyrazole-1-carboxylate (0.17 g, 0.93 mmol) was heated in MeOH:water (10:1, 5 mL) at 90° C. for 18 hours. The solvents were removed in vacuo and the crude residue was purified by silica gel column chromatography (Combiflash Rf, 0-15% MeOH in DCM). The purified fractions were combined, the solvent was removed in vacuo and the solid was sonicated in cyclohexane and filtered. The residue was dried in vacuo to give the title compound 35 as a light yellow solid (0.060 g, 52%). ¹H NMR (300 MHz, d₆-DMSO) δ 1.34 (d, J=7.04 Hz, 3H), 2.92-3.11 (m, 4H), 3.86 (q, J=7.04 Hz, 1H), 6.85 (brs, 1H), 7.13-7.25 (m, 4H), 7.36-7.44 (m, 1H), 7.57-87 (m, 2H), 8.37 (s, 1H), 9.63 (s, 1H). LCMS-C: rt 4.72 min; m/z 371 [M+H]⁺.

Example 36

Synthesis of 2-(2-(2-(5-chloro-2-(1-methyl-1H-pyrazol-4-ylamino)pyrimidin-4-yl)ethyl)phenyl)propanamide (36)

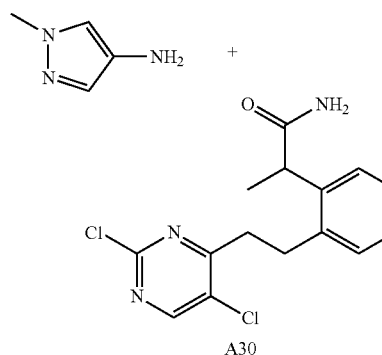

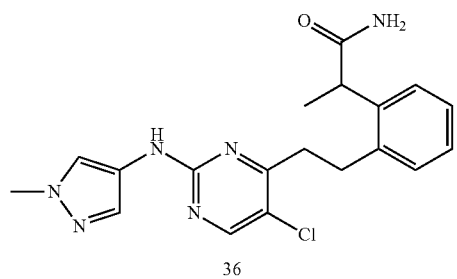

2-(2-(2-(5-Chloro-2-(1-methyl-1H-pyrazol-4-ylamino)pyrimidin-4-yl)ethyl)phenyl)propanamide (36)

A solution of 2-(2-(2-(2,5-dichloropyrimidin-4-yl)ethyl)phenyl)propanamide A30 (50 mg, 0.15 mmol), 4-amino-1-methylpyrazole (15 mg, 0.015 mmol) and p-toluenesulfonic acid (3.0 mg, 0.015 mmol) in 1,4-dioxane (2 mL) was heated at 80° C. under microwave irradiation for 3 hours, then at 120° C. for 3 hours and finally at 140° C. for 2 hours. The mixture was partitioned between water and EtOAc, the layers were separated and the aqueous phase was extracted with EtOAc (3 times). The combined organic extracts were washed with brine, dried (Na₂SO₄) and the solvent evaporated in vacuo to give the crude product. Purification by silica gel column chromatography (Combiflash Rf, 0-10% MeOH in DCM) gave the title compound 36 as a pale solid (0.020 g, 34%). ¹H NMR (300 MHz, CDCl₃) δ 1.57 (d, J=7.26 Hz, 3H), 3.04-3.15 (m, 4H), 3.91 (s, 3H), 4.00 (q, J=6.97 Hz, 1H), 5.59 (brs, 2H), 7.19-7.31 (m, 3H), 7.34 (brs, 1H), 7.38-7.41 (m, 1H), 7.49 (s, 1H), 7.71 (s, 1H), 8.25 (s, 1H). LCMS-B: rt 6.09 min; m/z 385 [M+H]⁺.

Example 37

Synthesis of 2-(2-(2-(5-chloro-2-((6-(piperidin-4-yl)pyridin-3-yl)amino)pyrimidin-4-yl)ethyl)phenyl)propanamide (37)

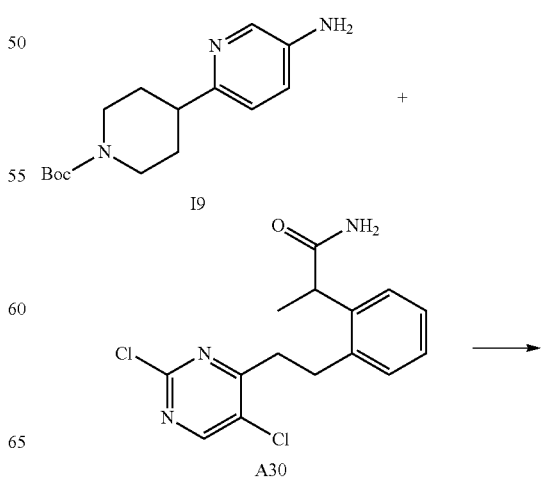

-continued

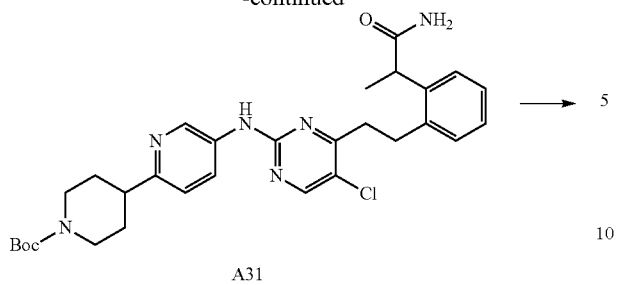

A31

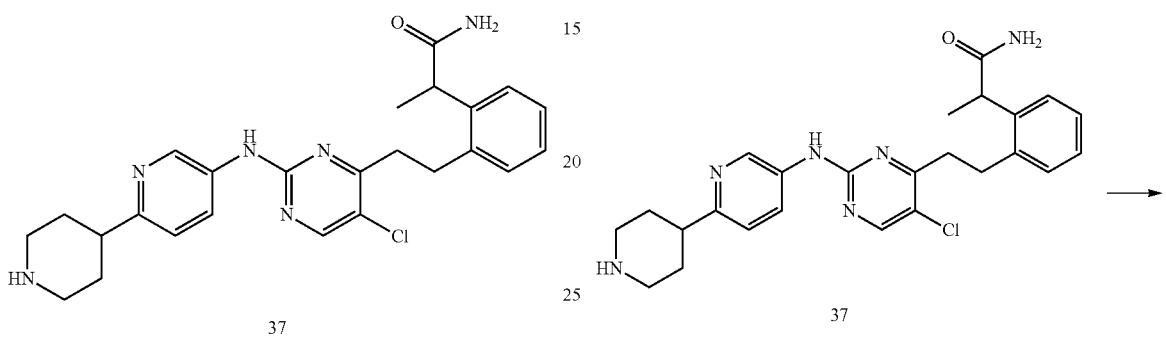

(a) tert-Butyl 4-(5-((4-(2-(1-amino-1-oxopropan-2-yl)phenethyl)-5-chloropyrimidin-2-yl)amino)pyridin-2-yl)piperidine-1-carboxylate (A31)

A suspension of 2-(2-(2-(2,5-dichloropyrimidin-4-yl)ethyl)phenyl)propanamide A30 (50.0 mg, 0.154 mmol), Cs₂CO₃ (151 mg, 0.463 mmol) and tert-butyl 4-(4-aminophenyl)piperidine-1-carboxylate 19 (85.6 mg, 0.308 mmol) in 1,4-dioxane (1.0 mL) was sonicated for 10 minutes, followed by the addition of Xantphos (3.57 mg, 6.18 µmol) and palladium(II) acetate (0.692 mg, 3.08 µmol). The reaction was heated under microwave irradiation for 20 minutes at 120° C. then filtered through Celite. The filter cake was washed with EtOAc, the solvent was removed under reduced pressure and the crude material was purified by silica gel column chromatography (Combiflash Rf, 0-90% EtOAc in cyclohexane) to afford the title compound A31 (34 mg, 39%). LCMS-C: rt 6.33 min; m/z 565.2 [M+H]⁺.

(b) 2-(2-(2-(5-Chloro-2-(((6-(piperidin-4-yl)pyridin-3-yl)amino)pyrimidin-4-yl)ethyl)phenyl)propanamide (37)

TFA (0.71 mL) was added to a solution of tert-butyl 4-(5-((4-(2-(1-amino-1-oxopropan-2-yl)phenethyl)-5-chloropyrimidin-2-yl)amino)pyridin-2-yl)piperidine-1-carboxylate A31 (34 mg, 0.06 mmol) in DCM (7 mL) and the mixture was stirred at room temperature overnight. The volatiles were removed in vacuo before the addition of 2.0 M NaOH solution (2 mL) and EtOAc. The phases were separated and the aqueous phase was extracted with EtOAc. The combined organic phases were washed with water, dried over Na₂SO₄ and the solvent removed under reduced pressure to give the title compound 37 (23 mg, 82%). LCMS-C: rt 6.02 min; m/z 465.3 [M+H]⁺.

Example 38

Synthesis of 2-(2-(2-(5-chloro-2-(6-(1-methylpiperidin-4-yl)pyridin-3-ylamino)pyrimidin-4-yl)ethyl)phenyl)propanamide (38)

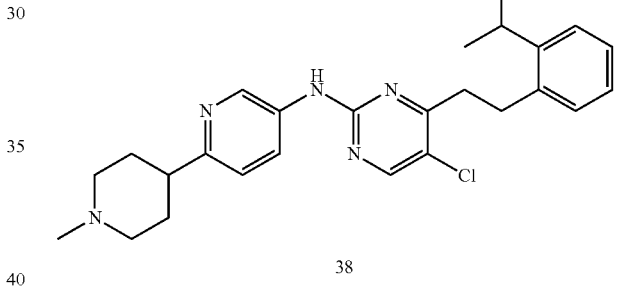

2-(2-(2-(5-Chloro-2-(((6-(1-methylpiperidin-4-yl)pyridin-3-yl)amino)pyrimidin-4-yl)ethyl)phenyl)propanamide (38)

Formaldehyde (31.2 µL, 0.419 mmol, 37 wt % in H₂O) was added to a suspension of 2-(2-(2-(5-chloro-2-((6-(piperidin-4-yl)pyridin-3-yl)amino)pyrimidin-4-yl)ethyl)phenyl)propanamide 37 (39.0 mg, 0.084 mmol) in MeOH (2.0 mL) under an atmosphere of nitrogen. Sodium triacetoxyborohydride (178 mg, 0.839 mmol) was added in one portion and the reaction mixture was stirred at room temperature for 2.5 hours. The volatiles were removed in vacuo and the residue was diluted with EtOAc (10 mL) and sat. aq. NaHCO₃ (10 mL). The layers were separated and the aqueous layer was extracted with EtOAc (2×10 mL). The combined organic layers were washed with water (20 mL) and brine (15 mL) and dried over Na₂SO₄. The solvent was removed under reduced pressure and the resulting solid was suspended in DCM (20 mL) and cyclohexane (30 mL). The solid was filtered to give the title compound 38 (34 mg, 84%). LCMS-C: rt 4.19 min; m/z 479.2 [M+H]⁺.

Example 39

Synthesis of 2-(2-(2-(5-chloro-2-(pyridin-3-ylamino)pyrimidin-4-yl)ethyl)phenyl)propanamide (39)

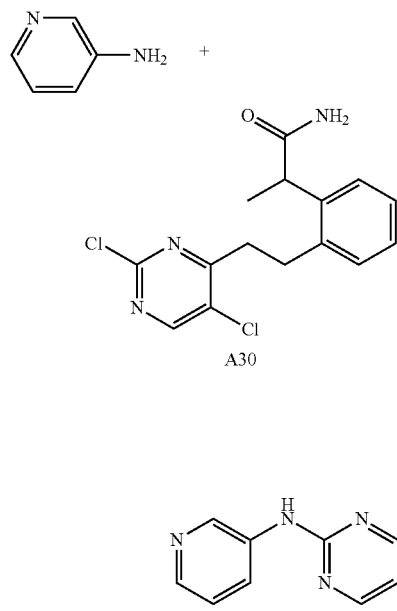

2-(2-(2-(5-Chloro-2-(pyridin-3-ylamino)pyrimidin-4-ylethyl)phenyl)propanamide (39)

A mixture of 2-(2-(2-(5-chloro-2-(1-methyl-1H-pyrazol-4-ylamino)pyrimidin-4-ylethyl)phenyl)propanamide A30 (0.080 g, 0.25 mmol), 3-aminopyridine (0.046 g, 0.49 mmol), Xantphos (0.0057 g, 0.010 mmol) and Cs$_2$CO$_3$ (0.24 g, 0.74 mmol) in 1,4-dioxane (3 mL) was bubbled with nitrogen for 10 minutes. Palladium (II) acetate (0.0011 g, 0.0049 mmol) was added and the mixture was heated at 120° C. under microwave irradiation for 28 minutes. The volatiles were removed in vacuo and the residue was purified by silica gel column chromatography (Combiflash Rf, 0-10% MeOH in DCM) to give the title compound 39 as a pink solid (0.029 g, 31%). LCMS-C: rt 4.30 min; m/z 382 [M+H]$^+$.

Example 40

Synthesis of 2-(2-(2-(5-chloro-2-(pyrimidin-5-ylamino)pyrimidin-4-yl)ethyl)phenyl)propanamide (40)

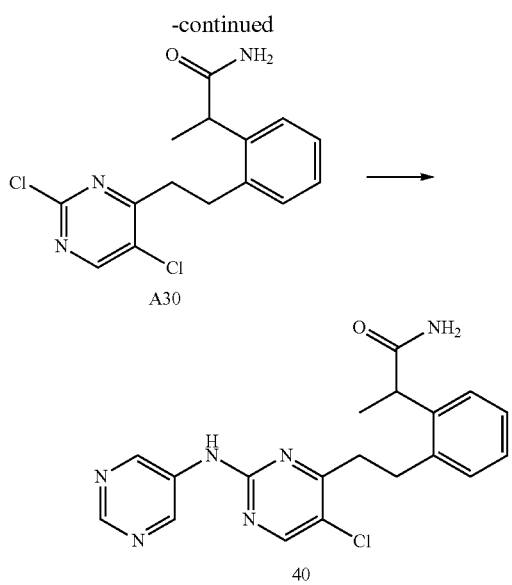

2-(2-(2-(5-Chloro-2-(pyrimidin-5-ylamino)pyrimidin-4-yl)ethyl)phenyl)propanamide (40)

A mixture of 2-(2-(2-(5-chloro-2-(1-methyl-1H-pyrazol-4-ylamino)pyrimidin-4-ylethyl)phenyl)propanamide A30 (0.080 g, 0.25 mmol), 5-aminopyrimidine (0.047 g, 0.49 mmol), Xantphos (0.0057 g, 0.010 mmol) and Cs$_2$CO$_3$ (0.24 g, 0.74 mmol) in 1,4-dioxane (3 mL) was bubbled with nitrogen for 10 minutes. Palladium (II) acetate (0.0011 g, 0.0049 mmol) was added and the mixture was heated at 120° C. under microwave irradiation for 20 minutes. The volatiles were removed in vacuo and the residue was purified by silica gel column chromatography (Combiflash Rf, 0-10% MeOH in DCM) to give the title compound 40 as an off white solid (0.030 g, 32%). LCMS-C: rt 4.85 min; m/z 383 [M+H]$^+$.

Example 41

Synthesis of 2-(2-(2-(5-chloro-2-(6-methylpyridin-3-ylamino)pyrimidin-4-yl)ethyl)phenyl)propanamide (41)

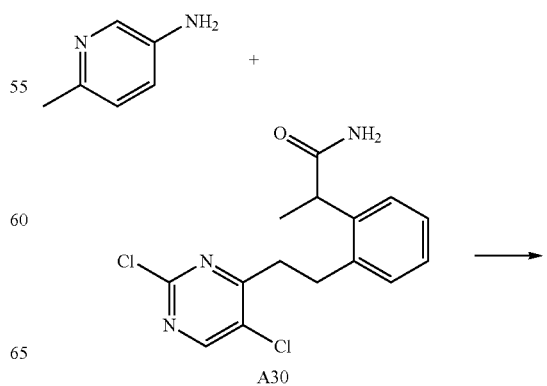

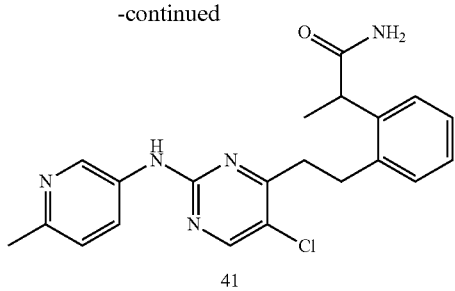

41

2-(2-(2-(5-chloro-2-(6-methylpyridin-3-ylamino)
pyrimidin-4-yl)ethyl)phenyl)propanamide (41)

A mixture of 2-(2-(2-(5-chloro-2-(1-methyl-1H-pyrazol-4-ylamino)pyrimidin-4-yl)ethyl)phenyl)propanamide WAK-011-06-05 (0.080 g, 0.25 mmol), 5-amino-2-methylpyridine (0.053 g, 0.49 mmol), Xantphos (0.0057 g, 0.010 mmol) and Cs$_2$CO$_3$ (0.24 g, 0.74 mmol) in 1,4-dioxane (3 mL) was bubbled with nitrogen for 10 minutes. Palladium (II) acetate (0.0011 g, 0.0049 mmol) was added and the mixture was heated at 120° C. under microwave irradiation for 20 minutes. The volatiles were removed in vacuo and the residue was purified by silica gel column chromatography (Combiflash Rf, 0-10% MeOH in DCM) to give the title compound 41 as a light yellow solid (0.032 g, 33%). LCMS-C: rt 4.24 min; m/z 396 [M+H]$^+$.

Example 42

Synthesis of 2-(2-(2-(5-chloro-2-(pyridazin-4-ylamino)pyrimidin-4-yl)ethyl)phenyl)propanamide (42)

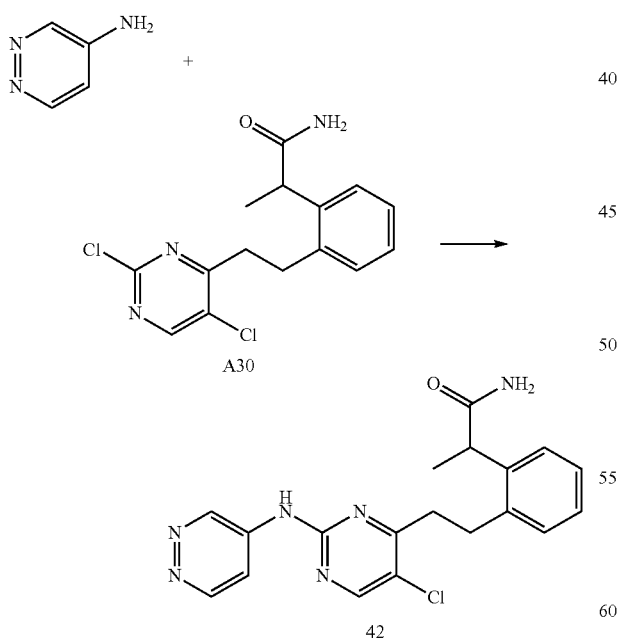

2-(2-(2-(5-Chloro-2-(pyridazin-4-ylamino)pyrimidin-4-yl)ethyl)phenyl)propanamide (42)

A mixture of 2-(2-(2-(2,5-Dichloropyrimidin-4-yl)ethyl) phenyl)propanamide (A30) 2-(2-(2-(2,5-Dichloropyrimidin-4-yl)ethyl)phenyl)propanamide (A30 (0.080 g, 0.25 mmol), 4-aminopyridazine (0.046 g, 0.49 mmol), Xantphos (0.0057 g, 0.010 mmol) and Cs$_2$CO$_3$ (0.24 g, 0.74 mmol) in 1,4-dioxane (3 mL) was bubbled with nitrogen for 10 minutes. Palladium (II) acetate (0.0011 g, 0.0049 mmol) was added and the mixture was heated at 120° C. under microwave irradiation for 28 minutes. The volatiles were removed in vacuo and the residue was purified by silica gel column chromatography (Combiflash Rf, 0-15% MeOH in DCM) to give the title compound 42 as a light yellow solid (0.020 g, 21%). LCMS-C: rt 4.23 min; m/z 383 [M+H]$^+$.

Example 43

Synthesis of 2-(2-(2-(5-chloro-2-(1-(piperidin-4-yl)-1H-pyrazol-4-ylamino)pyrimidin-4-yl)ethyl)phenyl)propanamide (43)

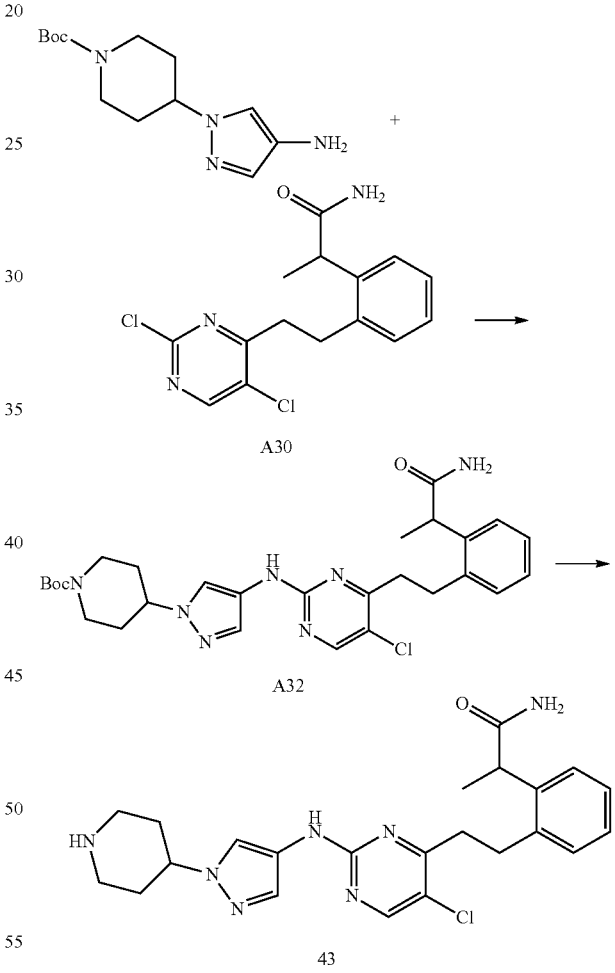

(a) tert-Butyl 4-(4-(4-(2-(1-amino-1-oxopropan-2-yl) phenethyl)-5-chloropyrimidin-2-ylamino)-1H-pyrazol-1-yl)piperidine-1-carboxylate (A32)

A stirred solution of 2-(2-(2-(2,5-Dichloropyrimidin-4-yl) ethyl)phenyl)propanamide (A30) (0.120 g, 0.370 mmol), tert-butyl 4-(4-amino-1H-pyrazol-1-yl)piperidine-1-carboxylate (0.177 g, 0.666 mmol) in n-butanol (3 mL) and glacial acetic acid (0.004 mL, 0.074 mmol) was stirred at 150° C. in the microwave for 30 minutes. After cooling, the solvent was removed to afford a crude purple oil which was purified by silica gel column chromatography (Combiflash Rf, 0-30% MeOH in DCM) to give the title compound A32 as a red oil (0.090 g, 44% yield). LCMS-C: rt 5.44 min; m/z 554 [M+H]+.

(b) 2-(2-(2-(5-Chloro-2-(1-(piperidin-4-yl)-1H-pyrazol-4-ylamino)pyrimidin-4-yl)ethyl)phenyl)propanamide (43)

To a stirred solution of tert-butyl 4-(4-(4-(2-(1-amino-1-oxopropan-2-yl)phenethyl)-5-chloropyrimidin-2-ylamino)-1H-pyrazol-1-yl)piperidine-1-carboxylate A32 (0.090 g, 0.162 mmol) in DCM (5 mL) was added TFA (2.0 mL) and the mixture was stirred at room temperature for 1.5 hours. The solvent was removed and the residue was suspended in EtOAc (5 mL) and washed with 1M HCl. The aqueous layer was basified with 1M NaOH and extracted with EtOAc (2×5 mL). The combined organic layers were dried (MgSO4), filtered and concentrated in vacuo to give a crude purple oil which was purified by flash chromatography (Combiflash Rf, 0-30% MeOH in DCM) to give the title compound 43 as a red oil (0.019 g, 26% yield). LCMS-C: rt 4.24 min; m/z 454 [M+H]+.

Example 44

Synthesis of 2-(2-(2-(5-chloro-2-(1-(1-methylpiperidin-4-yl)-1H-pyrazol-4-ylamino)pyrimidin-4-yl)ethyl)phenyl)propanamide (44)

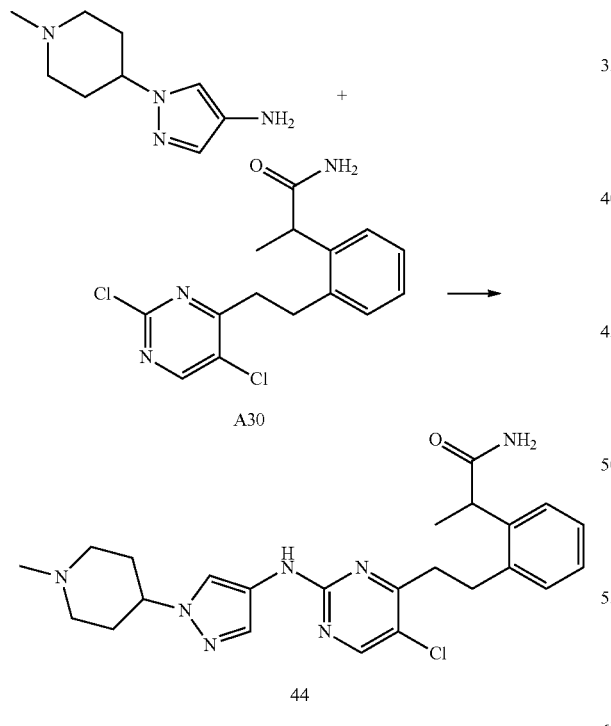

2-(2-(2-(5-Chloro-2-(1-(1-methylpiperidin-4-yl)-1H-pyrazol-4-ylamino)pyrimidin-4-yl)ethyl)phenyl)propanamide (44)

A stirred solution of 1-(1-methylpiperidin-4-yl)-1H-pyrazol-4-amine (0.117 g, 0.648 mmol), 2-(2-(2-(2,5-dichloropyrimidin-4-yl)ethyl)phenyl)propanamide A30 (0.060 g, 0.185 mmol) in MeOH (10 mL) and water (1.0 mL) was stirred at 70° C. for 16 hours. Additional 1-(1-methylpiperidin-4-yl)-1H-pyrazol-4-amine (0.052 g, 0.29 mmol) was added and the reaction was stirred for 16 hours at 70° C. After cooling the solvent was removed to afford an oil which was purified by HPLC (Gradient: 30-100%, acetonitrile 0.1% formic acid in water 0.1% formic acid, 12 min) to give the title compound 44 as a red gum (0.0018 g, 2% yield). LCMS-C: rt 4.28 min; m/z 468 [M+H]+.

Example 45

Synthesis of 2-(2-(2-(5-Chloro-2-((1-methyl-1H-pyrazol-4-yl)amino)pyrimidin-4-yl)ethyl)phenyl)-2-methylpropanamide (45)

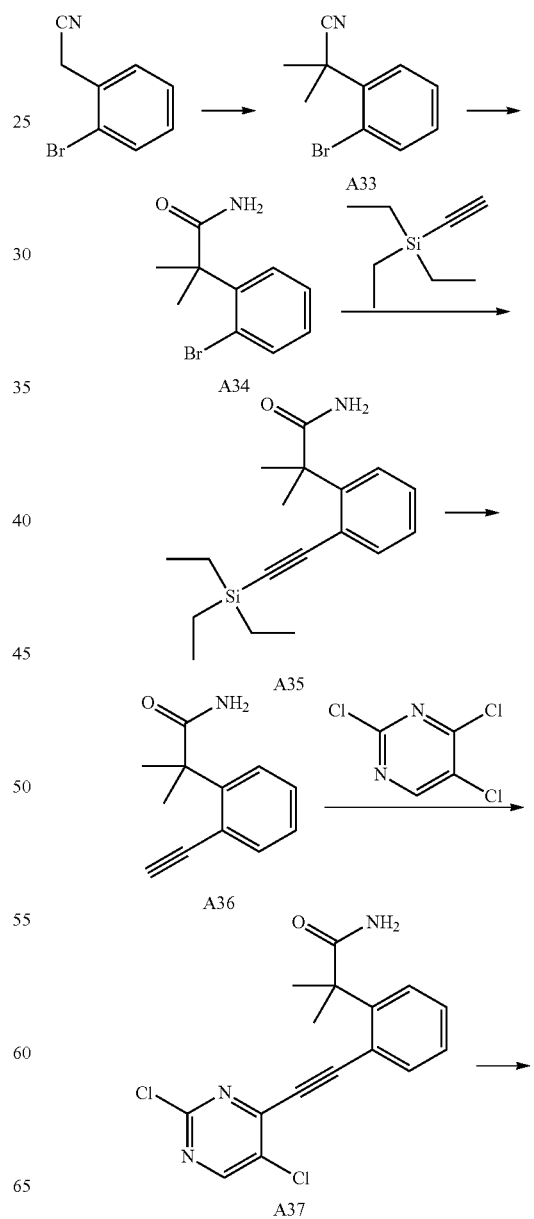

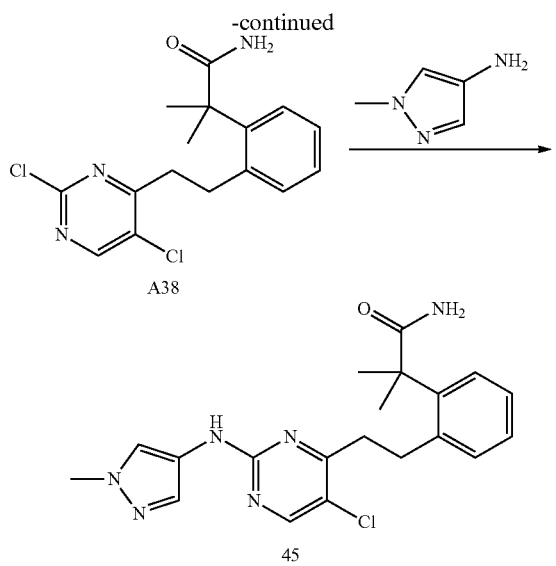

(a) 2-(2-Bromophenyl)-2-methylpropanenitrile (A33)

A suspension of t-BuOK (0.898 g, 8.00 mmol) in anhydrous THF (3 mL) and anhydrous NMP (3 mL) was cooled to 0° C. under a $N_2$ atmosphere. To this suspension, 2-(2-bromophenyl)acetonitrile (0.392 g, 2.00 mmol) was added and the mixture was allowed to stir at 0° C. for 10 minutes. Iodomethane (0.50 mL, 8.0 mmol) was added carefully over a period of 5 minutes and the resulting mixture was stirred for an additional 1 hour between 0° C. and 10° C. Excess t-BuOK was quenched by the addition of sat. aq. $NaHCO_3$ and the aqueous phase was extracted with EtOAc (3×40 mL). The combined organics were washed with brine, dried ($MgSO_4$) and the solvent removed in vacuo to give a yellow residue. Purification by column chromatography (Biotage Isolera, 24 g $SiO_2$ cartridge, 0-15% EtOAc in petroleum benzine 40-60° C.) gave the title compound A33 as a colourless oil (0.377 g, 84%). LCMS-D: rt 3.48 min; m/z 197/199 [M-CN]$^+$.

(b) 2-(2-Bromophenyl)-2-methylpropanamide (A34)

A mixture of 2-(2-bromophenyl)-2-methylpropanenitrile A33 (0.377 g, 1.68 mmol), NaOH (0.135 g, 3.37 mmol) and t-BuOH (4 mL) was stirred in a sealed vessel at 100° C. for 40 hours. The reaction mixture was cooled, diluted with DCM and filtered through Celite. The filtrate solvent was removed in vacuo and the residue was purified by column chromatography (Biotage Isolera, 24 g $SiO_2$ cartridge, 0-100% EtOAc in petroleum benzine 40-60° C.) to give the title compound A34 as a colourless oil (0.192 g, 48%). LCMS-D: rt 3.06 min; m/z 242/244 [M+H]$^+$.

(c) 2-Methyl-2-(2-((triethylsilyl)ethynyl)phenyl) propanamide (A35)

A mixture of 2-(2-bromophenyl)-2-methylpropanamide A34 (0.196 g, 0.810 mmol), CuI (0.008 g, 0.040 mmol), tri-tert-butylphosphonium tetrafluoroborate (0.012 g, 0.040 mmol), $PdCl_2(PPh_3)_2$ (0.028 g, 0.040 mmol) and (triethylsilyl)acetylene (0.174 mL, 0.971 mmol) in DMF (5 mL) was bubbled with $N_2$ for 10 minutes. $Et_3N$ (5 mL) was added and the mixture was stirred under nitrogen at 65° C. for 4 hours. The mixture was cooled and the volatiles were removed in vacuo. The dark brown residue was adsorbed onto silica and purified by column chromatography (Biotage Isolera, 24 g $SiO_2$ cartridge, 0-100% EtOAc in petroleum benzine 40-60° C.) to give the title compound A35 as a brown solid (0.116 g, 48%). LCMS-D: rt 3.84 min; m/z 302 [M+H]$^+$.

(d) 2-(2-Ethynylphenyl)-2-methylpropanamide (A36)

A solution of 2-methyl-2-(2-((triethylsilyl)ethynyl)phenyl)propanamide A35 (0.116 g, 0.385 mmol) in THF (5 mL) was stirred with TBAF (1.0 M in THF, 0.40 mL, 0.40 mmol) at 0° C. for 2 minutes. Sat. aq. $NaHCO_3$ (20 mL) was added and the aqueous phase was extracted with EtOAc (3×30 mL). The combined organics were washed with brine, dried ($MgSO_4$) and the solvent was removed in vacuo. The resultant yellow oil was purified by column chromatography (Biotage Isolera, 24 g $SiO_2$ cartridge, 20-100% EtOAc in petroleum benzine 40-60° C.) to give the title compound A36 as a yellow solid (0.060 g, 83%). LCMS-D: rt 3.02 min; m/z 188 [M+H]$^+$.

(e) 2-(2-((2,5-Dichloropyrimidin-4-yl)ethynyl)phenyl)-2-methylpropanamide (A37)

A mixture of 2-(2-ethynylphenyl)-2-methylpropanamide A36 (0.060 g, 0.32 mmol), 2,4,5-trichloropyrimidine (48 µL, 0.42 mmol) and $Et_3N$ (0.18 mL, 1.3 mmol) in 1,4-dioxane (5 mL) was bubbled with $N_2$ for 10 minutes. CuI (0.001 g, 0.006 mmol) and $PdCl_2(PPh_3)_2$ (0.002 g, 0.003 mmol) were added and the reaction mixture was stirred at room temperature under a $N_2$ atmosphere for 5.5 hours. The volatiles were removed in vacuo and the residue was purified by column chromatography (Biotage Isolera, 12 g $SiO_2$ cartridge, 10-100% EtOAc in petroleum benzine 40-60° C.) to give the title compound A37 as an off-white solid (0.067 g, 63%). LCMS-D: rt 3.33 min; m/z 334 [M+H]$^+$.

(f) 2-(2-(2-(2,5-Dichloropyrimidin-4-yl)ethyl)phenyl)-2-methylpropanamide (A38)

A mixture of 2-(2-((2,5-dichloropyrimidin-4-yl)ethynyl) phenyl)-2-methylpropanamide A37 (0.067 g, 0.20 mmol) and $PtO_2$ (0.014 g, 0.060 mmol) in MeOH (3.0 mL) and DMF (3.0 mL) was stirred in an atmosphere of $H_2$ for 64 hours. The mixture was diluted with EtOAc, filtered through Celite and the filtrate solvent was removed in vacuo. The residue was purified by column chromatography (Biotage Isolera, 12 g $SiO_2$, 0-100% EtOAc in petroleum benzine 40-60° C.) to give the title compound A38 as an off-white solid (0.042 g, 62%). LCMS-D: rt 3.37 min; m/z 338 [M+H]$^+$.

(g) 2-(2-(2-(5-Chloro-2-((1-methyl-1H-pyrazol-4-yl) amino)pyrimidin-4-yl)ethyl)phenyl)-2-methylpropanamide (45)

A mixture of 2-(2-(2-(2,5-dichloropyrimidin-4-yl)ethyl) phenyl)-2-methylpropanamide A38 (0.042 g, 0.12 mmol), 1-methyl-1H-pyrazol-4-amine (0.022 g, 0.23 mmol), and p-toluenesulfonic acid monohydrate (0.002 g, 0.012 mmol) in 1,4-dioxane (4.0 mL) was heated in the microwave at 120° C. for 3 hours. After cooling, the volatiles were removed in vacuo and the residue was adsorbed onto silica. Purification by column chromatography (Biotage Isolera, 12 g $SiO_2$, 0-5% MeOH in DCM) gave the title compound 45 as an off-white solid (0.009 g, 18%). LCMS-D: rt 3.29 min; m/z 399 [M+H]⁺.

Example 46

Synthesis of 1-(2-(2-(2-((1H-Pyrazol-4-yl)amino)-5-methylpyrimidin-4-yl)ethyl)phenyl)cyclopropanecarboxamide (46)

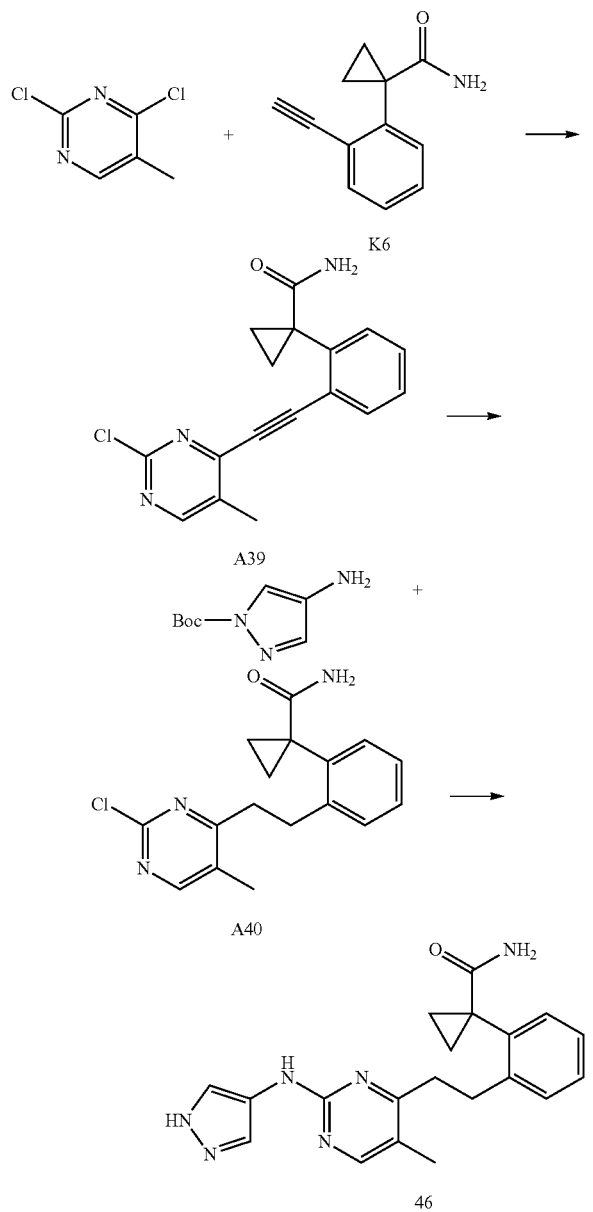

(a) 1-(2-((2-Chloro-5-methylpyrimidin-4-yl)ethynyl)phenyl)cyclopropanecarboxamide (A39)

A mixture of 1-(2-ethynylphenyl)cyclopropanecarboxamide K6 (2.29 g, 12.4 mmol), 2,4-dichloro-5-methylpyrimidine (2.62 g, 16.1 mmol), CuI (0.047 g, 0.25 mmol) and PdCl₂(PPh₃)₂ (0.087 g, 0.12 mmol) in dioxane (25 mL) was bubbled with N₂ for 10 minutes. Et₃N (10 mL) was added and the mixture was stirred under nitrogen at 70° C. for 1 hour. The reaction mixture was cooled and adsorbed onto silica. Purification by column chromatography (Biotage Isolera, 120 g SiO₂, 0-10% MeOH in CHCl₃) gave the title compound A39 as a yellow oil (1.85 g, 48%). LCMS-D: rt 3.24 min; m/z 312 [M+H]⁺.

(b) 1-(2-(2-(2-Chloro-5-methylpyrimidin-4-yl)ethyl)phenyl)cyclopropanecarboxamide (A40)

A mixture of 1-(2-((2-chloro-5-methylpyrimidin-4-yl)ethynyl)phenyl)cyclopropanecarboxamide A39 (1.85 g, 5.93 mmol) and PtO₂ (0.404 g, 1.78 mmol) in MeOH (10 mL) and DMF (40 mL) was stirred under an atmosphere of H₂ for 110 hours at room temperature. The mixture was filtered through Celite and the volatiles were removed in vacuo. The residue was purified by column chromatography (Biotage Isolera, 40 g SiO₂, 0-100% EtOAc in petroleum benzine 40-60° C.) to give the title compound A40 as a white solid (1.65 g, 88%). LCMS-D: rt 3.20 min; m/z 316 [M+H]⁺.

(c) 1-(2-(2-(2-((1H-Pyrazol-4-yl)amino)-5-methylpyrimidin-4-yl)ethyl)phenyl)cyclopropanecarboxamide (46)

A mixture of 1-(2-(2-(2-chloro-5-methylpyrimidin-4-yl)ethyl)phenyl)cyclopropanecarboxamide A40 (0.147 g, 0.465 mmol), tert-butyl 4-amino-1H-pyrazole-1-carboxylate (0.102 g, 0.559 mmol), Cs₂CO₃ (0.455 g, 1.40 mmol), Xantphos (0.011 g, 0.019 mmol) and Pd(OAc)₂ (0.002 g, 0.009 mmol) in 1,4-dioxane (5 mL) was bubbled with N₂ for 10 minutes before being heated in the microwave for 20 minutes at 120° C. The reaction mixture was cooled to room temperature, adsorbed onto silica, and purified by column chromatography (Biotage Isolera, 24 g SiO₂ cartridge, 20-100% EtOAc in petroleum benzine 40-60° C., then 0-20% MeOH in EtOAc) to give a white solid. This solid was taken up in DCM and precipitated by the addition of cyclohexane. The suspension was sonicated for 10 minutes and the precipitate was isolated by vacuum filtration and washed with Et₂O to give the title compound 46 as a white solid (0.021 g, 12%). LCMS-D: rt 2.98 min; m/z 363 [M+H]⁺.

Example 47

Synthesis of 1-(2-(2-(5-methyl-2-((1-methyl-1H-pyrazol-4-yl)amino)pyrimidin-4-yl)ethyl)phenyl)cyclopropanecarboxamide (47)

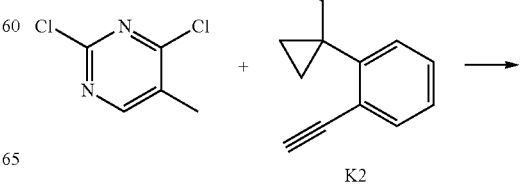

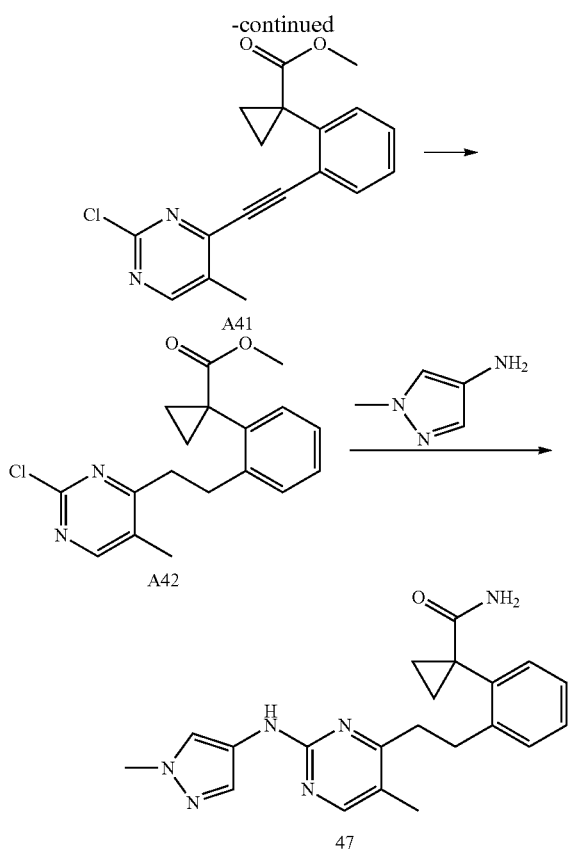

(a) Methyl 1-(2-((2-chloro-5-methylpyrimidin-4-yl)ethynyl)phenyl)cyclopropanecarboxylate (A41)

A mixture of methyl 1-(2-ethynylphenyl)cyclopropanecarboxylate K2 (1.34 g, 6.67 mmol), 2,4,-dichloro-5-methylpyrimidine (1.41 g, 8.67 mmol), CuI (0.063 g, 0.33 mmol), $PdCl_2(PPh_3)_2$ (0.234 g, 0.333 mmol) and tri-t-butylphosphonium tetrafluoroborate (0.097 g, 0.33 mmol) in 1,4-dioxane (15 mL) was bubbled with $N_2$ for 10 minutes. DIPEA (3.48 mL, 20.0 mmol) was added and the reaction mixture was stirred under $N_2$ at 80° C. for 3 hours. The reaction mixture was cooled and the volatiles were removed in vacuo to give a black residue that was purified by column chromatography (Biotage Isolera, 2×40 g $SiO_2$ cartridges, 0-50% EtOAc in petroleum benzine 40-60° C.) to give the impure title compound A41 as a yellow oil (estimated 80% purity, 1.352 g, 50%). LCMS-A: rt 6.79 min; m/z 327 [M+H]$^+$.

(b) Methyl 1-(2-(2-(2-chloro-5-methylpyrimidin-4-yl)ethyl)phenyl)cyclopropanecarboxylate (A42)

A solution of methyl 1-(2-((2-chloro-5-methylpyrimidin-4-yl)ethynyl)phenyl)cyclopropanecarboxylate A41 (estimated 80% purity, 1.35 g, 3.31 mmol) in DMF (15 mL) and MeOH (5 mL) was stirred with $PtO_2$ (0.235 g, 1.03 mmol) under an atmosphere of $H_2$ for 16 hours at room temperature. The reaction mixture was diluted with EtOAc (50 mL) and filtered through Celite. The volatiles were removed in vacuo and the black residue was purified by column chromatography (Biotage Isolera, 40 g $SiO_2$ cartridge, 0-25% EtOAc in petroleum benzine 40-60° C. then 40 g $SiO_2$ cartridge, 0-5% MeOH in DCM) to give the impure title compound A42 (estimated 78% purity, 0.922 g, 66%). LCMS-D: rt 3.58 min; m/z 331 [M+H]$^+$.

(c) 1-(2-(2-(5-Methyl-2-((1-methyl-1H-pyrazol-4-yl)amino)pyrimidin-4-yl)ethyl)phenyl)cyclopropanecarboxamide (47)

A mixture of 1-methyl-1H-pyrazol-4-amine (0.294 g, 3.02 mmol), methyl 1-(2-(2-(2-chloro-5-methylpyrimidin-4-yl)ethyl)phenyl)cyclopropanecarboxylate A42 (0.500 g, estimated 78% purity, 1.18 mmol), Xantphos (0.035 g, 0.060 mmol) and $Cs_2CO_3$ (1.48 g, 4.53 mmol) in 1,4-dioxane (5 mL) was bubbled with $N_2$ for 10 minutes. Palladium (II) acetate (0.007 g, 0.030 mmol) was added and the mixture was stirred in the microwave at 120° C. for 20 minutes. The volatiles were removed in vacuo and the black residue was purified by chromatography (Biotage Isolera, 2×40 g $SiO_2$ cartridges, 50-100% EtOAc in petroleum benzine 40-60° C. and then 0-10% MeOH in EtOAc) to give a yellow oil. This oil was purified further by column chromatography (0-5% MeOH in DCM) to give a yellow solid. A mixture of this solid and $LiOH.H_2O$ (0.234 g, 5.57 mmol) in THF (7 mL), MeOH (7 mL) and $H_2O$ (1.5 mL) was stirred at room temperature for 24 hours. Another portion of $LiOH.H_2O$ (0.234 g, 5.57 mmol) was added to the reaction mixture and stirring was continued for 72 hours at room temperature and then 24 hours at 35° C. The volatiles were removed in vacuo before $H_2O$ (10 mL) and aqueous HCl (2 M, 10 mL) were added. The aqueous phase was extracted with EtOAc (3×30 mL), the organics were combined, washed with brine, dried ($MgSO_4$) and the solvent removed under reduced pressure to give a yellow oil. A mixture of this oil, HOBt (0.072 g, 0.535 mmol), EDCl.HCl (0.103 g, 0.535 mmol) and DIPEA (0.23 mL, 1.34 mmol) in THF (6 mL) and DMF (1 mL) was stirred at room temperature for 10 minutes before ammonium carbonate (0.257 g, 2.68 mmol) was added. The mixture was stirred for a further 24 hours at room temperature and then 24 hours at 35° C. Sat. aqueous $NaHCO_3$ (30 mL) was added and the mixture was extracted with EtOAc (3×30 mL). The organics were combined, washed with brine and the solvent was removed in vacuo to give a yellow oil that was purified by column chromatography (Biotage Isolera, 40 g $SiO_2$, 50-100% EtOAc in petroleum benzine 40-60° C. and then 0-10% MeOH in EtOAc). The purified fractions were combined and the solvent removed in vacuo to give a yellow solid. Further purification by column chromatography (Biotage Isolera, 40 g $SiO_2$ cartridge, 0-5% MeOH in $CHCl_3$) gave a yellow solid. Prep-LCMS of this material gave the title compound 47 as a white solid (0.005 g, 1.1%). LCMS-D: rt 3.03 min; m/z 377 [M+H]$^+$.

Example 48

Synthesis of 1-(2-(2-(5-methyl-2-((1-(1-methylpiperidin-4-yl)-1H-pyrazol-4-yl)amino)pyrimidin-4-yl)ethyl)phenyl)cyclopropanecarboxamide (48)

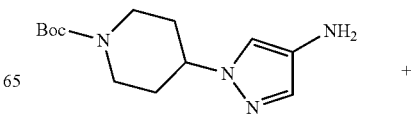

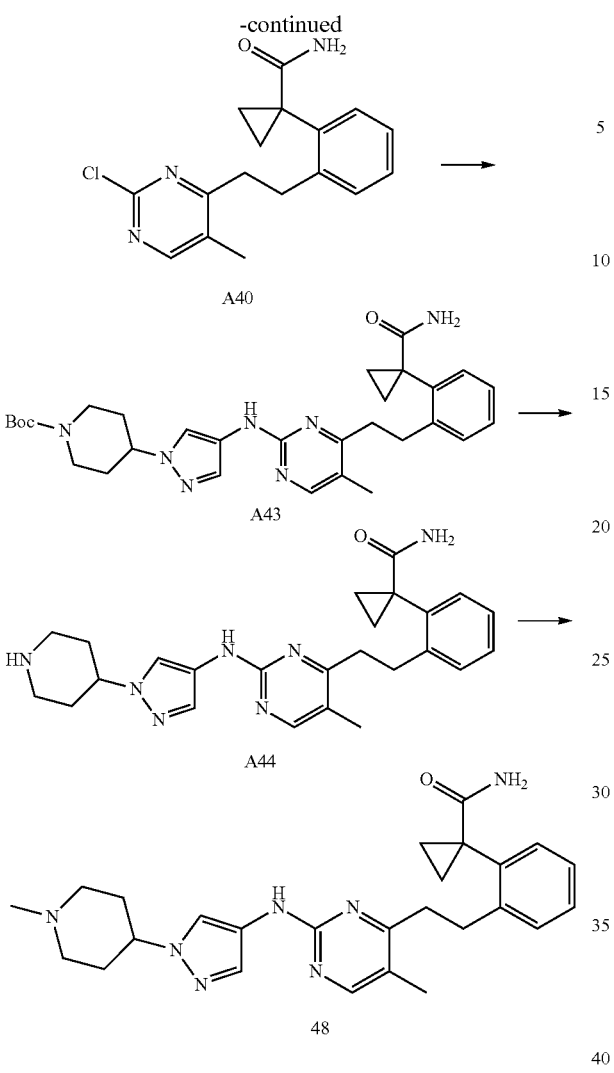

(a) tert-Butyl 4-(4-((4-(2-(1-carbamoylcyclopropyl)phenethyl)-5-methylpyrimidin-2-yl)amino)-1H-pyrazol-1-yl)piperidine-1-carboxylate (A43)

A mixture of 1-(2-(2-(2-chloro-5-methylpyrimidin-4-yl)ethyl)phenyl)cyclopropanecarboxamide A40 (0.250 g, 0.792 mmol), tert-butyl 4-(4-amino-1H-pyrazol-1-yl)piperidine-1-carboxylate (0.422 g, 1.58 mmol), Pd(OAc)$_2$ (0.004 g, 0.016 mmol), Xantphos (0.018 g, 0.032 mmol) and Cs$_2$CO$_3$ (0.774 g, 2.38 mmol) in dioxane (15 mL) was bubbled with N$_2$ for 10 minutes and then stirred in the microwave at 120° C. for 20 minutes. The volatiles were removed in vacuo and the residue was adsorbed onto SiO$_2$ and purified by column chromatography (Biotage Isolera, 40 g SiO$_2$ cartridge, 0-100% EtOAc in petroleum benzine 40-60° C.) to give the title compound A43 as a brown solid (0.118 g, 27%). LCMS-D: rt 3.40 min; m/z 546 [M+H]$^+$.

(b) 1-(2-(2-(5-Methyl-2-((1-(piperidin-4-yl)-1H-pyrazol-4-yl)amino)pyrimidin-4-yl)ethyl)phenyl)cyclopropanecarboxamide (A44)

A solution of tert-butyl 4-(4-((4-(2-(1-carbamoylcyclopropyl)phenethyl)-5-methylpyrimidin-2-yl)amino)-1H-pyrazol-1-yl)piperidine-1-carboxylate A43 (0.113 g, 0.207 mmol) in DCM (10 mL) was treated with TFA (0.32 mL, 4.1 mmol) and stirred for 20 hours at room temperature. The volatiles were evaporated in vacuo and aq. NaOH (2 M, 40 mL) was added to the residue. The aqueous phase was extracted with EtOAc (3×40 mL) and the combined organics were washed with brine and dried over MgSO$_4$. The solvent was removed in vacuo and the solid was suspended in DCM. Cyclohexane was added and the suspension was sonicated for 10 minutes. The solid was isolated by vacuum filtration to give the title compound A44 as an off-white solid (0.066 g, 72%). LCMS-D: rt 2.88 min; m/z 446 [M+H]$^+$.

(c) 1-(2-(2-(5-Methyl-2-((1-(1-methylpiperidin-4-yl)-1H-pyrazol-4-yl)amino)pyrimidin-4-yl)ethyl)phenyl)cyclopropanecarboxamide (48)

To a solution of 1-(2-(2-(5-methyl-2-((1-(piperidin-4-yl)-1H-pyrazol-4-yl)amino)pyrimidin-4-yl)ethyl)phenyl)cyclopropanecarboxamide A44 (0.064 g, 0.14 mmol) in MeOH (12 mL) was added formaldehyde solution (37% in water, 32 μL, 0.43 mmol) and sodium triacetoxyborohydride (0.122 g, 0.575 mmol) under a nitrogen atmosphere. The mixture was stirred at room temperature for 4 hours before concentrating under reduced pressure. The mixture was diluted with sat. aq. NaHCO$_3$ (20 mL) and the aqueous phase was extracted with EtOAc (3×25 mL). The combined organics were washed with brine, and dried (MgSO$_4$) before the solvent was removed in vacuo to give the title compound 48 as a white solid (0.035 g, 53%). LCMS-D: rt 2.89 min; m/z 460 [M+H]$^+$.

Example 49

Synthesis of 1-(2-(2-(5-Methyl-2-((6-(1-methylpiperidin-4-yl)pyridin-3-yl)amino)pyrimidin-4-yl)ethyl)phenyl)cyclopropanecarboxamide (49)

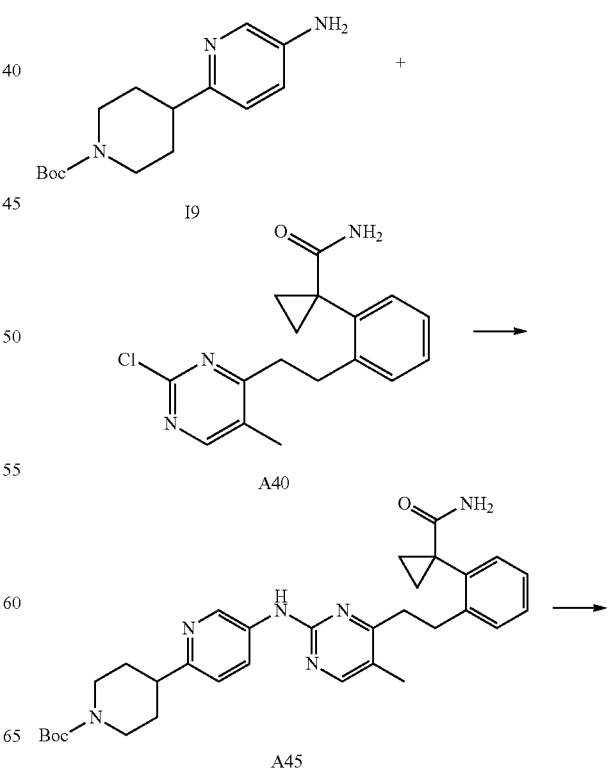

-continued

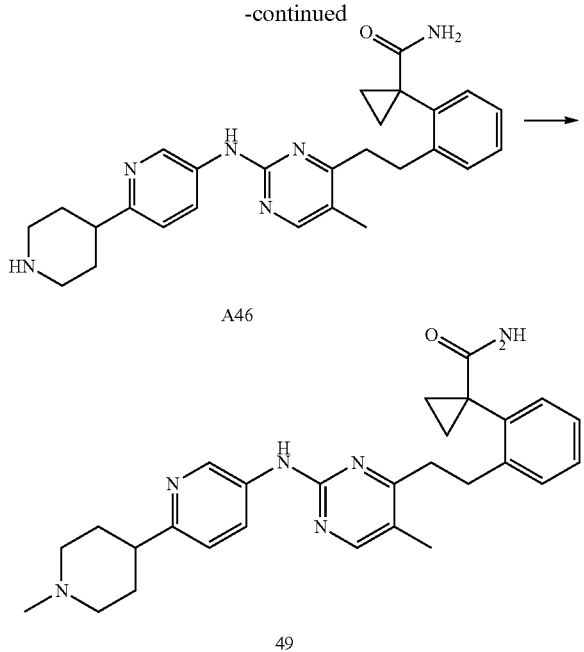

(c) 1-(2-(2-(5-Methyl-2-((6-(1-methylpiperidin-4-yl) pyridin-3-yl)amino)pyrimidin-4-yl)ethyl)phenyl) cyclopropanecarboxamide (49)

A solution of 1-(2-(2-(5-methyl-2-((6-(piperidin-4-yl)pyridin-3-yl)amino)pyrimidin-4-yl)ethyl)phenyl)cyclopropanecarboxamide A46 (0.121 g, 0.265 mmol) in MeOH (10 mL) was treated with formaldehyde solution (37% in water, 59 µL, 0.80 mmol) and sodium triacetoxyborohydride (0.225 g, 1.06 mmol) and stirred at room temperature for 3 hours. The mixture was concentrated in vacuo, aq. NaOH (2 M, ~30 mL) was added and the aqueous phase was extracted with EtOAc (3×30 mL). The organics were combined, washed with brine, dried (MgSO$_4$) and the solvent evaporated under reduced pressure to give a colourless oil. The oil was taken up in DCM and cyclohexane was added until a white precipitate formed. The suspension was sonicated for 10 minutes and the solid was isolated by vacuum filtration and dried under high vacuum for 4 hours to give the title compound 49 as a white solid (0.051 g, 41%). LCMS-D: rt 3.13 min; m/z 471 [M+H]$^+$.

Example 50

Synthesis of 1-(2-(2-(2-((4-(1-Aminoethyl)phenyl) amino)-5-methylpyrimidin-4-yl)ethyl)phenyl)cyclopropanecarboxamide (50)

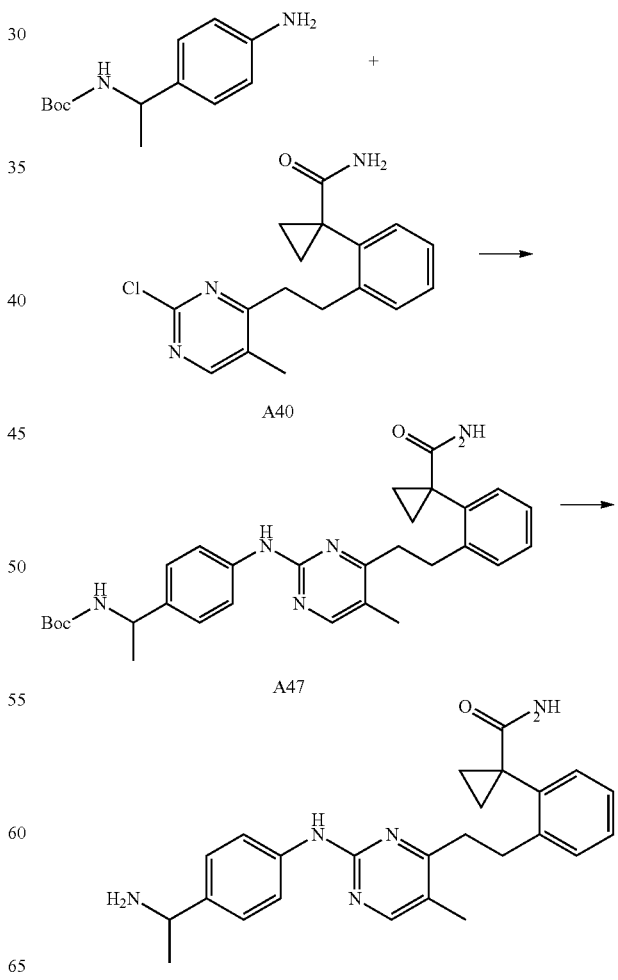

(a) tert-Butyl 4-(5-((4-(2-(1-carbamoylcyclopropyl) phenethyl)-5-methylpyrimidin-2-yl)amino)pyridin-2-yl)piperidine-1-carboxylate (A45)

A mixture of 1-(2-(2-(2-chloro-5-methylpyrimidin-4-yl)ethyl)phenyl)cyclopropanecarboxamide A40 (0.240 g, 0.761 mmol), tert-butyl 4-(5-aminopyridin-2-yl)piperidine-1-carboxylate (0.422 g, 1.52 mmol), Pd(OAc)$_2$ (0.003 g, 0.015 mmol), Xantphos (0.018 g, 0.030 mmol) and Cs$_2$CO$_3$ (0.744 g, 2.28 mmol) in dioxane (8 mL) was bubbled with N$_2$ for 10 minutes and then stirred in the microwave at 120° C. for 20 minutes. The volatiles were removed in vacuo and the residue was adsorbed onto SiO$_2$ and purified by column chromatography (Biotage Isolera, 40 g SiO$_2$ cartridge, 0-100% EtOAc in petroleum benzine 40-60° C. then 0-20% MeOH in EtOAc) to give the title compound A45 as a white solid (0.212 g, 50%). LCMS-D: rt 3.20 min; m/z 557 [M+H]$^+$.

(b) 1-(2-(2-(5-Methyl-2-((6-(piperidin-4-yl)pyridin-3-yl)amino)pyrimidin-4-yl)ethyl)phenyl)cyclopropanecarboxamide (A46)

A solution of tert-butyl 4-(5-((4-(2-(1-carbamoylcyclopropyl)phenethyl)-5-methylpyrimidin-2-yl)amino)pyridin-2-yl)piperidine-1-carboxylate A45 (0.200 g, 0.359 mmol) in DCM (10 mL) was treated with TFA (0.41 mL, 5.4 mmol) and stirred at room temperature for 4 hours. An extra aliquot of TFA (0.14 mL, 1.8 mmol) was added to the reaction mixture and stirring was continued for 1 hour at room temperature. Sat. aq. NaHCO$_3$ (~20 mL) was carefully added to the mixture followed by aq. NaOH (2 M, ~20 mL). DCM was removed in vacuo and the aqueous mixture was extracted with EtOAc (3×30 mL). The organic extracts were combined, washed with brine, dried (MgSO$_4$) and the solvent removed in vacuo. The residue was dissolved in DCM before cyclohexane was added to form a white precipitate. The suspension was sonicated for 10 minutes and filtered to give the title compound A46 as a white solid (0.129 g, 79%). LCMS-D: rt 3.08 min; m/z 457 [M+H]$^+$.

(a) tert-Butyl (1-(4-((4-(2-(1-carbamoylcyclopropyl) phenethyl)-5-methylpyrimidin-2-yl)amino)phenyl) ethyl)carbamate (A47)

A mixture of 1-(2-(2-(2-chloro-5-methylpyrimidin-4-yl) ethyl)phenyl)cyclopropanecarboxamide A40 (0.300 g, 0.950 mmol), tert-butyl (1-(4-aminophenyl)ethyl)carbamate (0.449 g, 1.90 mmol), Pd(OAc)₂ (0.004 g, 0.019 mmol), xantphos (0.022 g, 0.038 mmol) and Cs₂CO₃ (0.929 g, 2.85 mmol) in dioxane (15 mL) was bubbled with N₂ for 10 minutes and then stirred in the microwave at 120° C. for 20 minutes. The volatiles were removed in vacuo and the residue was adsorbed onto SiO₂ and purified by column chromatography (Biotage Isolera, 40 g SiO₂ cartridge, 0-100% EtOAc in petroleum benzine 40-60° C.) to give the title compound A47 as a white solid (0.110 g, 22%). LCMS-D: rt 3.52 min; m/z 516 [M+H]⁺.

(b) 1-(2-(2-(2-((4-(1-Aminoethyl)phenyl)amino)-5-methylpyrimidin-4-yl)ethyl)phenyl)cyclopropanecarboxamide (50)

A solution of tert-butyl (1-(4-((4-(2-(1-carbamoylcyclopropyl)phenethyl)-5-methylpyrimidin-2-yl)amino)phenyl) ethyl)carbamate A47 (0.110 g, 0.213 mmol) in DCM (10 mL) was treated with TFA (0.33 mL, 4.3 mmol) and stirred for 6 hours at room temperature. The volatiles were evaporated in vacuo before aq. NaOH (2 M, 30 mL) was added to the residue. The aqueous phase was extracted with EtOAc (3×30 mL) and the combined organics were washed with brine and dried over MgSO₄. The solvent was removed in vacuo to give an off-white solid that still contained starting material. The solid was taken up in DCM (20 mL) and treated with TFA (0.17 mL, 2.2 mmol). The mixture was stirred at room temperature for 24 hours before the volatiles were removed in vacuo. Aq. NaOH (2 M, 30 mL) was added and the aqueous phase was extracted with EtOAc (3×30 mL). The organics were combined, washed with brine, dried (MgSO₄) and the solvent removed in vacuo. The resultant white solid was dissolved in DCM and the desired product was precipitated by the addition of cyclohexane. The precipitate was isolated by vacuum filtration to give the title compound 50 (0.037 g, 42%) as a white solid. LCMS-A: rt 2.98 min; m/z 399 [M-NH₂]+.

Example 51

Synthesis of 2-(2-(2-(5-Methyl-2-((1-methyl-1H-pyrazol-4-yl)amino)pyrimidin-4-yl)ethyl)phenyl) propanamide (51)

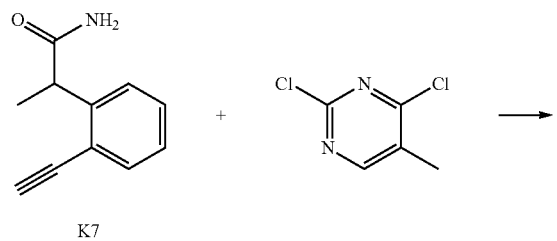

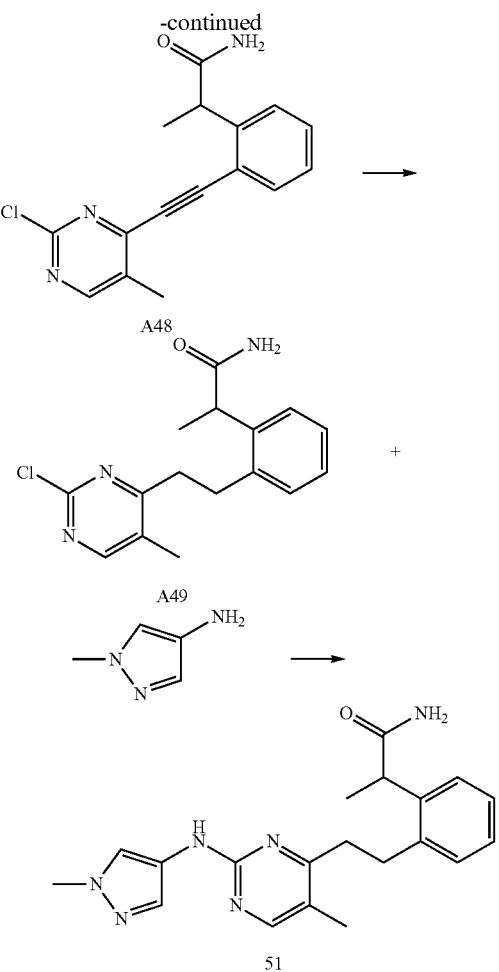

(a) 2-(2-((2-Chloro-5-methylpyrimidin-4-yl)ethynyl) phenyl)propanamide (A48)

A suspension of 2-(2-ethynylphenyl)propanamide K7 (2.00 g, 11.5 mmol), 2,4,-dichloro-5-methylpyrimidine (2.45 g, 15.0 mmol), CuI (0.044 g, 0.33 mmol), PdCl₂(PPh₃)₂ (0.162 g, 0.231 mmol) and tri-t-butylphosphonium tetrafluoroborate (0.067 g, 0.23 mmol) in DMF (15 mL) was bubbled with N₂ for 10 minutes. Et₃N (10 mL) was added and the reaction mixture was stirred under N₂ at 60° C. for 2.5 hours. The mixture was cooled, diluted with Et₂O and the precipitate was isolated by filtration and washed with Et₂O then water to give the title compound A48 as a white solid (2.08 g, 60%). LCMS-A: rt 5.86 min; m/z 300 [M+H]⁺.

(b) 2-(2-(2-(2-Chloro-5-methylpyrimidin-4-yl)ethyl) phenyl)propanamide (A49)

A solution of 2-(2-((2-chloro-5-methylpyrimidin-4-yl) ethynyl)phenyl)propanamide A48 (2.08 g, 6.95 mmol) in DMF (110 mL) and MeOH (10 mL) was stirred with PtO₂ (0.395 g, 1.74 mmol) under an atmosphere of H₂ for 16 hours at room temperature. An extra portion of PtO₂ (0.189 g, 0.832 mmol) was added and stirring was continued under H₂ for 72 hours at room temperature. The mixture was diluted with EtOAc (200 mL) and filtered through Celite. The volatiles were removed in vacuo and the residue was purified by column chromatography (Biotage Isolera, 120 g SiO₂ cartridge, 10-100% EtOAc in petroleum benzine 40-60° C.) to give the title compound A49 as a white solid (1.51 g, 72%). LCMS-D: rt 3.15 min; m/z 304 [M+H]⁺.

(c) 2-(2-(2-(5-Methyl-2-((1-methyl-1H-pyrazol-4-yl)amino)pyrimidin-4-yl)ethyl)phenyl)propanamide (51)

A mixture of 2-(2-(2-(2-chloro-5-methylpyrimidin-4-yl)ethyl)phenyl)propanamide A49 (0.250 g, 0.823 mmol), 1-methyl-1H-pyrazol-4-amine (0.096 g, 0.99 mmol), and p-toluenesulfonic acid monohydrate (0.016 g, 0.082 mmol) in 1,4-dioxane (5 mL) was irradiated in the microwave at 120° C. for 3 hours. The volatiles were removed in vacuo and the residue was adsorbed onto silica and purified by column chromatography (Biotage Isolera, 40 g SiO₂ cartridge, 50-100% EtOAc in petroleum benzine 40-60° C., then 0-10% MeOH in EtOAc). The fractions containing suspected product were combined and the solvent removed in vacuo to give a green solid. The solid was adsorbed onto silica and purified by column chromatography (Biotage Isolera, 40 g SiO₂ cartridge, 0-10% MeOH in CHCl₃) to give the title compound 51 as a white solid (0.178 g, 59%); $^1$H NMR (400 MHz, d₆-DMSO) δ ppm 9.16 (s, 1H), 8.11 (s, 1H), 7.85 (s, 1H), 7.46 (s, 1H), 7.41-7.35 (m, 1H), 7.24 (s, 1H), 7.20-7.10 (m, 3H), 6.87 (s, 1H), 3.86 (q, J=7.1, 7.0, 7.0 Hz, 1H), 3.78 (s, 3H), 3.23-3.11 (m, 1H), 3.08-2.97 (m, 1H), 2.96-2.78 (m, 2H), 2.05 (s, 3H), 1.33 (d, J=6.9 Hz, 3H). LCMS-D: rt 2.99 min; m/z 365 [M+H]⁺.

Example 51-1A and 51-2A

Separation of 2-(2-(2-(5-Methyl-2-((1-methyl-1H-pyrazol-4-yl)amino)pyrimidin-4-yl)ethyl)phenyl)propanamide (51)

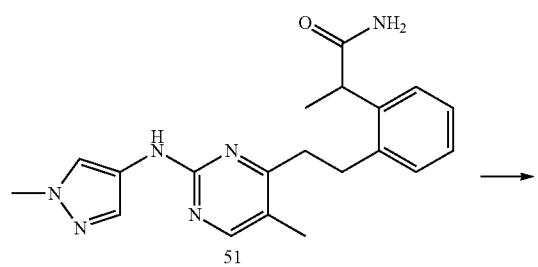

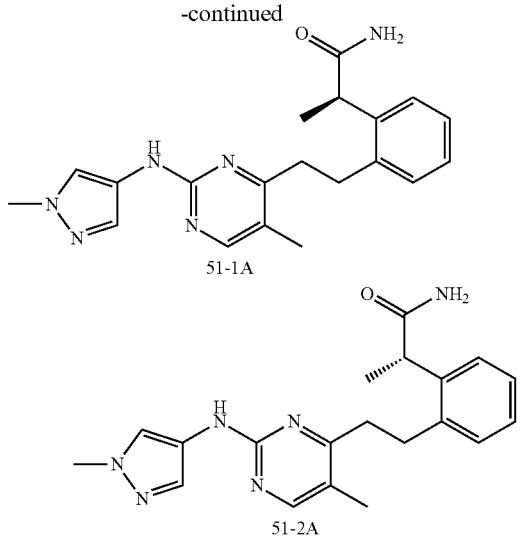

2-(2-(2-(5-Methyl-2-((1-methyl-1H-pyrazol-4-yl)amino)pyrimidin-4-yl)ethyl)phenyl)propanamide (51) was separated at using the chiral separation method A Enantiomer A of 2-(2-(2-(5-methyl-2-((1-methyl-1H-pyrazol-4-yl)amino)pyrimidin-4-yl)ethyl)phenyl)propanamide (51-1A), Chiral Characterisation Method E: rt 12.11 min, enantiomeric purity>99%.

Enantiomer B of 2-(2-(2-(5-methyl-2-((1-methyl-1H-pyrazol-4-yl)amino)pyrimidin-4-yl)ethyl)phenyl)propanamide (51-2A), Chiral Characterisation Method E: rt 14.72 min, enantiomeric purity>99%.

Example 52

Synthesis of 1-(2-(2-(2-((4-(piperidin-4-yl)phenyl)amino)-5-(trifluoromethyl)pyrimidin-4-yl)ethyl)phenyl)cyclobutanecarboxamide (52)

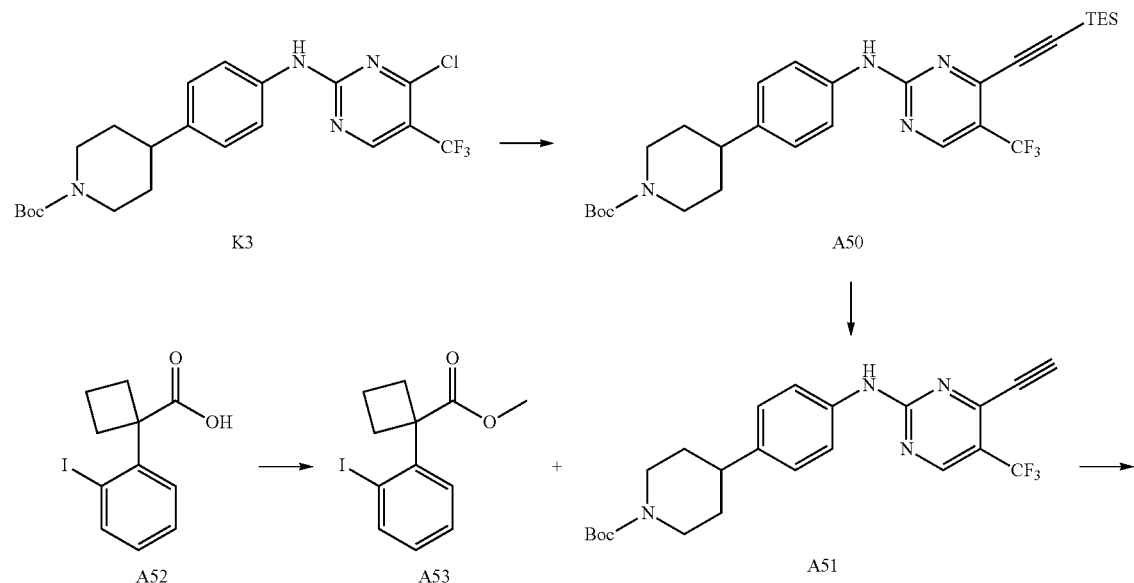

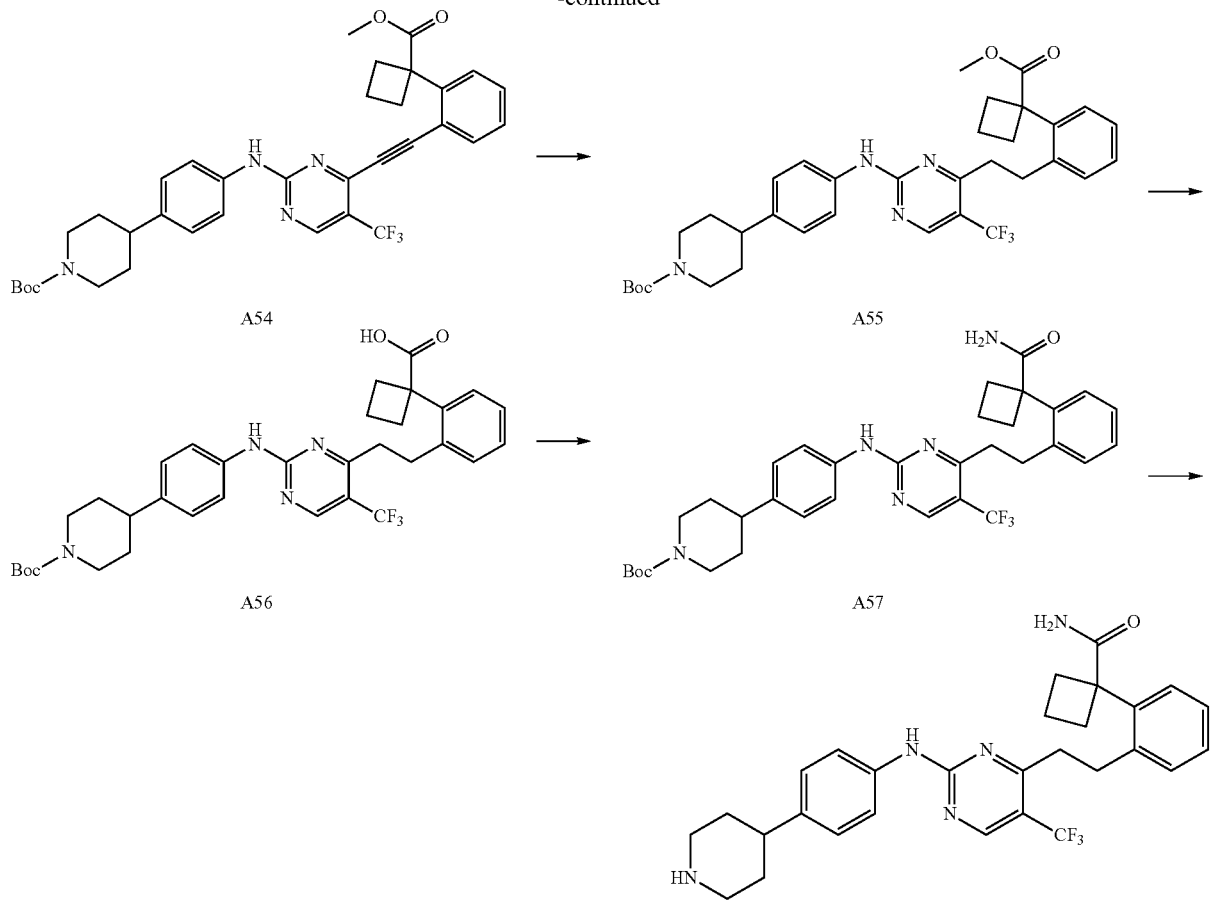

(a) tert-Butyl 4-(4-((5-(trifluoromethyl)-4-((triethylsilyl)ethynyl)pyrimidin-2-yl)amino)phenyl)piperidine-1-carboxylate (A50)

A suspension of tert-butyl 4-(4-((4-chloro-5-(trifluoromethyl)pyrimidin-2-yl)amino)phenyl)piperidine-1-carboxylate K3 (5.10 g, 11.2 mmol), PdCl$_2$(PPh$_3$)$_2$ (392 mg, 0.558 mmol), PPh$_3$ (146 mg, 0.558 mmol) and CuI (106 mg, 0.558 mmol) in THF (200 mL) and Et$_3$N (7.78 mL, 55.8 mmol) was sonicated for 10 minutes. TES acetylene (3.00 mL, 16.7 mmol) was added and the mixture was stirred at 30° C. overnight. The crude mixture was adsorbed onto silica gel and purified by silica gel column chromatography (Biotage Isolera, 0-50% EtOAc in petroleum benzine 40-60° C.) to give the title compound A50 as a yellow foam (4.64 g, 74%). LCMS-A: rt 7.737 min; m/z 561 [M+H]$^+$.

(b) tert-Butyl 4-(4-((4-ethynyl-5-(trifluoromethyl)pyrimidin-2-yl)amino)phenyl)piperidine-1-carboxylate (A51)

A mixture of K2CO$_3$ (1.72 g, 12.4 mmol) and tert-butyl 4-(4-((5-(trifluoromethyl)-4-((triethylsilyl)ethynyl)pyrimidin-2-yl)amino)phenyl)piperidine-1-carboxylate A50 (4.64 g, 8.28 mmol) in MeOH (250 mL) was stirred for 15 minutes at room temperature. The mixture was diluted with water (250 mL) and extracted with DCM (3×250 mL). The organics were combined and adsorbed onto silica gel. Purification by silica gel column chromatography (Biotage Isolera, 0-100% EtOAc in petroleum benzine 40-60° C.) gave the title compound A51 as a yellow solid (2.196 g, 59%). LCMS-A: rt 6.615 min; m/z 445 [M−H]$^−$.

(c) 1-(2-Iodophenyl)cyclobutanecarboxylic acid (A52)

A solution of 1-phenyl-1-cyclobutanecarboxylic acid (2.00 g, 11.4 mmol) in DMF (10 mL) containing palladium (II) acetate (0.109 g, 0.567 mmol), iodine (2.16 g, 8.51 mmol) and (diacetoxyiodo)benzene (2.47 g, 8.51 mmol) was stirred at 60° C. for 18 hours in the absence of light. Additional iodine (2.16 g, 8.51 mmol) and (diacetoxyiodo)benzene (2.47 g, 8.51 mmol) were added and stirring was continued at 60° C. for 8 hours. A final addition of iodine (2.16 g, 8.51 mmol) and (diacetoxyiodo)benzene (2.47 g, 8.51 mmol) was performed and stirring was continued at 60° C. for 16 hours. The reaction mixture was partitioned between EtOAc and water and the aqueous phase was extracted several times with EtOAc. The combined organic fractions were washed with 10% sodium metabisulfate (3×30 mL), 10% citric acid (2×30 mL), water, brine, and then dried (MgSO$_4$), filtered and the solvent evaporated. The crude product was dry loaded onto silica gel and the product was separated using silica column chromatography (Biotage Isolera, 40 g SiO$_2$ Cartridge, 0-100% EtOAc in petroleum benzine 40-60° C.) to give the title compound A52 as a cream solid (425 mg, 12%). LCMS-A: rt 5.711 min.

(d) Methyl 1-(2-iodophenyl)cyclobutanecarboxylate (A53)

A solution of 1-(2-iodophenyl)cyclobutanecarboxylic acid A52 (425 mg, 1.41 mmol) in MeOH (25 mL) and conc. $H_2SO_4$ (1.0 mL) was stirred at 60° C. overnight. The volatiles were removed in vacuo and the resulting residue diluted in EtOAc (50 mL) and sat. soln. $Na_2CO_3$ (50 mL). The aqueous layer was extracted with EtOAc (3×50 mL), the combined organic fractions were dried ($MgSO_4$) and the volatiles removed in vacuo to give the title compound A53 as a clear oil (361 mg, 81%). LCMS-A: rt 7.020 min; m/z 317 $[M+H]^+$.

(e) tert-Butyl 4-(4-((4-((2-(1-(methoxycarbonyl)cyclobutyl)phenyl)ethynyl)-5-(trifluoromethyl)pyrimidin-2-yl)amino)phenyl)piperidine-1-carboxylate (A54)

A suspension of tert-butyl 4-(4-((4-ethynyl-5-(trifluoromethyl)pyrimidin-2-yl)amino)phenyl)piperidine-1-carboxylate A51 (169 mg, 0.380 mmol), methyl 1-(2-iodophenyl)cyclobutanecarboxylate A53 (100 mg, 0.316 mmol), $PPh_3$ (8 mg, 0.03 mmol) and CuI (3 mg, 0.02 mmol) in DMF (3 mL) and $Et_3N$ (0.5 mL) was sonicated for 10 minutes before $PdCl_2(PPh_3)_2$ (22 mg, 0.032 mmol) was added. The reaction mixture was irradiated in the microwave at 120° C. for 20 minutes, adsorbed onto silica gel and purified using column chromatography (Biotage Isolera, 40 g $SiO_2$ cartridge, 0-30% EtOAc in petroleum benzine 40-60° C. (column run twice)) to give the title compound A54 as a yellow oil (33 mg, 16%). LCMS-A: rt 7.919 min; m/z 635 $[M+H]^+$.

(f) tert-Butyl 4-(4-((4-(2-(1-(methoxycarbonyl)cyclobutyl)phenethyl)-5-(trifluoromethyl)pyrimidin-2-yl)amino)phenyl)piperidine-1-carboxylate (A55)

Pd/C 10% (40 mg) was added to a solution of tert-butyl 4-(4-((4-((2-(1-(methoxycarbonyl)cyclobutyl)phenyl)ethynyl)-5-(trifluoromethyl)pyrimidin-2-yl)amino)phenyl)piperidine-1-carboxylate A54 (33 mg, 0.052 mmol) in EtOAc (10 mL) and $Et_3N$ (0.5 mL). The mixture was stirred under a hydrogen atmosphere overnight and then filtered through Celite. The filter cake was washed with EtOAc (50 mL) and the volatiles were removed in vacuo to give the title compound A55 as a yellow oil (31 mg, 93%). LCMS-A: rt 8.013 min; m/z 639.3 $[M+H]^+$.

(g) 1-(2-(2-(2-((4-(1-(tert-Butoxycarbonyl)piperidin-4-yl)phenyl)amino)-5-(trifluoromethyl)pyrimidin-4-yl)ethyl)phenyl)cyclobutanecarboxylic acid (A56)

$LiOH.H_2O$ (41 mg, 0.97 mmol) was added to a solution of tert-butyl 4-(4-((4-(2-(1-(methoxycarbonyl)cyclobutyl)phenethyl)-5-(trifluoromethyl)pyrimidin-2-yl)amino)phenyl)piperidine-1-carboxylate A55 (31 mg, 0.049 mmol) in THF (5 mL) and $H_2O$ (0.5 mL) and the mixture was stirred at 40° C. overnight. Additional $LiOH.H_2O$ (400 mg, 9.53 mmol) was added and the mixture was heated at reflux for 12 days. Upon cooling DCM (50 mL) and water (50 mL) were added and the aqueous layer was extracted with EtOAc (2×50 mL). The combined organics were dried ($Na_2SO_4$) and the volatiles were removed in vacuo to give the title compound A56 as a yellow oil (30 mg, 98%). LCMS-A: rt 7.586 min; m/z 625 $[M+H]^+$.

(h) tert-Butyl 4-(4-((4-(2-(1-carbamoylcyclobutyl)phenethyl)-5-(trifluoromethyl)pyrimidin-2-yl)amino)phenyl)piperidine-1-carboxylate (A57)

Ammonium carbonate (92 mg 0.96 mmol) was added to a suspension of 1-(2-(2-(2-((4-(1-(tert-butoxycarbonyl)piperidin-4-yl)phenyl)amino)-5-(trifluoromethyl)pyrimidin-4-yl)ethyl)phenyl)cyclobutanecarboxylic acid A56 (30 mg, 0.048 mmol), HOBt (32 mg, 0.24 mmol) and EDCl.HCl (46 mg, 0.24 mmol) in $Et_3N$ (0.2 mL) and DMF (10 mL) and the resulting mixture was stirred at 40° C. overnight. The volatiles were removed in vacuo and the resulting residue was dissolved in DCM (50 mL), washed with water (50 mL), separated and adsorbed onto silica gel. Purification by column chromatography (Biotage Isolera, 12 g $SiO_2$ cartridge, 0-100% EtOAc in peteroleum benzine 40-60° C.) gave the title compound A57 as a yellow solid (6 mg, 20%). LCMS-A: rt 8.604 min; m/z 624.3 $[M+H]^+$.

(i) 1-(2-(2-(2-((4-(Piperidin-4-yl)phenyl)amino)-5-(trifluoromethyl)pyrimidin-4-yl)ethyl)phenyl)cyclobutanecarboxamide (52)

A mixture of TFA (0.5 mL) and tert-butyl 4-(4-((4-(2-(1-carbamoylcyclobutyl)phenethyl)-5-(trifluoromethyl)pyrimidin-2-yl)amino)phenyl)piperidine-1-carboxylate A57 (6.0 mg, 9.6 µL) in DCM (5 mL) was stirred at room temperature overnight. The volatiles were removed in vacuo before 2 M aq. NaOH (5 mL) was added to form a precipitate. The solid was collected by filtration and washed with cyclohexane (10 mL) to give the title compound 52 as a tan solid (1.5 mg, 30%). LCMS-A: rt 4.994 min; m/z 524.3 $[M+H]^+$.

Example 53

Synthesis of 1-(3-(2-(2-((1-(piperidin-4-yl)-1H-pyrazol-4-yl)amino)-5-(trifluoromethyl)pyrimidin-4-yl)ethyl)phenyl)cyclopropanecarboxamide (53)

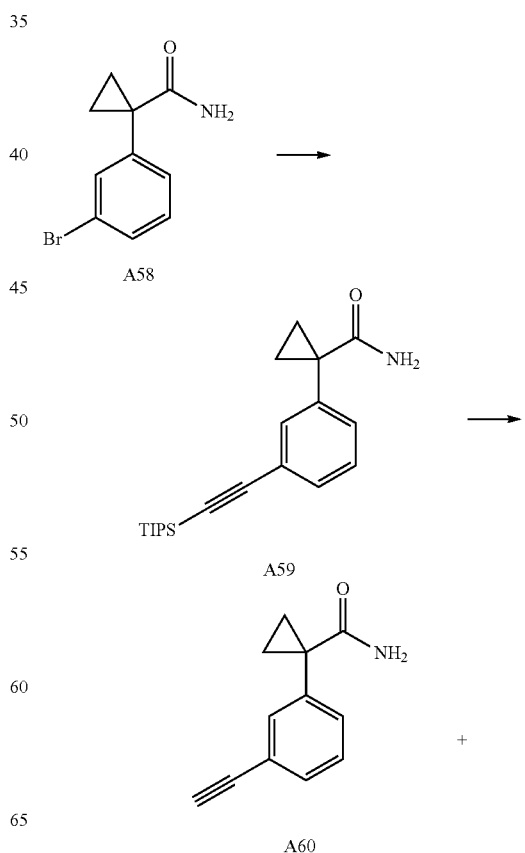

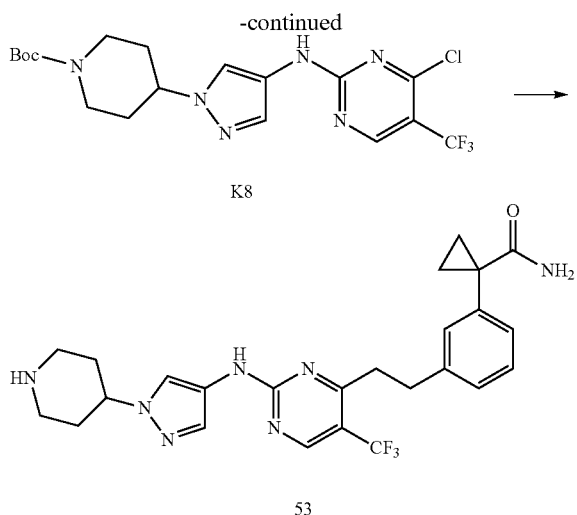

(a) 1-(3-Bromophenyl)cyclopropanecarboxamide (A58)

Ammonium carbonate (7.97 g 83.0 mmol) was added to a suspension of 1-(3-bromophenyl)cyclopropylacetic acid (2.00 g, 8.30 mmol), HOBt (1.68 g, 12.4 mmol) and EDCl.HCl (2.39 g, 12.4 mmol) in Et$_3$N (5 mL) and DMF (25 mL) and the mixture was stirred at room temperature overnight. EtOAc (150 mL) was added and the organic layer was washed with sat. NaHCO$_3$ solution (100 mL), 0.5 M citric acid solution (3×100 mL), water (100 mL), brine (50 mL) and dried (Na$_2$SO$_4$). The volatiles were removed in vacuo to yield the title compound A58 as a white solid (1.78 g, 89%). LCMS-A: rt 5.807 min; m/z 241 [M+H]$^+$.

(b) 1-(3-((Triisopropylsilyl)ethynyl)phenyl)cyclopropanecarboxamide (A59)

A suspension of 1-(3-bromophenyl)cyclopropanecarboxamide A58 (1.00 g, 4.17 mmol), TIPS acetylene (3.74 mL, 16.7 mmol), PPh$_3$ (55 mg, 0.21 mmol) and CuI (40 mg, 0.21 mmol) in Et$_3$N (4 mL) and DMF (15 mL) was sonicated for 10 minutes. PdCl$_2$(PPh$_3$)$_2$ (146 mg, 0.208 mmol) was added and the mixture was heated to 80° C. for 16 hours. The crude mixture was adsorbed onto silica gel and purified by column chromatography (Biotage Isolera, 40 g SiO$_2$ cartridge, 0-100% EtOAc in petroleum benzine 40-60° C.) to give the title compound A59 as a white solid (1.20 g, 84%). LCMS-A: rt 8.081 min; m/z 342.4 [M+H]$^+$.

(c) 1-(3-Ethynylphenyl)cyclopropanecarboxamide (A60)

A 1.0 M TBAF solution in THF (10.5 mL, 10.5 mmol) was added to a solution of 1-(3-((triisopropylsilyl)ethynyl)phenyl)cyclopropanecarboxamide A59 (1.20 g, 3.50 mmol) in THF (50 mL) and stirred for 15 minutes. The mixture was diluted with water (200 mL) and EtOAc (200 mL) before the organic fraction was separated and washed with 0.5 M citric acid solution (200 mL), water (200 mL), brine (50 mL) and dried (Na$_2$SO$_4$). The volatiles were removed in vacuo and the resulting solid was suspended in cyclohexane (50 mL) and sonicated for 10 minutes. The solid was collected by filtration and dried to give the title compound A60 as a tan solid (386 mg, 59%). LCMS-A: rt 5.635 min; m/z 186.2 [M+H]$^+$.

(d) 1-(3-(2-(2-((1-(Piperidin-4-yl)-1H-pyrazol-4-yl)amino)-5-(trifluoromethyl)pyrimidin-4-yl)ethyl)phenyl)cyclopropanecarboxamide (53)

A suspension of tert-butyl 4-(4-((4-chloro-5-(trifluoromethyl)pyrimidin-2-yl)amino)-1H-pyrazol-1-yl)piperidine-1-carboxylate K8 (483 mg, 1.08 mmol), 1-(3-ethynylphenyl)cyclopropanecarboxamide A60 (200 mg, 1.08 mmol), PPh$_3$ (14 mg, 0.054 mmol) and CuI (10 mg, 0.054 mmol) in Et$_3$N (1 mL) and DMF (4 mL) was sonicated for 10 minutes, PdCl$_2$(PPh$_3$)$_2$ (38 mg, 0.054 mmol) was added and the reaction mixture was irradiated in the microwave at 120° C. for 40 minutes. The mixture was adsorbed onto silica gel and purified by column chromatography (Biotage Isolera, 40 g SiO$_2$ cartridge, 0-100% EtOAc in petroleum benzine 40-60° C.) to give a yellow oil. Further purification by column chromatography (Biotage Isolera, 40 g SiO$_2$ cartridge, 0-100% MeOH in EtOAc) gave a yellow oil which was taken up in EtOAc (20 mL) and DMF (2 mL). Pd/C 10% (100 mg) was added to this solution and the mixture was stirred overnight under an atmosphere of hydrogen at room temperature. The mixture was filtered through Celite and the filter cake was washed with EtOAc (50 mL). The washings were combined and the volatiles were removed in vacuo to give a yellow oil that was adsorbed onto silica gel and purified by silica gel column chromatography (Biotope Isolera, 40 g SiO$_2$ cartridge, 0-100% EtOAc in petroleum benzine 40-60° C. then 0-20% MeOH in EtOAc). Further purification by silica column chromatography (Biotage Isolera, 25 g SiO$_2$ cartridge, 0-100% EtOAc in petroleum benzine 40-60° C. then 0-20% MeOH in EtOAc) gave a crude material that was dissolved in DCM (20 mL). TFA (1 mL) was added to this solution and the mixture was stirred at room temperature overnight. The volatiles were removed in vacuo and the resulting solid was sonicated for 10 minutes in sat. Na$_2$CO$_3$ (aq.) (25 mL). The precipitate was collected by filtration and washed with water (25 mL), toluene (50 mL) and air dried to give the title compound 53 as a yellow solid (15 mg, 32%). LCMS-A: rt 4.784 min; m/z 500.3 [M+H]$^+$.

Example 54

Synthesis of 2-(2-(2-(2-((1H-pyrazol-4-yl)amino)-5-(trifluoromethyl)pyrimidin-4-yl)ethyl)phenyl)propanamide (54)

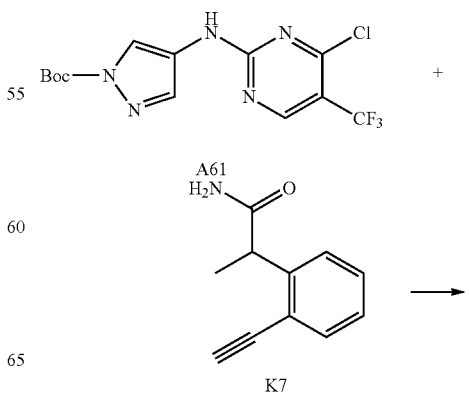

163

-continued

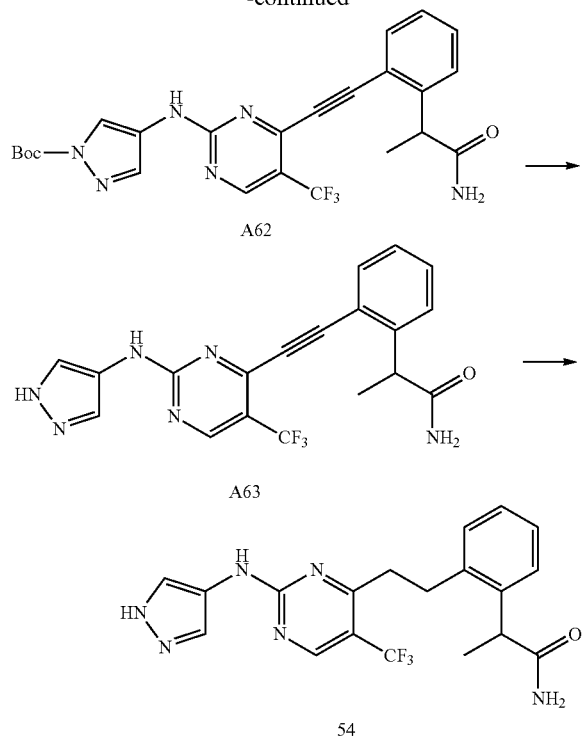

(a) tert-Butyl 4-((4-chloro-5-(trifluoromethyl)pyrimidin-2-yl)amino)-1H-pyrazole-1-carboxylate (A61)

A 1.0 M solution of zinc chloride in Et$_2$O (4.0 mL, 4.0 mmol) was added to 2,4-dichloro-5-trifluoromethylpyrimidine (0.49 mL, 3.6 mmol) in a 1:1 mixture of DCE/t-BuOH (40 mL) at 0° C. under a nitrogen atmosphere. The mixture was stirred for 1 hour before tert-butyl 4-amino-1H-pyrazole-1-carboxylate (0.606 g, 3.31 mmol) and triethylamine (0.51 mL, 3.7 mmol) in a 1:1 mixture of DCE/t-BuOH (30 mL) was added. The mixture was allowed to warm to room temperature and stirred for 20 hours before concentrating in vacuo and adding gradually to 100 mL water. The resulting precipitate was removed by vacuum filtration and washed with DCM. The filtrate was purified using silica gel column chromatography (0-30% EtOAc in DCM) to give the title compound A61 (0.170 g, 14%). LCMS-D: rt 3.622 min; m/z 362.1 [M−H]$^-$.

(b) tert-Butyl 4-((4-((2-(1-amino-1-oxopropan-2-yl)phenyl)ethynyl)-5-(trifluoromethyl)pyrimidin-2-yl)amino)-1H-pyrazole-1-carboxylate (A62)

A degassed mixture of tert-butyl 4-((4-chloro-5-(trifluoromethyl)pyrimidin-2-yl)amino)-1H-pyrazole-1-carboxylate A61 (0.373 g, 1.03 mmol), 2-(2-ethynylphenyl)propanamide K7 (0.452 g, 2.40 mmol), PdCl$_2$(PPh$_3$)$_2$ (0.015 g, 0.02 mmol), t-Bu$_3$PH.BF$_4$ (0.011 g, 0.038 mmol) and CuI (0.007 g, 0.04 mmol) in 1,4-dioxane (6.0 mL) and DIPEA (0.90 mL, 5.2 mmol) was heated in the microwave at 100° C. for 30 minutes. The mixture was concentrated under reduced pressure and purified using silica gel column chromatography (0-100% EtOAc in petroleum benzine 40-60° C.) to give the title compound A62 (0.309 g, 58%). LCMS-D: rt 3.533 min; m/z 502.2 499.2 [M−H]$^-$.

164

(c) 2-(2-((2-((1H-Pyrazol-4-yl)amino)-5-(trifluoromethyl)pyrimidin-4-yl)ethynyl)phenyl)propanamide (A63)

A mixture of tert-butyl 4-((4-((2-(1-amino-1-oxopropan-2-yl)phenyl)ethynyl)-5-(trifluoromethyl)pyrimidin-2-yl)amino)-1H-pyrazole-1-carboxylate A62 (0.31 g, 0.62 mmol) and TFA (0.90 mL, 12 mmol) in DCM (3.0 mL) was stirred for 2 hours at room temperature. The mixture was concentrated under reduced pressure and diluted with water (50 mL) before extracting with DCM (2×50 mL) and EtOAc (50 mL). The combined organic residues were concentrated and purified using silica gel column chromatography (50-100% EtOAc in petroleum benzine 40-60° C. then 0-10% MeOH in EtOAc) to give the title compound A63 (0.211 g, 85%). LCMS-D: rt 3.162 min; m/z 401.2 [M+H]$^+$.

(d) 2-(2-(2-(2-((1H-Pyrazol-4-yl)amino)-5-(trifluoromethyl)pyrimidin-4-ylethyl)phenyl)propanamide (54)

Et$_3$N (0.5 mL) was added to 2-(2-((2-((1H-pyrazol-4-yl)amino)-5-(trifluoromethyl)pyrimidin-4-yl)ethynyl)phenyl)propanamide A63 (0.211 g, 0.527 mmol) and 10% Pd/C (0.155 g) in DMF (4 mL) and EtOAc (16 mL) and the mixture was stirred under a hydrogen atmosphere for 16 hours. The mixture was filtered through Celite, concentrated under reduced pressure and purified using silica gel column chromatography (80-100% EtOAc in petroleum benzine 40-60° C. then 0-10% MeOH in EtOAc). The resulting product was further triturated with a mixture of Et$_2$O and acetone and the precipitate was collected by vacuum filtration to give the title compound 54 (0.055 g, 26%). LCMS-D: rt 3.178 min; m/z 405.2 [M+H]$^+$.

Example 55

Synthesis of 2-(2-(2-(2-((1-methyl-1H-pyrazol-4-yl)amino)-5-(trifluoromethyl)pyrimidin-4-yl)ethyl)phenyl)propanamide (55)

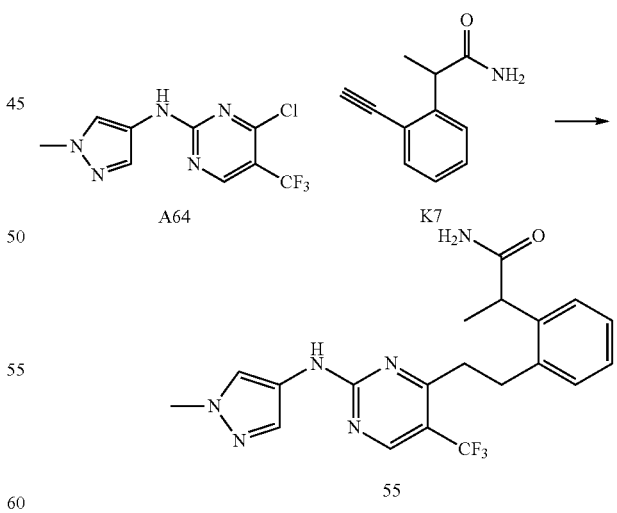

(a) 4-Chloro-N-(1-methyl-1H-pyrazol-4-yl)-5-(trifluoromethyl)pyrimidin-2-amine (A64)

A 1.0 M solution of ZnCl$_2$ in Et$_2$O (5.07 mL, 5.07 mmol) was added to a solution of 2,4-dichloro-5-(trifluoromethyl)

pyrimidine (1.00 g, 4.61 mmol) in t-BuOH (25 mL) and DCE (25 mL) and the mixture was stirred for 10 minutes. The mixture was diluted with t-BuOH (25 mL) and DCE (25 mL) before 1-methyl-1H-pyrazol-4-amine (492 mg, 5.07 mmol) and Et₃N (1.93 mL, 13.83 mmol) were added and stirring was continued at room temperature overnight. The volatiles were removed in vacuo and the resultant residue suspended in water (250 mL) and sonicated for 10 minutes. The solid was collected by vacuum filtration and the filter cake washed with water and then air dried. The solid was dissolved in DCM, adsorbed onto silica gel and purified by column chromatography (Biotage Isolera, 40 g SiO₂ cartridge, 0-100% EtOAc in petroleum benzine 40-60° C.) to give the title compound A64 as a white solid (182 mg, 14%). LCMS-A: rt 6.113 min; m/z 278.1 [M+H]⁺.

(b) 2-(2-(2-(2-((1-Methyl-1H-pyrazol-4-yl)amino)-5-(trifluoromethyl)pyrimidin-4-yl)ethyl)phenyl)propanamide (55)

A suspension of 4-chloro-N-(1-methyl-1H-pyrazol-4-yl)-5-(trifluoromethyl)pyrimidin-2-amine A64 (182 mg, 0.656 mmol), 2-(2-ethynylphenyl)propanamide K7 (110 mg, 0.635 mmol), PPh₃ (8 mg, 0.032 mmol) and CuI (6 mg, 0.032 mmol) in Et₃N (1 mL) and DMF (3 mL) was sonicated for 10 minutes, PdCl₂(PPh₃)₂ (22 mg, 0.032 mmol) was added and the reaction mixture was irradiated in the microwave at 120° C. for 20 minutes. The resultant mixture was adsorbed onto silica gel and purified by column chromatography (Biotage Isolera, 40 g SiO₂ cartridge, 0-100% EtOAc in petroleum benzine 40-60° C. then 0-100% MeOH in EtOAc) to give a yellow solid. Further purification by silica gel column chromatography (Biotage Isolera, 40 g SiO₂ cartridge, 0-100% MeOH in EtOAc) gave a yellow solid (105 mg) that was taken up in EtOAc (10 mL) and DMF (2 mL). 10% Pd/C (50 mg) was added and the mixture was stirred at room temperature overnight under an atmosphere of hydrogen. The mixture was diluted with EtOAc (50 mL), filtered through Celite and the filter cake was washed with EtOAc (50 mL). The washings were combined and the volatiles were removed in vacuo. The resulting residue was adsorbed onto silica gel and purified by column chromatography (Biotage Isolera, 12 g SiO₂ cartridge, 0-100% MeOH in EtOAc) to give the title compound 55 as a tan solid (31 mg, 29%). LCMS-A: rt 5.931 min; m/z 419.2 [M+H]⁺.

Example 56

Synthesis of 2-(2-(2-(2-((1-(piperidin-4-yl)-1H-pyrazol-4-yl)amino)-5-(trifluoromethyl)pyrimidin-4-yl)ethyl)phenyl)propanamide (56)

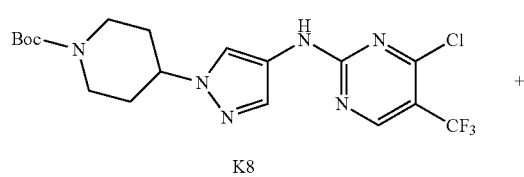

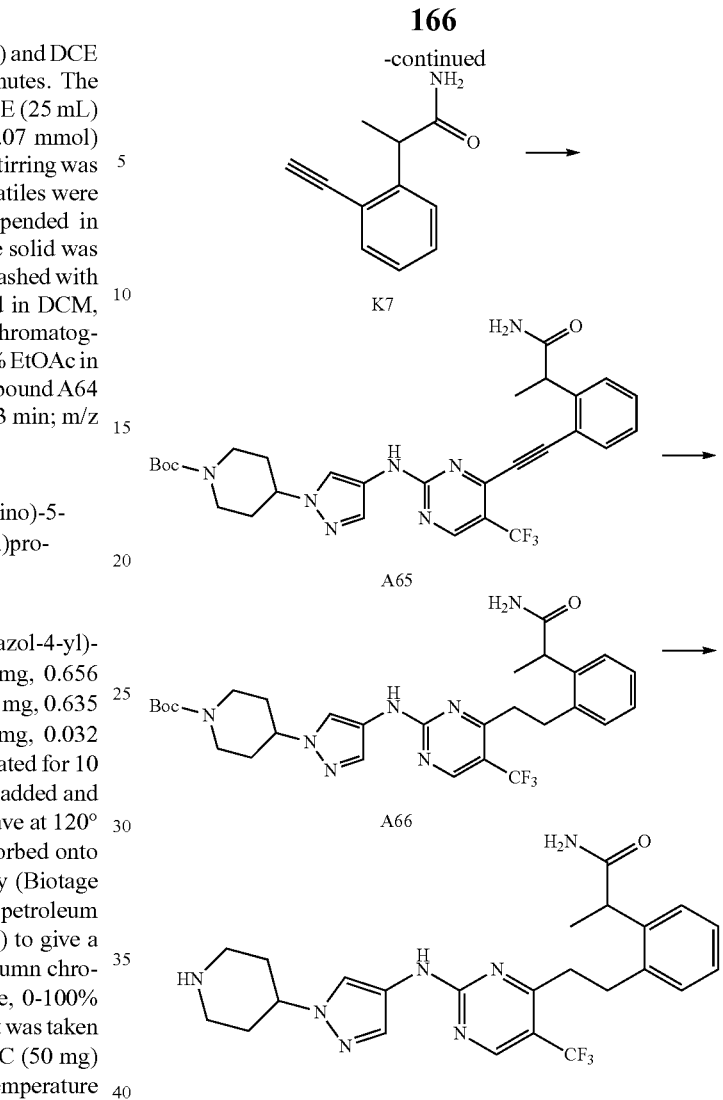

(a) tert-Butyl 4-(4-((4-((2-(1-amino-1-oxopropan-2-yl)phenyl)ethynyl)-5-(trifluoromethyl)pyrimidin-2-yl)amino)-1H-pyrazol-1-yl)piperidine-1-carboxylate (A65)

A mixture of tert-butyl 4-(4-((4-chloro-5-(trifluoromethyl)pyrimidin-2-yl)amino)-1H-pyrazol-1-yl)piperidine-1-carboxylate K8 (2.054 g, 4.597 mmol), 2-(2-ethynylphenyl)propanamide K7 (1.027 g, 5.929 mmol), CuI (0.017 g, 0.089 mmol), PdCl₂(PPh₃)₂ (0.062 g, 0.088 mmol) and t-Bu₃PH.BF₄ (0.025 g, 0.087 mmol) in dioxane (20 mL) and Et₃N (2.5 mL, 18 mmol) under a nitrogen atmosphere was heated in the microwave at 110° C. for 40 minutes. The mixture was concentrated under reduced pressure and purified using silica gel column chromatography (50-100% EtOAc in petroleum benzine 40-60° C.) to give the title compound A65 (2.121 g, 79%). ¹H NMR (400 MHz, d6-DMSO) δ 10.48-10.33 (m, 1H), 8.82-8.73 (m, 1H), 8.09-7.97 (m, 1H), 7.64-7.55 (m, 2H), 7.56-7.44 (m, 2H), 7.41-7.34 (m, 1H), 7.29-7.22 (m, 1H), 7.01 (s, 1H), 4.39-4.29 (m, 1H), 4.18-3.99 (m, 3H), 2.99-2.80 (m, 2H), 2.02-1.94 (m, 2H), 1.83-1.70 (m, 2H), 1.41 (s, 9H), 1.39-1.31 (m, 3H).

(b) tert-Butyl 4-(4-((4-(2-(1-amino-1-oxopropan-2-yl)phenethyl)-5-(trifluoromethyl)pyrimidin-2-yl)amino)-1H-pyrazol-1-yl)piperidine-1-carboxylate (A66)

A solution of tert-butyl 4-(4-((4-((2-(1-amino-1-oxopropan-2-yl)phenyl)ethynyl)-5-(trifluoromethyl)pyrimidin-2-yl)amino)-1H-pyrazol-1-yl)piperidine-1-carboxylate A65 (3.30 g, 5.66 mmol) in DMF (50 mL) and TEA (5 mL) was stirred with 10% Pd/C (wetted with ca. 53% water, 3.00 g) under an atmosphere of H$_2$ for 20 hours at 35° C. The mixture was filtered through Celite and the solvent was removed in vacuo. Purification by column chromatography (Biotage Isolera, 120 g SiO$_2$ cartridge, 20-100% EtOAc in petroleum benzine 40-60° C.) gave the title compound A66 as a yellow solid (3.32 g, 99%). LCMS-D: rt 3.54 min; m/z 588 [M+H]$^+$.

(c) 2-(2-(2-(2-((1-(piperidin-4-yl)-1H-pyrazol-4-yl)amino)-5-(trifluoromethyl)pyrimidin-4-ylethyl)phenyl)propanamide (56)

A solution of tert-butyl 4-(4-((4-(2-(1-amino-1-oxopropan-2-yl)phenethyl)-5-(trifluoromethyl)pyrimidin-2-yl)amino)-1H-pyrazol-1-yl)piperidine-1-carboxylate A66 (3.41 g, 5.80 mmol) in DCM (50 mL) was cooled to 0° C. and treated with TFA (4.44 mL, 0.058 mol). The mixture was stirred at 0° C. for 1 hour and then at room temperature for 3 hours. An extra aliquot of TFA (2.2 mL, 0.029 mol) was added to the mixture and stirring was continued for 2 hours at room temperature. Sat. aq. NaHCO$_3$ (~50 mL) was carefully added, followed by aq. NaOH (2 M, ~50 mL). DCM was removed in vacuo and the resultant aqueous mixture was diluted with H$_2$O (~50 mL). The white suspension was sonicated for 10 minutes and vacuum filtered. The isolated solid was washed with water and air dried to give the title compound 56 as a white solid (2.8 g, 99%). $^1$H NMR (400 MHz, d6-DMSO) δ 10.20-10.08 (m, 1H), 8.69-8.56 (m, 1H), 8.02-7.93 (m, 1H), 7.58 (s, 1H), 7.44-7.35 (m, 1H), 7.27-7.14 (m, 4H), 6.92-6.80 (m, 1H), 4.21-4.08 (m, 1H), 3.91-3.79 (m, 1H), 3.18-2.91 (m, 6H), 2.61-2.50 (m, 2H), 1.92-1.86 (m, 2H), 1.81-1.68 (m, 2H), 1.33 (d, J=6.9 Hz, 3H). LCMS-A: rt 4.79 min; m/z 488 [M+H]$^+$.

Example 56-1A and 56-2A

Separation of 2-(2-(2-(2-((1-(piperidin-4-yl)-1H-pyrazol-4-yl)amino)-5-(trifluoromethyl)pyrimidin-4-yl)ethyl)phenyl)propanamide (56)

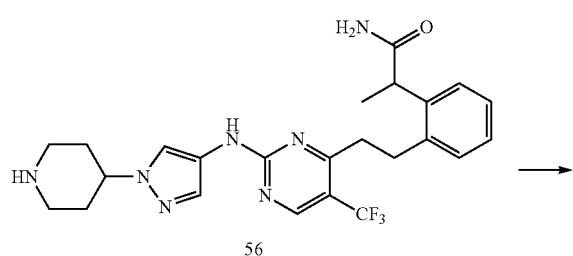

56

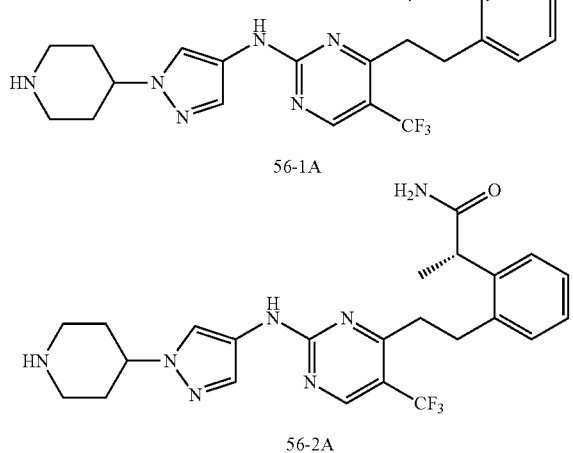

56-1A 56-2A

Racemic 2-(2-(2-(2-((1-(Piperidin-4-yl)-1H-pyrazol-4-yl)amino)-5-(trifluoromethyl)pyrimidin-4-yl)ethyl)phenyl)propanamide was separated using the chiral separation Method D.

Enantiomer A of 2-(2-(2-(2-((1-(piperidin-4-yl)-1H-pyrazol-4-yl)amino)-5-(trifluoromethyl)pyrimidin-4-yl)ethyl)phenyl)propanamide (56-1A), Chiral Characterisation Method F: rt 9.16 min, enantiomeric purity>99%.

Enantiomer B of 2-(2-(2-(2-((1-(piperidin-4-yl)-1H-pyrazol-4-yl)amino)-5-(trifluoromethyl)pyrimidin-4-yl)ethyl)phenyl)propanamide (56-2A), Chiral Characterisation Method F: rt 6.31 min, enantiomeric purity 97.6%.

Example 57

Synthesis of 2-(2-(2-(2-((1-(1-Methylpiperidin-4-yl)-1H-pyrazol-4-yl)amino)-5-(trifluoromethyl)pyrimidin-4-yl)ethyl)phenyl)propanamide (57)

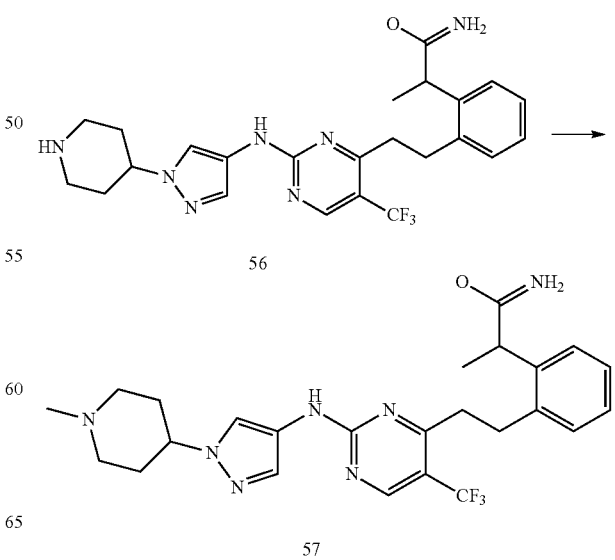

56

57

2-(2-(2-(2-((1-(1-Methylpiperidin-4-yl)-1H-pyrazol-4-yl)amino)-5-(trifluoromethyl)pyrimidin-4-yl)ethyl)phenyl)propanamide (57)

To a solution of 2-(2-(2-(2-((1-(piperidin-4-yl)-1H-pyrazol-4-yl)amino)-5-(trifluoromethyl)pyrimidin-4-yl)ethyl)phenyl)propanamide 56 (1.14 g, 2.33 mmol) in MeOH (40 mL) was added formaldehyde solution (37% in water, 0.52 mL, 7.0 mmol) and sodium triacetoxyborohydride (1.98 g, 9.33 mmol) under a nitrogen atmosphere. The mixture was stirred at room temperature for 4 hours before concentrating under reduced pressure. The mixture was diluted with sat. aq. NaHCO$_3$ (75 mL) and the aqueous phase was extracted with EtOAc (3×50 mL). The combined organics were washed with brine and dried (MgSO$_4$) before the solvent was removed in vacuo to give the product as a white solid (1.05 g, 90%). $^1$H NMR (400 MHz, d$_6$-DMSO) δ 10.22-10.09 (m, 1H), 8.69-8.55 (m, 1H), 8.04-7.95 (m, 1H), 7.58 (s, 1H), 7.43-7.35 (m, 1H), 7.29-7.12 (m, 4H), 6.96-6.84 (m, 1H), 4.13-4.01 (m, 1H), 3.90-3.79 (m, 1H), 3.27-2.88 (m, 4H), 2.83 (d, J=10.0 Hz, 2H), 2.19 (s, 3H), 2.07-1.87 (m, 6H), 1.33 (d, J=6.8 Hz, 3H). LCMS-D: rt 3.03 min; m/z 502 [M+H]$^+$.

Example 57-1A and 57-2A

Separation of 2-(2-(2-(2-((1-(1-Methylpiperidin-4-yl)-1H-pyrazol-4-yl)amino)-5-(trifluoromethyl)pyrimidin-4-yl)ethyl)phenyl)propanamide (57)

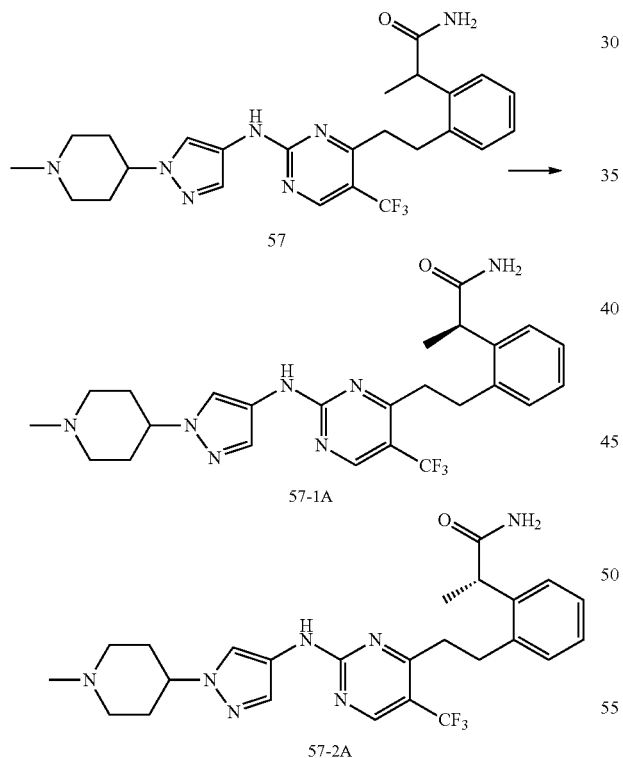

2-(2-(2-(2-((1-(1-Methylpiperidin-4-yl)-1H-pyrazol-4-yl)amino)-5-(trifluoromethyl)pyrimidin-4-yl)ethyl)phenyl)propanamide (57) was separated using the chiral separation Method B.

Enantiomer A of 2-(2-(2-(2-((1-(1-Methylpiperidin-4-yl)-1H-pyrazol-4-yl)amino)-5-(trifluoromethyl)pyrimidin-4-yl)ethyl)phenyl)propanamide (57-1A), Chiral Characterisation Method G: rt 14.23 min, enantiomeric purity>99%.

Enantiomer B of 2-(2-(2-(2-((1-(1-Methylpiperidin-4-yl)-1H-pyrazol-4-yl)amino)-5-(trifluoromethyl)pyrimidin-4-yl)ethyl)phenyl)propanamide (57-2A), Chiral Characterisation Method G: rt 20.34 min, enantiomeric purity>99%.

Example 58

Synthesis of 2-(2-(2-(2-((1-(1-acetylpiperidin-4-yl)-1H-pyrazol-4-yl)amino)-5-(trifluoromethyl)pyrimidin-4-yl)ethyl)phenyl)propanamide (58)

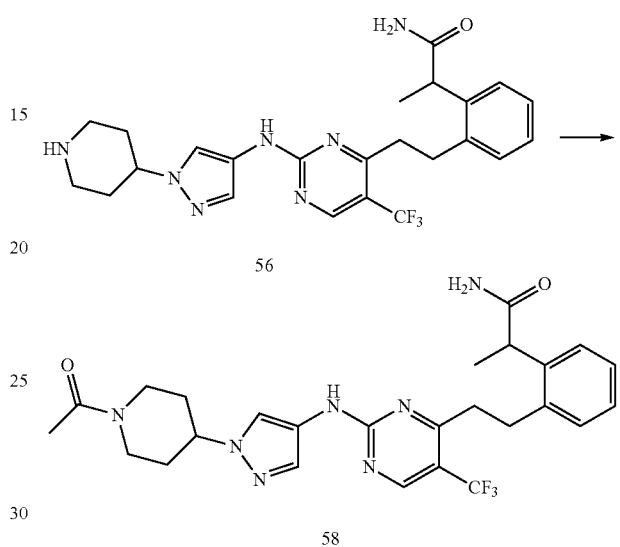

2-(2-(2-(2-((1-(1-Acetylpiperidin-4-yl)-1H-pyrazol-4-yl)amino)-5-(trifluoromethyl)pyrimidin-4-yl)ethyl)phenyl)propanamide (58)

Acetic anhydride (15 µL, 0.15 mmol) was added to a solution of 2-(2-(2-(2-((1-(piperidin-4-yl)-1H-pyrazol-4-yl)amino)-5-(trifluoromethyl)pyrimidin-4-yl)ethyl)phenyl)propanamide 56 (50 mg, 0.10 mmol) in DCM (5 mL) and pyridine (12 µL, 0.15 mmol) and the mixture was stirred at room temperature overnight. The volatiles were removed in vacuo and the resultant solid was suspended in water (25 mL) and sonicated for 5 minutes. The solid was collected by filtration and washed with sat. aq. Na$_2$CO$_3$ (20 mL), water (50 mL) then petroleum benzine 40-60° C. to give the title compound 58 as a white solid (42 mg, 77%). LCMS-D: rt 3.176 min; m/z 530.4 [M+H]$^+$.

Example 59

Synthesis of 2-(2-(2-(2-((1-(1-ethylpiperidin-4-yl)-1H-pyrazol-4-yl)amino)-5-(trifluoromethyl)pyrimidin-4-yl)ethyl)phenyl)propanamide (59)

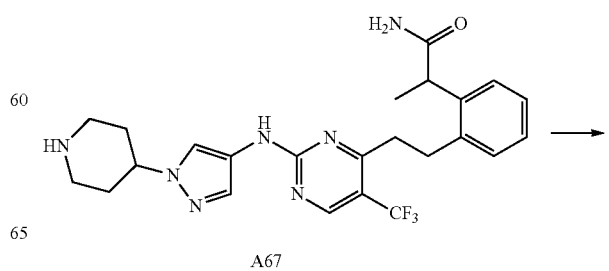

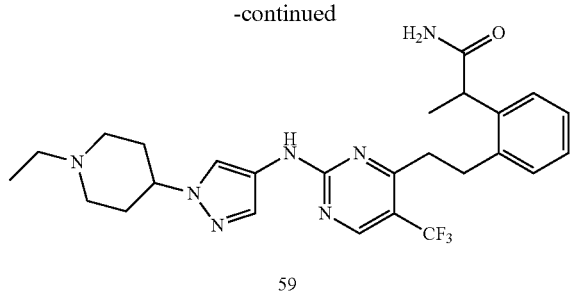

59

2-(2-(2-(2-((1-(1-Ethylpiperidin-4-yl)-1H-pyrazol-4-yl)amino)-5-(trifluoromethyl)pyrimidin-4-yl)ethyl)phenyl)propanamide (59)

Acetaldehyde (17 µL, 0.31 mmol) was added to a solution of 2-(2-(2-(2-((1-(piperidin-4-yl)-1H-pyrazol-4-yl)amino)-5-(trifluoromethyl)pyrimidin-4-yl)ethyl)phenyl)propanamide A67 (50 mg, 0.10 mmol) in EtOH (20 mL). After 10 minutes, NaHB(OAc)$_3$ (86 mg, 0.41 mmol) was added and the mixture was stirred for 3 hours. The reaction was quenched with water (20 mL) and the volatiles were removed in vacuo. The resultant solid was suspended in water (25 mL), sonicated for 10 minutes, collected by filtration and then dissolved in acetone (3 mL). Addition of petroleum benzine 40-60° C. gave a precipitate that was collected by filtration to give the title compound 59 as a tan solid (42 mg, 79%). LCMS-A: rt 4.808 min; m/z 516.3 [M+H]$^+$.

Example 60

Synthesis of 2-(2-(2-(2-((1-(1-isopropylpiperidin-4-yl)-1H-pyrazol-4-yl)amino)-5-(trifluoromethyl)pyrimidin-4-yl)ethyl)phenyl)propanamide (60)

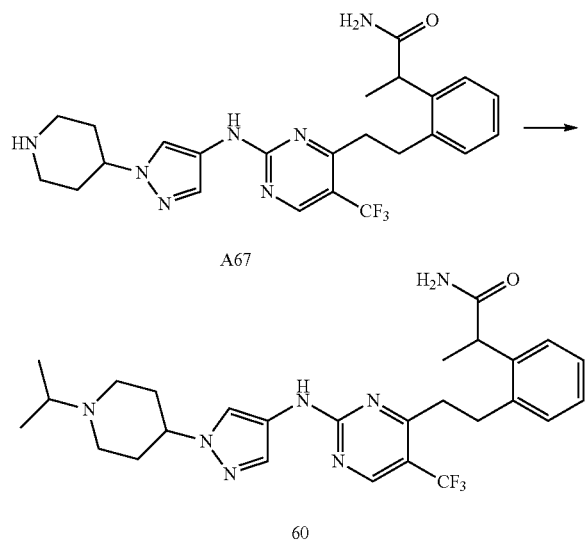

2-(2-(2-(2-((1-(1-Isopropylpiperidin-4-yl)-1H-pyrazol-4-yl)amino)-5-(trifluoromethyl)pyrimidin-4-yl)ethyl)phenyl)propanamide (60)

A suspension of 2-(2-(2-(2-((1-(piperidin-4-yl)-1H-pyrazol-4-yl)amino)-5-(trifluoromethyl)pyrimidin-4-yl)ethyl)phenyl)propanamide A67 (80 mg, 0.16 mmol), 2-iodopropane (25 µL, 0.25 mmol) and K2CO$_3$ (68 mg, 0.49 mmol) in MeCN (5 mL) was irradiated in the microwave at 120° C. for 40 minutes. Additional 2-iodopropane (25 µL, 0.25 mmol) was added and the reaction mixture was irradiated in the microwave at 120° C. for another 40 minutes. Upon cooling, the liquid was decanted from the solid and the volatiles were removed in vacuo. The resultant solid was suspended in water (50 mL) and sonicated for 10 minutes before being filtered. The solid was dissolved in acetone (3 mL) and precipitated by the addition of petroleum benzine 40-60° C. before being collected by filtration and dried under high vacuum to give the title compound 60 as a tan solid (61 mg, 70%). LCMS-D: rt 3.060 min; m/z 530.4 [M+H]$^+$.

Example 61

Synthesis of 2-(2-(2-(2-((6-Methoxypyridin-3-yl)amino)-5-(trifluoromethyl)pyrimidin-4-yl)ethyl)phenyl)propanamide (61)

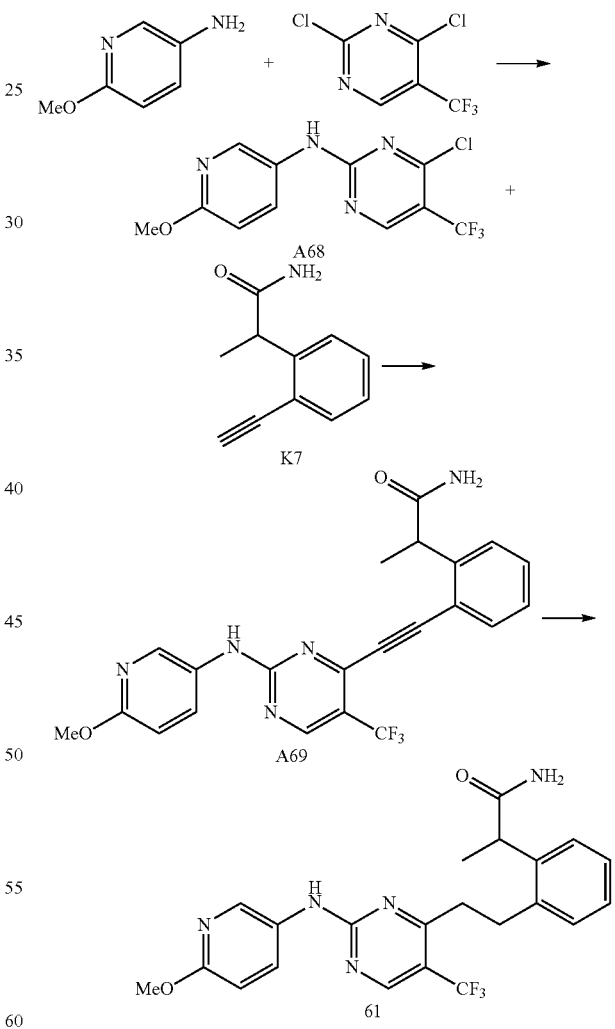

(a) 4-Chloro-N-(6-methoxypyridin-3-yl)-5-(trifluoromethyl)pyrimidin-2-amine (A68)

A 1.0 M solution of ZnCl$_2$ in Et$_2$O (5.07 mL, 5.07 mmol) was added to a solution of 2,4-dichloro-5-(trifluoromethyl)

pyrimidine (1.00 g, 4.61 mmol) in t-BuOH (25 mL) and DCE (25 mL). The mixture was stirred for 10 minutes and then diluted with t-BuOH (25 mL) and DCE (25 mL) before 5-amino-2-methoxypyridine (629 mg, 5.07 mmol) and Et₃N (1.93 mL, 13.8 mmol) were added. The mixture was stirred at room temperature overnight and the volatiles were removed in vacuo. The resultant residue was suspended in water (250 mL) and sonicated for 10 minutes before the solid was isolated by vacuum filtration. The filter cake was washed with water and air dried and then dissolved in DCM and adsorbed onto silica gel. Purification by column chromatography (Biotage Isolera, 40 g SiO₂ cartridge, 0-100% EtOAc in petroleum benzine 40-60° C.) gave the title compound A68 as a white solid (944 mg, 67%). LCMS-A: rt 6.62 min; m/z 305 [M+H]⁺.

(b) 2-(2-((2-((6-Methoxypyridin-3-yl)amino)-5-(trifluoromethyl)pyrimidin-4-yl)ethynyl)phenyl)propanamide (A69)

A mixture of 2-(2-ethynylphenyl)propanamide K7 (0.120 g, 0.693 mmol), 4-chloro-N-(6-methoxypyridin-3-yl)-5-(trifluoromethyl)pyrimidin-2-amine A68 (0.211 g, 0.693 mmol), CuI (0.013 g, 0.069 mmol), t-Bu₃PHBF₄ (0.020 g, 0.069 mmol) and PdCl₂(PPh₃)₂ (0.024 g, 0.035 mmol) in DMF (3 mL) was bubbled with N₂ for 5 minutes. Et₃N (1 mL) was added and the reaction mixture was stirred in the microwave at 120° C. for 15 minutes. The volatiles were removed in vacuo and the black residue was adsorbed onto silica. Purification by column chromatography (Biotage Isolera, 40 g SiO₂ cartridge, 0-100% EtOAc in petroleum benzine 40-60° C.) gave the title compound A69 as a yellow solid (0.198 g, 65%). LCMS-D: rt 3.43 min; m/z 442 [M+H]⁺.

(c) 2-(2-(2-(2-((6-Methoxypyridin-3-yl)amino)-5-(trifluoromethyl)pyrimidin-4-yl)ethyl)phenyl)propanamide (61)

A solution of 2-(2-((2-((6-methoxypyridin-3-yl)amino)-5-(trifluoromethyl)pyrimidin-4-yl)ethynyl)phenyl)propanamide A69 (0.198 g, 0.449 mmol) in EtOAc (20 mL) and MeOH (10 mL) was stirred over 10% Pd/C (wetted with ca. 53% water, 0.150 g) under an atmosphere of hydrogen for 16 hours. The mixture was filtered through Celite and the solvent was removed in vacuo. Purification by column chromatography (Biotage Isolera, 40 g SiO₂, 0-80% EtOAc in petroleum benzine 40-60° C.) gave the title compound 61 as a white solid (0.126 g, 63%). LCMS-D: rt 3.43 min; m/z 446 [M+H]⁺.

Example 62

Synthesis of 2-(2-(2-(2-((6-(piperidin-4-yl)pyridin-3-yl)amino)-5-(trifluoromethyl)pyrimidin-4-yl)ethyl)phenyl)propanamide (62)

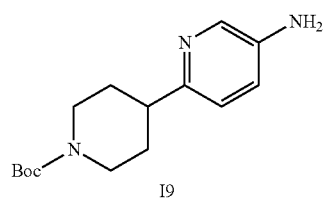

I9

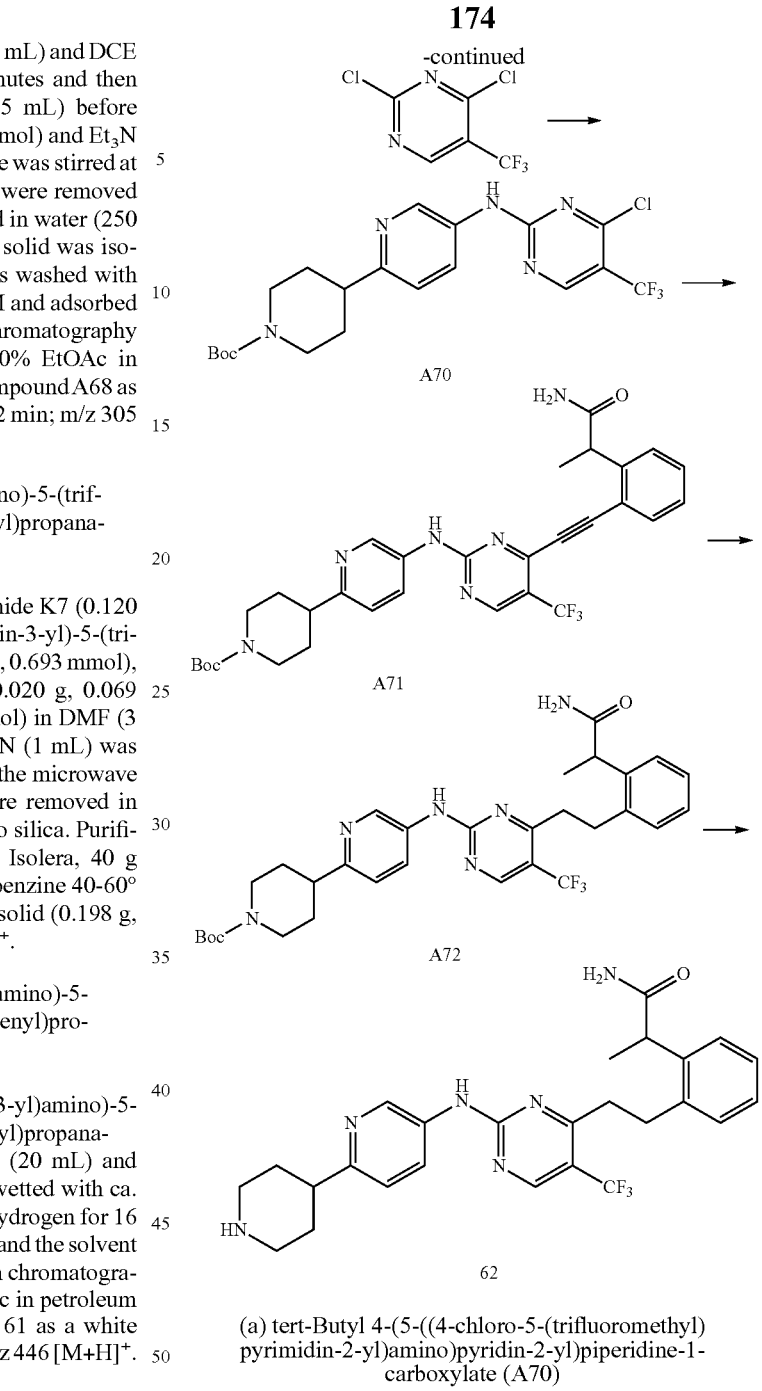

(a) tert-Butyl 4-(5-((4-chloro-5-(trifluoromethyl)pyrimidin-2-yl)amino)pyridin-2-yl)piperidine-1-carboxylate (A70)

2,4-Dichloro-5-(trifluoromethyl)pyrimidine (411 mg, 1.89 mmol) was stirred in 1:1 t-BuOH:DCE (100 mL) at room temperature. A 1.0 M ZnCl₂ solution in Et₂O (2.16 mL, 2.16 mmol) was added cautiously and after addition the mixture was stirred at room temperature for 20 minutes. tert-Butyl 4-(5-aminopyridin-2-yl)piperidine-1-carboxylate I9 (500 mg, 1.80 mmol) was added followed by NEt₃ (0.30 mL, 2.16 mmol) and the mixture was stirred at room temperature for 44 hours. The organic solvents were evaporated to dryness and the crude tan solid was suspended in water (250 mL) and sonicated for 10 minutes. The solid was isolated by filtration, washed with water (2×100 mL) and air-dried to give a cream solid. The solid was adsorbed onto silica and purified by silica gel column chromatography (40 g SiO₂ cartridge, 0-100% EtOAc in petroleum benzine 40-60° C.) to give the title compound A70 as an off white solid (346 mg, 42%). LCMS-A: rt 5.949 min; m/z 458 [M+H]⁺.

(b) tert-Butyl 4-(5-((4-((2-(1-amino-1-oxopropan-2-yl)phenyl)ethynyl)-5-(trifluoromethyl)pyrimidin-2-yl)amino)pyridin-2-yl)piperidine-1-carboxylate (A71)

To a mixture of tert-butyl 4-(5-((4-chloro-5-(trifluoromethyl)pyrimidin-2-yl)amino)pyridin-2-yl)piperidine-1-carboxylate A70 (0.397 g, 0.867 mmol), 2-(2-ethynylphenyl)propanamide K7 (0.195 g, 1.13 mmol), CuI (0.011 g, 0.057 mmol), $PdCl_2(PPh_3)_2$ (0.039 g, 0.056 mmol) and $t\text{-Bu}_3PH.BF_4$ (0.017 g, 0.058 mmol) under a nitrogen atmosphere was added dioxane (12 mL) and DIPEA (0.60 mL, 3.4 mmol). The mixture was stirred at room temperature for 96 hours before being concentrated under reduced pressure and purifying by silica gel column chromatography (Biotage Isolera, $SiO_2$ cartridge, 0-100% EtOAc in petroleum benzine 40-60° C. and 0-20% MeOH in EtOAc) to give the title compound A71 (0.139 g, 27%). LCMS-D: rt 3.626 min; m/z 595.3 $[M+H]^+$.

(c) tert-Butyl 4-(5-((4-(2-(1-amino-1-oxopropan-2-yl)phenethyl)-5-(trifluoromethyl)pyrimidin-2-yl)amino)pyridin-2-yl)piperidine-1-carboxylate (A72)

A mixture of tert-Butyl 4-(5-((4-((2-(1-amino-1-oxopropan-2-yl)phenyl)ethynyl)-5-(trifluoromethyl)pyrimidin-2-yl)amino)pyridin-2-yl)piperidine-1-carboxylate A71 (0.139 g, 0.234 mmol) and 10% Pd/C (0.156 g) in DMF (3.0 mL) and $Et_3N$ (0.30 mL) was stirred under a hydrogen atmosphere for 112 hours. The mixture was filtered through Celite and concentrated under reduced pressure before being purified using silica gel column chromatography (Biotage Isolera, $SiO_2$ cartridge, 0-100% EtOAc in petroleum benzine 40-60° C., 0-20% MeOH in EtOAc) to give the title compound A72 (0.060 g, 42%). LCMS-D: rt 3.568 min; m/z 599.4 $[M+H]^+$.

(d) 2-(2-(2-(2-((6-(Piperidin-4-yl)pyridin-3-yl)amino)-5-(trifluoromethyl)pyrimidin-4-yl)ethyl)phenyl)propanamide (62)

TFA (0.50 mL, 6.5 mmol) was added to tert-butyl 4-(5-((4-(2-(1-amino-1-oxopropan-2-yl)phenethyl)-5-(trifluoromethyl)pyrimidin-2-yl)amino)pyridin-2-yl)piperidine-1-carboxylate A72 (0.060 g, 0.099 mmol) in DCM (5 mL) and the mixture was stirred for 2 hours. The mixture was concentrated under reduced pressure and quenched with 25% aq. NaOH (20 mL). The aqueous phase was extracted with EtOAc (3×20 mL) before the combined organics were dried (phase separation cartridge) and concentrated under reduced pressure. The suspension was sonicated with hexane and concentrated under reduced pressure to give the title compound (0.066 g, 134% residual solvent/water). LCMS-D: rt 3.025 min; m/z 499.3 $[M+H]^+$.

Example 63

Synthesis of 2-(2-(2-(2-((6-(1-methylpiperidin-4-yl)pyridin-3-yl)amino)-5-(trifluoromethyl)pyrimidin-4-yl)ethyl)phenyl)propanamide (63)

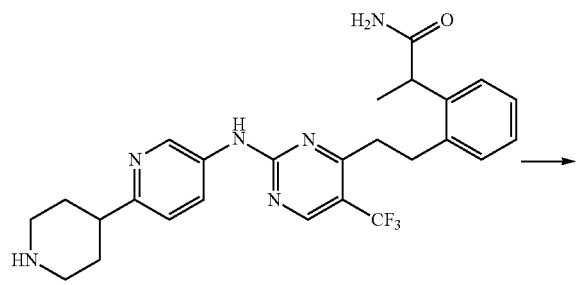

62

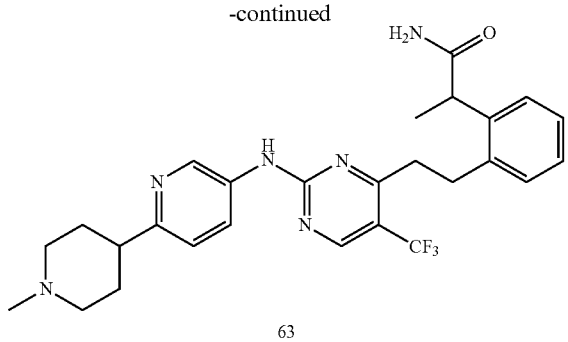

63

2-(2-(2-(2-((6-(1-Methylpiperidin-4-yl)pyridin-3-yl)amino)-5-(trifluoromethyl)pyrimidin-4-yl)ethyl)phenyl)propanamide (63)

To a mixture of 2-(2-(2-(2-((6-(piperidin-4-yl)pyridin-3-yl)amino)-5-(trifluoromethyl)pyrimidin-4-yl)ethyl)phenyl)propanamide 62 (0.064 g, 0.13 mmol) in anhydrous MeOH (2.0 mL) was added 37% aqueous formaldehyde (0.04 mL, 0.5 mmol) and sodium triacetoxyborohydride (0.138 g, 0.649 mmol). The mixture was stirred for 3 hours at room temperature under a nitrogen atmosphere and then quenched by the addition of sat. aq. $NaHCO_3$ (30 mL). The aqueous phase was extracted with EtOAc (2×20 mL), the combined organics were dried using a phase separation cartridge and then concentrated under reduced pressure. The organic residues were purified by prep-LCMS to give the title compound 63 (0.020 g, 30%) as the formic acid salt (2 equivs. determined by $^1H$ NMR). LCMS-A: rt 4.786 min; m/z 513.3 $[M+H]^+$.

Example 64

Synthesis of 1-(2-(2-(2-((6-Methoxypyridin-3-yl)amino)-5-(trifluoromethyl)pyrimidin-4-yl)ethyl)phenyl)cyclopropanecarboxamide (64)

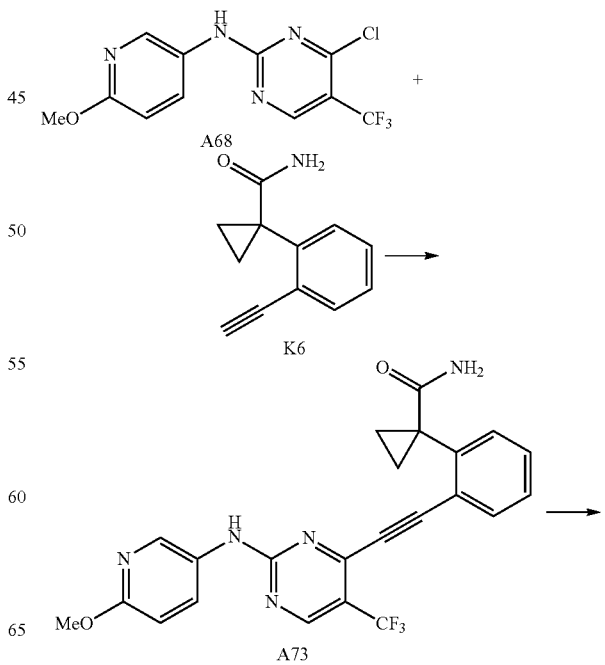

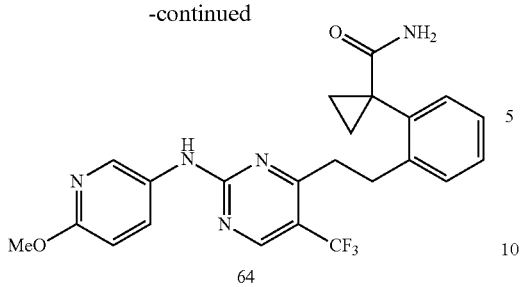

(a) 1-(2-((2-((6-Methoxypyridin-3-yl)amino)-5-(trifluoromethyl)pyrimidin-4-yl)ethynyl)phenyl)cyclopropanecarboxamide (A73)

A mixture of 1-(2-ethynylphenyl)cyclopropanecarboxamide K6 (0.120 g, 0.648 mmol), 4-chloro-N-(6-methoxypyridin-3-yl)-5-(trifluoromethyl)pyrimidin-2-amine A68 (0.197 g, 0.648 mmol), CuI (0.012 g, 0.065 mmol), t-Bu₃PHBF₄ (0.019 g, 0.065 mmol) and PdCl₂(PPh₃)₂ (0.023 g, 0.032 mmol) in DMF (3 mL) was bubbled with N₂ for 5 minutes. Et₃N (1 mL) was added and the reaction mixture was stirred in the microwave at 120° C. for 15 minutes. The volatiles were removed in vacuo and the black residue was adsorbed onto silica. Purification by column chromatography (Biotage Isolera, 40 g SiO₂ cartridge, 0-100% EtOAc in petroleum benzine 40-60° C.) gave the title compound A73 as a yellow solid (0.229 g, 78%). LCMS-D: rt 3.47 min; m/z 454 [M+H]⁺.

(b) 1-(2-(2-(2-((6-Methoxypyridin-3-yl)amino)-5-(trifluoromethyl)pyrimidin-4-yl)ethyl)phenyl)cyclopropanecarboxamide (64)

A solution of 1-(2-((2-((6-methoxypyridin-3-yl)amino)-5-(trifluoromethyl)pyrimidin-4-yl)ethynyl)phenyl)cyclopropanecarboxamide A73 (0.229 g, 0.505 mmol) in EtOAc (20 mL) was stirred over 10% Pd/C (wetted with ca. 53% water, 0.150 g) under an atmosphere of hydrogen for 16 hours. The mixture was filtered through Celite and the solvent was removed in vacuo. Purification by column chromatography (Biotage Isolera, 40 g SiO₂, 0-80% EtOAc in petroleum benzine 40-60° C.) gave an off-white solid contaminated with alkyne starting material. The solid was dissolved in EtOAc (20 mL) and MeOH (10 mL) and stirred over 10% Pd/C (wetted with ca. 53% water, 0.130 g) for 16 hours under an atmosphere of hydrogen. The mixture was filtered through Celite and the solvent was removed in vacuo to give the title compound 64 as a white solid (0.130 g, 56%). LCMS-D: rt 3.51 min; m/z 458 [M+H]⁺.

Example 65

Synthesis of 1-(2-(2-(2-((1-Methyl-1H-pyrazol-4-yl)amino)-5-(trifluoromethyl)pyrimidin-4-yl)ethyl)phenyl)cyclopropanecarboxamide (65)

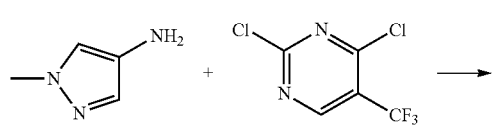

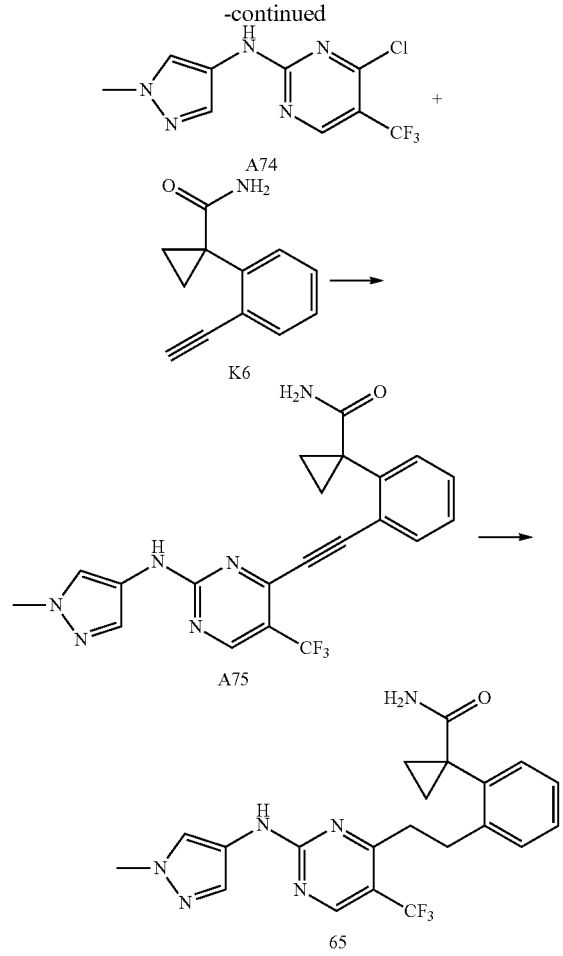

(a) 4-Chloro-N-(1-methyl-1H-pyrazol-4-yl)-5-(trifluoromethyl)pyrimidin-2-amine (A74)

ZnCl₂ in Et₂O (1M, 23.2 mL, 23.2 mmol) was added to 2,4-dichloro-5-trifluoromethylpyrimidine (5.2 mL, 39 mmol) in DCE:t-BuOH (1:1, 150 mL) under a nitrogen atmosphere. The mixture was stirred for 45 minutes before addition of 1-methyl-1H-pyrazol-4-amine (1.880 g, 19.36 mmol) in DCE/t-BuOH (1:1, 150 mL) and DIPEA (3.2 mL, 18 mmol). The mixture was heated to 50° C. for 16 hours, cooled and filtered using vacuum filtration. The solid was washed with MeOH and the filtrate concentrated under reduced pressure before being poured into water. The resulting precipitate was collected under vacuum filtration and washed with water then petroleum benzine 40-60° C. and finally dissolved in Et₂O and filtered. The Et₂O filtrate was concentrated under reduced pressure to give the crude product which was further purified in batches by a combination of trituration with Et₂O and cyclohexane or silica gel column chromatography (0-30% EtOAc in petroleum benzine 40-60° C.) then combined to give the title compound A74 (1.6 g, 30%). ¹H NMR (400 MHz, d-DMSO) δ ppm 10.66-10.58 (m, 1H), 8.77-8.68 (m, 1H), 7.93-7.86 (m, 1H), 7.53 (s, 1H), 3.88-3.78 (m, 3H).

(b) 1-(2-((2-((1-Methyl-1H-pyrazol-4-yl)amino)-5-(trifluoromethyl)pyrimidin-4-yl)ethynyl)phenyl)cyclopropanecarboxamide (A75)

To a degassed mixture of 4-chloro-N-(1-methyl-1H-pyrazol-4-yl)-5-(trifluoromethyl)pyrimidin-2-amine A74 (0.178 g, 0.640 mmol), 1-(2-ethynylphenyl)cyclopropanecarboxamide K6 (0.172 g, 0.928 mmol), PdCl$_2$(PPh$_3$)$_2$ (0.005 g, 0.007 mmol), t-Bu$_3$PH.BF$_4$ (0.005 g, 0.02 mmol) and copper (I) iodide (0.003 g, 0.02 mmol) in DMF (8.0 mL) was added DIPEA (0.33 mL, 1.9 mmol). The mixture was heated in the microwave for 2×20 minutes at 100° C. before being concentrated under reduced pressure. Purification by silica gel column chromatography (Isolera, 0-100% EtOAc petroleum benzine 40-60° C. then 0-20% MeOH in EtOAc) gave the title compound A75 (0.120 g, 44%). LCMS-D: rt 3.30 min; m/z 427.2 [M+H]$^+$.

(c) 1-(2-(2-(2-((1-Methyl-1H-pyrazol-4-yl)amino)-5-(trifluoromethyl)pyrimidin-4-yl)ethyl)phenyl)cyclopropanecarboxamide (65)

A mixture of 1-(2-(2-((1-methyl-1H-pyrazol-4-yl)amino)-5-(trifluoromethyl)pyrimidin-4-yl)ethynyl)phenyl)cyclopropanecarboxamide A75 (0.120 g, 0.281 mmol) and 10% Pd/C (0.135 g) in DMF (3 mL), EtOAc (5 mL) and Et$_3$N (0.5 mL) was stirred under a hydrogen atmosphere for 16 hours. The mixture was filtered through Celite and concentrated under reduced pressure before purification by silica gel column chromatography (0-15% MeOH in EtOAc). The product was triturated with Et$_2$O and the resulting precipitate was collected to give the title compound 65 (0.090 g, 74%). LCMS-D: rt 3.316 min; m/z 431.2 [M+H]$^+$.

Examples 66

Synthesis of 1-(2-(2-(2-((1-(piperidin-4-yl)-1H-pyrazol-4-yl)amino)-5-(trifluoromethyl)pyrimidin-4-yl)ethyl)phenyl)cyclopropanecarboxamide (66)

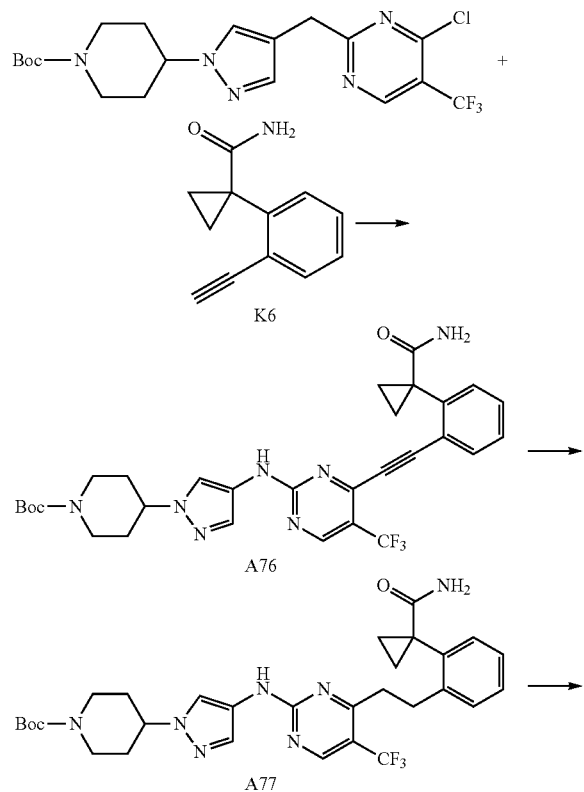

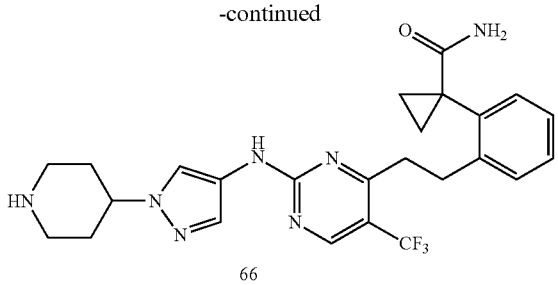

(a) tert-Butyl 4-(4-((4-((2-(1-carbamoylcyclopropyl)phenyl)ethynyl)-5-(trifluoromethyl)pyrimidin-2-yl)amino)-1H-pyrazol-1-yl)piperidine-1-carboxylate (A76)

A mixture of 1-(2-ethynylphenyl)cyclopropanecarboxamide K6 (0.250 g, 1.35 mmol), tert-butyl 4-(4-((4-chloro-5-(trifluoromethyl)pyrimidin-2-yl)amino)-1H-pyrazol-1-yl)piperidine-1-carboxylate K8 (0.603 g, 1.35 mmol), CuI (0.026 g, 0.135 mmol), t-Bu$_3$PHBF$_4$ (0.039 g, 0.135 mmol) and PdCl$_2$(PPh$_3$)$_2$ (0.047 g, 0.067 mmol) in DMF (10 mL) was bubbled with N$_2$ for 5 minutes. Et$_3$N (3 mL) was added and the reaction mixture was stirred in the microwave at 120° C. for 20 minutes. The volatiles were removed in vacuo and the black residue was adsorbed onto silica. Purification by column chromatography (Biotage Isolera, 40 g SiO$_2$ cartridge, 0-100% EtOAc in petroleum benzine 40-60° C.) gave a yellow solid which was purified further by two iterations of column chromatography (Biotage Isolera, 2×40 g SiO$_2$ cartridges, 0-10% MeOH in DCM then 40 g SiO$_2$ cartridge, 0-5% MeOH in DCM) to give the title compound A76 as a yellow solid (0.405 g, 50%). LCMS-D: rt 3.62 min; m/z 596 [M+H]$^+$.

(b) tert-Butyl 4-(4-((4-(2-(1-carbamoylcyclopropyl)phenethyl)-5-(trifluoromethyl)pyrimidin-2-yl)amino)-1H-pyrazol-1-yl)piperidine-1-carboxylate (A77)

A mixture of tert-butyl 4-(4-((4-((2-(1-carbamoylcyclopropyl)phenyl)ethynyl)-5-(trifluoromethyl)pyrimidin-2-yl)amino)-1H-pyrazol-1-yl)piperidine-1-carboxylate A76 (0.405 g, 0.680 mmol) and 10% Pd/C (wetted with ca. 53% water, 0.200 g) in EtOAc (30 mL) and MeOH (15 mL) was stirred under an atmosphere of H$_2$ at room temperature for 16 hours. The mixture was filtered through a plug of Celite and the filtrate was concentrated in vacuo. Purification by column chromatography (Biotage Isolera, 40 g SiO$_2$ cartridge, 0-10% MeOH in DCM) gave a yellow oil which was further purified by column chromatography (Biotage Isolera, 40 g SiO$_2$ cartridge, 10-90% EtOAc in petroleum benzine 40-60° C.) to give the title compound A77 as a yellow solid (0.213 g, 52%). LCMS-D: rt 3.62 min; m/z 600 [M+H]$^+$.

(c) 1-(2-(2-(2-((1-(Piperidin-4-yl)-1H-pyrazol-4-yl)amino)-5-(trifluoromethyl)pyrimidin-4-yl)ethyl)phenyl)cyclopropanecarboxamide (66)

A solution of tert-butyl 4-(4-((4-(2-(1-carbamoylcyclopropyl)phenethyl)-5-(trifluoromethyl)pyrimidin-2-yl)amino)-1H-pyrazol-1-yl)piperidine-1-carboxylate A77 (0.213 g, 0.355 mmol) in DCM (10 mL) was treated with TFA (1.09 mL, 14.2 mmol) and stirred for 16 hours at room temperature. The volatiles were evaporated in vacuo before aq. HCl (2 M, 25 mL) was added to the residue. The aqueous phase was extracted with EtOAc (3×25 mL) and the combined organics were washed with brine and dried over MgSO$_4$. The solvent was removed in vacuo and the crude product was purified by column chromatography (Biotage Isolera, 12 g C18 cartridge, 0-100% MeOH in H₂O) to give a yellow oil. This oil was taken up in a minimum amount of DCM and the desired product was precipitated by the addition of petroleum spirits. The solid was isolated by filtration to give the title compound 66 as a yellow solid (0.114 g, 64%). LCMS-D: rt 3.07 min; m/z 500 [M+H]⁺.

Example 67

Synthesis of 1-(2-(2-(2-((1-(1-Methylpiperidin-4-yl)-1H-pyrazol-4-yl)amino)-5-(trifluoromethyl)pyrimidin-4-yl)ethyl)phenyl)cyclopropanecarboxamide (67)

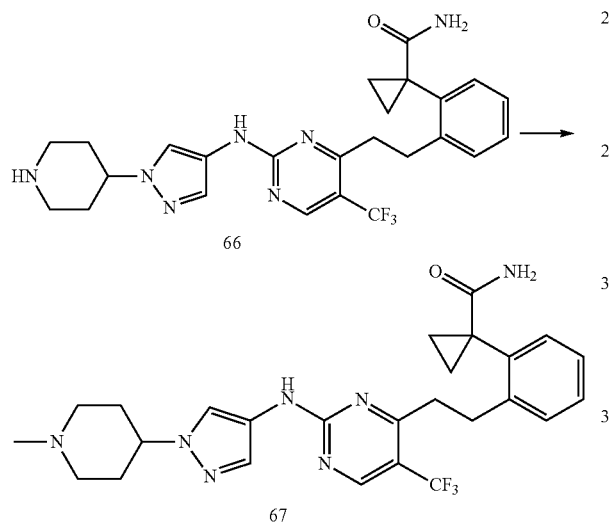

(a) 1-(2-(2-(2-((1-(1-Methylpiperidin-4-yl)-1H-pyrazol-4-yl)amino)-5-(trifluoromethyl)pyrimidin-4-yl)ethyl)phenyl)cyclopropanecarboxamide (67)

A mixture of 1-(2-(2-(2-((1-(piperidin-4-yl)-1H-pyrazol-4-yl)amino)-5-(trifluoromethyl)pyrimidin-4-yl)ethyl)phenyl)cyclopropanecarboxamide 66 (0.081 g, 0.16 mmol) and formaldehyde (37 wt % in H₂O; 36 µL, 0.49 mmol) in MeOH (5 mL) was stirred at room temperature for 10 minutes. Sodium triacetoxyborohydride (0.137 g, 0.649 mmol) was then added and stirring was continued for 3 hours at room temperature. The volatiles were removed in vacuo and sat. aq. NaHCO₃ (20 mL) was added to the residue. The aqueous phase was extracted with EtOAc (3×20 mL) and the combined organics were washed with brine, dried (MgSO₄) and the solvent was removed in vacuo. The yellow residue was taken up in MeOH and loaded onto an SCX cartridge (10 g). The column was eluted with 5 column volumes of MeOH and then 5 column volumes of 2% v/v aqueous ammonia in MeOH to release the amine product. The solvent was evaporated under reduced pressure, the residue was taken up in DCM and a solid was precipitated by the addition of petroleum benzine 40-60° C. The solid was isolated by filtration and air dried to give the title compound 67 as a yellow solid (0.048 g, 58%). LCMS-A: rt 4.82 min; m/z 514 [M+H]⁺.

Example 68

Synthesis of 1-(2-(2-(2-((6-(piperidin-4-yl)pyridin-3-yl)amino)-5-(trifluoromethyl)pyrimidin-4-yl)ethyl)phenyl)cyclopropanecarboxamide (68)

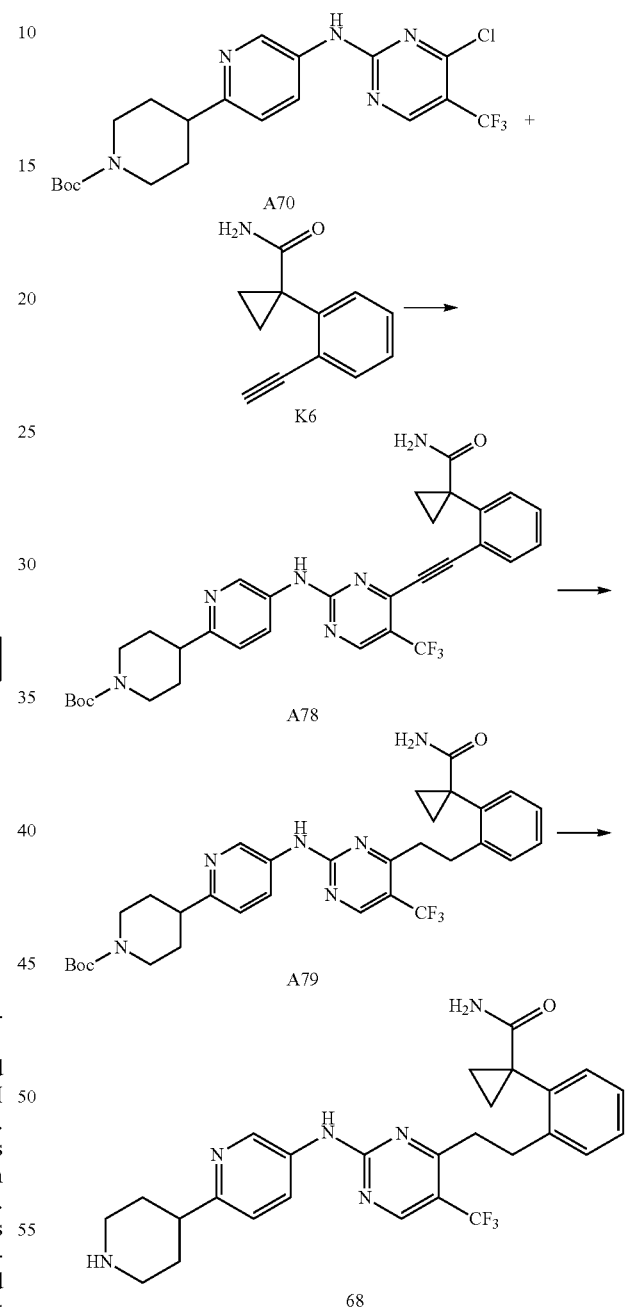

(a) tert-Butyl 4-(5-((4-((2-(1-carbamoylcyclopropyl)phenyl)ethynyl)-5-(trifluoromethyl)pyrimidin-2-yl)amino)pyridin-2-yl)piperidine-1-carboxylate (A78)

To a mixture of tert-butyl 4-(5-((4-chloro-5-(trifluoromethyl)pyrimidin-2-yl)amino)pyridin-2-yl)piperidine-1-carboxylate A70 (0.208 g, 0.453 mmol), 1-(2-ethynylphenyl)cyclopropanecarboxamide K6 (0.079 g, 0.42 mmol), CuI (0.003 g, 0.02 mmol), PdCl$_2$(PPh$_3$)$_2$ (0.017 g, 0.024 mmol) and t-Bu$_3$PH.BF$_4$ (0.009 g, 0.03 mmol) under a nitrogen atmosphere was added dioxane (6.0 mL) and DIPEA (0.23 mL, 1.3 mmol). The mixture was stirred at 85° C. for 4 hours and then concentrated under reduced pressure. Purification by silica gel column chromatography (Biotage Isolera, 0-100% EtOAc in Petroleum Benzine 40-60° C., 0-20% MeOH in EtOAc) gave the title compound A78 (0.118 g, 46%). LCMS-D: rt 3.645 min; m/z 607.4 [M+H]$^+$.

(b) tert-Butyl 4-(5-((4-(2-(1-carbamoylcyclopropyl)phenethyl)-5-(trifluoromethyl)pyrimidin-2-yl)amino)pyridin-2-yl)piperidine-1-carboxylate (A79)

DMF (3 mL) and Et$_3$N (0.30 mL) were added to a mixture of tert-butyl 4-(5-((4-((2-(1-carbamoylcyclopropyl)phenyl)ethynyl)-5-(trifluoromethyl)pyrimidin-2-yl)amino)pyridin-2-yl)piperidine-1-carboxylate A78 (0.118 g, 0.194 mmol) and 10% Pd/C (0.182 g). The mixture was stirred under a hydrogen atmosphere for 20 hours, filtered through Celite and the filtrate concentrated under reduced pressure. Purification by silica gel column chromatography (0-100% EtOAc in Petroleum Benzine 40-60° C.) gave the title compound A79 (0.080 g, 67%). LCMS-A: rt 5.852 min; m/z 611.3 [M+H]$^+$.

(c) 1-(2-(2-(2-((6-(Piperidin-4-yl)pyridin-3-yl)amino)-5-(trifluoromethyl)pyrimidin-4-yl)ethyl)phenyl)cyclopropanecarboxamide (68)

TFA (0.50 mL, 6.5 mmol) was added to a mixture of tert-Butyl 4-(5-((4-(2-(1-carbamoylcyclopropyl)phenethyl)-5-(trifluoromethyl)pyrimidin-2-yl)amino)pyridin-2-yl)piperidine-1-carboxylate A79 (0.080 g, 0.13 mmol) in DCM (5 mL) and the mixture stirred for 4 hours. The mixture was concentrated under reduced pressure and quenched with 25% aqueous NaOH (20 mL) before extracting with EtOAc (3×20 mL). The combined organic extracts were concentrated under reduced pressure and the above procedure repeated with DCM (1.5 mL) and TFA (0.2 mL) for 3 hours. The mixture was concentrated under reduced pressure and quenched with 25% aqueous NaOH (20 mL) before extracting with EtOAc (3×20 mL). The combined organic residues were dried (phase separation cartridge) and concentrated under reduced pressure to give the title compound 68 (0.069 g, quantitative). LCMS-A: rt 4.783 min; m/z 511.3 [M+H]$^+$.

Example 69

Synthesis of 1-(2-(2-(2-((6-(1-methylpiperidin-4-yl)pyridin-3-yl)amino)-5-(trifluoromethyl)pyrimidin-4-yl)ethyl)phenyl)cyclopropanecarboxamide (69)

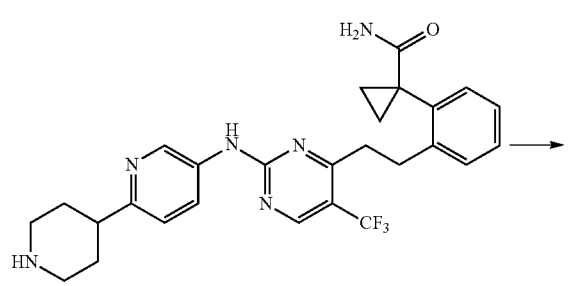

68

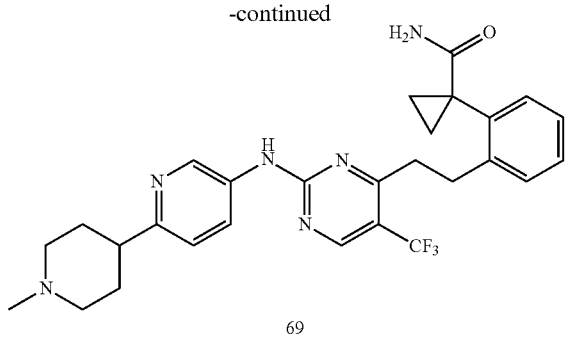

69

1-(2-(2-(2-((6-(1-Methylpiperidin-4-yl)pyridin-3-yl)amino)-5-(trifluoromethyl)pyrimidin-4-yl)ethyl)phenyl)cyclopropanecarboxamide (69)

To a mixture of 1-(2-(2-(2-((6-(piperidin-4-yl)pyridin-3-yl)amino)-5-(trifluoromethyl)pyrimidin-4-yl)ethyl)phenyl)cyclopropanecarboxamide 68 (0.069 g, 0.14 mmol) in anhydrous MeOH (2.0 mL) was added 37% aqueous formaldehyde (0.04 mL, 0.5 mmol) and sodium triacetoxyborohydride (0.147 g, 0.695 mmol). The mixture was stirred for 3 hours at room temperature under a nitrogen atmosphere and then quenched with sat. aq. NaHCO$_3$ (30 mL). The aqueous phase was extracted with EtOAc (2×20 mL) and the combined organics were dried using a phase separation cartridge and concentrated in vacuo. Purification by prep-LCMS gave the title compound 69 (0.020 g, 29%) as the formic acid salt (2 equivs. determined by $^1$H NMR). LCMS-A: rt 4.802 min; m/z 525.3 [M+H]$^+$.

Example 70

Synthesis of tert-Butyl 1-(4-(4-(2-(1-carbamoylcyclopropyl)phenethyl)-5-(trifluoromethyl)pyrimidin-2-ylamino)phenyl)ethylcarbamate (70)

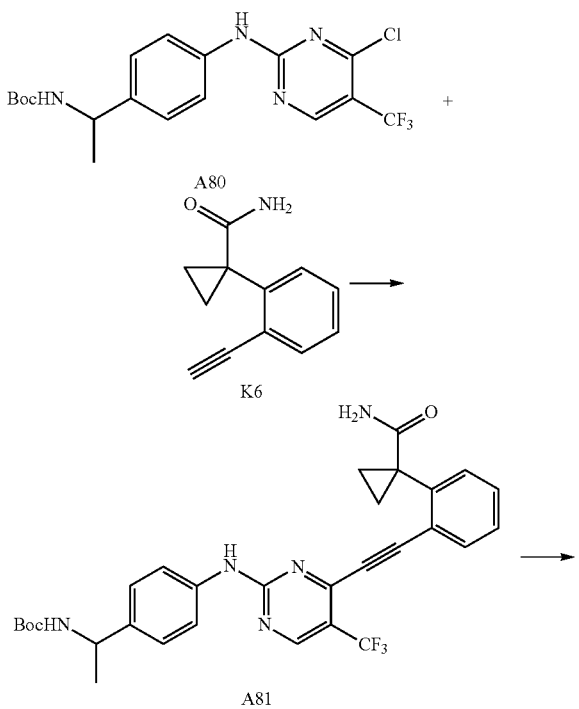

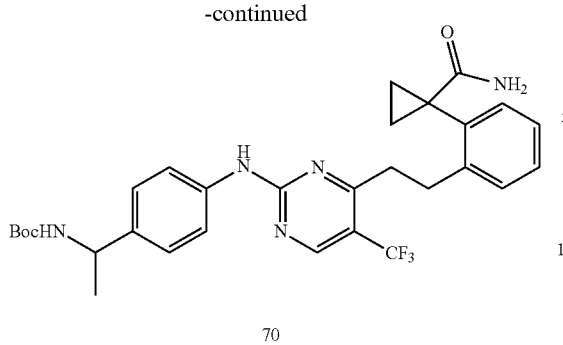

70

(a) tert-Butyl (1-(4-((4-chloro-5-(trifluoromethyl)pyrimidin-2-yl)amino)phenyl)ethyl)carbamate (A80)

2,4-Dichloro-5-(trifluoromethyl)pyrimidine (1.93 g, 8.89 mmol) was stirred in a 1:1 t-BuOH:DCE mixture (200 mL) at room temperature. A 1.0 M $ZnCl_2$ solution in $Et_2O$ (10.2 mL, 10.2 mmol) was added cautiously and the mixture was stirred at room temperature for 20 minutes. A 1:1 t-BuOH:DCE mixture (100 mL) was added followed by tert-butyl (1-(4-aminophenyl)ethyl)carbamate (2.00 g, 8.46 mmol) and $Et_3N$ (1.42 mL, 10.2 mmol). The mixture was stirred at room temperature overnight before the volatiles were evaporated in vacuo. EtOH (30 mL) was added, the suspension was sonicated for 1 minute before the solid was filtered, washed with EtOH (10 mL) and dried in vacuo to give the title compound A80 as a cream solid (3.2 g, 91%). LCMS-C: rt 4.88 min.

(b) tert-Butyl 1-(4-(4-((2-(1-carbamoylcyclopropyl)phenyl)ethynyl)-5-(trifluoromethyl)pyrimidin-2-ylamino)phenyl)ethylcarbamate (A81)

A solution of 1-(2-ethynylphenyl)cyclopropanecarboxamide K6 (0.15 g, 0.81 mmol) in DMF (3 mL) was added to a reaction vessel containing tert-butyl 1-(4-(4-chloro-5-(trifluoromethyl)pyrimidin-2-ylamino)phenyl)ethylcarbamate A80 (0.34 g, 0.81 mmol), $PdCl_2(PPh_3)_2$ (0.028 g, 0.040 mmol) tri-tert-butylphosphonium tetrafluoroborate (0.023 g, 0.081 mmol) and copper(I)iodide (0.015 g, 0.081 mmol). The mixture was bubbled with nitrogen for 10 minutes before $Et_3N$ (1.5 mL) was added. The mixture was heated at 120° C. under microwave irradiation for 15 minutes. The volatiles were removed in vacuo and the residue was purified by silica gel column chromatography (Combiflash Rf, 0-100% EtOAc in cyclohexane) to give the title compound A81 as a yellow oil (0.26 g, 56%). LCMS-C: rt 5.80 min; m/z 566 $[M+H]^+$.

(c) tert-Butyl 1-(4-(4-(2-(1-carbamoylcyclopropyl)phenethyl)-5-(trifluoromethyl)pyrimidin-2-ylamino)phenyl)ethylcarbamate (70)

A solution of tert-butyl 1-(4-(4-((2-(1-carbamoylcyclopropyl)phenyl)ethynyl)-5-(trifluoromethyl)pyrimidin-2-ylamino)phenyl)ethylcarbamate (0.25 g, 0.44 mmol) in EtOAc (12 mL) and DMF (2.0 mL) was stirred with Pd/C 10% (0.15 g) under an atmosphere of hydrogen for 16 hours at ambient temperature. The reaction mixture was diluted with EtOAc, filtered through a plug of Celite and washed with EtOAc. The solvents were removed in vacuo and the crude residue was purified by silica gel column chromatography (Combiflash Rf 0-100% EtOAc in cyclohexane) to give the title compound 70 as a colourless oil (0.14 g, 56%). LCMS-C: rt 5.88 min; m/z 570 $[M+H]^+$.

Example 70A

Synthesis of 1-(2-(2-(2-(4-(1-aminoethyl)phenylamino)-5-(trifluoromethyl)pyrimidin-4-yl)ethyl)phenyl)cyclopropanecarboxamide (70A)

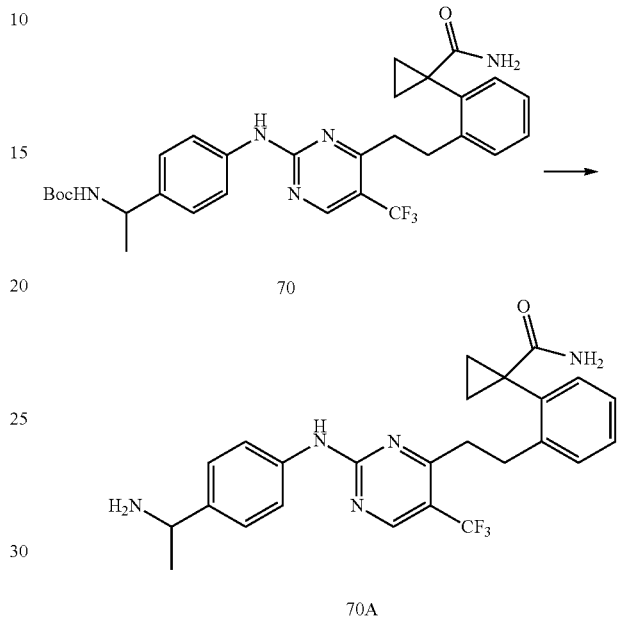

1-(2-(2-(2-(4-(1-Aminoethyl)phenylamino)-5-(trifluoromethyl)pyrimidin-4-yl)ethyl)phenyl)cyclopropanecarboxamide (70A)

To a solution of tert-butyl 1-(4-(4-(2-(1-carbamoylcyclopropyl)phenethyl)-5-(trifluoromethyl)pyrimidin-2-ylamino)phenyl)ethylcarbamate 70 (0.11 g, 0.19 mmol) in DCM (4 mL) was added trifluoroacetic acid (2 mL). The mixture was stirred at ambient temperature for 16 hours before the volatiles were removed in vacuo. The crude residue was purified using an SCX conditioned with MeOH, product was eluted off with 2 M ammonia in EtOH) to give the title compound 70A as a cream solid (0.073 g, 81%). LCMS-C: rt 4.48 min; m/z 470 $[M+H]^+$.

Example 71

Synthesis of 1-(2-(2-(2-(4-(1-acetamidoethyl)phenylamino)-5-(trifluoromethyl)pyrimidin-4-yl)ethyl)phenyl)cyclopropanecarboxamide (71)

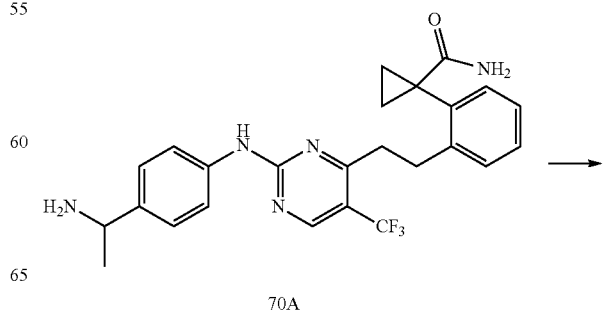

70A

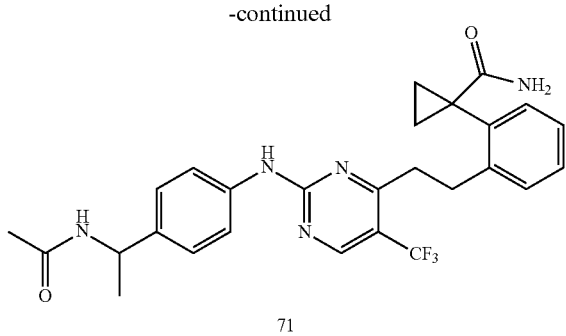

71

1-(2-(2-(2-(4-(1-Acetamidoethyl)phenylamino)-5-(trifluoromethyl)pyrimidin-4-yl)ethyl)phenyl)cyclopropanecarboxamide (71)

To a solution of 1-(2-(2-(2-(4-(1-aminoethyl)phenylamino)-5-(trifluoromethyl)pyrimidin-4-yl)ethyl)phenyl)cyclopropanecarboxamide 70A (0.015 g, 0.032 mmol) in DCM (1 mL) was added pyridine (0.0040 mL, 0.050 mmol) and acetic anhydride (0.0050 mL, 0.053 mmol) and the reaction mixture was stirred at ambient temperature overnight. The mixture was partitioned between water and EtOAc, the layers were separated and the water layer was extracted with EtOAc (2 times). The combined organic extracts were washed with brine, dried (Na$_2$SO$_4$) and evaporated in vacuo to give the title compound 71 as a light brown solid (0.016 g, 98%). LCMS-C: rt 5.24 min; m/z 512 [M+H]$^+$.

In addition to the Examples provided above, and the description of the synthesis of those compounds, it would be appreciated by a person skilled in the art that the following compounds could also be prepared:

Example 72

Synthesis of 1-(2-(2-(2-((6-(1-aminoethyl)pyridin-3-yl)amino)-5-(trifluoromethyl)pyrimidin-4-yl)ethyl)phenyl)cyclopropanecarboxamide

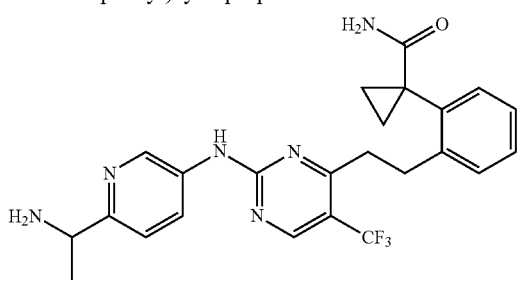

This compound is prepared according to the methods described for Example 2.

Example 73

Synthesis of 1-(2-(2-(2-((6-(1-(methylamino)ethyl)pyridin-3-yl)amino)-5-(trifluoromethyl)pyrimidin-4-yl)ethyl)phenyl)cyclopropanecarboxamide

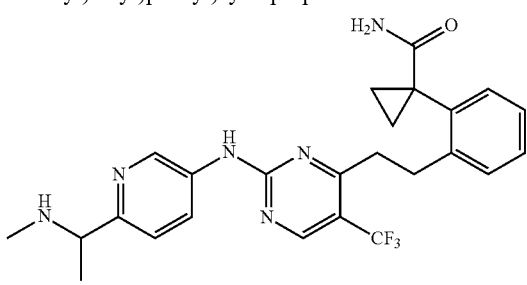

This compound is prepared via a methyl ketone intermediate corresponding to Example 32 followed by reductive amination with methylamine as described in Scheme V.

Example 74

Synthesis of 1-(2-(2-(2-((6-(1-(azetidin-1-yl)ethyl)pyridin-3-yl)amino)-5-(trifluoromethyl)pyrimidin-4-yl)ethyl)phenyl)cyclopropanecarboxamide

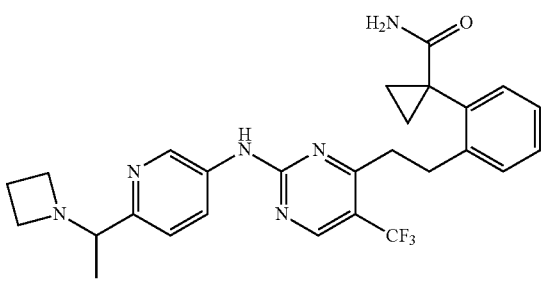 [SMILES: CC(c1ccc(Nc2ncc(C(F)(F)F)c(CCc3ccccc3C3(C(N)=O)CC3)n2)cn1)N1CCC1]

This compound is prepared via a methyl ketone intermediate corresponding to Example 32 followed by reductive amination with azetidine as described in Scheme V.

Example 75

Synthesis of 1-(2-(2-(2-((6-(1-morpholinoethyl)pyridin-3-yl)amino)-5-(trifluoromethyl)pyrimidin-4-yl)ethyl)phenyl)cyclopropanecarboxamide

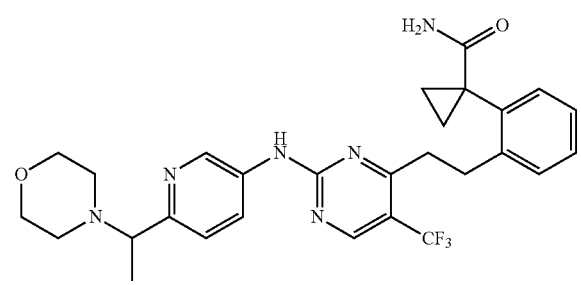 [SMILES: CC(c1ccc(Nc2ncc(C(F)(F)F)c(CCc3ccccc3C3(C(N)=O)CC3)n2)cn1)N1CCOCC1]

This compound is prepared via a methyl ketone intermediate corresponding to Example 32 followed by reductive amination with morpholine as described in Scheme V.

Example 76

Synthesis of [Insert Compound Name]

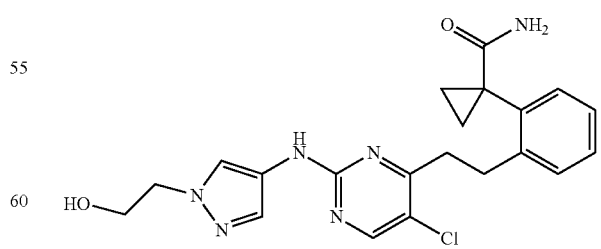

1-(2-(2-(2,5-dichloropyrimidin-4-yl)ethyl)phenyl)cyclopropanecarboxamide A14 and 1-ethanol-1H-pyrazole-4-amine were reacted as described for Example 34 to give Example 76 as a light yellow solid (0.064 g, 63%). LCMS-C: rt 4.78 min; m/z 427 [M+H]$^+$.

Example 77

Synthesis of [Insert Compound Name]

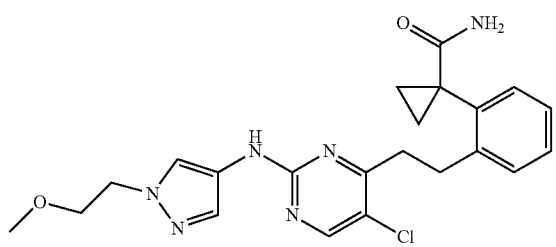 [SMILES: COCCn1cc(Nc2ncc(Cl)c(CCc3ccccc3C3(C(N)=O)CC3)n2)cn1]

1-(2-(2-(2,5-dichloropyrimidin-4-yl)ethyl)phenyl)cyclo-propanecarboxamide A14 and 1-methoxyethanol-1H-pyrazole-4-amine were reacted as described for Example 34 to give Example 77 as a light yellow oil (0.060 g, 57%). LCMS-B: rt 6.43 min; m/z 441 [M+H]$^+$.

Biological Assays

The activity of compounds of the invention can be profiled using biochemical and cellular assays.

Primary potency at VEGFR3 can be assessed using an Alpha Screen™ technology biochemical assay.

The ability of compounds of the invention to inhibit VEGFR3 within cells can be assessed with an ELISA type assay.

VEGFR3 Biochemical Assay

Compounds of the invention may be tested for in vitro activity in the following assay: A biotin labelled peptide is used as substrate (amino acid sequence: Biotin-Glu-Gly-Pro-Trp-Leu-Glu-Glu-Glu-Glu-Glu-Ala-Tyr-Gly-Trp-Met-Asp-Phe-NH$_2$). VEGFR3 cytoplasmic domain (amino acids 798-1298) was purchased as N-terminal GST-fusion protein ("the enzyme"). The 15 μL assay reactions are run in Greiner brand white 384-well low volume plates. All reactions contained 10 mM HEPES pH 7.4, mM MgCl$_2$, 0.01% (v/v) Tween-20, 50 μM Na$_3$VO$_4$, 0.01% (w/v) albumin from chicken egg white, 1 mM Dithiothreitol, 111 nM peptide substrate, 500 μM ATP, and 3.8 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 90 minutes at 30 degree Celsius. The reactions were stopped with the detection reagents added at the same time as follows: Product formation was quantified as amplified luminescence between PerkinElmer AlphaScreen™ beads, using Streptavidin-coated donor and anti-phosphotyrosine (P-Tyr-100) acceptor beads. To each reaction, 5 μL containing 10 mM HEPES pH 7.4, 25 mM NaCl, 100 mM EDTA, 0.01% (v/v) Tween-20, and 6.25 μg/mL of each bead type were added. Plates were incubated for 6 hours before being read on a PerkinElmer EnVision™ plate reader in HTS Alphascreen™ mode. IC$_{50}$ values were obtained by calculating percent inhibition (% I) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC$_{50}$ value, and D is the slope factor.

The above assay was also run in a modified form in some cases (indicated below with *). In these cases, VEGFR3 cytoplasmic domain (amino acids 818-1177, lacking 949-1002 of UniProt accession number P35916) was expressed and purified as N-terminal Hexa-His-fusion protein ("the enzyme"), rather than using the N-terminal GST-fusion protein. The assay conditions were the same as above but with 1 μM ATP and 8 ng/reaction of the enzyme. The comparable performance of both assay versions was monitored using benchmark compounds as described in the literature.

| VEGFR3 Biochemical assay results | |
|---|---|
| Compound | IC$_{50}$ (nM) |
| 1 | 91 |
| 1-1A | 103 |
| 1-2A | 75 |
| 2 | 10 |
| 3 | 9 |
| 4 | 22 |
| 5 | 28 |
| 6 | 8 |
| 7 | 10 |
| 8 | 10 |
| 9 | 26 |
| 10 | 92 |
| 11 | 1302 |
| 12 | 39 |
| 13 | 4 |
| 14 | 6 |
| 15 | 11 |
| 16 | 1 |
| 17 | 9 |
| 18 | 3 |
| 19 | 3 |
| 20 | 7 |
| 21 | 7 |
| 22 | 20 |
| 23 | 11 |
| 24 | 2 |
| 24A | 14 |
| 25 | 7 |
| 26 | 12 |
| 27 | 47 |
| 28 | 268 |
| 29 | 8 |
| 30 | 4 |
| 31 | 48 |
| 32 | 44 |
| 33 | 60 |
| 34 | 7 |
| 35 | 9 |
| 36 | 16 |
| 37 | 31 |
| 38 | 32 |
| 39 | 44 |
| 40 | 160 |
| 41 | 45 |
| 42 | 154 |
| 43 | 12 |
| 44 | 9 |
| 45 | 3 |
| 46 | 13 |
| 47 | 5 |
| 48 | 12 |
| 49 | 23 |
| 50 | 46 |
| 51 | 15 |
| 51-1A | 25 |
| 51-2A | 41 |
| 52 | 23 |
| 53 | 228 |
| 54 | 17 |
| 55 | 15 |
| 56 | 27 |
| 56-1A | 31 |
| 56-2A | 93 |
| 57 | 27 |
| 58 | 22 |
| 59 | 86 |

-continued

VEGFR3 Biochemical assay results

| Compound | IC$_{50}$ (nM) |
|---|---|
| 60 | 89 |
| 61 | 118 |
| 62 | 492 |
| 63 | 28 |
| 64 | 8 |
| 65 | 3 |
| 66 | 7 |
| 67 | 7 |
| 68 | 28 |
| 69 | 63 |
| 70 | 64 |
| 70A | 22 |
| 71 | 10 |
| 76 | 4 |
| 77 | 3 |

VEGFR3 Phospho ELISA Assay

Compounds of the invention may be tested for in vitro activity in the following assay:

Adult human dermal lymphatic microvascular endothelial cells (HMVEC-dLyAD) (Cat# CC-2810, Lonza) were seeded into clear-bottom, TC treated 12 well plates (Cat #665180, Greiner Bio-One) in EGM-2MV (Cat# CC-3202, Lonza) at 180,000 cells/well (volume 1 mL), and the plates incubated at 37° C. and 5% CO$_2$ for 6 hours. The media was replaced with EBM-2 (Cat # CC-3156, Lonza)+0.1% BSA (Cat# A8412, Sigma) and cells incubated for a further period (overnight at 37° C. and 5% CO$_2$).

96 well Maxisorp immuno plates (Cat #439454, Nunc) were coated with 100 µL of Total VEGFR3 capture antibody (Part #841888, Human Total VEGFR3/FLT4 ELISA Kit, Cat # DYC3491, R&D Systems), or Phospho VEGFR3 Capture antibody (Part #841885, Human Phospho VEGFR3/FLT4 ELISA Kit, Cat# DYC2724, R&D Systems). The plates were covered and incubated at room temperature overnight.

The coating antibody was flicked out and the plates washed three times with Wash Buffer (Phosphate buffered saline (137 mM NaCl, 2.7 nM KCl, 8.1 nM Na$_2$HPO$_4$, 1.5 mL KH$_2$PO$_4$, pH 7.2-7.4), 0.05% Tween 20). 300 µL of blocking buffer (5% v/v Tween 20, 5% w/v sucrose in PBS) was then added to wells and plate incubated for 2 hours at room temperature. Blocking solution is flicked out and plates washed three times and tapped dry.

Compound dilution series were prepared in EBM-2 (Cat # CC-3156, Lonza)+0.1% BSA (Cat#A8412, Sigma) with constant 0.1% DMSO concentration. 439 µL of sample or vehicle control was added to the cell monolayers. Cells are treated for 1 hour at 37° C. and 5% CO$_2$. 250 ng/mL Recombinant human VEGFC (Cat #2179-VC, R & D Systems) added to wells and plates incubated for an additional 10 minutes at 37° C. and 5% CO$_2$.

The media and compounds were removed and the cell monolayer washed once in Dulbecco's Phosphate Buffered Saline (Cat #21600-044, Invitrogen). 130 µL of Lysis buffer added to wells and cell lysate harvested and transferred to tubes and stored on ice. Complete lysis buffer was prepared by adding 10 µL Protease Inhibitor Cocktail (Cat # P8340, Sigma-Aldrich), 10 µL PMSF (Phenylmethanesulfonyl fluoride, Cat # P7626, Sigma-Aldrich, prepared as 500 mM DMSO stock) per 1 mL of Phosphosafe™ Extraction Reagent (Cat #71296, Merck).

The harvested samples were then diluted 1:2 in IC Diluent #18 (5% Tween 20/PBS) and 100 µL transferred to the Total and Phospho VEGFR3 coated, blocked and washed 96 well plates and incubated for 2 hours at room temperature. The plates were then washed three times in wash buffer as described above and tapped dry. For detection of Total VEGFR3 100 µL of Detection antibody (Total VEGFR3 Detection Antibody Part#841888 in Total VEGFR3 kit) diluted in IC Diluent #1 (1% w/v BSA (Cat # A7906, Sigma-Aldrich)/PBS) was added to wells and the plate incubated for 2 hours at room temperature. The plate was then washed three times in wash buffer and tapped dry. 100 µL of streptavidin-HPR diluted in IC diluent #1 Streptavidin-HRP, Part #890803 in Total VEGFR3 kit) was added to wells and incubated at room temperature for 20 minutes followed by washing as described above. 100 µL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 µL stop solution (2 M H$_2$SO$_4$).

Total VEGFR3 levels were quantified using a Multiskan Ascent plate reader and Ascent software fitted with 450 nm filter.

For detection of Phospho VEGFR3, 100 µL of Detection antibody (Anti-Phospho-Tyrosine-HRP Detection Antibody, Part #841403 in Phospho VEGFR3 kit) was diluted in IC Diluent #1 (1% w/v BSA/PBS), added to the wells and the plate incubated for 2 hours at room temperature. The plate was then washed three times in wash buffer as described above and tapped dry. 100 µL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 µL stop solution (2 M H$_2$SO$_4$).

Phospho VEGFR3 levels were quantified using a Multiscan ascent plate reader and ascent software fitted with 450 nm filter.

IC$_{50}$ values are determined by first calculating the level of phospho VEGFR3 relative to Total VEGFR3 according to the following formula:

$$SRP = \frac{SP}{ST}$$

Where SRP is the Sample Relative Phospho level, SP is Phospho VEGFR3 reading and ST is Total VEGFR3 reading.

Percent inhibition (% I) for each lysate relative to vehicle control (VEGFC stimulated) is then calculated according to the following formula:

$$\%I = \frac{SRP\ \text{Vehicle} - SRP\ \text{Test}}{SRP\ \text{Vehicle}} * 100$$

Where SRP is the Sample Relative Phospho level as calculated above.

% I is plotted against compound concentration and data fitted using a Sigmoidal dose response with IC50 determined from curve.

VEGFR3 Phospho ELISA assay results

| Compound | IC$_{50}$ (nM) |
|---|---|
| 1 | 173 |
| 1-1A | 329 |
| 1-2A | 315 |
| 2 | 26 |

-continued

VEGFR3 Phospho ELISA assay results

| Compound | IC$_{50}$ (nM) |
|---|---|
| 3 | 27 |
| 4 | 38 |
| 5 | 51 |
| 6 | 17 |
| 7 | 38 |
| 8 | 19 |
| 9 | 75 |
| 12 | 267 |
| 13 | 9 |
| 14 | 30 |
| 15 | 51 |
| 16 | 4 |
| 17 | 62 |
| 18 | 5 |
| 19 | 11 |
| 20 | 38 |
| 21 | 14 |
| 24 | 25 |
| 35 | 64 |
| 36 | 76 |
| 44 | 52 |
| 45 | 23 |
| 51 | 526 |
| 56 | 68 |
| 57 | 27 |
| 57-1A | 38 |
| 57-2A | 19 |
| 64 | 394 |
| 68 | 51 |

VEGFR2 Phospho ELISA Assay

Compounds of the invention may be tested for in vitro activity in the following assay:

Adult human umbilical vein endothelial cells (HUVEC) (Cat# CC-2519, Lonza) were seeded into clear-bottom, TC treated 12 well plates (Cat #665180, Greiner Bio-One) in EGM-2 (Cat# CC-3162, Lonza) at 180,000 cells/well (volume 1 mL), and the plates incubated at 37° C. and 5% CO$_2$ for 6 hours. The media was replaced with EBM-2 (Cat # CC-3156, Lonza)+0.1% BSA (Cat# A8412, Sigma) and cells incubated for a further period (overnight at 37° C. and 5% CO$_2$).

96 well Maxisorp immuno plates (Cat #439454, Nunc) were coated with 100 µL of Total VEGFR2 capture antibody (Part #841434, Human Total VEGFR2/FLT4 ELISA Kit, Cat # DYC1780, R&D Systems), or Phospho VEGFR2 Capture antibody (Part #841419, Human Phospho VEGFR2/FLT4 ELISA Kit, Cat# DYC1766, R&D Systems). The plates were covered and incubated at room temperature overnight.

The coating antibody was flicked out and the plates washed three times with Wash Buffer (Phosphate buffered saline (137 mM NaCl, 2.7 nM KCl, 8.1 nM Na$_2$HPO$_4$, 1.5 mL KH$_2$PO$_4$, pH 7.2-7.4), 0.05% Tween 20). 300 µL of Blocking buffer (1% v/v BSA (Cat# A8412, Sigma) in PBS) was then added to wells and plate incubated for 2 hours at room temperature. Blocking solution is flicked out and plates washed three times and tapped dry.

Compound dilution series were prepared in EBM-2 (Cat # CC-3156, Lonza)+0.1% BSA (Cat# A8412, Sigma) with constant 0.1% DMSO concentration. 427.5 µL of sample or vehicle control was added to the cell monolayers. Cells are treated for 1 hour at 37° C. and 5% CO$_2$. 50 ng/mL Recombinant human VEGF (Cat #293-VC, R & D Systems) added to wells and plates incubated for an additional 10 minutes at 37° C. and 5% CO$_2$.

The media and compounds were removed and the cell monolayer washed once in Dulbecco's Phosphate Buffered Saline (Cat #21600-044, Invitrogen). 130 µL of Lysis buffer added to wells and cell lysate harvested and transferred to tubes and stored on ice. Complete lysis buffer was prepared by adding 10 µL Protease Inhibitor Cocktail (Cat # P8340, Sigma-Aldrich), 10 µL PMSF (Phenylmethanesulfonyl fluoride, Cat # P7626, Sigma-Aldrich, prepared as 500 mM DMSO stock) per 1 mL of Phosphosafe™ Extraction Reagent (Cat #71296, Merck).

The harvested samples were then diluted 1:2 in IC Diluent #12 (1% NP-40, 20 nM Tris (pH 8.0), 137 mM NaCl, 10% glycerol, 2 mM EDTA, 1 mM activated sodium orthovanadate) and 100 µL transferred to the Total and Phospho VEGFR2 coated, blocked and washed 96 well plates and incubated for 2 hours at room temperature. The plates were then washed three times in wash buffer as described above and tapped dry.

For detection of Total VEGFR2 100 µL of Detection antibody (Total VEGFR2 Detection Antibody Part#841435 in Total VEGFR2 kit) diluted in IC Diluent #14 (20 mM Tris, 137 mM CaCl$_2$, 0.05% Tween20, 0.1% BSA) was added to wells and the plate incubated for 2 hours at room temperature. The plate was then washed three times in wash buffer and tapped dry. 100 µL of streptavidin-HPR diluted in IC diluent #14 Streptavidin-HRP, Part #890803 in Total VEGFR2 kit) was added to wells and incubated at room temperature for 20 minutes followed by washing as described above. 100 µL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 µL stop solution (2 M H$_2$SO$_4$).

Total VEGFR2 levels were quantified using a Multiskan Ascent plate reader and Ascent software fitted with 450 nm filter.

For detection of Phospho VEGFR2, 100 µL of Detection antibody (Anti-Phospho-Tyrosine-HRP Detection Antibody, Part #841403 in Phospho VEGFR2 kit) was diluted in IC Diluent 14 (20 mM Tris, 137 mM CaCl$_2$, 0.05% Tween20, 0.1% BSA), was added to the wells and the plate incubated for 2 hours at room temperature. The plate was then washed three times in wash buffer as described above and tapped dry. 100 µL Substrate solution (3,3',5,5'-Tetramethylbenzidine (TMB) Liquid Substrate System for ELISA, Cat # T0440, Sigma-Aldrich) was added and the plate incubated for 20 minutes in the dark at room temperature followed by the addition of 50 µL stop solution (2 M H$_2$SO$_4$).

Phospho VEGFR2 levels were quantified using a Multiscan ascent plate reader and ascent software fitted with 450 nm filter.

IC$_{50}$ values are determined by first calculating the level of phospho VEGFR2 relative to Total VEGFR2 according to the following formula:

$$SRP = \frac{SP}{ST}$$

where SRP is the Sample Relative Phospho level, SP is Phospho VEGFR2 reading and ST is Total VEGFR2 reading.

Percent inhibition (% I) for each lysate relative to vehicle control (VEGF-A stimulated) is then calculated according to the following formula:

$$\%I = \frac{SRP\ \text{Vehicle} - SRP\ \text{Test}}{SRP\ \text{Vehicle}} * 100$$

where SRP is the Sample Relative Phospho level as calculated above.

% I is plotted against compound concentration and data fitted using a Sigmoidal dose response with $IC_{50}$ determined from plotted curve.

| VEGFR2 Phospho ELISA assay results | |
|---|---|
| Compound | $IC_{50}$ (nM) |
| 1 | >10000 |
| 2 | 283 |
| 3 | 1789 |
| 4 | 2036 |
| 5 | 4083 |
| 6 | 6608 |
| 7 | 629 |
| 8 | 897 |
| 9 | >10000 |
| 12 | >10000 |
| 13 | 257 |
| 14 | 357 |
| 15 | 1996 |
| 16 | 46 |
| 17 | 393 |
| 18 | 21 |
| 19 | 248 |
| 20 | 1755 |
| 21 | 73 |
| 24A | 209 |
| 35 | 3786 |
| 36 | 8171 |
| 44 | 138 |
| 45 | 370 |
| 56 | 2224 |
| 57 | 394 |
| 57-1A | 518 |
| 57-2A | 382 |
| 68 | 4083 |

P397Y-FAK Inhibition MSD Platform Cellular Biomarker Assay

Compounds of the invention may be tested for in vitro activity in the following assay:

96-well plates (cat#MA6000, Meso Scale Discovery) are coated with 30 µL/well of mouse monoclonal FAK antibody [63D5] (cat#ab72140, Abcam) pre-diluted in PBS to a concentration of 1 mg/mL. The plates are sealed with adhesive film and incubated for 16 hours at 4° C. The antibody is then flicked out of the plates and 150 µL of 3% [w/v] Blocker A (cat#R93AA-1, Meso Scale Discovery) is added. The plates are resealed with adhesive film and incubated at room temperature on a shaker set at medium speed for 2 hours. The plates are then washed three times with a solution containing 50 mM Tris-HCl pH 7.5, 0.15 M NaCl and 0.02% Tween-20, before cell lysate addition described below.

Cells are split 1:2 into T150 cell culture flasks 2 days prior to compound treatment. On the day prior to compound treatment, 200 µL media containing 20,000 cells is seeded into all wells of white, clear-bottom, TC treated, µclear, 96-well microtitre plates (cat#655098, Greiner Bio-One), and the plates are incubated at 37° C. and 5% $CO_2$ for 36 hours. 1 µL/well of compound is then added from dilution series prepared in DMSO. Negative control wells receive the same volume of DMSO without compounds, and positive control wells receive 2 µM of a control compound in the same volume of DMSO. Cells are treated for 1 hour at 37° C. and 5% $CO_2$. The media/compounds are then flicked off and 55 µL/well of ice-cold complete lysis buffer is added. Complete lysis buffer is prepared by adding 1 tablet PhosSTOP complete phosphatase inhibitor (cat#04906837001, Roche) and 1 tablet Complete, Mini, EDTA-free, protease inhibitor (cat#04693159001, Roche) per 10 mL of incomplete lysis buffer (150 mM NaCl, 20 mM Tris-HCl pH 7.5, 1 mM EDTA, 1 mM EGTA, 1% Triton-X 100). Plates are incubated on ice for 30 minutes, with 30 seconds high speed plate shaking every 5 minutes. 40 µL/well of cell lysate is transferred to the coated, blocked and washed 96-well microtitre plates described above. The 96-well plates are sealed with adhesive film and incubated for 16 hours at 4° C. The plates are then washed three times with a solution containing 50 mM Tris-HCl pH 7.5, 0.15 M NaCl and 0.02% Tween-20 and tapped dry. 25 µL/well of detection solution (1% [w/v] Blocker A (cat#R93AA-1, Meso Scale Discovery) in 50 mM Tris-HCl pH 7.5, 0.15 M NaCl and 0.02% Tween-20, with 1:600 rabbit polyclonal FAK phospho Y397 antibody (cat#ab39967, Abcam), 1:1000 anti-rabbit sulfo-tag antibody (cat#R32AB-1 Meso Scale Discovery) and 1:40 reconstituted Blocker D-M (cat#D609-0100, Rockland Immunochemicals for Research)) is added, and the plates resealed with adhesive film and incubated for 1 hour at room temperature on a plate shaker set to medium speed. Plates are then washed three times with a solution containing 50 mM Tris-HCl pH 7.5, 0.15 M NaCl and 0.02% Tween-20 and tapped dry. 150 µL/well of Read Buffer T+Surfactant (cat#R92TC-1, Meso Scale Discovery) is then added, and pFAK-397 levels quantified using a Meso Scale Discovery SECTOR Imager 6000 instrument.

$IC_{50}$ values are determined by first calculating percent inhibition (% I) for each lysate relative to controls on the same plate (% I=(S−CP)/(CN−CP)) where S is the sample result, CN is the average result of DMSO only treated negative controls, and CP is the average result of 2 µM treated positive controls. % I is plotted against compound concentration [I] and the data fitted using the following equation, % I=(A+((B−A)/(1+((C/[I])^D)))), where A is the lower asymptote, B is the upper asymptote, C is the IC50 value, and D is the slope factor.

| P397Y-FAK Inhibition MSD platform cellular biomarker assay results for MDA-231-LNA cells | |
|---|---|
| Compound | $IC_{50}$ (nM) |
| 1 | 1178 |
| 2 | 80 |
| 3 | 672 |
| 4 | >2000 |
| 16 | 1159 |
| 54 | 88 |
| 55 | 115 |
| 56 | 517 |

B16F10 Melanoma Mouse Model
In-Life Study

Female BALB/c nu/nu mice at 6 to 8 weeks are inoculated with $4 \times 10^5$ murine B16F10 melanoma cells (ATCC CRL-6475) in Matrigel® suspension sub-dermally in the ear. 24 hours following inoculation treatment commences via oral gavage twice daily for 14 days. Animals are monitored daily for health, weight changes and the appearance and number of satellite lesions tracking down the ear.

On day 15 mice are sacrificed and ears removed and fixed in 4% paraformaldehyde. Ears are washed twice in PBS prior to being photographed then stored in PBS for whole mount immunohistochemistry analysis. Draining lymph nodes (superficial cervicals) are removed, examined for the presence of metastatic lesions and photographed prior to freezing in OTC medium.

Primary lesion size is determined through measurement of length and width. Lesion volume is calculated using the following equation ($V=W \times L^2)/2$).

Whole Mount Immunohistochemistry for Lymphatic and Blood Vessels

Cartilage is removed from the edge of the paraformaldehyde fixed ear prior to the ear being separated into the dorsal (with primary lesion) and ventral sections. Dorsal ear sections are premeablised in 0.3% Triton-x100 in PBS for 1 hour at 4° C. followed by blocking overnight at 4° C. in 1% BSA/0.3% Triton-x100/PBS on rotating wheel. Ears are then incubated for 24 hours in the primary antibody (Mouse LYVE-1 Biotinylated affinity 6402 purified pAB, R&D Systems, Cat # BAF2125 or Rat Anti-mouse CD31 (PECAM) Clone 390, eBioscience, Cat #14-0311) at 4° C. on rotating wheel followed by 6×1 hour washes in 0.3% Triton-x100/PBS at 4° C.

Ear are then incubated for 24 hours in the secondary detection reagent (Streptavidin Cy3 Conjugate, Sigma-Aldrich Cat # S-6402 or Alexa Fluor 488 Goat Anti-Rat IgI (H+L) Antibody, Invitrogen Molecular Probes Cat # A11006) at 4° C. on rotating wheel followed by 6×1 hour washes in 0.3% Triton-x100/PBS at 4° C.

Ear sections are refixed in 4% paraformaldehyde for 20 minutes then washed twice in PBS prior to mounting in whole mount slide with Prolong Gold antifade reagent with Dapi (Invitrogen Molecular Probes Cat# P36935).

Representative images of ears are taken on a Olympus BX51 microscope with DP72 CCD camera and associated software.

Caki-1 Tumor Model

Female BALB/c nu/nu mice at 6 to 8 weeks injected subcutaneously (s.c.) with the human renal cancer cell line Caki-1 (ATCC HTB-46). Cells are resuspended in Dulbecco's PBS (Sigma-Aldrich) and 5×10^6 cells are injected s.c near the third mammary fat pad. Tumors are grown to an average size of 150 mm³ prior to commencement of treatment. Treatment can consist of a repeat oral gavage at varying doses dose. Tumour growth and animal health is monitored over the course of the study. Tumor growth is represented as mean tumor volume in mm³. Animals are euthanized and tumors excised for either histologic examination including development of lymphatic vessels and blood vessels within the tumor and target engagement (phosphorylated VEGFR3) using immunohistochemistry or alternatively using tumor lysates to quantitate in situ inhibition of the target (phosphorylated VEGFR3).

The invention claimed is:

1. A compound of the formula (I), or a stereoisomer, or a salt or a solvate thereof:

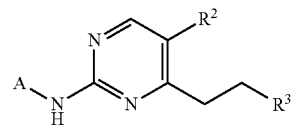

wherein:

A is an optionally substituted 5 or 6 membered heteroaryl group linked to the NH group through an aromatic ring carbon atom, in which the heteroaryl ring system contains 1 to 4 heteroatoms selected from N, O and S, and;

A may bear a substituent $R^{1A}$ which is not alpha to the NH group and may optionally further bear one, two or three substituents $R^{1C}$, where $R^{1A}$ is selected from:

(i) $CH(R^{C1})NZ^1Z^3$, where $R^{C1}$ is selected from H, $C_{1-2}$ alkyl, $Z^1$ is selected from H, $C_{1-3}$ alkyl optionally substituted by OH, $C(=O)OC_{1-4}$ alkyl and $C(=O)Me$ and $Z^3$ is H, or $Z^1$ and $Z^3$ together with the N to which they are attached form a 4-6 membered heterocycle containing at least one N and optionally one O;

(ii) $XNHZ^2$, where X is selected from $CMe_2$, cyclopropylidene, cyclobutylidene, cyclopentylidene and oxetanylidine and $Z^2$ is selected from H, $C_{1-3}$ alkyl optionally substituted by OH, $C(=O)OC_{1-3}$ alkyl and $C(=O)Me$;

(iii) a group selected from $R^{1A1}$ to $R^{1A13}$:

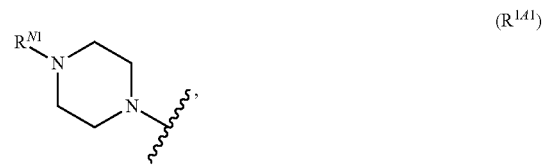

-continued

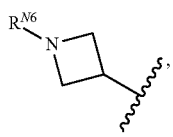 (R$^{146}$)

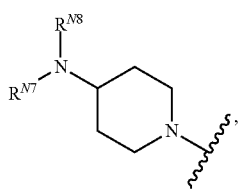 (R$^{147}$)

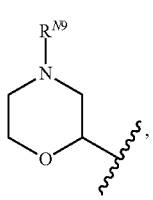 (R$^{148}$)

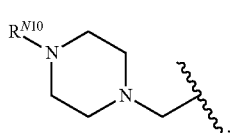 (R$^{149}$)

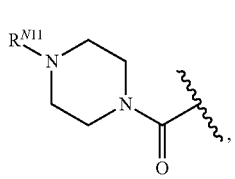 (R$^{1410}$)

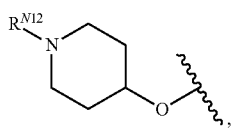 (R$^{1411}$)

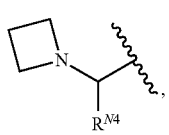 (R$^{1412}$)

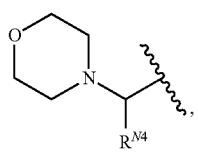 (R$^{1413}$)

wherein:
$R^{N1}$ is selected from H, $C_{1-4}$ alkyl, $C_{3-4}$ cycloalkyl and C(=O)Me;
$R^{N2}$ is selected from H, $C_{1-4}$ alkyl, $C_{3-4}$ cycloalkyl and C(=O)Me;
$R^{N3}$ is selected from H, $C_{1-4}$ alkyl, $C_{3-4}$ cycloalkyl and C(=O)Me;
$R^{N4}$ is selected from H and $CH_3$;
$R^{N5}$ is selected from H, $C_{1-4}$ alkyl, $C_{3-4}$ cycloalkyl and C(=O)Me;
$R^{N6}$ is selected from H, $C_{1-4}$ alkyl, $C_{3-4}$ cycloalkyl and C(=O)Me;
$R^{N7}$ and $R^{N8}$ are independently selected from H and $CH_3$;
$R^{N9}$ is selected from H, $C_{1-4}$ alkyl, $C_{3-4}$ cycloalkyl and C(=O)Me;
$R^{N10}$ is selected from H, $C_{1-4}$ alkyl, $C_{3-4}$ cycloalkyl and C(=O)Me;
$R^{N11}$ is selected from H, $C_{1-4}$ alkyl, $C_{3-4}$ cycloalkyl and C(=O)Me; and
$R^{N12}$ is selected from H, $C_{1-4}$ alkyl, $C_{3-4}$ cycloalkyl and C(=O)Me and where each $R^{1C}$ is independently selected from:
(i) $C_{1-3}$ alkyl optionally substituted with one to three substituents selected from F, OH and O—($C_{1-3}$ alkyl);
(ii) F;
(iii) Cl;
(iv) O—($C_{1-3}$ alkyl);
(v) CN;
(vi) =O; and
(vii) C(=O) $C_{1-3}$ alkyl $R^2$ is selected from H, halo, $C_{1-4}$ alkyl, $CF_3$, $CF_2H$, CN and O—($C_{1-3}$ alkyl);
$R^3$ is selected from substituted phenyl and a substituted 6 membered heteroaryl group, where the heteroaryl ring system contains 1 or 2 N heteroatoms, where $R^3$ bears a substituent $R^4$ either alpha or beta to the —$C_2H_4$— group, and may additionally bear further substituents selected from F, methyl and $CF_3$; and $R^4$ is —Y—C(O)N($R^{N13}$)$Z^4$, where Y is selected from —CHCH$_3$—, —CH(CH$_2$CH$_3$)—, —C(CH$_3$)$_2$— and $C_{3-5}$ cycloalkylidene; $R^{N13}$ is selected from H and $CH_3$; and $Z^4$ is selected from H, $CH_3$ and $OCH_3$.

2. A compound, or a stereoisomer, or a salt, or a solvate thereof, according to claim 1, wherein A is an optionally substituted 6 membered heteroaryl group.

3. A compound, or a stereoisomer, or a salt, or a solvate thereof, according to claim 2, wherein A is optionally substituted pyridyl.

4. A compound, or a stereoisomer, or a salt, or a solvate thereof, according to claim 3, wherein A is selected from:

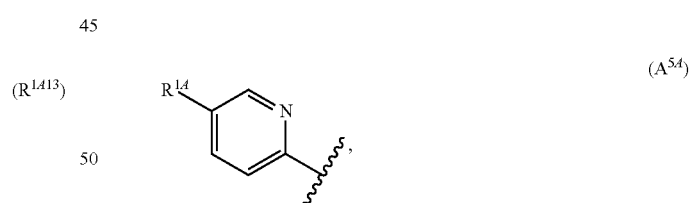 (A$^{54}$)

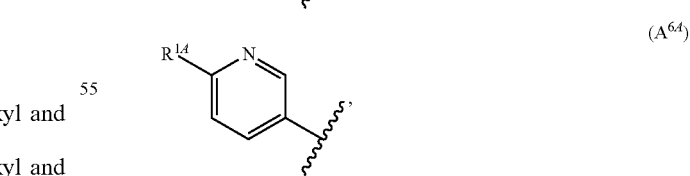 (A$^{64}$)

 (A$^{74}$)

-continued

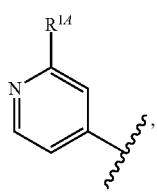
(A^{8A})

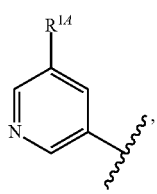
(A^{9A})

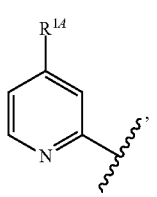
(A^{10A})

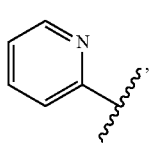
(A^{11A})

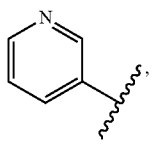
(A^{12A})

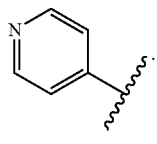
(A^{13A})

5. A compound, or a stereoisomer, or a salt, or a solvate thereof, according to claim 4, wherein A is

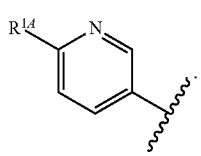
(A^{6A})

6. A compound, or a stereoisomer, or a salt, or a solvate thereof, according to claim 1, wherein A is an optionally substituted 5 membered heteroaryl group.

7. A compound, or a stereoisomer, or a salt, or a solvate thereof, according to claim 6, wherein A is optionally substituted pyrazolyl.

8. A compound, or a stereoisomer, or a salt, or a solvate thereof, according to claim 7, wherein A is selected from:

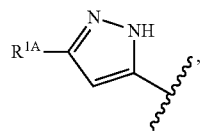
(A^{14A})

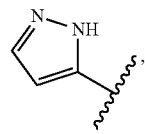
(A^{15A})

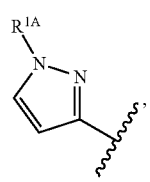
(A^{16A})

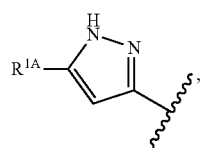
(A^{17A})

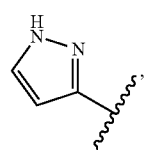
(A^{18A})

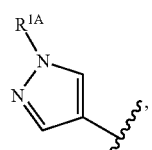
(A^{19A})

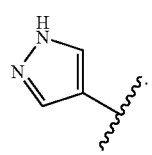
(A^{20A})

9. A compound, or a stereoisomer, or a salt, or a solvate thereof, according to claim 8, wherein A is

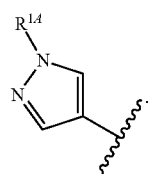
(A^{19A})

10. A compound, or a stereoisomer, or a salt, or a solvate thereof, according to claim 1, wherein A is selected from:

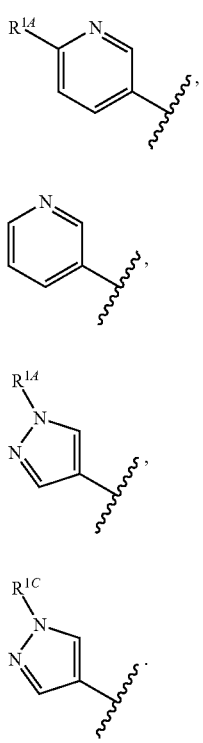

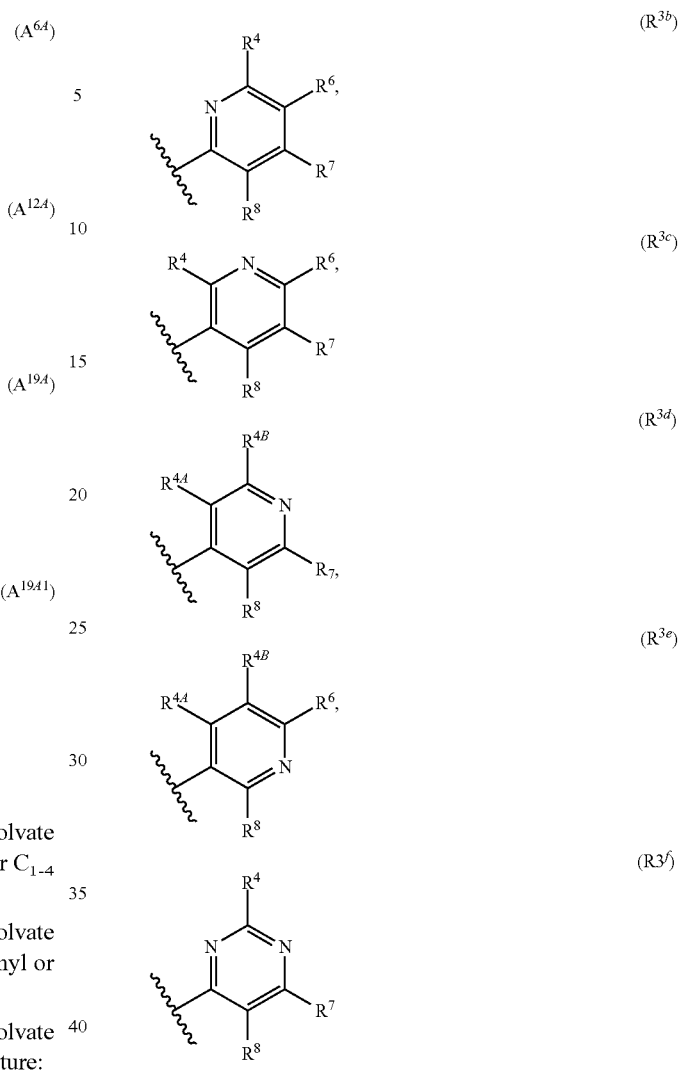

11. A compound, or a stereoisomer, or a salt, or a solvate thereof, according to claim 1, wherein $R^2$ is H, F, Cl, or $C_{1-4}$ alkyl, $CF_3$, $CF_2H$, CN or methoxy.

12. A compound, or a stereoisomer, or a salt, or a solvate thereof, according to claim 11, wherein $R^2$ is Cl, methyl or $CF_3$.

13. A compound, or a stereoisomer, or a salt, or a solvate thereof, according to claim 1, wherein $R^3$ has the structure:

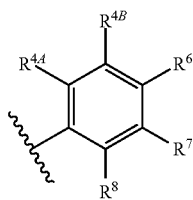

where $R^6$, $R^7$ and $R^8$ are independently selected from H, F, methyl and $CF_3$; and one of $R^{4A}$ and $R^{4B}$ is $R^4$, and the other of $R^{4A}$ and $R^{4B}$ is selected from H, F, methyl and $CF_3$.

14. A compound, or a stereoisomer, or a salt, or a solvate thereof, according to claim 1, wherein $R^3$ is a substituted 6 membered heteroaryl group, where the heteroaryl ring system contains 1 or 2 N heteroatoms.

15. A compound, or a stereoisomer, or a salt, or a solvate thereof, according to claim 14, wherein $R^3$ is selected from one of the following structures:

where $R^6$, $R^7$ and $R^8$ (if present) are independently selected from H, F, methyl and $CF_3$;

one of $R^{4A}$ and $R^{4B}$ (if present) is $R^4$, and the other is selected from H, F, methyl and $CF_3$.

16. A compound, or a stereoisomer, or a salt, or a solvate thereof, according to claim 1, wherein $R^{N13}$ is H or Me.

17. A compound, or a stereoisomer, or a salt, or a solvate thereof, according to claim 1, wherein $Z^4$ is H, Me or OMe.

18. A compound, or a stereoisomer, or a salt, or a solvate thereof, according to claim 1, wherein Y is selected from —CHCH$_3$—, —CH(CH$_2$CH$_3$)—, —C(CH$_3$)$_2$— and $C_{3-5}$ cycloalkylidene.

19. A compound of formula (I), or a stereoisomer, or a salt, or a solvate thereof, according to claim 1, wherein:

A is an optionally substituted 5 or 6 membered heteroaryl group linked to the NH group through an aromatic ring carbon atom, in which the heteroaryl ring system contains 1 or 2 heteroatoms selected from N and O, and;

A may bear a substituent $R^{1A}$ which is not alpha to the NH group, and may optionally further bear one or two substituents $R^{1C}$, where $R^{1A}$ is selected from:

(i) CH($R^{C1}$)NZ$^1$Z$^3$, where $R^{C1}$ is selected from H, $C_{1-2}$ alkyl, $Z^1$ is selected from H and $C_{1-3}$ alkyl substituted by C(=O)OC$_{1-4}$ alkyl or C(=O)Me and $Z^3$ is H, or $Z^1$ and Z³ together with the N to which they are attached form a 4-6 membered heterocycle containing one N and optionally one O;

(iii) a group selected from:

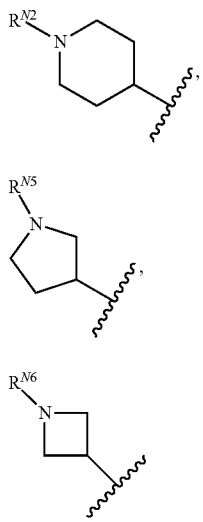

wherein:

$R^{N2}$ is selected from H, $C_{1-3}$ alkyl and C(=O)Me;

$R^{N5}$ is selected from H and $C_{1-4}$ alkyl;

$R^{N6}$ is H; and where each $R^{1C}$ is independently selected from:

(i) $C_{1-3}$ alkyl optionally substituted with one to three substituents selected from F, OH and O—($C_{1-3}$ alkyl);

(ii) O—($C_{1-3}$ alkyl);

CN; and (iv) C(=O)Me;

$R^2$ is selected from halo, $CH_3$ and $CF_3$;

$R^3$ is substituted phenyl, where $R^3$ bears a substituent $R^4$ either alpha or beta to the —$C_2H_4$— group, and may additionally bear a further substituent F; and $R^4$ is —Y—C(O)N($R^{N13}$)$Z^4$, where Y is selected from —CHCH$_3$—, —CH(CH$_2$CH$_3$)—, —C(CH$_3$)$_2$—, and $C_{3-4}$ cycloalkylidene; $R^{N13}$ is H; and $Z^4$ is H.

20. A compound of formula (I), or a stereoisomer, or a salt, or a solvate thereof, according to claim 1 wherein:

A is an optionally substituted 5 or 6 membered heteroaryl group linked to the NH group through an aromatic ring carbon atom, in which the heteroaryl ring system contains 1 or 2 heteroatoms selected from N and O, and;

A may bear a substituent $R^{1A}$ which is not alpha to the NH group, and may optionally further bear one or two substituents $R^{1C}$, where $R^{1A}$ is selected from:

(i) CH($R^{C1}$)N$Z^1Z^3$, where $R^{C1}$ is selected from H, $C_{1-2}$ alkyl, $Z^1$ is selected from H and $C_{1-3}$ alkyl substituted by C(=O)O$C_{1-4}$ alkyl or C(=O)Me and $Z^3$ is H;

(iii) a group selected from:

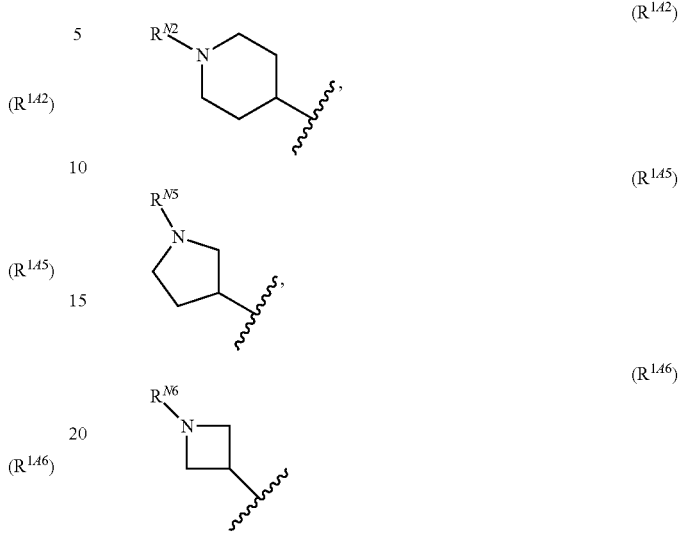

wherein:

$R^{N2}$ is selected from H, $C_{1-3}$ alkyl and C(=O)Me;

$R^{N5}$ is selected from H and $C_1$ alkyl;

$R^{N6}$ is H; and where each $R^{1C}$ is independently selected from:

(i) $C_{1-3}$ alkyl optionally substituted with one to three substituents independently selected from F, OH and O—($C_{1-3}$ alkyl);

(ii) O—($C_{1-3}$ alkyl);

(iii) CN; and (iv) C(=O)Me;

$R^2$ is selected from halo, $CH_3$ and $CF_3$;

$R^3$ is substituted phenyl, where $R^3$ bears a substituent $R^4$ either alpha or beta to the —$C_2H_4$— group, and may additionally bear a further substituent F; and $R^4$ is —Y—C(O)N($R^{N13}$)$Z^4$, where Y is selected from —CHCH$_3$—, —CH(CH$_2$CH$_3$)—, —C(CH$_3$)$_2$—, and $C_{3-4}$ cycloalkylidene; $R^{N13}$ is H; and $Z^4$ is H.

21. A compound of formula (I), or a stereoisomer, or a salt, or a solvate thereof, according to claim 1 wherein:

A is an optionally substituted 5 or 6 membered heteroaryl group linked to the NH group through an aromatic ring carbon atom, in which the heteroaryl ring system contains 1 or 2 heteroatoms selected from N and O, and;

A may bear a substituent $R^{1A}$ which is not alpha to the NH group, and may optionally further bear one or two substituents $R^{1C}$, where $R^{1A}$ is selected from:

(i) CH($R^{C1}$)N$Z^1Z^3$, where $R^{C1}$ is methyl, $Z^1$ is H and $Z^3$ is H;

(iii) a group selected from:

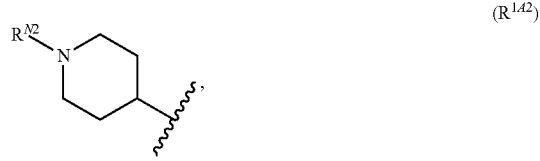

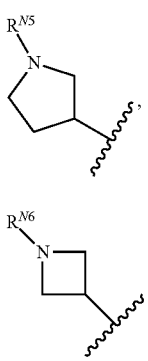

wherein:
$R^{N2}$ is selected from H and methyl;
$R^{N5}$ is selected from H and methyl;
$R^{N6}$ is H;
and where each $R^{1C}$ is independently selected from:
(i) $CH_3$ or $CF_3$;
$R^2$ is selected from halo and $CF_3$;
$R^3$ is substituted phenyl, where
   $R^3$ bears a substituent $R^4$ either alpha or beta to the $-C_2H_4-$ group, and may additionally bear a further substituent F; and
$R^4$ is $-Y-C(O)N(R^{N13})Z^4$, where Y is selected from $-CHCH_3-$, $-CH(CH_2CH_3)-$, $-C(CH_3)_2-$, and $C_3$ cycloalkylidene; $R^{N13}$ is H; and $Z^4$ is H.

22. A compound of formula (I), or a stereoisomer, or a salt, or a solvate thereof, of claim 1 wherein:
A is an optionally substituted pyrazolyl or pyridyl group linked to the NH group through an aromatic ring carbon atom, in which the heteroaryl ring system contains 1 or 2 heteroatoms selected from N and O, and;
A may bear a substituent $R^{1A}$ which is not alpha to the NH group, and may optionally further bear one or two substituents $R^{1C}$, where $R^{1A}$ is:

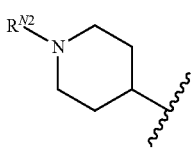

wherein:
$R^{N2}$ is methyl; and
where each $R^{1C}$ is independently selected from:
(i) $CH_3$ or $CF_3$;
$R^2$ is selected from Cl and $CF_3$;
$R^3$ is substituted phenyl, where
   $R^3$ bears a substituent $R^4$ alpha to the $-C_2H_4-$ group, and may additionally bear a further substituent F; and
$R^4$ is $-Y-C(O)N(R^{N13})Z^4$, where Y is selected from $-CHCH_3-$ and $C_3$ cycloalkylidene; $R^{N13}$ is H; and $Z^4$ is H.

23. A compound of formula (I), or a stereoisomer, or a salt, or a solvate thereof, according to claim 1
wherein:
A is an optionally substituted pyridyl, wherein A may bear one substituent $R^{1A}$ which is not alpha to the NH group, where $R^{1A}$ is selected from a group selected from:

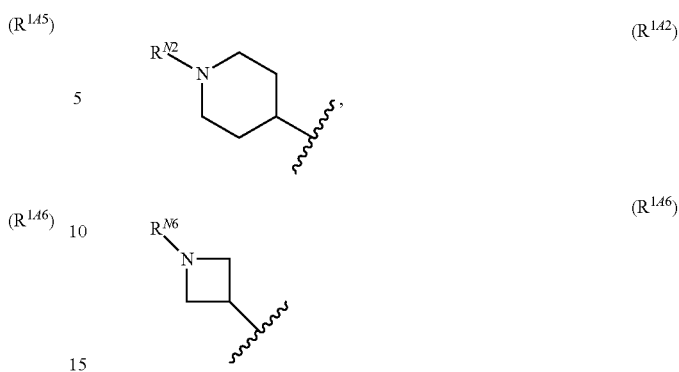

wherein:
$R^{N2}$ is selected from H and methyl;
$R^{N6}$ is selected from H and methyl;
$R^2$ is selected from Cl, methyl and $CF_3$; and
$R^4$ is $-Y-C(O)NH_2$, where Y is selected from $-CHCH_3-$, $-C(CH_3)_2-$, cyclopropylidene and cyclobutylidene.

24. A compound of formula (I), or a stereoisomer, or a salt, or a solvate thereof, according to claim 1
wherein:
A is an optionally substituted pyridyl, wherein A may bear one substituent $R^{1A}$ which is not alpha to the NH group, where $R^{1A}$ is selected from a group selected from:

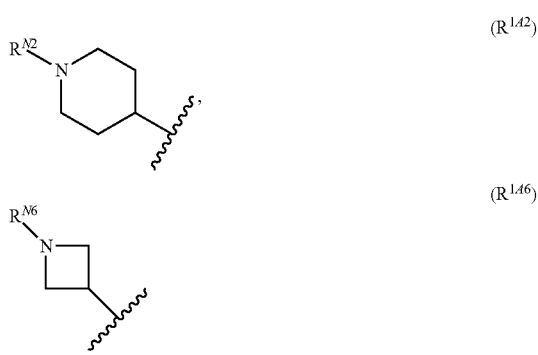

wherein:
$R^{N2}$ is selected from H and methyl;
$R^{N6}$ is selected from H and methyl;
$R^2$ is selected from Cl, methyl and $CF_3$; and
$R^4$ is $-Y-C(O)NH_2$, where Y is selected from $-C(CH_3)_2-$, cyclopropylidene and cyclobutylidene.

25. A compound of formula (I), or a stereoisomer, or a salt, or a solvate thereof, according to claim 1
wherein
A is selected from an optionally substituted 5 or 6 membered heteroaryl group which contains 1 or 2 heteroatoms selected from N and O, wherein A may bear one substituent $R^{1A}$ which is not alpha to the NH group, where $R^{1A}$ is selected from $R^{1A2}$, $R^{1A3}$ and $R^{1A6}$

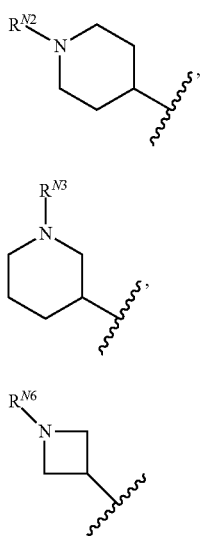

wherein:
$R^{N2}$ is selected from H and $C_{1-4}$ alkyl;
$R^{N3}$ is selected from H, $C_{1-3}$ alkyl, and C(=O)Me;
$R^{N6}$ is selected from H and $C_{1-4}$alkyl;
and may optionally further bear one substituent $R^{1C}$ selected from $CF_3$, $C_{1-3}$alkyl, $CH_2CF_3$, CN, C(=O)($C_{1-3}$alkyl), $CH(CH_3)NH_2$, $CHCF_2$, $OCH_3$, $CH(CH_3)NHCH_3$, $C_{1-3}$alkylOH and $C_{1-3}$alkylOMe;
$R^2$ is selected from halo, $C_{1-4}$alkyl and $CF_3$; and
$R^4$ is —Y—C(=O)$NH_2$, where Y is selected from —$CHCH_3$—, —C($CH_3$)$_2$—, cyclopropylidene and cyclobutylidene.

26. A compound selected from the group consisting of the following compounds:
- 1-(2-(2-(2-((6-(piperidin-4-yl)pyridin-3-yl)amino)-5-(trifluoromethyl)pyrimidin-4-yl)ethyl)phenyl)cyclopropanecarboxamide (5);
- 1-(2-(2-(5-chloro-2-(pyridin-3-ylamino)pyrimidin-4-yl)ethyl)phenyl)cyclopropanecarboxamide (6);
- 1-(2-(2-(5-chloro-2-((6-(trifluoromethyl)pyridin-3-yl)amino)pyrimidin-4-yl)ethyl)phenyl)cyclopropanecarboxamide (9);
- 1-(2-(2-(5-(trifluoromethyl)-2-((6-(trifluoromethyl)pyridin-3-yl)amino)pyrimidin-4-yl)ethyl)phenyl)cyclopropanecarboxamide (10);
- 1-(2-(2-(5-chloro-2-(oxazol-2-ylamino)pyrimidin-4-yl)ethyl)phenyl)cyclopropanecarboxamide (11);
- 1-(2-(2-(5-chloro-2-(pyrimidin-5-ylamino)pyrimidin-4-yl)ethyl)phenyl)cyclopropanecarboxamide (12);
- 1-(2-(2-(5-Chloro-2-((1-methyl-1H-pyrazol-4-yl)amino)pyrimidin-4-yl)ethyl)phenyl)cyclopropanecarboxamide (13);
- 1-(2-(2-(2-((1-(azetidin-3-yl)-1H-pyrazol-4-yl)amino)-5-chloropyrimidin-4-yl)ethyl)phenyl)cyclopropanecarboxamide (14);
- 1-(2-(2-(5-chloro-2-((6-(piperidin-4-yl)pyridin-3-yl)amino)pyrimidin-4-yl)ethyl)phenyl)cyclopropanecarboxamide (15);
- 1-(2-(2-(5-chloro-2-(5-(1-methylpiperidin-3-yl)pyridin-3-ylamino)pyrimidin-4-yl)ethyl)phenyl)cyclopropanecarboxamide (16);
- 1-(2-(2-(5-chloro-2-((1-(piperidin-4-yl)-1H-pyrazol-4-yl)amino)pyrimidin-4-yl)ethyl)phenyl)cyclopropanecarboxamide (17);
- 1-(2-(2-(5-chloro-2-((1-(1-methylpiperidin-4-yl)-1H-pyrazol-4-yl)amino)pyrimidin-4-yl)ethyl)phenyl)cyclopropanecarboxamide (18);
- 1-(2-(2-(2-(1H-pyrazol-4-ylamino)-5-chloropyrimidin-4-yl)ethyl)phenyl)cyclopropanecarboxamide (19);
- 1-(2-(2-(5-chloro-2-(1-(pyrrolidin-3-yl)-1H-pyrazol-4-ylamino) pyrimidin-4-yl)ethyl)phenyl)cyclopropanecarboxamide (20);
- 1-(2-(2-(5-chloro-2-(1-(1-methylpyrrolidin-3-yl)-1H-pyrazol-4-ylamino)pyrimidin-4-yl)ethyl)phenyl)cyclopropanecarboxamide (21);
- 1-(2-(2-(5-chloro-2-(pyridazin-4-ylamino)pyrimidin-4-yl)ethyl)phenyl)cyclopropanecarboxamide (22);
- 1-(2-(2-(5-Chloro-2-((3-methyl-1H-pyrazol-4-yl)amino)pyrimidin-4-yl)ethyl)phenyl)cyclopropanecarboxamide (25);
- 1-(2-(2-(5-Chloro-2-((1,3-dimethyl-1H-pyrazol-4-yl)amino)pyrimidin-4-yl)ethyl)phenyl)cyclopropanecarboxamide (26);
- 1-(2-(2-(5-chloro-2-((5-methyl-1H-pyrazol-3-yl)amino)pyrimidin-4-yl)ethyl)phenyl)cyclopropanecarboxamide (27);
- 1-(2-(2-(5-Chloro-2-((1-methyl-1H-pyrazol-3-yl)amino)pyrimidin-4-yl)ethyl)phenyl)cyclopropanecarboxamide (28);
- 1-(2-(2-(5-chloro-2-((1-(2,2,2-trifluoroethyl)-1H-pyrazol-4-yl)amino)pyrimidin-4-yl)ethyl)phenyl)cyclopropanecarboxamide (29);
- 1-(2-(2-(5-chloro-2-((1-isopropyl-1H-pyrazol-4-yl)amino)pyrimidin-4-yl)ethyl)phenyl)cyclopropanecarboxamide (30);
- 1-(2-(2-(5-chloro-2-((6-cyanopyridin-3-yl)amino)pyrimidin-4-yl)ethyl)phenyl)cyclopropanecarboxamide (31);
- 1-(2-(2-(2-((6-acetylpyridin-3-yl)amino)-5-chloropyrimidin-4-yl)ethyl)phenyl)cyclopropanecarboxamide (32);
- 1-(2-(2-(2-((6-(1-aminoethyl)pyridin-3-yl)amino)-5-chloropyrimidin-4-yl)ethyl)phenyl)cyclopropanecarboxamide (33)
- 1-(2-(2-(5-chloro-2-((1-(difluoromethyl)-1H-pyrazol-4-yl)amino)pyrimidin-4-yl)ethyl)phenyl)cyclopropanecarboxamide (34);
- 2-(2-(2-(2-(1H-pyrazol-4-ylamino)-5-chloropyrimidin-4-yl)ethyl)phenyl) propanamide (35);
- 2-(2-(2-(5-chloro-2-(1-methyl-1H-pyrazol-4-ylamino)pyrimidin-4-yl)ethyl)phenyl) propanamide (36);
- 2-(2-(2-(5-chloro-2-((6-(piperidin-4-yl)pyridin-3-yl)amino)pyrimidin-4-yl)ethyl)phenyl)propanamide (37);
- 2-(2-(2-(5-chloro-2-(6-(1-methylpiperidin-4-yl)pyridin-3-ylamino)pyrimidin-4-yl)ethyl)phenyl)propanamide (38);
- 2-(2-(2-(5-chloro-2-(pyridin-3-ylamino)pyrimidin-4-yl)ethyl)phenyl) propanamide (39);
- 2-(2-(2-(5-chloro-2-(pyrimidin-5-ylamino)pyrimidin-4-yl)ethyl)phenyl) propanamide (40)
- 2-(2-(2-(5-chloro-2-(6-methylpyridin-3-ylamino)pyrimidin-4-yl)ethyl)phenyl) propanamide (41);
- 2-(2-(2-(5-chloro-2-(pyridazin-4-ylamino)pyrimidin-4-yl)ethyl)phenyl) propanamide (42);
- 2-(2-(2-(5-chloro-2-(1-(piperidin-4-yl)-1H-pyrazol-4-ylamino)pyrimidin-4-yl)ethyl)phenyl)propanamide (43);
- 2-(2-(2-(5-chloro-2-(1-(1-methylpiperidin-4-yl)-1H-pyrazol-4-ylamino)pyrimidin-4-yl)ethyl)phenyl)propanamide (44);
- 2-(2-(2-(5-Chloro-2-((1-methyl-1H-pyrazol-4-yl)amino)pyrimidin-4-yl)ethyl)phenyl)-2-methylpropanamide (45);

1-(2-(2-(2-((1H-Pyrazol-4-yl)amino)-5-methylpyrimidin-4-yl)ethyl)phenyl)cyclopropanecarboxamide (46)

1-(2-(2-(5-methyl-2-((1-methyl-1H-pyrazol-4-yl)amino)pyrimidin-4-yl)ethyl)phenyl)cyclopropanecarboxamide (47);

1-(2-(2-(5-methyl-2-((1-(1-methylpiperidin-4-yl)-1H-pyrazol-4-yl)amino)pyrimidin-4-yl)ethyl)phenyl)cyclopropanecarboxamide (48);

1-(2-(2-(5-Methyl-2-((6-(1-methylpiperidin-4-yl)pyridin-3-yl)amino)pyrimidin-4-yl)ethyl)phenyl)cyclopropanecarboxamide (49);

2-(2-(2-(5-Methyl-2-((1-methyl-1H-pyrazol-4-yl)amino)pyrimidin-4-yl)ethyl)phenyl)propanamide (51);

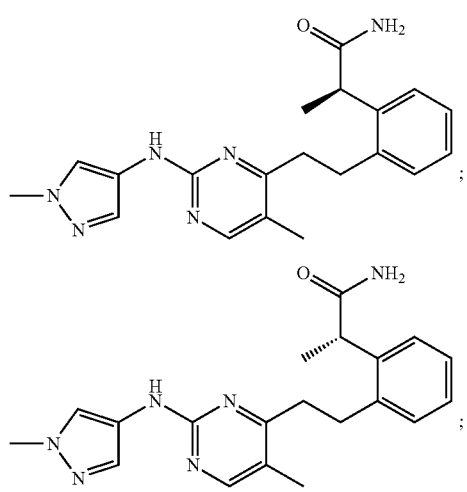

1-(3-(2-(2-((1-(piperidin-4-yl)-1H-pyrazol-4-yl)amino)-5-(trifluoromethyl)pyrimidin-4-yl)ethyl)phenyl)cyclopropanecarboxamide (53);

2-(2-(2-(2-((1H-pyrazol-4-yl)amino)-5-(trifluoromethyl)pyrimidin-4-yl)ethyl)phenyl)propanamide (54);

2-(2-(2-(2-((1-methyl-1H-pyrazol-4-yl)amino)-5-(trifluoromethyl)pyrimidin-4-yl)ethyl)phenyl)propanamide (55);

2-(2-(2-(2-((1-(piperidin-4-yl)-1H-pyrazol-4-yl)amino)-5-(trifluoromethyl)pyrimidin-4-yl)ethyl)phenyl)propanamide (56);

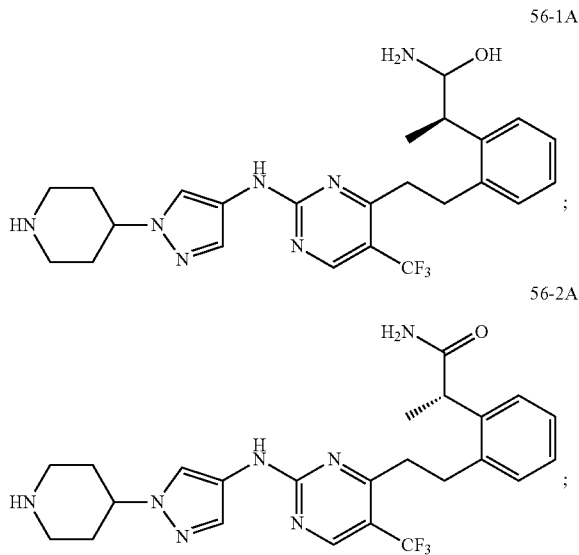

2-(2-(2-(2-((1-(1-Methylpiperidin-4-yl)-1H-pyrazol-4-yl)amino)-5-(trifluoromethyl)pyrimidin-4-yl)ethyl)phenyl)propanamide (57);

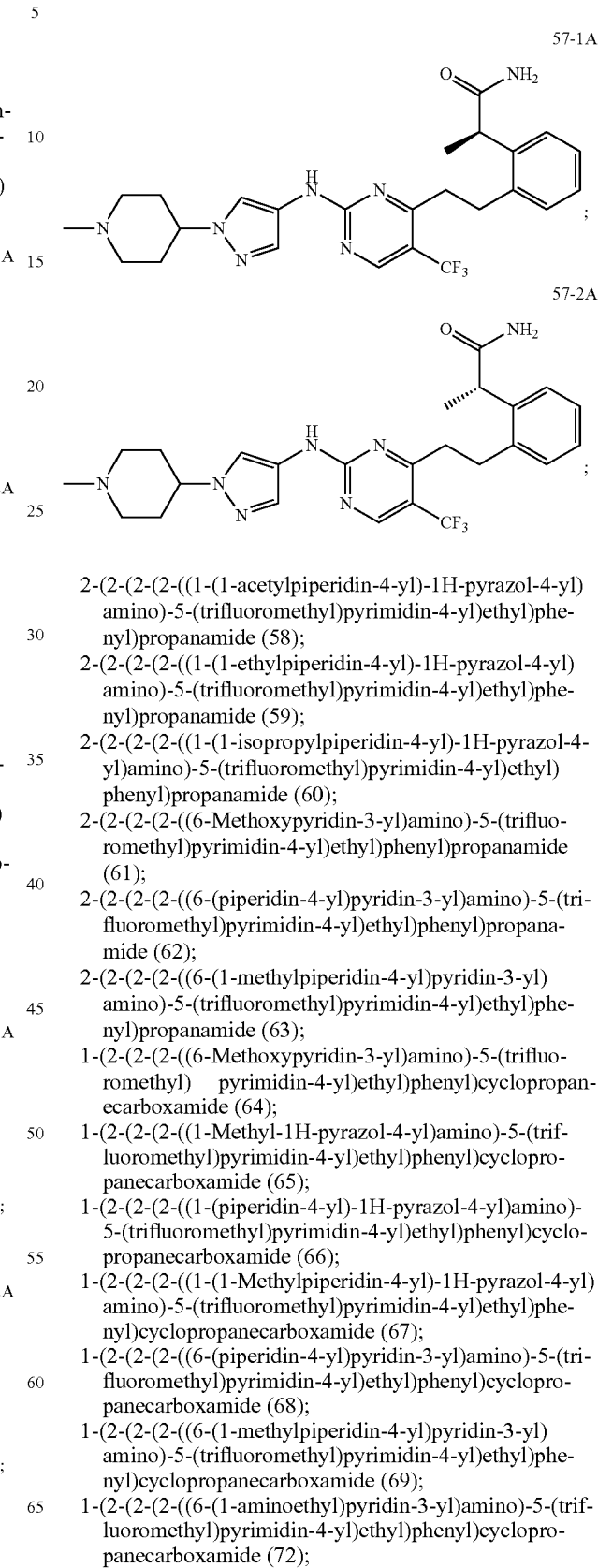

2-(2-(2-(2-((1-(1-acetylpiperidin-4-yl)-1H-pyrazol-4-yl)amino)-5-(trifluoromethyl)pyrimidin-4-yl)ethyl)phenyl)propanamide (58);

2-(2-(2-(2-((1-(1-ethylpiperidin-4-yl)-1H-pyrazol-4-yl)amino)-5-(trifluoromethyl)pyrimidin-4-yl)ethyl)phenyl)propanamide (59);

2-(2-(2-(2-((1-(1-isopropylpiperidin-4-yl)-1H-pyrazol-4-yl)amino)-5-(trifluoromethyl)pyrimidin-4-yl)ethyl)phenyl)propanamide (60);

2-(2-(2-(2-((6-Methoxypyridin-3-yl)amino)-5-(trifluoromethyl)pyrimidin-4-yl)ethyl)phenyl)propanamide (61);

2-(2-(2-(2-((6-(piperidin-4-yl)pyridin-3-yl)amino)-5-(trifluoromethyl)pyrimidin-4-yl)ethyl)phenyl)propanamide (62);

2-(2-(2-(2-((6-(1-methylpiperidin-4-yl)pyridin-3-yl)amino)-5-(trifluoromethyl)pyrimidin-4-yl)ethyl)phenyl)propanamide (63);

1-(2-(2-(2-((6-Methoxypyridin-3-yl)amino)-5-(trifluoromethyl) pyrimidin-4-yl)ethyl)phenyl)cyclopropanecarboxamide (64);

1-(2-(2-(2-((1-Methyl-1H-pyrazol-4-yl)amino)-5-(trifluoromethyl)pyrimidin-4-yl)ethyl)phenyl)cyclopropanecarboxamide (65);

1-(2-(2-(2-((1-(piperidin-4-yl)-1H-pyrazol-4-yl)amino)-5-(trifluoromethyl)pyrimidin-4-yl)ethyl)phenyl)cyclopropanecarboxamide (66);

1-(2-(2-(2-((1-(1-Methylpiperidin-4-yl)-1H-pyrazol-4-yl)amino)-5-(trifluoromethyl)pyrimidin-4-yl)ethyl)phenyl)cyclopropanecarboxamide (67);

1-(2-(2-(2-((6-(piperidin-4-yl)pyridin-3-yl)amino)-5-(trifluoromethyl)pyrimidin-4-yl)ethyl)phenyl)cyclopropanecarboxamide (68);

1-(2-(2-(2-((6-(1-methylpiperidin-4-yl)pyridin-3-yl)amino)-5-(trifluoromethyl)pyrimidin-4-yl)ethyl)phenyl)cyclopropanecarboxamide (69);

1-(2-(2-(2-((6-(1-aminoethyl)pyridin-3-yl)amino)-5-(trifluoromethyl)pyrimidin-4-yl)ethyl)phenyl)cyclopropanecarboxamide (72);

1-(2-(2-(2-((6-(1-(methylamino)ethyl)pyridin-3-yl) amino)-5-(trifluoromethyl)pyrimidin-4-yl)ethyl)phenyl)cyclopropanecarboxamide (73);
1-(2-(2-(2-((6-(1-(azetidin-1-yl)ethyl)pyridin-3-yl) amino)-5-(trifluoromethyl)pyrimidin-4-yl)ethyl)phenyl)cyclopropanecarboxamide (74);
1-(2-(2-(2-((6-(1-morpholinoethyl)pyridin-3-yl)amino)-5-(trifluoromethyl)pyrimidin-4-yl)ethyl)phenyl)cyclopropanecarboxamide (75);

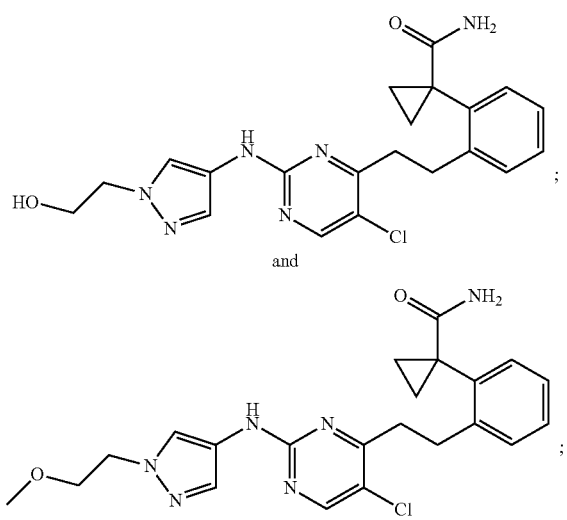

and or a stereoisomer, a salt or a solvate thereof.

27. A process for the preparation of a compound, or a stereoisomer, a salt or a solvate thereof, according to claim 1, comprising reacting a compound of formula F1

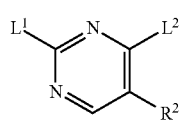

F1 with a compound of formula A-NH$_2$ to displace the group L$^1$ and with a compound of the formula HC≡R$^3$ to displace the group L$^2$; or
with a compound of formula HC≡R$^3$ to displace the group L$^2$, and with a compound of formula A-NH$_2$ to displace the group L$^2$,
wherein R$^2$, A and R$^3$ areas defined in formula (I) in claim 1 and L$^1$ and L$^2$ are leaving groups.

28. A pharmaceutical agent comprising a compound, or a stereoisomer, a salt or a solvate thereof, according to claim 1.

29. A composition comprising a compound, or a stereoisomer, a salt or a solvate thereof, according to claim 1, and a pharmaceutically acceptable carrier or diluent.

30. A method of inhibiting VEGFR3 in vitro or in vivo, comprising contacting a cell with an effective amount of a compound, or a stereoisomer, a salt or a solvate thereof, according to claim 1.

31. A method for treating a cancer selected from melanoma, breast cancer and head and neck cancer, comprising administering an effective amount of a compound, or a stereoisomer, or a salt, or a solvate thereof, according to claim 1 to a subject in need thereof.

32. The composition of claim 29, further comprising an anti-tumour agent selected from the group consisting of an antiproliferative drug, an antineoplastic drug, a cytostatic agent, an anti-invasion agent, an inhibitor of growth factor function, an antiangiogenic agent, an antilymphangiogenic agent, a vascular damaging agent, and combinations thereof.

33. A compound according to claim 1, wherein R$^{1A}$ is:

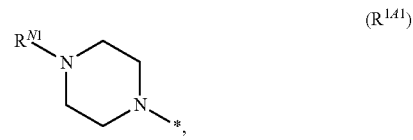

(R$^{141}$)

wherein R$^{N1}$ is C(═O)Me, H, methyl or ethyl.

34. A compound according to claim 1, wherein R$^{1A}$ is:

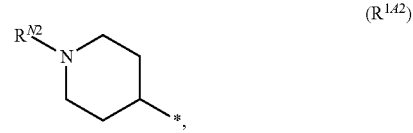

(R$^{142}$)

wherein R$^{N2}$ is selected from H, methyl and ethyl.

35. A compound according to claim 1, wherein R$^{1A}$ is:

(R$^{143}$)

wherein R$^{N3}$ is selected from H and methyl.

36. A compound according to claim 1, wherein R$^{1A}$ is:

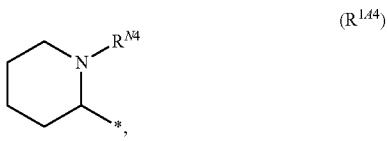

(R$^{144}$)

wherein R$^{N4}$ is selected from H and methyl.

37. A compound according to claim 1, wherein R$^{1A}$ is:

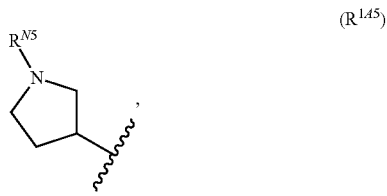

(R$^{145}$)

wherein R$^{N5}$ is selected from H and methyl.

38. A compound according to claim 1, wherein $R^{14}$ is:

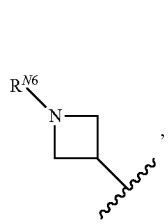  ($R^{147}$)

wherein $R^{N6}$ is selected from H and methyl.

39. A compound according to claim 1, wherein $R^{14}$ is:

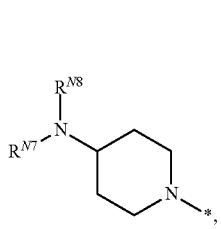  ($R^{147}$)

wherein $R^{N7}$ and $R^{N8}$ are both H or both methyl.

40. A compound according to claim 1, wherein $R^{14}$ is:

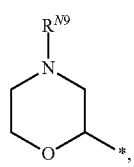  ($R^{148}$)

wherein $R^{N9}$ is H.

41. A compound according to claim 1, wherein $R^{14}$ is:

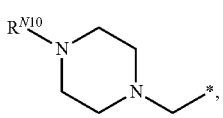  ($R^{149}$)

wherein $R^{N10}$ is selected from H and methyl.

42. A compound according to claim 1, wherein $R^{14}$ is:

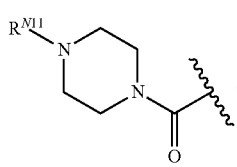  ($R^{1410}$)

wherein $R^{N11}$ is selected from H and methyl.

43. A compound according to claim 1, wherein $R^{14}$ is:

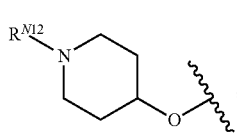  ($R^{1411}$)

where $R^{N12}$ is selected from H and methyl.

44. A compound according to claim 1, wherein $R^{14}$ is selected from:

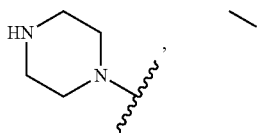

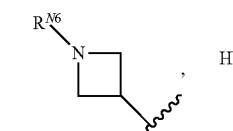

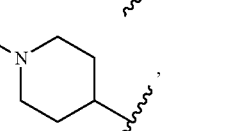

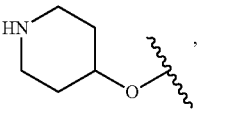

45. A compound according to claim 1, where no $R^{1B}$ substituents are present on A.

46. A compound according to claim 1, where $R^{1B}$ is methyl.

47. A compound according to claim 1, where a single $R^{1B}$ substituent is present.

48. A compound according to claim 1, where no $R^{1C}$ substituents are present on A.

49. A compound according to claim 1, where $R^{1C}$ is methyl or $CF_3$.

50. A compound according to claim 1, where a single $R^{1C}$ substituent is present.

51. A compound according to claim 13, wherein the group of $R^{4A}$ and $R^{4B}$ that is not $R^4$, and $R^6$, $R^7$ and $R^8$ are all H.

52. A compound according to claim 13, wherein one of the group of $R^{4A}$ and $R^{4B}$ that is not $R^4$, $R^6$, $R^7$ and $R^8$ is not H.

53. A compound according to claim 52, wherein the group that is not H is either $R^6$ or $R^7$.

54. A compound according to claim 13, wherein the group $R^{4A}$ is $R^4$, and $R^{4B}$, $R^6$, $R^7$ and $R^8$ are all H.

55. A compound according to claim 15, wherein the group of $R^{4A}$ and $R^{4B}$ (if present) that is not $R^4$, and $R^6$, $R^7$ and $R^8$ (if present) are all H.

56. A compound according to claim 15, wherein one of the group of $R^{4A}$ and $R^{4B}$ (if present) that is not $R^4$, and $R^6$, $R^7$ and $R^8$ (if present) is not H.

57. A compound according to claim 15, wherein $R^3$ is of structure $R^{3d}$ and $R^{3e}$.

58. A compound according to claim 1, wherein $R^4$ is alpha to the —$C_2H_4$— group.

59. A compound according to claim 1, wherein $R^4$ is beta to the —$C_2H_4$— group.

60. A compound according to claim 1, wherein Y is selected from $CHCH_3$—, —$CH(CH_2CH_3)$—, —$C(CH_3)_2$—, and $C_{3-4}$ cycloalkylidene.

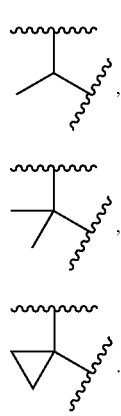
($Y^a$)
($Y^b$)
($Y^c$)
61. A compound according to claim 1, wherein Y is selected from —CH(CH$_2$CH$_3$)—, —C(CH$_3$)$_2$—, and C$_{3-4}$ cycloalkylidene.
* * * * *